ID 007294500B2

United States Patent
Boot et al.

(10) Patent No.: US 7,294,500 B2
(45) Date of Patent: Nov. 13, 2007

(54) MOSAIC INFECTIOUS BURSAL DISEASE VIRUS VACCINES

(75) Inventors: Hendrik Johannis Boot, Amersfoort (NL); Anna Agnes H. M. ter Huurne, Lelystad (NL); Bernardus Petrus H. Peeters, Lelystad (NL)

(73) Assignee: ID-Lelystad, Instituut voor Dierhouderij en Diergezondheid B.V., Lelystad (NL)

( * ) Notice: Subject to any disclaimer, the term of this patent is extended or adjusted under 35 U.S.C. 154(b) by 490 days.

(21) Appl. No.: 10/046,671

(22) Filed: Jan. 14, 2002

(65) Prior Publication Data

US 2003/0152592 A1    Aug. 14, 2003

Related U.S. Application Data

(63) Continuation of application No. PCT/NL00/00493, filed on Jul. 13, 2000.

(30) Foreign Application Priority Data

Jul. 14, 1999    (EP)    ................... 99202316

(51) Int. Cl.
C12N 7/02    (2006.01)
C12N 7/00    (2006.01)
C12N 15/86    (2006.01)

(52) U.S. Cl. ............... 435/239; 435/235.1; 435/456; 435/463; 435/464; 435/466

(58) Field of Classification Search .............. 435/236
See application file for complete search history.

(56) References Cited

U.S. PATENT DOCUMENTS

| 4,824,668 | A | | 4/1989 | Melchior, Jr. et al. |
| 5,788,970 | A | | 8/1998 | Vakharia et al. |
| 5,830,723 | A | | 11/1998 | Foster et al. |
| 5,871,744 | A | * | 2/1999 | Vakharia et al. ......... 424/205.1 |
| 6,017,759 | A | | 1/2000 | Vakharia et al. |

FOREIGN PATENT DOCUMENTS

| WO | WO95/26196 | 10/1995 |
| WO | WO98/06827 | 2/1998 |
| WO | WO98/09646 | 3/1998 |
| WO | WO 01/04319 A1 | 1/2001 |

OTHER PUBLICATIONS

Muller, H. and Becht, H. "Biosynthesis of virus-specific proteins in cells infected with infectious bursal disease virus and their significance as structural elements for infectious virus and incomplete particles" J. Virology vol. 44(1982), pp. 384-392.*
Mundt E. "Tissue culture infectivity of different strains of infectious busal disease virus is determined by distinct amino acid in V2" J. Gen. Virology vol. 80(1999), pp. 2067-2076.*
PCT International Search Report, PCT/NL00/00493 dated Oct. 30, 2000.
Lim et al., Adaptation of Very Virulent Infectious Bursal Disease Virus to Chicken Embryonic Fibroblasts by Site-Directed Mutagenesis of Residues 279 and 284 of Viral Coat Protein VP2, Journal of Virology, Apr. 1999, pp. 2854-2862, vol. 73, No. 4.
Muller et al., Biosynthesis of Virus-Specific Proteins in Cells Infected with Infectious Bursal Disease Virus and Their Significance as Structural Elements for Infectious Virus and Incomplete Particles, Journal of Virology, Oct. 1982, pp. 384-392, vol. 44, No. 1.
Mundt, Tissue culture infectivity of different strains of infectious bursal disease virus is determined by distinct amino acids in VP2, Journal of General Virology, 1999, pp. 2067-2076, vol. 80.
PCT International Search Report, PCT/US95/03772, dated Jul. 19, 1995, 3 pages.
PCT International Search Report, PCT/US97/14391, dated Feb. 13, 1998, 2 pages.

* cited by examiner

*Primary Examiner*—Bruce R. Campell
*Assistant Examiner*—Bo Peng
(74) *Attorney, Agent, or Firm*—TraskBritt

(57) ABSTRACT

The invention relates to Infectious Bursal Disease Virus ("IBDV") and vaccines therefor. Provided are infectious recombinant Infectious Bursal Disease Virus ("rIBDV") essentially incapable of growing in a cell that is not derived from a bursa cell, or an infectious rIBDV having retained at least part of the very virulent characteristics of a very virulent Infectious Bursal Disease Virus ("vvIBDV").

11 Claims, 50 Drawing Sheets

```
CONSENSUS: ggatacgatc ggtctgaccc cggggagtc acccggggac aggcygwcaa ggycttgttc   60
CEF94-A:   .......... .......... .......... .......... ...c.t.... ..t.......   60
D6948-A:   .......... .......... .......... .......... ...t.a.... ..c.......   60
TY89-A:    ---------- ---------- ---------- ---------- ---------- ----------   60

CONSENSUS: caggatggaa ctcctccttc tacaaygcta tcattgatgg tyagtagaga tcagacaaac  120
CEF94-A:   .......... .......... ......c... .......... .......c.. ..........  120
D6948-A:   .......... .......... ......t... .......... ......t... ..........  120
TY89-A:    ---------- ---------- ---------- ---------- ---------- ----------  120

CONSENSUS: gatcgcagcg atgacraacc tgcaagatca aacccaacag attgttccgt tcatacggag  180
CEF94-A:   .......... .......a.. .......... .......... .......... ..........  180
D6948-A:   .......... .......g.. .......... .......... ........g. ..........  180
TY89-A:    ---------- ---------- ---------- ---------- ---------- ----------  180

CONSENSUS: cctcctgatg ccaacaaccg daccggcgtc cattccggac gacaccctrg agaagcacac  240
CEF94-A:   .......... .......... .......... .......... .........g ..........  240
D6948-A:   .......... .......... .......... .......... .........a ..........  240
TY89-A:    ---------- ---------- ---------- ---------- ---------- ----------  240

CONSENSUS: tctcaggtca gagacctcga cctacaattt gactgtgggg gacacagggt cagggctaat  300
CEF94-A:   .......... .......... .......... .......... .......... ..........  300
D6948-A:   .......... .......... .......... .......... .......... ..........  300
TY89-A:    ---------- ---------- ---------- ---------- ---------- ----------  300

CONSENSUS: tgtcttttc cctggwttcc ctggctcaat tgtgggtgct cactacacac tgcagagcaa  360
CEF94-A:   .......... ......a... .......... .......... .......... ..........  360
D6948-A:   .......... ......t... .......... .......... .......... ..........  360
TY89-A:    ---------- ---------- ---------- ---------- ---------- ----------  360

CONSENSUS: tgggaactac aagttcgatc agatgctcct gactgcccag aacctaccgg ccagytacaa  420
CEF94-A:   .......... .......... .......... .......... .......... ....t.....  420
D6948-A:   .......... .......... .......... .......... .......... ....c.....  420
TY89-A:    ---------- ---------- ---------- ---------- ---------- ----------  420
```

FIG. 2B

```
CONSENSUS: ctactgcagg ctagtgagtc ggagtctcac agtgaggtca agcacactyc ctggtggcgt  480
CEF94-A:   .......... .......... .......... .......... .....t.... ..........  480
D6948-A:   .......... .......... .......... .......... .....c.... ..........  480
TY89-A:    ---------- ---------- ---------- ---------- ---------- ----------

CONSENSUS: ttatgcacta aayggcacca taaacgccgt gaccttccaa ggaagcctga gtgaactgac  540
CEF94-A:   ...c...... .c........ .......... .......... .......... ..........  540
D6948-A:   ...c...... .t........ .......... .......... .......... ..........  540
TY89-A:    ---------- ---------- ---------- ---------- ---------- ----------

CONSENSUS: agatgttagc tacaatgggt tgatgtctgc aacagccaac atcaacgaca aaatyggaa   600
CEF94-A:   .......... .......... .......... .......... .......... ....t.....  600
D6948-A:   .......... .......... .......... .......... .......... ....c.....  600
TY89-A:    ---------- ---------- ---------- ---------- ---------- ----------

CONSENSUS: cgtcctagta ggggaagggg tmaccgtcct cagcttaccc acatcatatg atcttgggta  660
CEF94-A:   .......... .......... .c........ .......... .......... ..........  660
D6948-A:   .......... .......... .a........ .......... .......... ..........  660
TY89-A:    ---------- ---------- ---------- ---------- ---------- ----------

CONSENSUS: tgtgagrcty ggtgacccca ttcccgcwat agggctygac ccaaaaatgg tagcmacatg  720
CEF94-A:   ...g..t... .......... ....a..... .....t.... .......... .....c....  720
D6948-A:   ...a..c... .......... ....t..... .....c.... .......... .....a....  720
TY89-A:    ---------- ---------- ---------- ---------- ---------- ----------

CONSENSUS: tgacagcagt gacaggccca gagtctacac cataactgca gccgatgatt accaattctc  780
CEF94-A:   .......... .......... .......... .......... .......... ..........  780
D6948-A:   .......... .......... .......... .......... .......... ..........  780
TY89-A:    ---------- ---------- ---------- ---------- ---------- ----------

CONSENSUS: atcacagtac caascaggtg gggtaacaat cacactgttc tcagcyaaya tygatgccat  840
CEF94-A:   ...c...... .......... .......... .......... .....c..c. .t........  840
D6948-A:   ...g...... .......... .......... .......... .....t..t. .c........  840
TY89-A:    ---------- ---------- ---------- ---------- ---------- ----------
```

FIG. 2C

```
CONSENSUS: cacaagcctc agcrtygggg gagarctcgt gtttcaaaca agcgtccamg gccttrtact 900
CEF94-A:   .........  ...g.t....  ....g.....  ..........  .......c..  .......g..  900
D6948-A:   .........  ...a.c....  .......a..  ..........  ........a.  .........a  900
TY89-A:    ---------  ----------  ----------  ----------  ----------  ----------  ---

CONSENSUS: gggygcyacc atctacctya taggctttga tgggacwgcg gtaatcacca grgctgtggc 960
CEF94-A:   ...c..c..  ..........  ....c.....  ..........  ....a.....  .......... 960
D6948-A:   ...t..t..  ..........  .......t..  ......t...  ..........  .........a 960
TY89-A:    ---------  ----------  ----------  ----------  ----------  ----------  ---

CONSENSUS: cgcaracaat gggctracgr ccggcacyga caaccttwtg ccattcaatm ttgtgattcc 1020
CEF94-A:   ....a....  ......g...a  .......c..  .......t..  .........a  .......... 1020
D6948-A:   ....g....  ....a...g.  .......t..  .........a  .......c..  .......... 1020
TY89-A:    ---------  ----------  ----------  ----------  ----------  ----------  ---

CONSENSUS: aacmarcgag ataacccagc caatcacatc catcaaactg gagatagtga cctccaaaag 1080
CEF94-A:   ...a.a...  ..........  ..........  ..........  ..........  .......... 1080
D6948-A:   ...c.g...  ..........  ..........  ..........  ..........  .......... 1080
TY89-A:    ---------  ----------  ----------  ----------  ----------  ----------  ---

CONSENSUS: tggtggtcag gcrggggatc agatgtcrtg gtcrgcaagw gggagcctag cagtgacgat 1140
CEF94-A:   .........  ..a.......  ......g...  ...g..a...  ..........  .......... 1140
D6948-A:   ...c.g...  ......g...  .......a..  ......a..t  ..........  .......... 1140
TY89-A:    ---------  ----------  ----------  ----------  ----------  ----------  ---

CONSENSUS: ccayggtggc aactatccag gggccctccg tcccgtcacr ctagtrgcct acgaaagagt 1200
CEF94-A:   ...t.....  ..........  ..........  ........g.  .......g..  .......... 1200
D6948-A:   ...c.....  ..........  ..........  .........a  ........a.  .......... 1200
TY89-A:    ---------  ----------  ----------  ----------  ----------  ----------  ---

CONSENSUS: ggcaacagga tcygtcgtta cggtcgcygg ggtgagcaac ttcgagctga tcccaaatcc 1260
CEF94-A:   .........  .c........  ......t...  ..........  ..........  .......... 1260
D6948-A:   .........  ..t.......  .....c....  ..........  ..........  .......... 1260
TY89-A:    ---------  ----------  ----------  ----------  ----------  ----------  ---
```

FIG. 2D

```
CONSENSUS: tgaactagca aagaacctgg tyacagaata cggccgattt gacccaggag ccatgaacta  1320
CEF94-A:   .......... .......... .t........ .......... .......... ..........  1320
D6948-A:   .......... .......... .c........ .......... .......... ..........  1320
TY89-A:    ---------- ---------- ---------- ---------- ---------- ----------

CONSENSUS: cacaaaattg atactgagtg agagggaccg tcttgcatc  aagaccgtmt ggccaacaag  1380
CEF94-A:   .......... .......... .......... .......... ......c... ..........  1380
D6948-A:   .......... .......... .......... .......... .......a.. ..........  1380
TY89-A:    ---------- ---------- ---------- ---------- ---------- ----------

CONSENSUS: ggagtacact gactttcgyg artacttcat ggaggtggcc gacctcaact ctcccctgaa  1440
CEF94-A:   .......... .......t.. ..a....... .......... .......... ..........  1440
D6948-A:   .......... .......c.. ..g....... .......... .......... ..........  1440
TY89-A:    ---------- ---------- ---------- ---------- ---------- ----------

CONSENSUS: gattgcagga gcattyggct tcaaagacat aatccgggcc mtaaggagga tagctgtgcc  1500
CEF94-A:   .......... .......c.. .......... .......... a......... ..........  1500
D6948-A:   .......... .......t.. .......... .......... c......... ..........  1500
TY89-A:    ---------- ---------- ---------- ---------- ---------- ----------

CONSENSUS: ggtggtctcy acaytgttcc caccygccgc tcccctagcc catgcaattg gggaaggtgt  1560
CEF94-A:   ........c. ...t...... .....t.... .......... .......... ..........  1560
D6948-A:   ........t. ...c...... .....c.... .......... .......... ..........  1560
TY89-A:    ---------- ---------- ---------- ---------- ---------- ----------

CONSENSUS: agactacctg ctgggcgatg aggcacaggc tgcttcagga actgctcgag ccgcgtcagg  1620
CEF94-A:   .......... .......... .......... .......... .......... ..........  1620
D6948-A:   .......... .......... .......... .......... .......... ..........  1620
TY89-A:    ---------- ---------- ---------- ---------- ---------- ----------

CONSENSUS: aaaagcaaga gctgcctcag gccgcataag gcagctract ctcgccgccg acaagggta   1680
CEF94-A:   .......... .......... .......... .......g.. .......... ..........  1680
D6948-A:   .......... .......... .......... .......a.. .......... ..........  1680
TY89-A:    ---------- ---------- ---------- ---------- ---------- ----------
```

FIG. 2E

```
CONSENSUS: cgaggtagtc gcgaatctrt tycaggtgcc ccagaatccy gtagtcgacg ggattctygc 1740
CEF94-A:   .......... .........a .c........ .........c .......... .....t.... 1740
D6948-A:   .......... .........g .t........ .........t .......... .....c.... 1740
TY89-A:    ---------- ---------- ---------- ---------- ---------- ---------- 1740

CONSENSUS: ttcacctggg rtactccgcg gygcacacaa cctcgactgc gtgttragag agggtgccac 1800
CEF94-A:   .......... g......... .t........ .......... ......a... .......... 1800
D6948-A:   .......... a......... .c........ .......... ......g... .......... 1800
TY89-A:    ---------- ---------- ---------- ---------- ---------- ---------- 1800

CONSENSUS: gctattccct gtggtyatya cgacagtgga agaygccatg acacccaaag caytgaacag 1860
CEF94-A:   .......... .....t.t.. .......... ...c...... .......... ..t....... 1860
D6948-A:   .......... .....c.c.. .......... ...t...... .......... ..c....... 1860
TY89-A:    ---------- ---------- ---------- ---------- ---------- ---------- 1860

CONSENSUS: caaaatgttt gctgtcattg aaggcgtgcg agaagayctc caacctccwt ctcaaagagg 1920
CEF94-A:   .......... .......... .......... .....c.... .......t.. .......... 1920
D6948-A:   .......... .......... .......... .....t.... ........a. .......... 1920
TY89-A:    ---------- ---------- ---------- ---------- ---------- ---------- 1920

CONSENSUS: atccttcata cgaactctct cyggacayag agtctatgga tatgctccag atgggtact 1980
CEF94-A:   .......... .......... .t....c... .......... .......... .......... 1980
D6948-A:   .......... .......... .c....t... .......... .......... .......... 1980
TY89-A:    ---------- ---------- ---------- ---------- ---------- ---------- 1980

CONSENSUS: tccactggag actgggagag aytacaccgt kgtcccaata gatgatgtct gggacgacag 2040
CEF94-A:   .......... .......... .c........ t......... .......... .......... 2040
D6948-A:   .......... .......... .t........ g......... .......... .......... 2040
TY89-A:    ---------- ---------- ---------- ---------- ---------- ---------- 2040

CONSENSUS: cattatgctg tccaaagayc ccatacctcc tattgtggga aacagyggaa ayctagccat 2100
CEF94-A:   .......... .......t.. .......... .......... .......t.. .....t.... 2100
D6948-A:   .......... .......c.. .......... .......... .......c.. .....c.... 2100
TY89-A:    ---------- ---------- ---------- ---------- ---------- ---------- 2100
```

FIG. 2F

```
CONSENSUS: agcttacatg gatgtgtttc gacccaaagt cccmatccat gtggcyatga cgggagccct 2160
CEF94-A:   .......... .......... .......... ...a...... .....t.... .......... 2160
D6948-A:   .......... .......... .......... .....c.... .....c.... .......... 2160
TY89-A:    ---------- ---------- ---------- ---------- ---------- ----------

CONSENSUS: caaygcytrt ggcgagattg agaamgtrag cttagaagc accaagctcg ccactgcaca 2220
CEF94-A:   ...t..t.g. .......... ....a..a.. .......... .......... .......... 2220
D6948-A:   ...c..c.a. .......... ....c..g.. .......... .......... .......... 2220
TY89-A:    ---------- ---------- ---------- ---------- ---------- ----------

CONSENSUS: ccgacttggc ctyaagttgg ctggtcccgg wgcattygay gtraacaccg ggyccaactg 2280
CEF94-A:   .......... ...t...... .......... a......c.t .....a.... .....c.... 2280
D6948-A:   .......... ...c...... .......... t......t.c ......g... .....t.... 2280
TY89-A:    ---------- ---------- ---------- ---------- ---------- ----------

CONSENSUS: ggcracgtty atcaaacgtt tycctcacaa tccmcgmgac tgggacaggy tmccytacct 2340
CEF94-A:   ...a...c.. .......... ....c..... ...a..c... .......c.. ..c..c.... 2340
D6948-A:   ...g...t.. .......... ....t..... ...a..c... .......c.. ..c..t.... 2340
TY89-A:    ---------- ---...c... ....c..... ...c..a... .......t.. ..a..c....   44

CONSENSUS: caacctwccm tayctyccac cmamwgcwgg acgycagtwc sayctkgccm tggchgchtc 2400
CEF94-A:   .......a.a ..c..t.... .c.at..a.. .......c.. c..c..t...a .....t.a.. 2400
D6948-A:   .......t.a ..c..t.... .c.at..a.. .......c.. g.c..g...a .....c..t. 2400
TY89-A:    .......t.c ..t..c.... .a.ca..t.. .......t.. c..t..g...c .....a..c.  104

CONSENSUS: mgagttcaaa gagacccccmg aactcgarrr ygcygtsmgw gcmatggamg cwgcwgcmaa 2460
CEF94-A:   a......... .......c.. ......gag t.c..ca.a ..a.....a. .a..a..c.. 2460
D6948-A:   a......... .......c.. ......gag c.c..ca.a ..c.....a. .a..a..c.. 2460
TY89-A:    c......... .......a.. ......aga c..t..gc.t ..a.....c. .t..t..a..  164

CONSENSUS: cgtsgaccca ytrttccrmt cwgcdctcmr bgtsttcatg tggytggaag araayggggat 2520
CEF94-A:   ...g...... c.a....aa. .t.a...ag t..g...... ...c...... ...g..t... 2520
D6948-A:   ...g...... c.g....aa. .t..g..ag c..g...... ...c...... ...g..t... 2520
TY89-A:    ...c...... t.g....gc. .a..t...ca g..c...... ...t...... ...a..c...  224
```

```
CONSENSUS: tgtracygay atggcyaact tcgcmctcag cgacccgaac gcmcaymgga tgmrmaattt 2580
CEF94-A:   ...g..t..c ........c. ........a. .......... ..c..tc... ..cga..... 2580
D6948-A:   ...g..t..t ........c. ........a. .......... ..c..tc... ..cgc..... 2580
TY89-A:    ...a..c..c ........t. ........c. .......... ..a..ca... ..aaa..... 284

CONSENSUS: ycthgcaaay gcwccmcarg cmggmagcaa gtcgcaragr gccaagtayg gsacrgcwgg 2640
CEF94-A:   t..t...... ..a..a..a. a..c...... .......a.g .........c ...g..a..a 2640
D6948-A:   t..c...... ..a..a..a. a..c...... .........a .........c ...g..a..a 2640
TY89-A:    c..a...... ..t..c..g. .c..a..... .......g..g .......t. ...c..g..t 344

CONSENSUS: ctacggagtg gaggcymgrg gccccacdcc agargargca cagagggara aagacacacg 2700
CEF94-A:   .......... ...tc.g... .........a ....g..a.. .......... .......... 2700
D6948-A:   .......... ...cc.g... .........t ....g..a.. ..........a .......... 2700
TY89-A:    .......... ...ta.a... .........g ....a..g.. .......g.. .......... 404

CONSENSUS: gatctcmaag aagatggara cbatgggcat ctacttygca acaccrgaat gggtagcact 2760
CEF94-A:   .......... .......a.. ..c....... .......... .......a.. .......... 2760
D6948-A:   .......... .......a.. ..t....... .......t.. .......a.. .......... 2760
TY89-A:    .......... .......c.. ..g....... .......c.. .......g.. .......... 464

CONSENSUS: caayggggcac cgrggsccaa gccccggcca gctvaagtac tggcaraaca camgagaaat 2820
CEF94-A:   ...t...... ..a..g.... .......... ........a. .......g.. .......c.. 2820
D6948-A:   ...t...... ..g..g.... .......... ........g. .......g.. .......c.. 2820
TY89-A:    ...c...... ..a..c.... .......... ........c. .......a.. .......a.. 524

CONSENSUS: accdgahccm aacgaggact aycyagacta ygtgcaygcr gagaagagcc ggttggcrtc 2880
CEF94-A:   ...g..c..a ........ .t.t......c ....t..a.. .......... .......a.. 2880
D6948-A:   ...t..t..a ........ .c.t......c ....t..a.. .......... .......a.. 2880
TY89-A:    ...a..a..c ........ .c.c......t ....c..g.. .......... .......g.. 584

CONSENSUS: agaagaacar rtcytaaggg cagcyacgtc gatctacggg gctccaggac aggcwgarcc 2940
CEF94-A:   .........a a..c...... .......t.. .......... .......... ....a..g.. 2940
D6948-A:   .........a a..c...... .......t.. .......... .......... ....a..g.. 2940
TY89-A:    .........g g..t...... .......c.. .......... .......... ....t..a.. 644
```

FIG. 2H

```
CONSENSUS: accccaagcy ttcatagacg aagtygccar rgtctatgaa atcaaccatg grcgtggycc  3000
CEF94-A:   .........t .......... .....t...a a......... .......... .a.....c..  3000
D6948-A:   .........c .......... ...c...a.a .......... .......... .g.....c..  3000
TY89-A:    .........c .......... ...c.....g g......... .......... .g.....t..  704

CONSENSUS: maaccargar cagatgaarg ayctgctcyt gactgcgatg gagatgaagc atcgcaatcc  3060
CEF94-A:   a.....a..a .........a .....t...t .......... .......... ..........  3060
D6948-A:   c.....a..a .........a .....t....c .......... .......... ..........  3060
TY89-A:    a......g..g .........g .c........ .......... .......... ..........  764

CONSENSUS: caggcgggct cyaccaaagc cmaagccaaa acccaatgct ccawcacaga dacccccctgg  3120
CEF94-A:   .........  .t........ ..c....... .......... .....a.... ..........  3120
D6948-A:   .........  .c........ ..c....... .......... ......a... ..........  3120
TY89-A:    .........  .c........ ..a....... .......... .....t.... ..........  824

CONSENSUS: wcggctgggc cgctggatca ggrcbgtctc tgaygaggac ytkgagtgag gywcctgga   3180
CEF94-A:   t........  .......... ..a.c..... .....t.... c.t....... .ta.......  3180
D6948-A:   t........  .......... ..g.t..... .....t.... c.t....... .ct.......  3180
TY89-A:    a........  .......... ..a.g..... ......c.... t.g....... .ct.......  884

CONSENSUS: gtctcccgac accacccgcg caggygtgga caccaattmr kmmhtaswrm atycsaaatt  3240
CEF94-A:   .........  .......... ......t... .......... ..cg gact..caac ..c.c.....  3240
D6948-A:   .........  .......... .........c .......... ..cg gcca..caac ..c.c.....  3240
TY89-A:    .........  .......... ......t... .......... ...aa tcac..gtga ..t.g.....  944

CONSENSUS: ggatccgttc gcgggtcccc                                              3260
CEF94-A:   .........  ..........                                              3260
D6948-A:   .........  ..........                                              3260
TY89-A:    .........  ..........                                              964
```

FIG. 3A

```
CONSENSUS:  ggatacgatg ggtctgaccc tctggggagtc acgaattaac gtggctacta ggggygatrm   60
CEF94-B:    .......... .......... .......... .......... .......... ....c...aa   60
D6948-B:    .......... .......... .......... .......... .......... ....t...gc   60

CONSENSUS:  ccrccgctrg ctgccacgtt agtggctcct cttcttgatg attctrccac catgagtgac  120
CEF94-B:    ..g...g... .......... .......... .......... .......g.. ..........  120
D6948-B:    ..a.....a. .......... .......... .......... .......a.. ..........  120

CONSENSUS:  rttttcaaya gtccacaggc gcgaagcamg atmtcagcag cgttcggcat aaagcctacw  180
CEF94-B:    a.......c. .......... .......... ..c....... .......... ........t   180
D6948-B:    g.......t. .......... .......... ..a....... .......... ........a   180

CONSENSUS:  gctggacarg aygtggaaga actcytgatc cctaargtyt gggtgccacc tgaggatccs  240
CEF94-B:    .......a.. .c........ .......t.. ....a..t.. .......... .........g  240
D6948-B:    .......g.. .t........ .......c.. .....g..c. .......... .........c  240

CONSENSUS:  ytkgccagcc ctagtcgwct ggcmaagttc ctcagrgara acggctacaa rrttytgcag  300
CEF94-B:    c.t....... ......a... ...a...... .......a.g .......... ag..t.....  300
D6948-B:    t.g....... ......t... ...c...... .......g..a .......... ga..c.....  300

CONSENSUS:  ccacggtctc trccygagaa tgaggagtat gagaccgayc aaatactccc wgacytagcw  360
CEF94-B:    .......... .g..c..... .......... .........c .......... a..t.....a  360
D6948-B:    .......... .a..t..... .......... .........t .......... t..c.....t  360

CONSENSUS:  tggatgmgrc agatagargg rgctgtttta aaaccmacyc tatctctccc yattggagay  420
CEF94-B:    ....c.a... ......a..g ........g. .......c.t .......... t.......t   420
D6948-B:    ....a.g... ......g..a ........a. .......a.c .......... c.......c   420

CONSENSUS:  caggagtact tcccwaarta ctacccaaca caycgcccka gcaaggaraa gcccaatgcg  480
CEF94-B:    .......... ....a..g.. .......... ..t....t.. ........g. ..........  480
D6948-B:    .......... ....t..a.. .......... ..c....g.. ........a. ..........  480
```

FIG. 3B

```
CONSENSUS: tacccgccmg ayatcgcayt actcaagcag atgatytacy tgtttctcca ggttccmgag 540
CEF94-B:   .........a ..c......c .......... ......t..c .......... ......a... 540
D6948-B:   .......... ..t......t .......... ......c..t .......... ......c... 540

CONSENSUS: gccammgakr rcctwaarga tgargtmacc ctmytraccc aaaacatwag rgayaargcc 600
CEF94-B:   ....ac..gg g...a..g.. ....a..a.. ..ct.g.... .......a.. g..c..g... 600
D6948-B:   ...ca..ta  a..t..a... ....g..c.. ...ac.a... .......t.. a..t..a... 600

CONSENSUS: tayggragtg ggacctacat gggacargcm acymgacttg tkgcyatgaa rgaggtygcc 660
CEF94-B:   ..t..a.... .......... ......a..a ..tc...... .g..c..... g......c.. 660
D6948-B:   ..c..g.... .......... ......g..c ..ca...... .t..t..... a......t.. 660

CONSENSUS: actggragaa acccaaacaa rgatcctcta aagcttgggt acacytttga gagcatmgcs 720
CEF94-B:   ......a... .......... g......... .......... ...t...... .......c.g 720
D6948-B:   ......g... .......... a......... .......... ....c..... .......a.c 720

CONSENSUS: cagctacttg acatcacwyt accggtaggc ccaccggtg  aggatgacaa gccctgggtr 780
CEF94-B:   .......... .......ac. .......... .......... .......... .........g 780
D6948-B:   .......... .......tt. .......... .......... .......... .........a 780

CONSENSUS: ccactcacaa grgtgccgtc amggatgttg gtwctgacgg gmgacgtaga tggsgamttt 840
CEF94-B:   .......... a......... ..c....... ....a..... .a........ ...c..c... 840
D6948-B:   .......... g......... ..a....... ....t..... ..c....... ...g..a... 840

CONSENSUS: gaggttgarg aytaccttcc caaaatcaac ctcaagtcat caagtggact rccmtatgtw 900
CEF94-B:   ........a. ..t....... .......... .......... .......... a..a.....a 900
D6948-B:   ........g. ..c....... .......... .......... .......... g..c.....t 900

CONSENSUS: ggtcgcacca aaggagarac wattggsgag atgatagcya tmtcraacca gtttctymga 960
CEF94-B:   .......... .......g.. a......c.. .........t .c..a..... ......ca.. 960
D6948-B:   .......... .......a.. t......g.. .........c .a..g..... ......tc.. 960
```

FIG. 3C

```
CONSENSUS: gagctatcar crctgytgaa gcarggtgca gggacaaarg ggtcraacaa gaagaagctr 1020
CEF94-B:   .........a .a...t.... ....a..... .........g .......... ..........a 1020
D6948-B:   .........g .g....c... ....g..... .........a .......g.. ...........g 1020

CONSENSUS: ctcagcatgy taagtgacta ytggtactta tcatgyggc ttttgtttcc maaggctgar 1080
CEF94-B:   ........t. .......... .t........ .......... .......... a..........a 1080
D6948-B:   ........c. .......... .c........ .......t.. .......... c..........g 1080

CONSENSUS: aggtacgaca aaagyacatg gctcaccaag acccgkaaca tatggtcagc tccatcmcca 1140
CEF94-B:   .......... .....t.... .......... .......g.. .......... ......c... 1140
D6948-B:   .......... .....c.... .......... .......t.. .......... ......a... 1140

CONSENSUS: acacacctca tgatctcwat gatmacctgg cccgtgatgt ccaayagccc aaayaacgtg 1200
CEF94-B:   .......... ......t... ...c...... .......... .....c.... ...t...... 1200
D6948-B:   .......... ......a... ...a...... .......... .....t.... ...c...... 1200

CONSENSUS: ttgaacattg argggtgtcc rtcactctac aarttcaacc cgttyagagg wggytraac 1260
CEF94-B:   .......... .a........ a......... .........a ....c..... a..t.g.... 1260
D6948-B:   .......... .g........ g......... .........g ....t..... t..c.a.... 1260

CONSENSUS: aggatcgtsg agtggatawt ggcycccggaw gaacccaagg cyytwgtata tgckgacaac 1320
CEF94-B:   .....c.... .......t.. ...c....a. .......... .tc.t..... ...g...... 1320
D6948-B:   .......g.. .......a.. ...t....t. .......... .ct.a..... ...t...... 1320

CONSENSUS: atatacattg tycactcmaa cacgtggtac tcaattgacc tagagaaggg tgaggcaaac 1380
CEF94-B:   .........  .c....a... .......... .......... .......... .......... 1380
D6948-B:   .........  .t....c... .......... .......... .......... .......... 1380

CONSENSUS: tgcackcgyc aacacatgca rgccgcmatg tactacatmc tyaccagagg rtggtcmgay 1440
CEF94-B:   ....t.c... .......... a......a.. .......c.. .c........ g.....a..c 1440
D6948-B:   ....g..t.. .......... g......c.. .......t.. .t........ a.....c..t 1440

CONSENSUS: aacggygacc cmatgttcaa tcaaracatgg gccacctttg csatgaacat tgccccwgct 1500
CEF94-B:   ....c..... .a........ ....a..... .......... .....c.... ......t... 1500
D6948-B:   ....t..... .c........ ....g..... .......... .....g.... ......a... 1500
```

FIG. 3D

```
CONSENSUS: ctagtkgtgg actcatcrtg yctgatwatg aacctkcara tyaagacmta tggtcaaggc 1560
CEF94-B:   .........  ....g.....  .c........  .......g..a  .t........c  ..........  1560
D6948-B:   ...t......  ......a...  .t........  .......t..g  .c........a  ..........  1560

CONSENSUS: agygggaatg cagcccacstt catcaacaac cayctyytka gcacsctwgt gctwgaccag 1620
CEF94-B:   ..c.......  ......g...  ..........  ..c..ct.g.  .......g..a  ...t......  1620
D6948-B:   ..t.......  ........c.  ..........  ..t..tc.t.  ..........c  ...t...a..  1620

CONSENSUS: tggaacytga tgarrcarcc yagwccagac agcgargagt tcaartcaat tgargacaag 1680
CEF94-B:   .....c....  ...ga..g..  ..c..a....  ..........  ........g.  .....g....  1680
D6948-B:   .....t....  ...ag..a..  ..t..t....  ..........  ........a.  .....a....  1680

CONSENSUS: ctrggyatca acttyaagat tgagaggtcc attgatgaya tyaggggcaa gctsagacag 1740
CEF94-B:   ..a..t....  ......t...  ..........  ........t.  ..c.......  .......g..c  1740
D6948-B:   ..g..c....  ......c...  ..........  ........c.  ..t.......  .......c..  1740

CONSENSUS: cttgtccycc ttgcacaacc agggtacctg agtggrgggg tygaaccaga rcaayccagc 1800
CEF94-B:   .......t..  ..........  ..........  .......g..  ..t.......  a...t.....  1800
D6948-B:   .......c..  ..........  ..........  .......a..  ..c.......  g...c.....  1800

CONSENSUS: ccaactgtwg agctkgacct actmggrtgg tcwgcwacwt acagcaaaga tctyggatc 1860
CEF94-B:   .......t..  ....t.....  ...a..g...  ..a..t..a.  ..........  ...c......  1860
D6948-B:   .......a..  ....g.....  ...c..a...  ..t..a..t.  ..........  ...t......  1860

CONSENSUS: tatgtgccgg tgcttgacaa ggaacgcyta ttttgytctg ctgcgtatcc caarggrgta 1920
CEF94-B:   ..........  ..........  ......c...  .......t..  ..........  ....g..a..  1920
D6948-B:   ..........  ..........  ......t...  .......c..  ..........  ....a..g..  1920

CONSENSUS: gagaayaara gyctcaartc caargtyggg atcgagcarg catacaargt wgtcaggtay 1980
CEF94-B:   ...c..g...  .t....g...  ......c...  ........g.  ........g.  a........t  1980
D6948-B:   ...t..a...  .c....a...  ......t...  ........a.  ........a.  t........c  1980

CONSENSUS: gaggcgttga ggttggtagg tggttggaac tacccactcc tgaacaaagc ytgcaagaay 2040
CEF94-B:   ..........  ..........  ..........  ..........  ..........  c........t  2040
D6948-B:   ..........  ..........  ..........  ..........  ..........  t........c  2040
```

FIG. 3E

```
CONSENSUS: aaygcargyg cmgctcggcg gcatctggag gccaagggt tcccrctcga ygagttcctm 2100
CEF94-B:   ..c...g.c. .c........ .......... .......... .a........ c......... 2100
D6948-B:   ..t...a.t. .a........ .......... .......... ....g..... t......... 2100

CONSENSUS: gccgagtggt cwgagytgtc mgagttcggw gargcttcg aaggcttcaa yatcaagctg 2160
CEF94-B:   .......... .t..c..... a...t..... .g.c...... .......... t......... 2160
D6948-B:   .......... .a..t..... c......a.. .a..t..... .......... .....c.... 2160

CONSENSUS: acmgtaacay ckgagagcct mgccgaactk aacarrccag tacccccaa rccyccaaat 2220
CEF94-B:   ..c.....t. .t..t..... a.........  ....g..... ......ag.. g..c...... 2220
D6948-B:   ..a.....c  .g........ c.........t .....ga... .......... a..t...... 2220

CONSENSUS: gtcaacagac cagtcaacac yggkggrctm aaggcagtca gcaaygccct caagaccggy 2280
CEF94-B:   .......... .......... t.g..a..c. .......... .......... .........t 2280
D6948-B:   .......... .......... c..t..g..a .......... .....t.... .........c 2280

CONSENSUS: cggtayagra aygaagccgg actragtggy ctcgtcctyc tagccacmgc mmgmagccgw 2340
CEF94-B:   ....c..g.. .......c.. ....g..... ........t. .......... aa.a......t 2340
D6948-B:   ....t..a.. .......t.. .......c.. ........c. .......c.. cc.c......a 2340

CONSENSUS: ctrcargayg cagtyaaggc caaggcagar gccgagaaac tccacaagtc yaagccmgay 2400
CEF94-B:   ..g..a..t. .....t.... .......... .......... .......... c.....a..c 2400
D6948-B:   ..a..g..c. .......c.. ........g. .......... .......... t.....c..t 2400

CONSENSUS: gaccccgatg cagactggtt ygaamgrtca gaaacyctgt cagacctkct ggagaaagcc 2460
CEF94-B:   .......... .......... c...a..a.. ......t... .........t .......... 2460
D6948-B:   .......... .......... t...c.g... ......c... .......g.. .......... 2460

CONSENSUS: gacatygcca gcaaggtcgc ycactcagca ctcgtggaaa caagcgacgc yctttgaagcr 2520
CEF94-B:   ....c..... .......... c......... .......... .......... c.........a 2520
D6948-B:   ....t..... .......... t......... .......... .......... t.........g 2520

CONSENSUS: gtycagtcra cytcmgtgta cacyccmaag tacccagarg tyaagaaccc acagaccgcc 2580
CEF94-B:   ..t...g... .t..c..... .....t..c. .......a.. .c........ .......... 2580
D6948-B:   ..c...a... .c..a..... .....c..a. .......g.. .t........ .......... 2580
```

FIG. 3F

```
CONSENSUS: tccaacccccg ttgtttgggct ccacctgccc gccaagagrg ccaccgtgt ccaggcmgct 2640
CEF94-B:   .......... .......... .......... .......... ........c. .......... 2640
D6948-B:   .......... .......... .......... .......a.. .......... ....a..... 2640

CONSENSUS: cttctcggag caggracgag cagaccaatg gggatggagg cyccaacacg gtccaagaac 2700
CEF94-B:   .......... ....a..... .......... .......... ..c....... .......... 2700
D6948-B:   .......... ....g..... .......... .......... ..t....... .......... 2700

CONSENSUS: gccgtgaaaa tggccaaamg gcggcaacgc caaaargaga gccgccaaya gccatgatgg 2760
CEF94-B:   .......... .........c .......... .......g.. ........c. .......... 2760
D6948-B:   .......... .........a .......... .......a.. ........t. .......... 2760

CONSENSUS: gaaccactca agaagaggac actaayccca gaccccgtat cccggcctt cgcctgcggg 2820
CEF94-B:   .......... .......... ......t... .......... .......... .......... 2820
D6948-B:   .......... .......... ......c... .......... .......... .......... 2820

CONSENSUS: ggccccc                                                          2827
CEF94-B:   .......                                                          2827
D6948-B:   .......                                                          2827
```

FIG. 4A

```
CONSENSUS: MTNLQDQTQQ IVPFIRSLLM PTTGPASIPD DTLEKHTLRS ETSTYNLTVG DTGSGLIVFF  60
CEF94-PP:  .......... .......... .......... .......... .......... ..........  60
D6948-PP:  ---------- ---------- ---------- ---------- ---------- ----------  60
TY89-PP:   ---------- ---------- ---------- ---------- ---------- ----------  60

CONSENSUS: PGFPGSIVGA HYTLQSNGNY KFDQMLLTAQ NLPASYNYCR LVSRSLTVRS STLPGGVYAL 120
CEF94-PP:  .......... .......... .......... .......... .......... .......... 120
D6948-PP:  ---------- ---------- ---------- ---------- ---------- ---------- 120
TY89-PP:   ---------- ---------- ---------- ---------- ---------- ---------- 120

CONSENSUS: NGTINAVTFQ GSLSELTDVS YNGLMSATAN INDKIGNVLV GEGVTVLSLP TSYDLGYVRL 180
CEF94-PP:  .......... .......... .......... .......... .......... .......... 180
D6948-PP:  ---------- ---------- ---------- ---------- ---------- ---------- 180
TY89-PP:   ---------- ---------- ---------- ---------- ---------- ---------- 180

CONSENSUS: GDPIPAIGLD PKMVATCDSS DRPRVYTITA ADDYQFSSQY Q.GGVTITLF SANIDAITSL 240
CEF94-PP:  .......... .......... .......... .......... P......... .......... 240
D6948-PP:  .......... .......... .......... .......... A......... .......... 240
TY89-PP:   ---------- ---------- ---------- ---------- ---------- ---------- 240

CONSENSUS: S.GGELVFQT SV.GL.LGAT IYLIGFDGTA VITRAVAA.N GLT.GTDNL. PFN.VIPT.E 300
CEF94-PP:  .V........ ..H..V.... .......... .......N.. ...T...L.. ....L....N 300
D6948-PP:  .I........ ..Q..I.... .......... .......D.. ....A....M ......I..S 300
TY89-PP:   ---------- ---------- ---------- ---------- ---------- ---------- 300

CONSENSUS: ITQPITSIKL EIVTSKSGGQ AGDQMSWSA. GSLAVTIHGG NYPGALRPVT LVAYERVATG 360
CEF94-PP:  .......... .......... ........R. .......... .......... .......... 360
D6948-PP:  .......... .......... ........S. .......... .......... .......... 360
TY89-PP:   ---------- ---------- ---------- ---------- ---------- ---------- 360

CONSENSUS: SVVTVAGVSN FELIPNPELA KNLVTEYGRF DPGAMNYTKL ILSERDRLGI KTVWPTREYT 420
CEF94-PP:  .......... .......... .......... .......... .......... .......... 420
D6948-PP:  .......... .......... .......... .......... .......... .......... 420
TY89-PP:   ---------- ---------- ---------- ---------- ---------- ---------- 420
```

FIG. 4B

```
CONSENSUS: DFREYFMEVA DLNSPLKIAG AFGFKDIIRA .RRIAVPVVS TLFPPAAPLA HAIGEGVDYL   480
CEF94-PP:  .......... .......... .......... I......... .......... ..........   480
D6948-PP:  .......... .......... .......... L......... .......... ..........   480
TY89-PP:   ---------- ---------- ---------- ---------- ---------- ----------

CONSENSUS: LGDEAQAASG TARAASGKAR AASGRIRQLT LAADKGYEVV ANLFQVPQNP VVDGILASPG   540
CEF94-PP:  .......... .......... .......... .......... .......... ..........   540
D6948-PP:  .......... .......... .......... .......... .......... ..........   540
TY89-PP:   ---------- ---------- ---------- ---------- ---------- ----------

CONSENSUS: .LRGAHNLDC VLREGATLFP VVITTVEDAM TPKALNSKMF AVIEGVREDL QPPSQRGSFI   600
CEF94-PP:  V......... .......... .......... .......... .......... ..........   600
D6948-PP:  I......... .......... .......... .......... .......... ..........   600
TY89-PP:   ---------- ---------- ---------- ---------- ---------- ----------

CONSENSUS: RTLSGHRVYG YAPDGVLPLE TGRDYTVVPI DDVWDDSIML SKDPIPPIVG NSGNLAIAYM   660
CEF94-PP:  .......... .......... .......... .......... .......... ..........   660
D6948-PP:  .......... .......... .......... .......... .......... ..........   660
TY89-PP:   ---------- ---------- ---------- ---------- ---------- ----------

CONSENSUS: DVFRPKVPIH VAMTGALNA. GEIE.VSFRS TKLATAHRLG LKLAGPGAFD VNTG.NWATF   720
CEF94-PP:  .......... ........C. ...K...... .......... .......... ....P.....   720
D6948-PP:  .......... ........Y. ...N...... .......... .......... .....S....   720
TY89-PP:   ---------- ---------- ---------- ---------- ---------- ----------

CONSENSUS: IKRFPHNPRD WDRLPYLNLP YLPPNAGRQY HLAMAASEFK ETPELESAVR AMEAAANVDP   780
CEF94-PP:  .......... .......... .......... ....D..... .......... ..........   780
D6948-PP:  .......... .......T.. .......F.. .......L.. .......D.. ......D...   780
TY89-PP:   ---------- ---------- ---------- ---------- ---------- ---------- 58

CONSENSUS: LFQSALSVFM WLEENGIVTD MANFALSDPN AHRMRNFLAN APQAGSKSQR AKYGTAGYGV   840
CEF94-PP:  .......... .......... .......... .......... .......... ..........   840
D6948-PP:  .......... .......... .......... .......... .......... ..........   840
TY89-PP:   ..R...Q... .......... .......... ....K..... .......... ..........   118
```

FIG. 4C

```
CONSENSUS: EARGPTPEEA QREKDTRISK KMETMGIYFA TPEWVALNGH RGPSPGQLKY WQNTREIPDP    900
CEF94-PP:  .......... .......... .......... .......... .......... ..........    900
D6948-PP:  .......... .......... .......... .......... .......... ..........    900
TY89-PP:   .......... .......... .......... .......... .......... .....E....    178

CONSENSUS: NEDYLDYVHA EKSRLASEEQ ILRAATSIYG APGQAEPPQA FIDEVAKVYE INHGRGPNQE    960
CEF94-PP:  .......... .......... .......... .......... .......... ..........    960
D6948-PP:  .......... .......... .......... .......... .......... ..........    960
TY89-PP:   ....P..... .......... .V........ .......... ......R... ..........    238

CONSENSUS: QMKDLLLTAM EMKHRNPRRA PPKPKPKPNA PTQRPPGRLG RWIRTVSDED LE           1012
CEF94-PP:  .......... .......... .L........ .......... .......... ..           1012
D6948-PP:  .......... .......... .......... .......... ....A..... ..           1012
TY89-PP:   .......... .......... .......... .....S.... .......... ..            290
```

FIG. 5A

```
CONSENSUS: MSD.FNSPQA RS.ISAAFGI KPTAGQDVEE LLIPKVWVPP EDPLASPSRL AKFLRENGYK   60
CEF94-VP1: ...I..... ..T....... .......... .......... .......... ..........   60
D6948-VP1: ...V..... ..K....... .......... .......... .......... ..........   60

CONSENSUS: .LQPRSLPEN EEYETDQILP DLAWMRQIEG AVLKPTLSLP IGDQEYFPKY YPTHRPSKEK  120
CEF94-VP1: V......... .......... .......... .......... .......... ..........  120
D6948-VP1: I......... .......... .......... .......... .......... ..........  120

CONSENSUS: PNAYPPDIAL LKQMIYLFLQ VPEA...LKD EVTLLTQNIR DKAYGSGTYM GQATRLVAMK  180
CEF94-VP1: .......... .......... ....NEG... .......... .......... ..........  180
D6948-VP1: .......... .......... ....TDN... .......... .......... ..........  180

CONSENSUS: EVATGRNPNK DPLKLGYTFE SIAQLLDITL PVGPPGEDDK PWVPLTRVPS RMLVLTGDVD  240
CEF94-VP1: .......... .......... .......... .......... .......... ..........  240
D6948-VP1: .......... .......... .......... .......... .......... ..........  240

CONSENSUS: G.FEVEDYLP KINLKSSSGL PYVGRTKGET IGEMIAISNQ FLRELS.LLK QGAGTKGSNK  300
CEF94-VP1: .D........ .......... .......... .......... ......T... ..........  300
D6948-VP1: .E........ .......... .......... .......... ......A... ..........  300

CONSENSUS: KKLLSMLSDY WYLSCGLLFP KAERYDKSTW LTKTRNIWSA PSPTHLMISM ITWPVMSNSP  360
CEF94-VP1: .......... .......... .......... .......... .......... ..........  360
D6948-VP1: .......... .......... .......... .......... .......... ..........  360

CONSENSUS: NNVLNIEGCP SLYKFNPFRG GLNRIVEWI. AP.EPKALVY ADNIYIVHSN TWYSIDLEKG  420
CEF94-VP1: .......... .......... ........L. ...E...... .......... ..........  420
D6948-VP1: .......... .......... ........M. ...D...... .......... ..........  420

CONSENSUS: EANCTRQHMQ AAMYYILTRG WSDNGDPMFN QTWATFAMNI APALVVDSSC LIMNLQIKTY  480
CEF94-VP1: .......... .......... .......... .......... .......... ..........  480
D6948-VP1: .......... .......... .......... .......... .......... ..........  480

CONSENSUS: GQGSGNAATF INNHLLSTLV LDQWNLM.QP .PDSEEFKSI EDKLGINFKI ERSIDDIRGK  540
CEF94-VP1: .......... .......... ......R..R R......... .......... ..........  540
D6948-VP1: .......... .......... ......K..S S......... .......... ..........  540
```

FIG. 5B

```
CONSENSUS: LRQLV.LAQP GYLSGGVEPE Q.SPTVELDL LGWSATYSKD LGIYVPVLDK ERLFCSAAYP  600
CEF94-VP1: .....L.... .......... .S........ .......... .......... ..........  600
D6948-VP1: .....P.... .......... .P........ .......... .......... ..........  600

CONSENSUS: KGVENKSLKS KVGIEQAYKV VRYEALRLVG GWNYPLLNKA CKNNA.AARR HLEAKGFPLD  660
CEF94-VP1: .......... .......... .......... .......... .....G.... ..........  660
D6948-VP1: .......... .......... .......... .......... .....S.... ..........  660

CONSENSUS: EFLAEWSELS EFGEAFEGFN IKLTVT.ESL AELN.PVPPK PPNVNRPVNT GGLKAVSNAL  720
CEF94-VP1: .......... .......... ......S... ....K..... .......... ..........  720
D6948-VP1: .......... .......... ......P... ....R..... .......... ..........  720

CONSENSUS: KTGRYRNEAG LSGLVLLATA RSRLQDAVKA KAEAEKLHKS KPDDPDADWF ERSETLSDLL  780
CEF94-VP1: .......... .......... .......... .......... .......... ..........  780
D6948-VP1: .......... .......... .......... .......... .......... ..........  780

CONSENSUS: EKADIASKVA HSALVETSDA LEAVQSTSVY TPKYPEVKNP QTASNPVVGL HLPAKRATGV  840
CEF94-VP1: .......... .......... .......... .......... .......... ..........  840
D6948-VP1: .......... .......... .......... .......... .......... ..........  840

CONSENSUS: QAALLGAGTS RPMGMEAPTR SKNAVKMAKR RQRQKESRQ. .                       881
CEF94-VP1: .......... .......... .......... .........Q P                       881
D6948-VP1: .......... .......... .......... .........- -                       879
```

FIG. 6

```
CONSENSUS: MVSRDQTNDR SDD.PARSNP TDCSVHTEPS DANNRTGVHS GRHP.EAHSQ VRDLDLQFDC   60
D6948-VP5: .......... ...E...... .......... .......... ....R..... ..........   60
CEF94-VP5: .......... ...K...... .......... .......... .....G.... ..........   60

CONSENSUS: GGHRVRANCL FPW.PWLNCG CSLHTAEQWE LQVRSDAPDC PEPTGQLQLL QASESESHSE  120
D6948-VP5: .......... ..F....... .......... .......... .......... ..........  120
CEF94-VP5: .......... ..I....... .......... .......... .......... ..........  120

CONSENSUS: VKHT.WWRLC TK.HHKRRDL PRKPE                                        145
D6948-VP5: ....P..... ..W....... .....                                        145
CEF94-VP5: ....S..... ..R....... .....                                        145
```

```
                                                          VP4 <-+-> VP3
                 SacII
CEF94-PP: 724-FPHNPRD WDRLPYLNLP YLPPNAGRQY HLAMAASEFK ETPELESAVR AMEAAANVDP 780
TY89-PP:  724-....... .......... ....T....F ...L...... ......D... ..D....... 780

CEF94-PP: LFQSALSVFM WLEENGIVTD MANFALSDPN AHRMRNFLAN APQAGSKSQR AKYGTAGYGV 840
TY89-PP:  ..R...Q... .......... .......... ....K..... .......... .......... 840

SacI
CEF94-PP: EARGPTPEEA QREKDTRISK KMETMGIYFA TPEWVALNGH RGPSPGQLKY WQNTREIPDP 900
TY89-PP:  .......... .......... .......... .......... .......... ........E. 900

CEF94-PP: NEDYLDYVHA EKSRLASEEQ ILRAATSIYG APGQAEPPQA FIDEVAKVYE INHGRGPNQE 960
TY89-PP:  ....P..... .......... V......... .......... ......R... .......... 960

CEF94-PP: QMKDLLLTAM EMKHRNPRRA LPKPKPKPNA PTQRPPGRLG RWIRTVSDED LE         1012
TY89-PP:  .......... .......... P......... .S........ .......... ..         1012
```

FIG. 14

```
                         VP4 ┌──→ VP3
           ┌SacII
CEF94-PP: 724-FPHNPRD WDRLPYLNLP YLPPNAGRQY HLAMAASEFK ETPELESAVR AMEAAANVDP 780
D6948:    ......... .......... .......T.. ...D...... .........D ........D. 780
TY89-PP:  724-...... .......... .......F.. .....L.... .......... ........D. 780

CEF94-PP: LFQSALSVFM WLEENGIVTD MANFALSDPN AHRMRNFLAN APQAGSKSQR AKYGTAGYGV 840
D6948:    .......... .......... .......... .......... .......... .......... 840
TY89-PP:  ..R...Q... .......... .....K.... .......... .......... .......... 840

┌SacI
CEF94-PP: EARGPTPEEA QREKDTRISK KMETMGIYFA TPEWVALNGH RGPSPGQLKY WQNTREIPDP 900
D6948:    .......... .......... .......... .......... .......... .......... 900
TY89-PP:  .......... .......... .......... .......... ..E....... .......... 900

CEF94-PP: NEDYLDYVHA EKSRLASEEQ ILRAATSIYG APGQAEPPQA FIDEVAKVYE INHGRGPNQE 960
D6948:    .......... .......... .......... .......... .......... .......... 960
TY89-PP:  ....P..... .......... .....V.... .......... ......R... .......... 960

CEF94-PP: QMKDLLLTAM EMKHRNPRRA LPKPKPKPNA PTQRPPGRLG RWIRTVSDED LE 1012
D6948:    .......... .......... P......... .......... ...A...... .. 1012
TY89-PP:  .......... .......... P......... .......S.. .......... .. 1012
```

FIG. 16

Mock | D6948 mD6948-s2VP3C1 | mD6948-s2VP3C3

FIG. 17

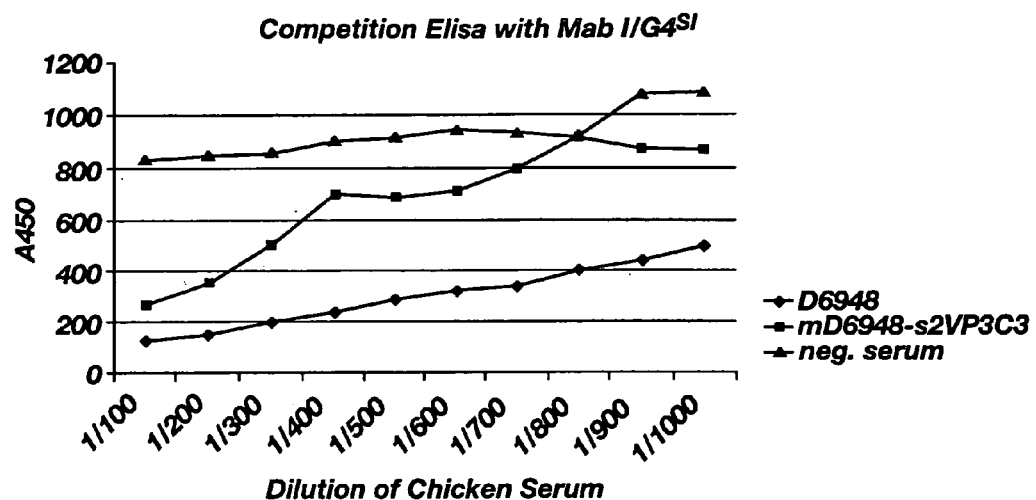
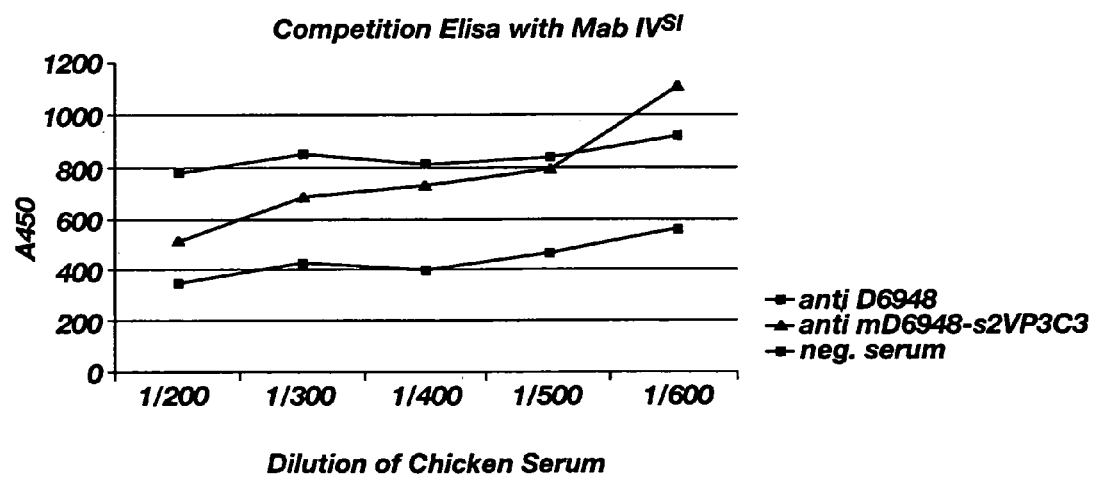
FIG. 18

FIG. 19

```
D6948-VP5: MLSLMVSRDQ TNDRSDDEPA RSNPTDCSVH TEPSDANNRT GVHSGRHPRE AHSQVRDLDL 60
CEF94-VP5: ----...... .......K.. .......... .......... ........G. .......... 56

D6948-VP5: QFDCGGHRVR ANCLFPWFPW LNCGCSLHTA EQWELQVRSD APDCPEPTGQ LQLLQASESE 120
CEF94-VP5: .......... .......I.. .......... .......... .......... .......... 116

D6948-VP5: SHSEVKHTPW WRLCTKWHHK RRDLPRKPE                                   149
CEF94-VP5: ........S. ......R... .........                                   145
```

FIG. 20A

```
D6948-PP:  MTNLQDQTQQ IVPFIRSLLM PTTGPASIPD DTLEKHTLRS ETSTYNLTVG DTGSGLIVFF  60
CEF94-PP:  .......... .......... .......... .......... .......... ..........  60

D6948-PP:  PGFPGSIVGA HYTLQSNGNY KFDQMLLTAQ NLPASYNYCR LVSRSLTVRS STLPGGVYAL 120
CEF94-PP:  .......... .......... .......... .......... .......... .......... 120

D6948-PP:  NGTINAVTFQ GSLSELTDVS YNGLMSATAN INDKIGNVLV GEGVTVLSLP TSYDLGYVRL 180
CEF94-PP:  .......... .......... .......... .......... .......... .......... 180

D6948-PP:  GDPIPAIGLD PKMVATCDSS DRPRVYTITA ADDYQFSSQY QAGGVTITLF SANIDAITSL 240
CEF94-PP:  .......... .......... .......... .......P.. .......... .......... 240

D6948-PP:  SIGGELVFQT SVQGLILGAT IYLIGFDGTA VITRAVAADN GLTAGTDNLM PFNIVIPTSE 300
CEF94-PP:  .V........ ..H..V.... .......... .......N.. ...T...L.. ...L....N. 300

D6948-PP:  ITQPITSIKL EIVTSKSGGQ AGDQMSWSAS GSLAVTIHGG NYPGALRPVT LVAYERVATG 360
CEF94-PP:  .......... .......... .........R .......... .......... .......... 360

D6948-PP:  SVVTVAGVSN FELIPNPELA KNLVTEYGRF DPGAMNYTKL ILSERDRLGI KTVWPTREYT 420
CEF94-PP:  .......... .......... .......... .......... .......... .......... 420

D6948-PP:  DFREYFMEVA DLNSPLKIAG AFGFKDIIRA LRRIAVPVVS TLFPPAAPLA HAIGEGVDYL 480
CEF94-PP:  .......... .......... .......... I......... .......... .......... 480

D6948-PP:  LGDEAQAASG TARAASGKAR AASGRIROLT LAADKGYEVV ANLFQVPQNP VVDGILASPG 540
CEF94-PP:  ────────── ────────── ────────── .......... .......... .......... 540

D6948-PP:  ILRGAHNLDC VLREGATLFP VVITTVEDAM TPKALNSKMF AVIEGVREDL QPPSQRGSFI 600
CEF94-PP:  V......... .......... .......... .......... .......... .......... 600

D6948-PP:  RTLSGHRVYG YAPDGVLPLE TGRDYTVVPI DDVWDDSIML SKDPIPPIVG NSGNLAIAYM 660
CEF94-PP:  .......... .......... .......... .......... .......... .......... 660

D6948-PP:  DVFRPKVPIH VAMTGALNAY GEIENVSFRS TKLATAHRLG LKLAGPGAFD VNTGSNWATF 720
CEF94-PP:  ........C. .........K .......... .......... .......... .......P.. 720
```

FIG. 20B

```
D6948-PP:  IKRFPHNPRD WDRLPYLNLP YLPPNAGRQY DLAMAASEFK ETPELESAVR AMEAAANVDP  780
CEF94-PP:  .......... .......... .......... .....H.... .......... ..........  780

D6948-PP:  LFQSALSVFM WLEENGIVTD MANFALSDPN AHRMRNFLAN APQAGSKSQR AKYGTAGYGV  840
CEF94-PP:  .......... .......... .......... .......... .......... ..........  840

D6948-PP:  EARGPTPEEA QREKDTRISK KMETMGIYFA TPEWVALNGH RGPSPGQLKY WQNTREIPDP  900
CEF94-PP:  .......... .......... .......... .......... .......... ..........  900

D6948-PP:  NEDYLDYVHA EKSRLASEEQ ILRAATSIYG APGQAEPPQA FIDEVAKVYE INHGRGPNQE  960
CEF94-PP:  .......... .......... .......... .......... .......... ..........  960

D6948-PP:  QMKDLLLTAM EMKHRNPRRA PPKPKPKPNA PTQRPPGRLG RWIRAVSDED LE          1012
CEF94-PP:  .......... .......... ......L... .......... .....T.... ..          1012
```

FIG. 21A

```
D6948-VP1: MSDVFNSPQA RSKISAAFGI KPTAGQDVEE LLIPKVWVPP EDPLASPSRL AKFLRENGYK  60
CEF94-VP1: ...I...... ...T...... .......... .......... .......... ..........  60

D6948-VP1: ILQPRSLPEN EEYETDQILP DLAWMRQIEG AVLKPTLSLP IGDQEYFPKY YPTHRPSKEK 120
CEF94-VP1: V......... .......... .......... .......... .......... .......... 120

D6948-VP1: PNAYPPDIAL LKQMIYLFLQ VPEATDNLKD EVTLLTQNIR DKAYGSGTYM GQATRLVAMK 180
CEF94-VP1: .......... .......... ...NEG.... .......... .......... .......... 180

D6948-VP1: EVATGRNPNK DPLKLGYTFE SIAQLLDITL PVGPPGEDDK PWVPLTRVPS RMLVLTGDVD 240
CEF94-VP1: .......... .......... .......... .......... .......... .......... 240

D6948-VP1: GEFEVEDYLP KINLKSSSGL PYVGRTKGET IGEMIAISNQ FLRELSALLK QGAGTKGSNK 300
CEF94-VP1: .D........ .......... .......... .......... ....T..... .......... 300

D6948-VP1: KKLLSMLSDY WYLSCGLLFP KAERYDKSTW LTKTRNIWSA PSPTHLMISM ITWPVMSNSP 360
CEF94-VP1: .......... .......... .......... .......... .......... .......... 360

D6948-VP1: NNVLNIEGCP SLYKFNPFRG GLNRIVEWIM APDEPKALVY ADNIYIVHSN TWYSIDLEKG 420
CEF94-VP1: .......... .......... .......L.. .....E.... .......... .......... 420

D6948-VP1: EANCTRQHMQ AAMYYILTRG WSDNGDPMFN QTWATFAMNI APALVVDSSC LIMNLQIKTY 480
CEF94-VP1: .......... .......... .......... .......... .......... .......... 480

D6948-VP1: GQGSGNAATF INNHLLSTLV LDQWNLMKQP SPDSEEFKSI EDKLGINFKI ERSIDDIRGK 540
CEF94-VP1: .......... .......... ......R... ....R..... .......... .......... 540

D6948-VP1: LRQLVPLAQP GYLSGGVEPE QPSPTVELDL LGWSATYSKD LGIYVPVLDK ERLFCSAAYP 600
CEF94-VP1: ....L..... .......... ..S....... .......... .......... .......... 600

D6948-VP1: KGVENKSLKS KVGIEQAYKV VRYEALRLVG GWNYPLLNKA CKNNASAARR HLEAKGFPLD 660
CEF94-VP1: .......... .......... .......... .......G.. .......... .......... 660

D6948-VP1: EFLAEWSELS EFGEAFEGFN IKLTVTPESL AELNRPVPPK PPNVNRPVNT GGLKAVSNAL 720
CEF94-VP1: .......... .......... ........S. .........K .......... .......... 720
```

FIG. 21B

```
D6948-VP1: KTGRYRNEAG LSGLVLLATA RSRLQDAVKA KAEAEKLHKS KPDDPDADWF ERSETLSDLL 780
CEF94-VP1: .......... .......... .......... .......... .......... .......... 780

D6948-VP1: EKADIASKVA HSALVETSDA LEAVQSTSVY TPKYPEVKNP QTASNPVVGL HLPAKRATGV 840
CEF94-VP1: .......... .......... .......... .......... .......... .......... 840

D6948-VP1: QAALLGAGTS RPMGMEAPTR SKNAVKMAKR RQRQKESRQ- -                     879
CEF94-VP1: .......... .......... .......... .........Q P                     881
```

MOSAIC INFECTIOUS BURSAL DISEASE VIRUS VACCINES

CROSS-REFERENCE TO RELATED APPLICATION

This application is a continuation of International Application Number PCT/NL00/00493 filed on Jul. 13, 2000 designating the United States of America, International Publication No. WO 01/04319 (Jan. 18, 2001), the contents of the entirety of which is incorporated by this reference.

TECHNICAL FIELD

The invention relates generally to biotechnology and, more particularly, to Infectious Bursal Disease Virus ("IBDV") vaccines.

BACKGROUND

Infectious bursal disease ("IBD"), an infectious disease among young chickens, was first recognized in 1957 in Gumboro, Del., USA, and formally documented by Cosgrove (Cosgrove, 1962; Lasher and Shane, 1994). As a result, the disease is often referred to as "Gumboro". Not long after IBD was first reported, it was recognized in poultry populations throughout the world (Lasher and Shane, 1994). IBD is caused by a virus ("IBDV") classified as a Birnavirus (Dobos et al., 1979).

Two different IBDV serotypes exist: serotypes I and II (Jackwood et al., 1982; McFerran et al., 1980). Isolates belonging to serotype I are highly pathogenic for chickens. Serotype II isolates, which are mainly recovered from turkeys, have not been reported to induce clinical signs in chickens and are regarded as apathogenic (Ismail et al., 1988). Infectious bursal disease or Gumboro is a highly contagious disease for young chickens and is responsible for severe losses in the poultry industry. In birds surviving an acute infection, lymphoid cells in the bursa of Fabricius are destroyed, resulting in B-cell-dependent immunodeficiency. This causes increased susceptibility to disease caused by otherwise harmless agents. A central role in the pathogenesis of Gumboro is played by the bursa, which is representing the target organ of the virus.

IBDV infections were initially recognized by whitish or watery diarrhea, anorexia, depression, trembling, weakness, and death. This clinical IBD was generally seen in birds between three and eight weeks of age. The course of the disease runs approximately 10 days in a flock. Mortality usually ranges from 0–30 percent. Field reports suggest that leghorns are more susceptible to IBDV than broiler-type chickens. Subclinical IBD was later recognized and is generally considered a greater problem in commercial poultry than the clinical disease. It is generally seen in birds less than three weeks of age. This early infection results in a B-lymphocyte depletion of the bursa of Fabricius. The bird is immunologically crippled and unable to respond fully to vaccinations or field infections. In susceptible chickens, damage caused by IBDV can be seen within two to three days after exposure to virulent virus. Initially, the bursa swells (3 days post-exposure) with edema and hemorrhages and then begins to show atrophy (7–10 days). IBD virus is especially cytopathic to certain B-lymphocytes. The highest concentration of these specific B-lymphocytes is found in the bursa. Destruction of the B-lymphocytes by IBD field virus may result in an incomplete seeding of these cells in secondary lymphoid tissue. As a result of the depletion of B-lymphocytes, surviving birds are immunocompromised during the remainder of their lifetime.

IBDV is found worldwide, and IBDV-specific antibodies have even been found in Antarctic penguins (Gardner et al., 1997). The prevalence of clinical IBD is relatively low compared to the prevalence of subclinical IBD. IBDV is very resistant to common disinfectants and has been found in lesser mealworms, mites, and mosquitoes. These facts correlate with field experience of reoccurring IBD problems on a farm, despite clean-up efforts. Infection with IBDV results in a strong antibody response against IBD, which is capable of neutralizing this virus. Most likely as a result of vaccination, antigenic variant isolates of serotype I were isolated in the Delaware area (USA). These isolates have been shown to cause bursa atrophy in as little as three days post-infection without inflammation of the bursa. Despite their change in antigenicity, these antigenic variants do not form a distinct serotype. After the occurrence of antigenic variant IBDV isolates in the USA, the poultry industry in European countries was hit by outbreaks of IBD caused by a very virulent serotype I IBDV (vvIBDV) (Berg et al., 1991; Chettle et al., 1989; Kouwenhoven and Van den Bos, 1995). These very virulent field isolates were capable of establishing themselves in the face of high levels of maternal antibodies which normally were protective. These vvIBDV cause more severe clinical signs during an outbreak and are now found globally (e.g., Europe, Japan, Israel and Asia).

IBDV belongs to the family of Birna viruses which include Infectious Bursal Disease Virus (IBDV) isolated from chickens, Infectious Pancreatic Necrosis Virus (IPNV) isolated from Fish, *Drosophila* X Virus (DXV) isolated from fruit fly, and Tellina Virus (TV) and Oyster Virus (OV) both isolated from bivalve molluscs (Dobos et al., 1979). Birna viruses have a dsRNA genome which is divided over two genome segments (the A- and B-segment). The A-segment (3.3 kbp) contains two partly overlapping open reading frames (ORFs). The first, smallest ORF encodes the non-structural Viral Protein 5 (VP5, 17 kDa). The second ORF encodes a polyprotein (1012 amino acid, 110 kDa), which is autocatalytically cleaved. The exact positions of these cleavage sites are unknown.

From SDS-Page analysis of in vitro translated IBDV RNA, it is known that the polyprotein is rapidly cleaved into three proteins: pVP2 (48 kDa), VP4 (29 kDa) and VP3 (33 kDa). During in vivo virus maturation, pVP2 is processed into VP2 (38 kDa), probably resulting form site-specific cleavage of the pVP2 by a host cell-encoded protease (Kibenge et al., 1997). VP2 and VP3 are the two proteins that constitute the single shell of the virion. The B-segment (2.9 kbp) contains one large ORF, encoding the 91 kDa VP1 protein. This protein contains a consensus RNA-dependent RNA polymerase motive (Bruenn, 1991).

Furthermore, this protein has been reported to be linked to the 5'-ends of the genomic RNA segments (Viral Protein genome-linked, VPg). The nucleotide sequence of internal parts of a large number of IBDV isolates of classical, antigenic variant or very virulent origin has been determined and deposited in several databases such as GenBank. Furthermore, Mundt and Muller (Mundt and Muller, 1995) have determined the 5'- and 3'-termini of several IBDV isolates (CU-1, CU-1M, P-2 and 23/82), and by combining the internal and terminal sequences, Mundt and Muller established the complete nucleotide sequence of a serotype I A-segment (3261 bp) and B-segment (2827 bp). This provided the way to generate an infectious (recombinant) copy (rIBDV) of IBDV serotype I, by knowing the complete sequence dsRNA sequence of IBDV genome and by using one of several methods to generate infectious copy virus (see, for example, Boyer et al., Virology 198:415–426, 1994). Mundt and Vakharia indeed produced infectious rIBDV serotype I from cDNA (Mundt and Vakharia, 1996). Full-length cDNA of a serotype I IBDV, preceded by a T7 promoter, was thereby used as a template for T7 RNA polymerase using a method described by Weiland and Dreher (Weiland and Dreher, 1989). The in vitro-generated mRNA, containing a cap-structure at its 5'-end, was subsequently transfected into eukaryotic cells (VERO cells) using a liposome formulation (Lipofectin, GibcoBRL). The supernatant of the transfected cells contained infectious rIBDV after incubation during 36 h in the $CO_2$ incubator at 37° C. (Mundt and Vakharia, 1996; (WO 98/09646)). In addition, Lim et al. introduced two amino acid mutations (D279N and A284T) into the cDNA of vvIBDV isolate HK46 (Lim et al., 1999). These mutations were most probably based on data of Yamaguchi et al. (Yamaguchi et al., 1996), which showed that these specific mutations were found in two independent experiments in which very virulent IBDV isolates lost their very virulent character by adaptation and growth on primary CEF cells. Lim et al. obtained an rIBDV isolate which possessed the phenotype of a CEF-culture adapted isolate, i.e., an rIBDV isolate which can be propagated, i.e., is able to infect, multiply and be released for further replication, in vvIBDV non-permissive cells such as CEF cells. Noteworthy, Lim et al. were unable to produce an infectious vvIBDV isolate using the unmodified cDNA of the HK46 isolate (Lim et al., 1999). Furthermore, although cDNA of IBDV can be used to produce infectious IBDV, the exact mechanism of replication has not been elucidated yet. Data exist which are in support of a semi-conservative genome replication model for Birnaviradae (Bernard, 1980; Mertens et al., 1982).

Now and then, IBDV variants are detected in the field or are created in cell cultures in the laboratory (Muller, 1987) that are genetic re-assortments of serotype I and II strains of IBDV, in that they contain one genomic segment derived from the one serotype and another segment derived from the other serotype. Such segment re-assorted (srIBDV) strains (also called chimeric IBDV) not only occur in nature, but have recently been generated from cDNA as a well, by Vahkaria and Mundt (WO 98/09646).

Vaccination using attenuated field isolates worked sufficiently well until antigenic derivatives were found in the Delaware region of the USA starting in 1985 (isolates Del A, D, G and E) (Snyder, 1990). These field isolates were missing an important virus-neutralizing epitope. The change of this epitope is characterized by the lack of binding of the virus-neutralizing monoclonal antibody (Mab) B69 (Snyder et al., 1988a). The antibodies induced by vaccination with classical IBDV vaccines appeared to be less protective against these antigenic IBDV variants. Inactivated vaccines based upon antigenic IBDV variants were subsequently produced and were found to protect effectively against these antigenic variants of IBDV. After the Delaware variant, a second antigenic variant IBDV was isolated. This variant was recovered from the Delmarva region (USA) and was referred to as the GLS variant. The GLS variant is characterized by the absence of epitopes for both the virus-neutralizing Mab B69 and R63 (Snyder et al., 1988b). After identifying these antigenic variants, a large survey was performed within the USA by using a panel of nine Mabs against IBDV. This survey yielded an additional antigenic variant: the DS326 variant. This antigenic variant is characterized by the absence of epitopes for Mab 179 and BK44, in addition to those for Mabs B69 and R63 (Snyder, 1990). No further reports of antigenic variants have been published in the USA or in other parts of the world. Whether this is due to non-existence of new variant IBDV isolates or whether new antigenic variants just have not been detected due to the lack of extensive surveys or the lack of discriminating monoclonal antibodies is unclear.

The nucleotide sequence of the polyprotein-encoding part of the A-segment of the Del, the GLS and the DS326 antigenic variant IBDV isolates has been determined (Vakharia et al., 1994). Most of the amino acid changes were found in a specific region of the VP2 protein, the so-called hypervariable region. Furthermore, it was found that the epitopes which are capable of inducing neutralizing antibodies are conformation dependent and are clustered in the hypervariable region. This region consists of a domain with a high hydrophobicity index (amino acids 224 to 314 of pVP2, corresponding with amino acids 224 to 314 of the polyprotein) which is flanked by two small hydrophilic regions, each spanning about 14 amino acids (Vakharia et al., 1994; Heine et al., 1991). Amino acid substitution both within the hydrophobic region and within the hydrophilic regions might be involved in the antigenic variant character of these isolates.

After the problems caused by the antigenic variant IBDV isolates in the USA, the poultry industry in Europe was affected by very virulent IBDV (vvIBDV) isolates (Berg et al., 1991; Chettle et al., 1989). The vvIBDV isolates cause more severe clinical signs during an outbreak and are able to break through levels of antibodies which are protective against classical IBDV isolates. The molecular determinants which distinguish vvIBDV from classical IBDV isolates are not exactly known. It is known, however, that the pathogenicity of cell culture adapted very virulent IBDV isolates is severely reduced, compared with the non-adapted parental isolates (Yamaguchi et al., 1996). The correlation between CEF-adaptation and loss of the very virulent phenotype is likely to be due to the change in target cell tropism of the adapted virus. This change in cell tropism may be due to the loss of bursa cell receptor binding capability of the cell culture adapted very virulent IBDV isolate. Another possibility is that the cell culture adapted very virulent IBDV isolate is able to infect non-bursa cells, resulting in large reduction of IBDV load in the primary target cells (bursa cells). From the published results (Yamaguchi et al., 1996), it is clear that a recombinant IBDV (rIBDV) which is based upon the cDNA of a cell culture adapted very virulent isolate will never yield a vaccine which meets the demands of being able to break through high levels of maternal antibodies and induce a high enough immune response.

No specific antibodies that exclusively recognize the vvIBDV isolates have been described yet (Eterradossi et al., 1997). The lack of discriminating antibodies makes direct diagnosis difficult. Most attention has been given to sequence comparison between the hypervariable region of VP2 of classical isolates and of very virulent isolates. Sequence analysis of the vvIBDV isolate UK661 showed that only three unique (i.e., not found in non-vvIBDV isolates) amino acid substitutions are present within the hypervariable region of the VP2 protein. One amino acid substitution is present within the remaining part of the pVP2 protein, while 5 unique amino acid mutations are present within the VP4-encoding part of the polyprotein and 6 in the VP3-encoding part (Brown and Skinner, 1996). The smaller ORF of the UK661 isolate A-segment, encoding the VP5 protein, contains 2 unique amino acid substitutions. Additionally, 16 unique amino acid substitutions were found in the VP1 protein encoded by the B-segment of this vvIBDV isolate. The virulent phenotype of the vvIBDV might be influenced by each of the found amino acid substitutions, and even (silent) nucleotide substitutions within the coding or non-coding parts of either the A- or B-segment may contribute to the altered phenotype of the vvIBDV isolates in comparison with the classical or antigenic variant isolates. Serial passage on embryonated eggs of a vvIBDV isolate (OKYM) resulted in the appearance of a derivative isolate (OKYMT) which is able to grow on Chicken Embryo Fibroblast (CEF) cells and has lost its virulence. This adaptation was reported to be the result of 7 nucleotide substitutions in the polyprotein encoding part of the genome. Whether additional nucleotide substitutions (or deletions) were present in remaining parts of the A- or B-segment (e.g., untranslated regions, VP1-encoding region, and VP5-encoding region) was not determined (Yamaguchi et al., 1996). The reported nucleotide substitutions result in 5 amino acid substitutions. Three of these amino acid substitutions were located in the hydrophobic part of the hypervariable region (I256T, D279N, A284T) of VP2, one in the hydrophilic part located downstream of the hypervariable region (S315F) of VP2, and one in VP3 (A805T) (Yamaguchi et al., 1996). In an independent experiment, Yamaguchi et al. found that the adaptation of vvIBDV isolate TKSM into TKSMT resulted also in the A284T and D279N substitutions. The A284T substitution correlated in their analysis completely with adaptation onto CEF cells and loss of virulence. The D279N substitution was also present in both CEF-adapted vvIBDV isolates (OKYMT and TKSMT) and is potentially also important for growth on CEF cells and loss of virulence. The non-CEF adapted, classical IBDV isolate GBF-1 has, on the other hand, an asparagine at position 279, in combination with alanine at position 284, and cannot grow on CEF cells, so the single substitution D279N does not account for loss of virulence and growth on CEF cells. The amino acid changes in the VP2 apparently allow the modified IBDV to propagate on cells which do not have a receptor for wild-type IBDV. Cells possessing a wild-type IBDV receptor such as bursa cells are susceptible for classical and vvIBDV isolates. Recently, it was shown that amino acid substitution, A284T in combination with D279N, is indeed enough to turn a non-CEF-adapted very virulent IBDV isolate into a CEF-adapted isolate. Lim et al. introduced these two amino acid substitutions into the A-segment cDNA of vvIBDV isolate HK46 (Lim et al., 1999). After transfection of this cDNA, Lim et al. obtained an rIBDV isolate which possessed the phenotype of a CEF-culture-adapted isolate, i.e., an rIBDV isolate which is able to infect and multiply in CEF cells. The virulence of this rIBDV isolate was not assessed in chickens. Noteworthy, Lim et al. were unable to produce a recombinant infectious vvIBDV isolate using the unmodified cDNA of the HK46 isolate (Lim et al., 1999).

The goal of vaccination against IBD is prevention of subclinical and clinical IBD and the economic aspects of each. Effective vaccination for IBD can be divided into the following categories:

Protection of the developing bursa in broilers, breeders and layers.

Prevention of clinical disease in broilers, breeders and layers.

Priming and boosting of breeders.

To minimize the immunosuppressive effects of IBDV, the young chick must be protected. Protection of the very young can be achieved through high enough levels of maternal antibodies passed from the breeder hen to her progeny. Vaccination of the very young chick itself may not be successful since onset of protection after vaccination is between three and five days. When a bird, lacking maternal antibodies against IBDV, is exposed to a pathogenic IBDV field strain, damage will occur within 24–48 hours.

Generally, the early vaccinations of the breeders serve as priming. In most situations, this single vaccination is not considered to be adequate. "Boosting" is the term commonly associated with the administration of a final IBDV vaccination prior to the onset of lay. This is done to increase the circulating antibody in the hen and hence the maternal antibodies in the progeny. Both inactivated (oil emulsion vaccine) and live vaccines (IBDV) have been used for this purpose. The use of a live vaccine in an older bird will result in an increase of antibodies; however, large variations in antibody titers are often seen. These variations result in progeny becoming susceptible to field challenge from as early as a few days after hatching to 21 days after hatching. The use of inactivated IBDV vaccines gives a higher antibody titer as well as a decrease of variation between antibody titers of birds belonging to the same flock. The levels of maternal antibodies necessary to neutralize IBD vary with the invasiveness and pathogenicity of the field strain. In practical terms, if a very virulent IBDV isolate is present, higher maternal antibody levels are desired (see Table 1 for an overview of virulence of field isolates and strength of vaccines). Yet, for effective vaccination, avoiding interference with maternal antibodies is needed to induce a good immune response. Clinical IBD is typically seen between three and six weeks of age. The immune response of the chick must be stimulated as the passive protection is declining. The timing of the active vaccination may be estimated by the breeder or chick titer and the half-life of antibodies of approximately 3.5 days (De Wit and Van Loon, 1998; Kouwenhoven and Van den Bos, 1995). The levels of maternal antibodies tend to vary within a population. This variation might be a result of variation in the antibody levels of the breeder hen. Also, the mixing of progeny from several breeder flocks (e.g., combination of breeders of different age; breeders vaccinated with live vaccine and those with oil emulsion vaccine) results in variation of IBDV antibodies between chicks belonging to the same flock. If the coefficient of variation (CV) in mean maternal antibody titers is too wide, it may be recommended to vaccinate twice (with a 10 day interval) or to vaccinate early with a hot vaccine (in the presence of a high antigenic pressure).

The average titer of antibody against IBDV in a flock will decline in time (FIG. 1). As a result of the decrease in average antibody titers, an immunity gap will occur. The best results are obtained if the immunity gap is as short as possible and is as early as possible, within a minimum of 2 weeks after hatching. There should be at least sufficient immunity after active vaccination at the age of 4 weeks, since many handlings occur in the houses from that time point with risks of introducing field virus. Therefore, farmers like to vaccinate at 2 weeks or even before. Intermediate vaccines are often unable to break through the average IBDV antibody titer of the broiler at two weeks after hatching (FIG. 1). If there is a high variation in mean maternal antibody titers, some chicks will be effectively vaccinated with intermediate vaccines, others not. To circumvent those problems, hot vaccines are being used. A drawback of usage of hot vaccines is that the bursa of chickens with low-to-moderate maternal antibody titers will be (partly) damaged.

There is a wide variety of IBDV vaccines available. Important aspects in vaccination strategies are the ability of the virus to replicate in the face of maternal antibody (invasiveness of the vaccine) and the spectrum of antigenic content (including antigenic variants). The ability of a vaccine virus to replicate in the face of maternal antibodies allows live vaccines to be categorized into three main groups: mild, intermediate, and intermediate plus or hot vaccines (see Table 1).

The initial vaccines for IBD were derived from classical IBDV isolates. These vaccines were moderately pathogenic IBDV strains with low passage numbers in embryonated eggs. These were often used in breeder programs to induce high levels of circulating antibodies. However, when given to a young bird with moderate or low levels of maternal antibodies, these vaccines could cause extensive bursal atrophy resulting in immunosuppression. Mild vaccines were subsequently developed to be used in these young birds. The attenuation of classical IBDV was done in tissue culture systems. Traditionally, attenuated strains for vaccines are generated by adapting IBDV strains to chicken embryoblast (CEF) cells or other appropriate cells or cell lines through serial passages. These vaccines are not immunosuppressive even when used in birds having no maternal antibodies. However, moderate and high levels of antibodies easily neutralize them. As breeder programs developed (including the use of adjuvant, inactivated vaccines), higher levels of maternal antibodies were generated in progeny. This reduces the effectiveness of these mild vaccines.

Intermediate-strength vaccines were to overcome the inadequacies of the mild vaccines. Some of the intermediate-strength vaccines were developed by cloning a field isolate on chicken cell cultures. Intermediate-strength vaccines are capable of establishing immunity in birds with moderate levels of maternal antibodies. These vaccines will cause some bursal atrophy in birds without maternal antibodies, but are considered not immunosuppressive.

Hot (strong) or intermediate plus vaccines were developed after the first outbreaks with vvIBDV. These vvIBDV isolates could break through higher levels of maternal immunity than the vaccines that were on the market at that time. Vaccination with intermediate vaccines always came too late in situations with high infection pressure with vvIBDV. Hot vaccines consist of vvIBDV strains with low-to-moderate passage in embryonated eggs or bursa-derived IBDV of chickens infected with vvIBDV isolates. Adapting vvIBDV on cells traditionally used for the generation of vaccines in general fails, since either these cells are non-permissive for vvIBDV or, when adapted to the cells, the vvIBDV in question had lost its very virulent character, making it useless for hot or intermediate plus vaccines. Hot or intermediate plus vaccines are desirably able to circumvent maternal immunity at an earlier age than intermediate vaccines but spread more within a flock. If intermediate plus and hot vaccines are used in chickens with moderate-to-high levels of maternal antibodies, there is no negative side effect on the bursa (Kouwenhoven and Van den Bos, 1995). If these vaccines are used in chickens with low-to-moderate levels of maternal immunity, this causes depletion of lymphoid cells in the bursa and a severe depletion of peripheral blood-B cells is found (Ducatelle et al., 1995). Although a recovery of bursal function has been observed, these vaccines should be used with precautions.

Live vaccines must be given in a way in which the virus will preferably reach the bursa, where it will quickly multiply and induce an immune response. Possible routes for application of live vaccines include drinking water, spray, subcutaneous and in ovo. Inactivated IBD vaccines are used in broiler breeders. They differ in some of the same ways as live vaccines. Their efficacy depends upon the spectrum of antigens they contain. Injectable oil-emulsion products may be given subcutaneously or intramuscularly.

A continuous monitoring of the field situation using an integrated quality control scheme including serology can be a valuable tool for continuously adapting preventive vaccination programs to changing epidemiological conditions. Also, a continuous follow-up of the epidemiological situation will allow anticipation of the development of major epidemics (Ducatelle et al., 1995). However, the ability of diagnostic laboratories to monitor IBD with meaningful definitive data is difficult. Serology is important but can be confusing when all birds monitored from commercial broiler flocks have high levels of the same spectrum of circulating antibodies. Field evaluations of broilers to monitor the status of IBD are highly subjective: it is difficult to discriminate antibody titers obtained after vaccination from those induced by IBDV field infections. If it were possible to discriminate between IBDV antibody response to field virus and IBDV vaccination, it is possible to have "early warning" systems and to start IBDV eradication programs if desired. Only when there is a known difference between the antibody response to the used IBDV vaccine and IBDV field isolates, defined conclusion about whether (sub)clinical signs of IBDV are the result of live IBDV vaccination or of IBDV field isolates can be made.

The invention provides infectious recombinant Infectious Bursal Disease Virus (rIBDV) essentially incapable of growing in a cell that is not derived from a bursa cell or another cell comprising a wild-type IBDV receptor (a non-bursa cell). A bursa is a lymphoid organ, mostly comprising cells that are related to the immune system. In particular, it comprises lymphocytes or lymphocyte precursor cells of sometimes the T-cell but mainly the B-cell-type, and cells derived thereof, in close relation with monocytes or monocyte-derived cells such as macrophages, and also with follicular dendritic cells and antigen-presenting cells. In particular, the invention provides rIBDV that is essentially incapable of growing in a cell not listed among the above-identified bursa cells or cells derived thereof, such as dendritic cells, monocytes, lymphocytes or cells derived thereof. Herewith, the invention provides an rIBDV having retained an important characteristic, in that in comparison with commonly attenuated IBDV strains, it cannot or only little grow in non-bursa cells, such as the well-known CEF, QM5 or VERO cells, or other cells that are commonly used for propagating attenuated strains of IBDV. In particular, the invention provides an rIBDV essentially incapable of growing in a non-B-cell-derived cell. Essentially incapable of growing herein means that the isolate in question is not or only little capable to infect, multiply or be released for further replication. No such rIBDV isolates existed prior to this invention; all previously known rIBDV isolates grow in non-bursa cell-derived cells such as CEF cells (WO98/09646; Lim et al., 1999), thereby, for example, having lost those very virulent characteristics essential for maintaining in a vaccine strain designed to face the above-identified problems.

In a preferred embodiment, the invention provides are infectious rIBDV having retained at least part of the very virulent characteristics of a very virulent Infectious Bursal Disease Virus (vvIBDV) needed to provide protection against vvIBDV. In particular, vvIBDV is provided that is essentially incapable of growing in a non-bursa cell-derived cell. In particular, as, for example, demonstrated in the detailed description, the invention provides an rIBDV essentially incapable of growing in a CEF cell, a VERO cell or a QM5 cell, except, of course, in those CEF, VERO, QM5, or related cells having been provided with the necessary means (such as a transgenic receptor or replication system derived from a bursa cell or other characteristic of B-lymphoid cells which support the propagation of IBDV in an essentially non-lymphoid cell if this characteristic is present in such a non-B-lymphoid cell) needed for replication of classical or very virulent IBDV.

Furthermore, the invention provides an rIBDV wherein the amino acid sequence of protein VP2 comprises no asparagine at amino acid position 279, but, for example, comprises an amino acid particular for a strain with a very virulent character, such as with aspartic acid at amino acid position 279. Such rIBDV strains as provided by the invention have retained at least part of the very virulent characteristics of vvIBDV, as well as an rIBDV according to the invention wherein the amino acid sequence of protein VP2 comprises no threonine at amino acid position 284, but, for example, comprises an amino acid particular for a strain with a very virulent character, such as with alanine at amino acid position 284.

In a preferred embodiment, the invention provides an rIBDV according to the invention wherein the amino acid sequence of protein VP2 at least comprises a stretch of amino acids from about position 279 to 289, preferably from about position 229 to 314, most preferably from about position 214 to 328 as found in a vvIBDV isolate such as shown in Table 8.

The invention furthermore provides a method for obtaining an infectious recombinant copy of Infectious Bursal Disease Virus (rIBDV) essentially incapable of growing in a non-bursa cell-derived cell or having at least part of the very virulent characteristics of a very virulent Infectious Bursal Disease Virus (vvIBDV) comprising transfecting at least one first cell with a nucleic acid such as a cDNA or RNA comprising an IBDV genome at least partly derived from a vvIBDV, incubating the first cell in a culture medium, recovering rIBDV from the transfected first cell or culture medium, and propagating recovered rIBDV in at least one second cell which is permissive for vvIBDV. A vaccine derived from the recombinant virus as described is also part of this invention. Also, a vaccine comprising a chemically or physically inactivated recombinant virus or parts thereof is part of this invention.

Also, the attenuated derivatives of initially produced recombinant very virulent IBDV are part of this invention. Such a virus can be attenuated by known methods including serial passage, removing specific nucleic acid sequences, or site-directed mutagenesis. Physiologically acceptable carriers for vaccines of poultry are known in the art and need not be further described herein. Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IBDV. The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization. The vaccine can be administered by any suitable known method of inoculating poultry including nasally, ophthalmically, by injection, in drinking water, in the feed, by exposure, and the like. Preferably, the vaccine is administered by mass administration techniques such as in ovo vaccination, by placing the vaccine in drinking water or by spraying the animals' environment. When administered by injection, the vaccines are preferably administered parenterally. The vaccine of the present invention is administered to poultry to prevent IBD anytime before or after hatching. Poultry is defined to include but not be limited to chickens, roosters, hens, broilers, roasters, breeders, layers, turkeys and ducks. Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, eye drops, nose drops, and the like.

As explained above, there is need for an IBDV vaccine that can protect against field infections with IBDV, and preferably against very virulent IBDV (vvIBDV). It is clear that vaccines derived from attenuated classical strains and not from very virulent strains will not be able to sufficiently protect. However, as explained above, simply adapting and cultivating a vvIBDV strain on a cell or cell-line, such as VERO, CEF or QM5, as one skilled in the art would first do in order to obtain a vaccine strain from a vvIBDV strain, reduces it virulent phenotype such that no sufficient protection is to be expected. Therefore, a vaccine strain is needed that has at least partly maintained the very virulent or hot character, in order to provide sufficient protection; however, paradoxically, such a desirable vaccine strain would most likely not be able to be sufficiently or substantially propagated on appropriate cells, such as non-bursa cell-derived VERO, CEF or QM5, deemed needed to obtain the vaccine. In a preferred embodiment, the invention provides a method wherein the first cell is a non-bursa cell-derived cell non-permissive for vvIBDV, preferably wherein the first cell has additionally been provided with a helper virus or a viral protein (herein T7-polymerase is used) derived thereof. With the help of such a cell comprising a properly selected helper virus, e.g., expressing distinct IBDV or Birna virus viral proteins, or of a cell expressing IBDV or Birna virus viral proteins, (also called a complementary cell) also now defective or deficient rIBDV can be made.

The invention therewith also provides a method to generate Infectious Bursal Disease Virus, by combining cDNA sequences derived from very virulent IBDV (vvIBDV) isolates with cDNA sequences derived from either serotype I classical attenuated IBDV isolates, serotype I antigenic variants of IBDV, or serotype II IBDV isolates, wherein the infectious copy recombinant Infectious Bursal Disease Virus, having retained at least part of the very virulent characteristics of a very virulent Infectious Bursal Disease Virus, has at least retained the incapacity to substantially be propagated on a vvIBDV non-permissive cell such as a QM5 or CEF cell.

Preferably, a method as provided by the invention provides a vaccine comprising an IBDV genome wherein parts of segments A and/or B derived from a vvIBDV are used combined with parts of segments A and/or B derived from an attenuated IBDV, such as attenuated serotype I or I IBDV. Such an rIBDV is herein also called a mosaic IBDV (mIBDV). Herein we show that (mosaic) vvIBDV can be generated from cDNA by transfection of non-susceptible cells followed by amplification of the cDNA-derived rIBDV on susceptible cells. The invention provided herein provides a method to generate vvIBDV from the cloned, full-length cDNA of a vvIBDV isolate (see Table 5 and 6). After transfection of QM5 cells with cDNA of vvIBDV, it is essential that propagation of the generated vvIBDV virus takes place on cells which are permissive for vvIBDV. These permissive cells can, for example, be found among bursa cell-derived cells such as primary bursa cells, in chicken in embryo cells, chicken embryo's, or young chickens. Using the method described herein we have, for example, produced recombinant D6948 (rD6948) using the cDNA derived from the very virulent D6948 IBDV isolate. This rD6948 isolate has the same virulence as the parental D6948 isolate (Table 6).

Preferably, the invention provides a method wherein a permissive second cell is a primary bursa cell, thereby allowing initial propagation of the desired vaccine virus. As explained above, there is a need for a vaccine capable of breaking through maternal immunity of young chickens at an early stage. A desired vaccine should preferably be able to induce a high level of protection in vaccinated young chickens, and should, therefore, be as immunogenic as very virulent viruses or be almost as immunogenic.

The invention furthermore provides a method to engineer recombinant mosaic IBDV (mIBDV) vaccine which has one or more of the desired phenotypes, i.e., i) being able to break through high levels of maternal antibodies in young chickens and being highly immunogenic, and ii) having a reduced pathogenicity compared to wild-type very virulent IBDV isolates. In one embodiment, the invention provides an infectious mosaic IBDV (mIBDV) comprising an rIBDV wherein at least one genome segment comprises nucleic acid derived from at least two different Birna virus isolates. It is preferred that at least one of the isolates is a vvIBDV characterized by its incapacity to substantially be propagated on a vvIBDV non-permissive cell, such as a VERO, QM5 or CEF cell and/or characterized by its capacity to substantially be propagated on a vvIBDV-permissive cell, such as a primary bursa cell. For example, the invention provides mIBDV which consists partly of the genome derived from a classical attenuated isolate (such as CEF94) and partly derived from the genome of a vvIBDV isolate (such as D6948). A recombinant mosaic IBDV (mIBDV), made on the basis of infectious cDNA derived from a very virulent IBDV isolate (D6948) and combined with defined parts of cDNA derived from a cell culture adapted, serotype I, classical IBDV isolate (CEF94), results in an mIBDV isolate which has a reduced pathogenicity compared to wild-type vvIBDV isolates which are essentially not replicating on non-B-lymphoid-derived cells.

Furthermore, specific nucleotide substitutions which either do or do not lead to amino acid mutations, or deletion of specific parts of the IBDV genome, again lead to an altered phenotype of the generated mIBDV. For example, the replacement of the pVP2-coding region of CEF-94 cDNA with the corresponding region of cDNA of D6948 yielded plasmid pHB36-vvVP2. This plasmid was subsequently transfected into FPT7-infected (Britton et al., 1996) QM5 cells in combination with pHB-34Z. Supernatant of these transfected QM5 cells was subsequently transferred to fresh QM5 cells. None of these QM5 cells reacted positively in an IPMA using specific antibodies for the VP3 protein of IBDV. On the other hand, primary bursa cells, after being overlaid with supernatant of the transfected cells, reacted positively in the same IPMA. The functional feature of being able to enter permissive cells such as QM5 cells is apparently located in the pVP2 coding region of the A-segment. This invention provides a method to generate recombinant vvIBDV (such as rD6948) having a pVP2 sequence exactly as found in a wild-type vvIBDV (here D6948). All very virulent isolates of which the pVP2 sequences have been described thus far have an alanine at position 284 and cannot or only little be propagated on CEF cells (see Tables 7 and 8). On the other hand, when a threonine is present at position 284, propagation on CEF cells is possible, but this is associated with the lack of a very virulent phenotype (see Tables 7 and 8). Herein we describe a method to generate infectious recombinant IBDV (rIBDV) having the nucleotide sequence of a wild-type very virulent IBDV isolate, including the alanine codon for amino acid 284 and being unable to be propagated on CEF cells. Furthermore, in our rD6948 isolate we have an aspartic acid present at position 279 instead of an asparagine commonly found for virulent IBDV isolates which can be propagated on CEF cells (Tables 7 and 8). The rD6948 is truly a very virulent rIBDV, as it is unable to grow on CEF cells (Table 5) and induces similar clinical signs and mortality as wild-type very virulent D6948 isolate (Table 6). Although mIBDV isolate (mCEF94-vvVP2) did not cause any mortality or body weight loss in a 9-day course, in contrast to the D6948, rD6948 and srIBDV-DACB isolates (also having a functional VP2 protein derived from vvIBDV, see Table 6), it caused the same reduction in bursa weight after 9 days post-infection as the wild-type very virulent D6948 isolate.

In yet another embodiment, the invention provided a mosaic IBDV according to the invention wherein at least one of the isolates is a serotype II IBDV. Such an mIBDV, preferably lacking at least one immunodominant epitope specific for a serotype I IBDV as well, is an (r)D6948-derived vaccine virus such as mD6948-s2VP3C1, also having a functional VP2 protein derived from vvIBDV, allowing vaccination with a marker vaccine. Vaccination with an IBDV marker vaccine and subsequent testing with a corresponding diagnostic test enables the discrimination between antibodies induced by the vaccine and by infection with IBDV field isolates. This mIBDV can be differentiated from all other known wild-type IBDV isolates, either belonging to serotype I or serotype II, for example, by using a specific set of monoclonal antibodies. The generation of mIBDV from serotype I and II cDNA provides such an mIBDV marker vaccine that induces a serological response in chickens that can be differentiated from the serological response induced by IBDV field strains. The marker vaccine provided by the invention, lacking at least one immunodominant epitope, preferably a serotype I epitope, enables the discrimination between vaccinated and infected animals by means of a diagnostic serologic test. Such an mIBDV marker vaccine is preferably based upon vvIBDV and contains specific sequences originating from classical serotype I or serotype II IBDV. Such an mIBDV marker vaccine has one or more of the following characteristics: i) It induces a protective immune response against vvIBDV field viruses despite high levels of maternal antibodies. ii) It has a reduced pathogenicity compared to vaccines based upon wild-type vvIBDV. iii) It, for example, misses at least one serotype I-specific antigen which enables the serological discrimination of the mIBDV marker vaccine from all serotype I IBDV isolates.

Also, the invention provides a method to produce or generate tailor-made vaccines against specific antigenic variants of IBDV by incorporating the specific amino acid changes in an mIBDV vaccine virus. Depending on the composition, these mosaic IBD viruses (mIBDV) possess different phenotypes and different antigenic properties. A specific mutation in one of the viral proteins can have a profound effect on IBDV viability. We found that this is true in the case of a single nucleotide substitution, leading to a single amino acid mutation in VP4 (V582A). No rIBDV could be rescued from cDNA when this particular nucleotide substitution was present. Not only mutations within the VP4-encoding region itself, but also mutations or deletions in the region of the cleavage sites (pVP2-VP4 and VP4-VP3) may have a negative effect on replication of rIBDV. Mutations in the other viral proteins, or even deletion of an entire viral protein (i.e., VP5), influence the replication and or virulence as well. Two groups have constructed a VP5 minus rIBDV isolate, by introducing mutations in the cDNA of a CEF-adapted D78 IBDV isolate (Mundt et al., 1997; Yao et al., 1998). Apparently, the VP5 protein, which is a non-structural protein, is also a non-essential protein. Yao et al. reported that inactivation of the ORF for VP5 (replacement of the start codon by a stop codon) yielded infectious rIBDV (rD78NS which grows to slightly lower titers (in vitro) than rD78), while Mundt et al. reported that inactivation of the ORF for VP5 (replacement of the start codon by an arginine codon) yielded an rIBDV (IBDV/VP5–) which is able to grow to the same titers (in vitro) as the parental isolate. Furthermore, Yao et al. reported that rD78NS has decreased cytotoxic and apoptotic effects in cell culture (in vitro) and has a delay in replication compared to the parental isolate (in vivo), and failed to induce any pathological lesions or clinical signs of disease in infected chickens.

Mutations or deletions in the mIBDV cDNA yields an mIBDV with a desired phenotype, i.e., mIBDV which is based on a very virulent isolate but which has a reduced ability to replicate and hence a reduced pathogenicity. The introduction of cDNA sequences from a serotype II, cell culture adapted, IBDV isolate (TY89) into the mosaic virus gives us yet another opportunity to generate marker mIBDV vaccine which can be discriminated from wild-type serotype I IBDV, for example, by using specific monoclonal antibodies. Such mIBDV can be used to induce an antibody spectrum, which differs from the spectrum induced by IBDV field isolates. This enables the development of a serologic test to determine whether IBDV antibodies are the result of live mIBDV vaccination or of infection with IBDV field isolates. For example, the mCEF94-s2VP3C virus is recognized by serotype II-specific VP3 antibody (Mab T75), while it is also recognized by a serotype I-specific VP2 antibody (Mab 1.4). This particular rIBDV is, on the other hand, not recognized by a serotype I-specific VP3 antibody (Mab B10). No apparent difference is present between the replication of mCEF94-s2VP3C and rCEF94, indicating that the exchange of the VP3C-terminal part does not lead to major changes in replication ability in QM5 cells. When, on the other hand, the complete VP3-encoding region was exchanged, we observed a severe reduction in replication ability of the resulting virus (mCEF94-s2VP3). On the other hand, mCEF94-s2VP3N was not reacting with Mab C3 (VP3, serotype I) while it is fully reacting with Mab B10 (VP3, serotype I) and only partially with Mab T75 (VP3, serotype II). Replication of this mosaic IBDV on CEF cells is reduced compared to rCEF94. From the generated mIBDV, based on cDNA derived from serotype I (CEF94) and serotype II (TY89), it is clear that a serological marker based on VP3 has been identified. The replacement of the cDNA of (part of) VP3 of serotype I for the corresponding part of serotype II leads to a unique combination of IBDV antigens within one mIBDV isolate. An mIBDV isolate based on this combination of antigens can be used as an IBDV marker vaccine.

The introduction of the VP3 C-terminal part of TY89 (Serotype II) into the cDNA of D6948 yielded a mosaic IBDV (mD6948-s2VP3C1) which has a reduced virulence (no mortality, no body weight loss) compared to D6948 or rD6948 (Table 6). This mIBDV, or a comparable isolate which is more or less virulent, is also advantageously used as an IBDV marker vaccine to prevent infections with very virulent IBDV field isolates.

Furthermore, the invention provides using site-specific mutagenesis techniques to introduce any desired nucleotide mutation within the entire genome of mIBDV. Using this technique allows adapting mIBDV vaccines to future antigenic variations by including any mutation that has been found in antigenic variant IBDV field isolates. Furthermore, it is provided by the invention to exchange part of the genomic sequence of IBDV with the corresponding part of a Birna virus belonging to another genus (e.g., DXV, EPNV, OV, TV). Herewith, the invention provides new mosaic Birna (mBirna) viruses which have new characteristics resulting in new recombinant vaccines for IBDV or other Birna viruses. Also, the use of cDNA of other Birna viruses (e.g., DXV, IPNV, OV or TV) leads to new IBDV vaccines. In this approach, one or more of the IBDV immunodominant or neutralizing epitopes are exchanged with the corresponding parts of the protein of another Birna virus.

Of course, the invention also provides a method for producing an rIBDV according to the invention, the vector comprising heterologous nucleic acid sequences derived from another virus, or (micro)organism, whereby r- or mIBDV serves as a vector. For example, a method is provided to generate an infectious copy IBDV which expresses one or more antigens from other pathogens and which can be used to vaccinate against multiple diseases. Such an infectious copy IBDV, for example, comprises a heterologous cDNA encoding a heterologous protein obtained from a pathogen, for example, poultry pathogens. Also, a method is provided to generate a conditional lethal IBDV deletion mutant which can be used as a self-restricted, non-transmissible (carrier) vaccine. Such an IBDV deletion mutant is unable to express one of the IBDV proteins, and is phenotypically complemented by supplying the missing protein by other means.

The invention is further explained in the detailed description without limiting the invention thereto.

BRIEF DESCRIPTION OF THE FIGURES

FIG. 1: Antibody titres in broilers having high levels of maternal antibody at day 0.

FIGS. 2A–2G: Alignment of IBDV A-segment cDNA sequences CEF94-A (SEQ ID NO:71), D6948-A (SEQ ID NO:72), TY89-A (SEQ ID NO:73) and consensus sequence (SEQ ID NO:70).

FIGS. 3A–3F: Alignment of IBDV B-segment cDNA sequences CEF94-B (SEQ ID NO:75), D6948-B (SEQ ID NO:76) and consensus sequence (SEQ ID NO:74).

FIGS. 4A–4C: IBDV polyprotein alignment for CEF94-PP (SEQ ID NO:78), D6948-PP (SEQ ID NO:79), TY89-PP (SEQ ID NO:80) and consensus sequence (SEQ ID NO:81).

FIGS. 5A–5B: IBDV VP1 alignment for CEF94-VP1 (SEQ ID NO:82), D6948-VP1 (SEQ ID NO:83) and consensus sequence (SEQ ID NO:81).

FIG. 6: IBDV VP5 alignment for D6948-VP5 (SEQ ID NO:85), CEF94-VP5 (SEQ ID NO:86) and consensus sequence (SEQ ID NO:84).

FIG. 9: Comparison of the amino acid sequences of the VP3-encoding parts of the cDNAs of the cell culture adapted serotype I classical strain CEF94 (amino acids 724–1012 of SEQ ID NO:78) and the wild-type serotype II strain TY89 (amino acids 2–290 of SEQ ID NO:80). The sequence of the CEF94 protein is presented, while only those amino acids, which differ from the CEF94 sequence, are given for TY89. Identical amino acids are represented by a dot. Plasmid pHB36-s2VP3 encodes the entire given amino acid sequence of serotype II (TY89). The nucleotide sequences of the A-segment cDNAs, which were used to deduce the amino acid sequences, have been deposited in the GenBank database: A-segment CEF94 (AF194428, full-length) and TY89 (xxxxx, partially). The positions of the SacII and ScaI sites in the corresponding cDNA (FIG. 10) are indicated.

FIG. 14: Schematic representation of the plasmids containing the full-length (hybrid) A-segment cDNA sequences. The T7 promoter sequence, the hepatitis delta virus ribozyme (HDR), and the T7 terminator are only given for plasmids pHB-36W and pHB60, but is present in each plasmid. Open boxes indicate CEF94 cDNA; shaded boxes indicate D6948 cDNA, while black boxes indicate TY89 cDNA.

FIG. 16: Comparison of the amino acid sequence of VP3 of the classical, cell culture adapted serotype I CEF94 strain (amino acids 724–1012 of SEQ ID NO:78), the very virulent serotype I D6948 strain (amino acids 724–1012 of SEQ ID NO:79) and the wild-type serotype II TY89 strain (amino acids 2–290 of SEQ ID NO:80). The sequence of the CEF94 protein is presented, while only those amino acids that differ from the CEF94 sequence are given for D6948 and TY89. The positions of the SacII and ScaI endonuclease restriction sites in the corresponding cDNA (see FIG. 14) are indicated.

FIG. 17: Formalin-fixed bursa sections stained with Hematoxylin-Eosin (H & E). Layer-type SPF chickens infected with the indicated virus (upper right corner) at day 21 were euthanized at day 13 post-infection, and bursas were examined. The overall damage of the follicular structure was determined according to Bayyari et al. (1996) and is given in Table 13.

FIG. 18: Resulting data of the competition Elisa's. The CEF94 VP3 antigen was coated, and a diluted serum sample (taken at 13 days post-infection) of chickens infected with the indicated virus was mixed with either Mab IV$^{SI}$ or I/G4$^{SI}$. The amount of bound Mab was determined using Rabbit-anti-Mouse conjugated with peroxidase and a TMB as substrate.

FIGS. 19, 20A, 20B, 21A, and 21B: Amino acid comparison between the different ORFs of the cDNAs of wild-type vvIBDV isolate D6948 and the cell culture adapted classical isolate CEF94. The complete sequence of the D6948 proteins is given, while only those amino acids which differ from the D6948 sequence are given for CEF94 (below the D6948 sequence). The nucleotide sequences of the A- and B-segments, which were used to deduce the amino acid sequences, can be found in the GenBank database (accession numbers are given between parenthesis: A-segment D6948 (AF240686), CEF94 (AF194428), B-segment D6948 (AF240687), and CEF94 (AF194429). A) Amino acid sequence encoded by the first ORF (VP5) of the A-segments for D6948-VP5 (SEQ ID NO:87) and CEF94-VP5 (SEQ ID NO:86). B) Amino acid sequence encoded by the second ORF (polyprotein) of the A-segment for D6948-PP (SEQ ID NO:79) and CEF95-PP (SEQ ID NO:78). The VP4 of the polyprotein (underlined) is preceded by pVP2, while VP3 is located at the C-terminus (see FIG. 22). The putative cleavage sites between pVP2 and VP4, and between VP4 and as suggested by (18) have been used. Only recently it was shown that the actual cleavage sites are most likely located between amino acids 512–513 (pVP2-VP4) and 755–756

(VP4/VP3) (27). C) Amino acid sequence encoded by the single ORF encoded by the B-segment (VP1/VPg) for D6948-VP1 (SEQ ID NO:83) and CEF94-VP1 (SEQ ID NO:82). Dashes are given in the case where corresponding amino acids are missing. Amino acid changes which are found in all vvIBDV sequences are given in bold face. Amino acid residues that are reported to be involved in adaptation to non-B-lymphoid cells are given in italics.

Figure 22:
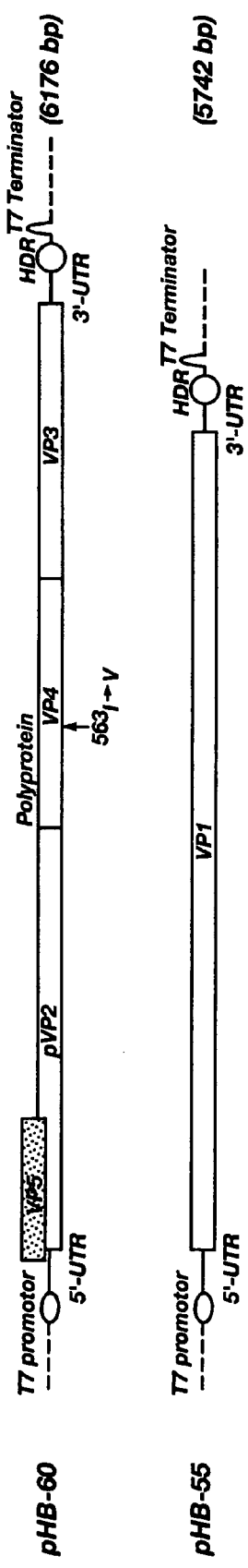

FIG. 22: Schematic representation of the plasmids containing the full-length cDNA sequence of the A-segment (pHB-60) and B-segment (pHB-55) of the wild-type very virulent IBDV isolate D6948. The cDNA sequence is preceded by a T7 promoter sequence and is followed by the hepatitis delta virus ribozyme (HDR), and a T7 terminator. The different ORFs are represented by open boxes.

Figure 23:
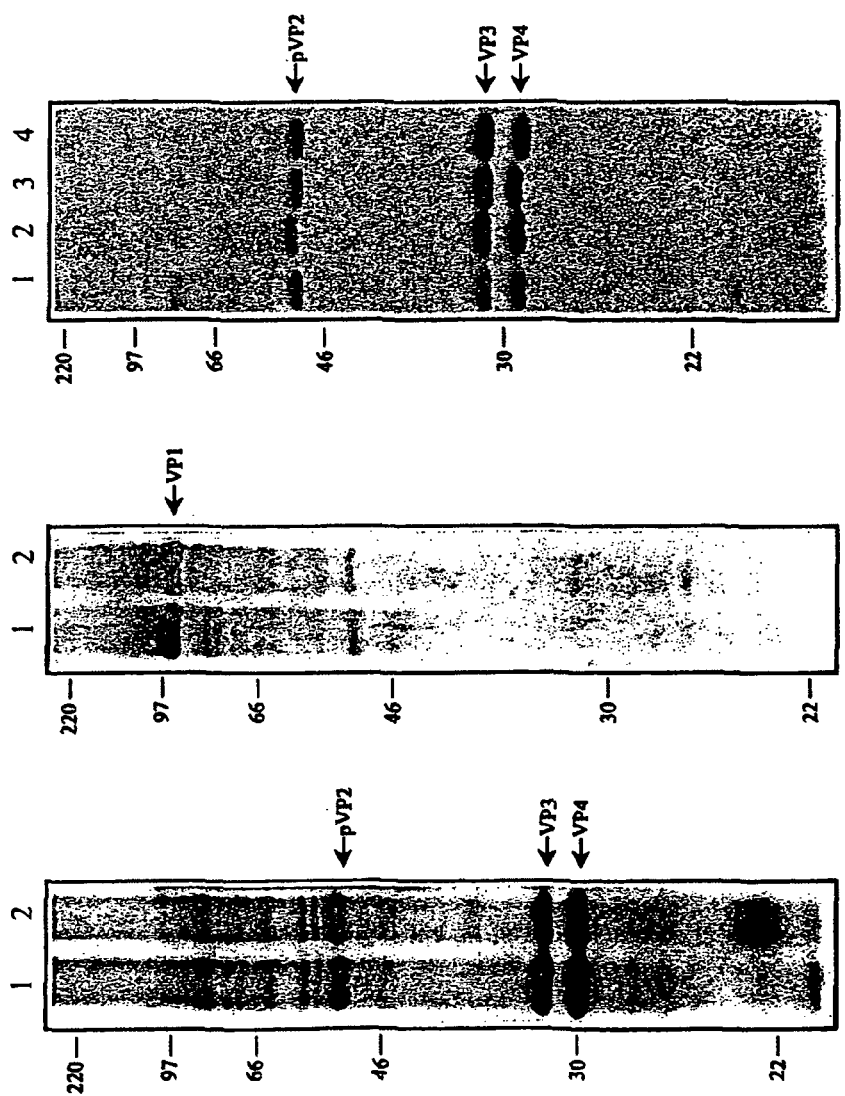

FIGS. 23A, 23B, and 23C: Autoradiogram of an SDS-PAGE analysis of a coupled in vitro transcription/translation reaction. a) Full-length A-segment plasmids of attenuated classical IBDV isolate CEF94 (lane 1) and wild-type very virulent IBDV isolate D6948 (lane 2). b) Full-length B-segment plasmids of CEF94 (lane 1) and D6948 (lane 2). c) Full-length A-segment CEF94 (lane 1) and full-length A-segment plasmid of the classical attenuated IBDV isolated (pHB-36) in which either pVP2 (pHB36-vvVP2, lane 2), VP3 (pHB36-vvVP3, lane 3), or VP4 (pHB36-vvVP4, lane 4) has been exchanged. The positions of the viral proteins are indicated on the right. The sizes of the marker proteins (Rainbow marker, Amersham) are indicated on the left.

Figure 24:
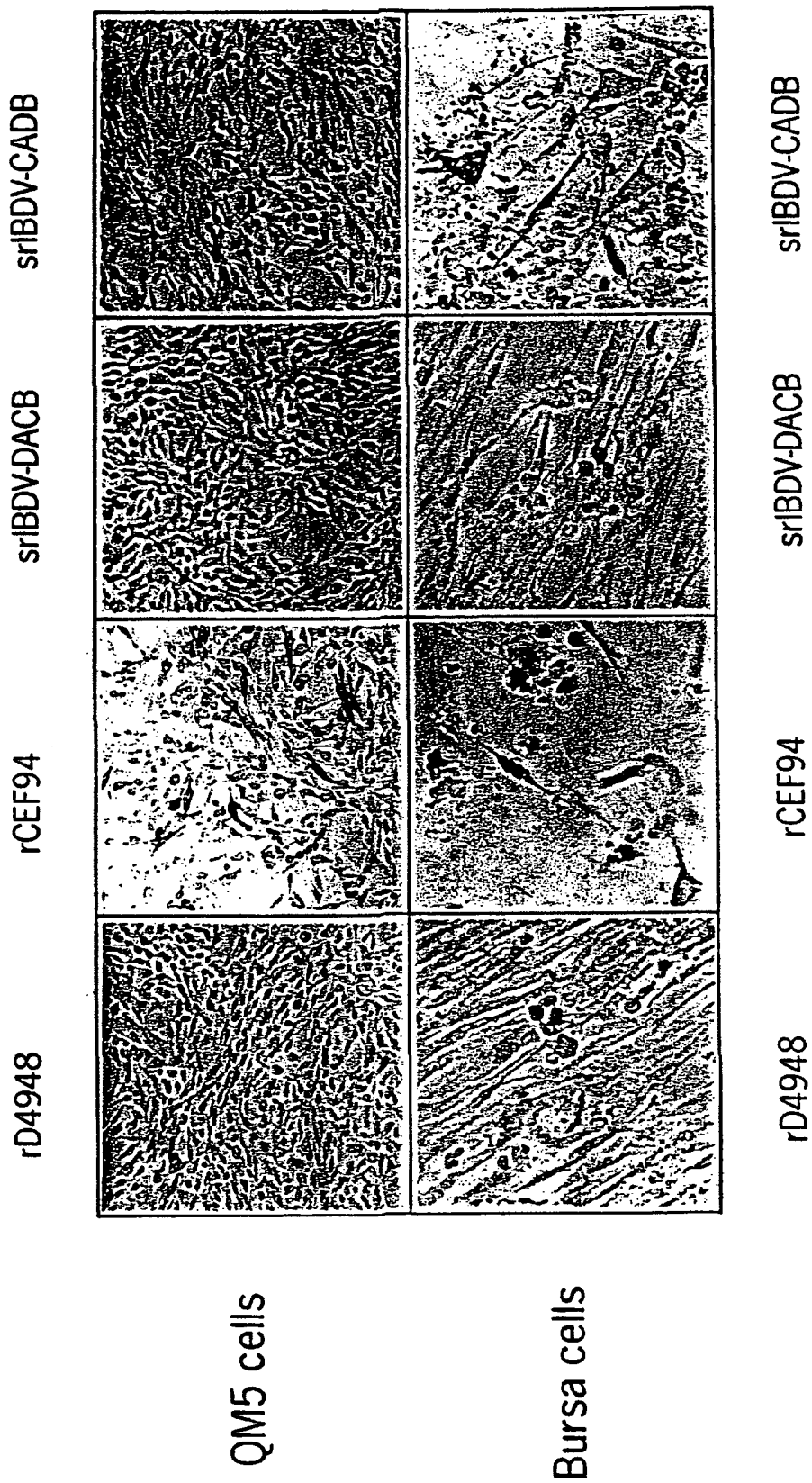

FIG. 24: Detection of IBDV using the VP3/4 polyclonal antiserum. Samples of supernatant of different plasmid transfections were used to infect QM5 or primary bursa cells. After infection, the QM5 cells were incubated for 24 h, while the primary bursa cells were incubated for 48 h. IBDV proteins were visualized by performing an Immunoperoxidase Monolayer Assay.

Figure 25:
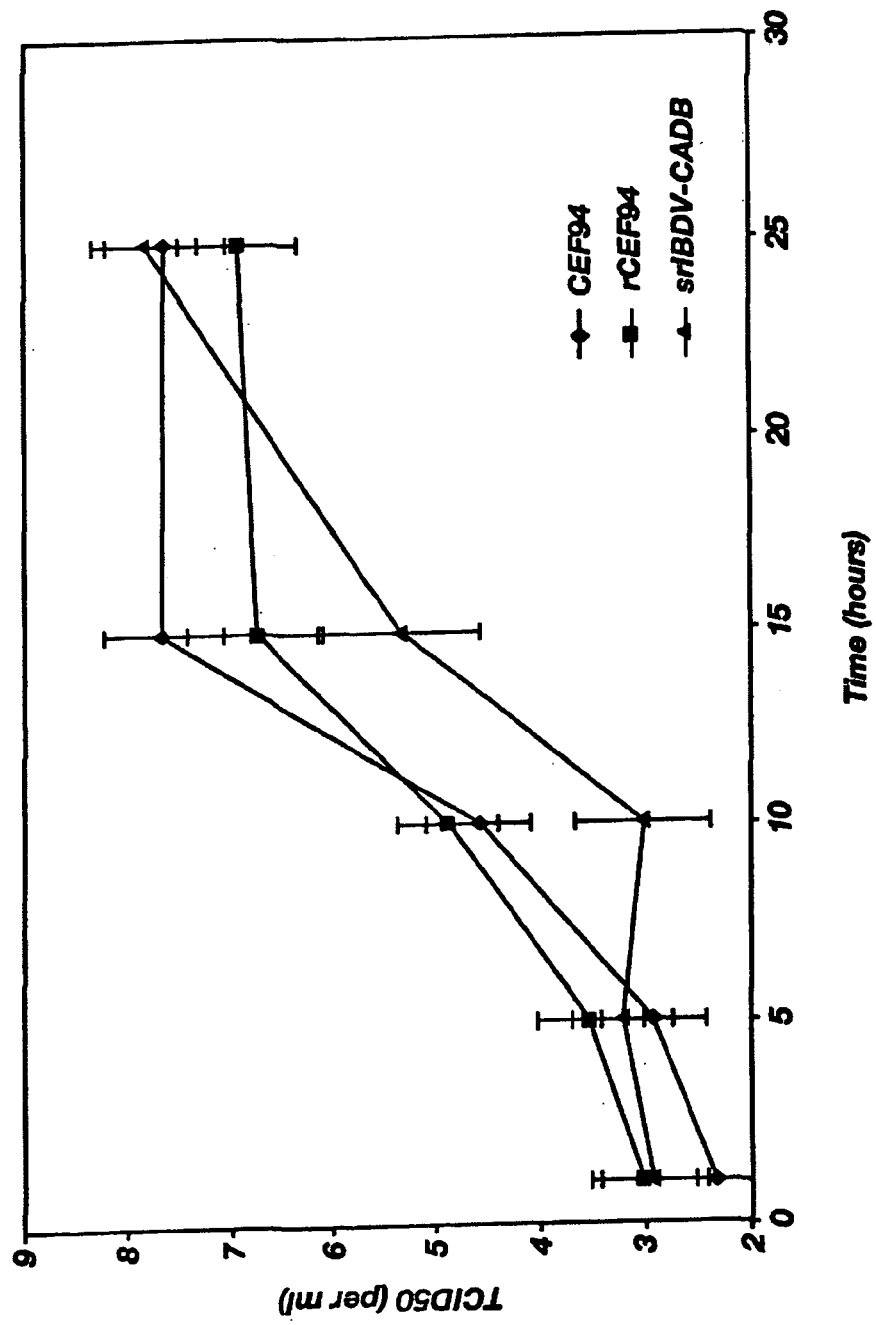

FIG. 25: Single-step growth curves of CEF94, rCEF94 and srIBDV-CADB. QM5 cells were infected with IBDV (m.o.i.=5, T=0 h) for one hour, washed three times, and covered with fresh medium. At different time points, samples were taken from the supernatant and the amount of IBDV ($TCID_{50}$ per ml) was determined. The $TCID_{50}$ value at each time point is the mean of three independent experiments; error bars represent standard deviations.

Figure 26:
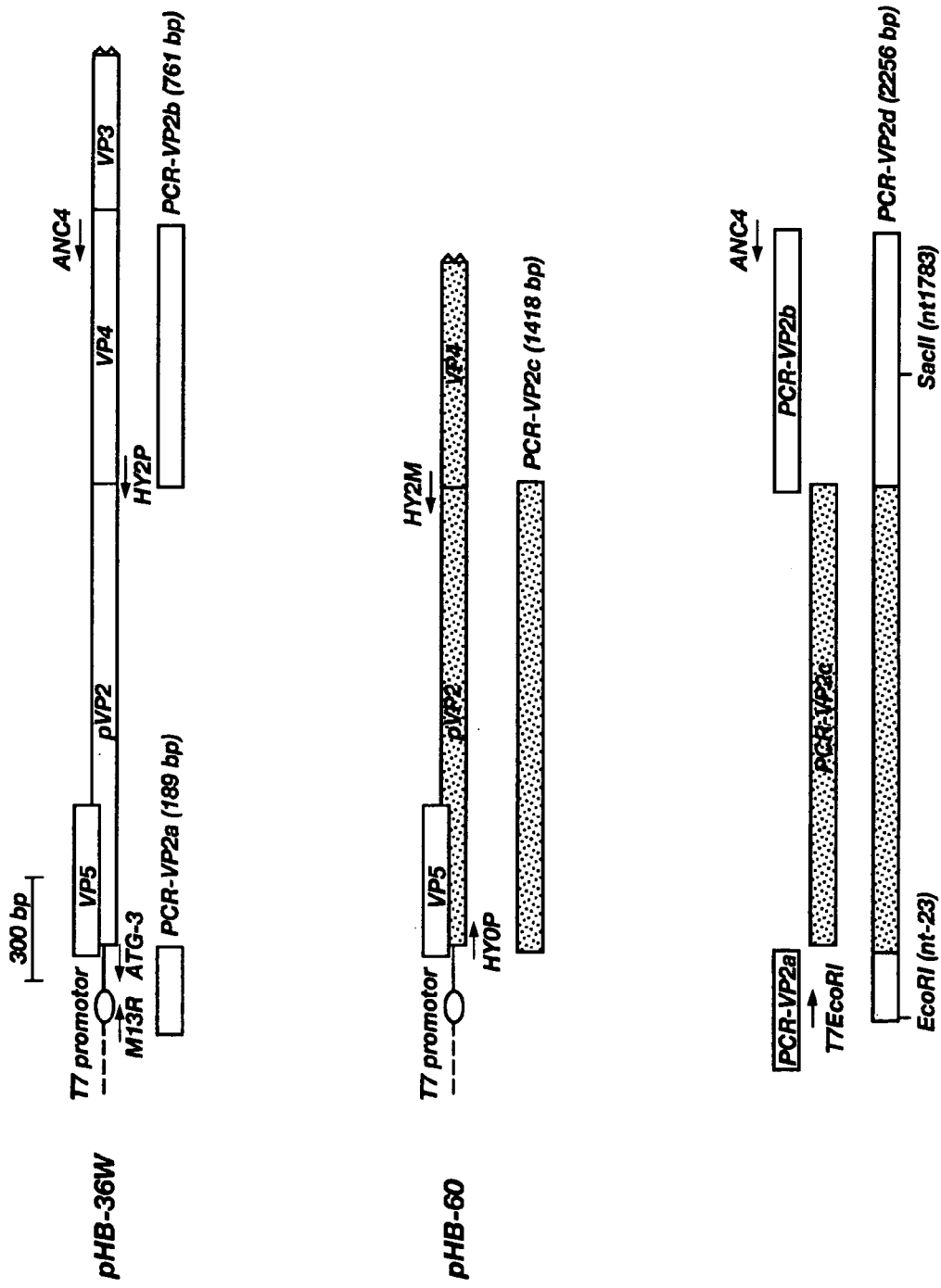

FIG. 26: Schematic representation of the construction of a mosaic PCR fragment having a middle part originating from D6948 cDNA (shaded boxes), and flanking parts originating from CEF94 cDNA (open boxes). For the construction of pHB-36-vvVP2, we first generated PCR fragments VP2a, VP2b, and VP2c. These PCR fragments were purified and subsequently used as template in a fusion PCR, yielding PCR fragment VP2d (17). This PCR fragment was subsequently purified and used to replace the corresponding part of the CEF94 A-segment cDNA, by using the indicated EcoRI and SacII restriction sites. pHB36-vvVP3 and -vvVP4 were generated using the same approach using different primers to generate the PCR fragments and different restriction sites to introduce the PCR fragments in the full-length A-segment clone (see Material and Method section and Table 16).

Figure 27:
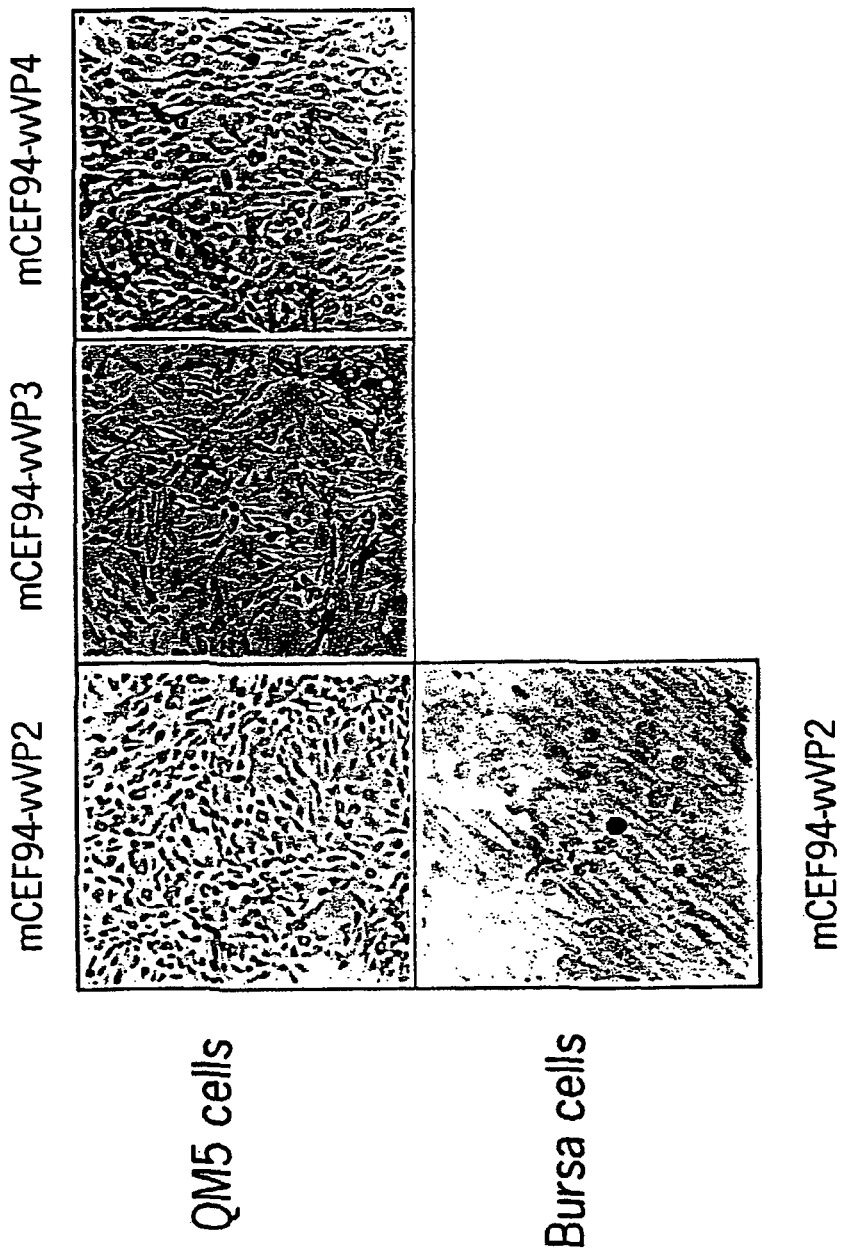

FIG. 27: Detection of mosaic IBDV using VP3/4 polyclonal antiserum. Samples of supernatant of different plasmid transfections were used to infect QM5 and primary bursa cells. After infection, the QM5 cells were incubated for 24 h, while the primary bursa cells were incubated for 48 h (FIG. 24). In contrast to the negative control (mock-infected), in which no B-lymphoid cells stained positive (data not shown), we found several stained B-lymphoid cells scattered throughout the culture tissue dish in the IPMA shown in the lower panel.

DETAILED DESCRIPTION OF THE INVENTION

Material and Methods

Viruses and Cells

The IBDV isolate CEF94 is a derivative of PV1 (Petek et al., 1973). After receiving the PV1 isolate in our laboratory in 1973, we have further adapted this isolate by repeated passage (>25 times) on either primary Chicken Embryo Fibroblast (CEF) cells or Bursa cells. The very virulent IBDV isolate D6948 was originally isolated in 1989 by the Poultry Health Service (Doom, the Netherlands). It was purified by 5 passages in embryonated eggs and one subsequent passage in SPF leghorn chickens. IBDV Serotype II isolate TY89 (McFerran et al., 1980) was maintained in our laboratory by a limited number of passages on CEF cells. Amplification of CEF-adapted isolates of IBDV (CEF94 and TY89) was performed by growing freshly prepared chicken embryo fibroblast (CEF) cells in a tissue culture flask (75 cm2) until near confluency. This cell culture was infected with either CEF94 or TY89 (m.o.i.=0.1) and incubated for 48 h at 37° C. in a 5% $CO_2$ incubator. The supernatant of this culture was centrifuged at 6000 g for 15 min. (pelleting of debris), transferred to clean tubes and subsequently centrifuged at 33,000 g for 3 h. The virus pellet was resuspended in PBS (1% of the initial culture volume). The very virulent IBDV isolate D6948 was propagated in our laboratory in 21-day-old chickens by inoculation of 200 ELD50 (Egg Lethal Doses) per chicken, nasally and by eye-drop. The bursas of Fabricius were collected from the infected chickens three days post-infection, and two volumes of tryptose phosphate buffer were added. This mixture was homogenized in a Sorval Omnimixer (3*10 sec, maximum speed) and subsequently clarified by centrifugation (6000 g, 10 min). The supernatant was transferred to clean tubes and extracted three times with freon and once with chloroform. Virus preparations were stored at −70° C. until further use. QM5 cells (Antin and Ordahl, 1991) were received from the laboratory of R. Duncan (Dalhouse University, Halifax, Nova Scotia, Canada) and maintained by using QT35 medium (Fort Dodge), in a $CO_2$ incubator (37° C.).

Isolation of Viral dsRNA

The genomic dsRNA was purified from the IBDV particles by digesting the viral proteins with Proteinase K (Amresco, 1.0 mg/ml) in the presence of 0.5% SDS during 2 h at 50° C. The viral dsRNA was purified by phenol/chloroform/isoamylalcohol (25:24:1) extraction (two times) and precipitation with ethanol (2.5V)/NaCl (0.1V, 5M, pH4.8) or with 2 M lithium chloride (Diaz-Ruiz and Kaper, 1978). The RNA was dissolved in DEPC-treated water (10% of the initial volume) and stored at −20° C. until further use. The integrity and purity of the viral RNA was checked on an agarose gel.

Rapid Amplification of cDNA Ends

The extreme 5'-termini of all genomic RNA strands (the coding and non-coding strands of both the A- and B-segment) of isolate CEF94 were determined. We used 2 μg of genomic dsRNA and 10 pmol of strand- and segment-specific primers in a total volume of 12 μl, for each determination. After incubation at 95° C. for five min., we transferred this mixture onto ice and added 4 μl of Superscript II first strand syntheses buffer (Gibco/BRL), 2 µl of 100 mM DTT and 2 µl of dNTPs (10 mM each). This mixture was subsequently incubated at 52° C. for 2 min, after which 1 µl of reverse transcriptase (Superscript II, Gibco/BRL) was added and incubation at 52° C. was continued for one hour. The reverse transcriptase was inactivated by the addition of 1 µl of 0.5 M EDTA. The genomic dsRNA was destroyed by the addition of 2 µl of 6 M NaOH and incubation at 65° C. for 30 min. For neutralization, 2 µl of 6 M Acetic acid was added, and cDNA was recovered by using a Qiaex DNA extraction kit (Qiagen) and finally dissolved in 6 µl water. In the anchor ligation reaction, we used 2.5 µl of the cDNA preparation, 4 pmol of the anchor, 5 µl T4 ligation buffer and 0.5 µl T4 RNA ligase (New England Biolabs). Incubation was performed at room temperature for 16 h and the reaction was stored at −20° C. To amplify the single-stranded cDNA which was ligated to the anchor, we used a nested primer in combination with the anchor primer. The PCR was performed by using the following conditions: 10 pmol of each specific primer, 10 pmol of the anchor primer, 4.5 or 5.5 mM $MgCl_2$, 1*Taq buffer (Perkin Elmer), 50 µM of each dNTP, 3 units of Taq polymerase (Perkin/Elmer), and 4 µl of the RNA ligation mixture as template, in a total volume of 50 µl. The amplification was performed by 35 cycles through the temperature levels of 92° C. (45 sec), 57 or 65° C. (45 sec), and 72° C. (90 sec). The resulting PCR products were agarose gel purified and digested with EcoRI and XbaI and ligated (T4 DNA Ligase, Pharmacia), in a pUC18 vector which had previously been digested with the same restriction enzymes. The resulting plasmids were amplified in E. coli and nucleotide sequence analysis was performed by using the M13F and M13R primers.

Generation of Full-Length A- and B-Segment Single-Stranded cDNA

To produce full-length single-stranded cDNA of both the A- and B-segments of CEF94 and D6948, we used a primer specific for the 3'-terminus of the coding strand in the reverse transcription reaction for initiation of the cDNA synthesis. As template we used 1 µg of genomic RNA and 2.5 pmol of ANC1 (A-segment-specific primer, Table 2) or BNC1 (B-segment-specific primer, Table 2) in a total volume of 10 µl. After incubation at 98° C. for two min., we transferred this mixture immediately onto ice and added 10 µl of RT-mix containing 2* Superscript II first strand syntheses buffer (Gibco/BRL), 20 mM DTT, 2 mM of each dNTP and 100 units of Superscript II (Gibco/BRL). In the case of the negative control reaction, the addition of Superscript II enzyme was omitted. All tubes were incubated at 50° C. for 30 min, after which time 0.5 units of RNase H were added and incubation was continued at 37° C. for 15 min. Water (80 µl) was added to each tube, and dsRNA and cDNA was purified by a phenol/chloroform/isoamylalcohol (25:24:1) extraction and precipitated by using a standard ethanol/NaAc precipitation protocol. Obtained pellets were dissolved in 20 µl of water and stored at −20° C.

Amplification of Full-Length cDNA Using a PCR-Based Protocol

The full-length single-stranded cDNA of both the A- and B-segments were amplified by using PCR. The primers which hybridize to the 3'-terminus of the non-coding strand of the A-segment (T7AC0, Table 2) and B-segment (T7BC1, Table 2) both have a non-hybridizing 5' extension of 24 nt containing a T7 promoter sequence and an EcoRI site. The primers that hybridize to the 5' terminus of the coding strand of the A-segment (ANC0, Table 2) and B-segment (BNC1, Table 2) match exactly. As template we used 5 µL of the above-mentioned RT reaction and the PCR was performed in the presence of 1* Expand High Fidelity buffer, 50 µM of each dNTP, 0.2 pmol of each primer, 1.5 units of Expand High Fidelity enzyme, and 2.0 mM MgCl2 (A-segment) or 4.0 mM MgCl2 (B-segment). Amplification was performed by cycling 35 times between 94° C. (15 sec), 58° C. (15 sec) and 72° C. (5 min) in the case of A-segment amplification (A-program) and cycling for 35 times between 94° C. (15 sec), 54° C. (15 sec) and 72° C. (5 min) in the case of B-segment amplification (B-program), using a Biometra T3 thermocycler. The yield of PCR products was checked on a 1.0% agarose gel.

Cloning and Analysis of the Generated PCR Fragments

The full-length PCR fragments which were generated three times independently from genomic dsRNA were isolated from the agarose gel by using a Qiaex gel purification kit (Qiagen) and ligated in the pGEM-Teasy (Promega) vector according to the suppliers instructions. The ligated plasmids were used to transform E. coli DH5-alpha cells which were subsequently grown under ampicillin selection (100 µg/ml) and in the presence of IPTG (0.8 mg per petri-dish)) and Bluo-gal (0.8 mg per petri-dish). Plasmid DNA of white colonies was prepared and analyzed by restriction enzyme digestion and agarose gel separation. The nucleotide sequences of the cloned cDNAs were determined by using an ABI310 automated sequencer and A- and B-segment-specific primers. The consensus nucleotide sequences of both segments of CEF94 and of both segments of D6948 were determined (FIGS. 2A–2G and 3A–3F) and the corresponding amino acid sequence of the open reading frames was deduced (FIGS. 4A–4C, 5A, 5B and 6). By using the cDNA of two independent clones, we restored one amino acid mutation present in the A-segment clone (V542A), resulting in pHB-36W, one amino acid mutation in the A-segment clone of D6948 (P677L), resulting in pHB-60, and one amino acid mutation in the B-segment of D6948 (Q291X), resulting in pHB-55. No amino acid mutations were present in the B-segment cDNA clone of CEF94 (pHB-34Z).

Introduction of a Hepatitis Delta Virus Ribozyme

The Hepatitis Delta Virus ribozyme was first introduced into the E. coli high copy number plasmid pUC-18 by digesting transcription vector 2.0 (Pattnaik et al., 1992) with restriction enzymes XbaI and SmaI. The resulting 236 bp fragment, which contains the Hepatitis Delta Virus Ribozyme and a T7 RNA polymerase terminator, was ligated in the pUC18 vector which previously was digested with XbaI and SmaI, yielding pUC-Ribo. Plasmids containing the A- and B-segment of CEF94 and D6948 were used as template in a full-length PCR using the above-described conditions and primers specific for either the A-segment (T7AC0 and ANC0) or B-segment (T7BC1 and BNC1). The PCR fragments were agarose gel purified (Qiaex), blunt-ended by using T4 DNA polymerase, and subsequently digested with EcoRI. The resulting DNA fragments were directionally cloned into the pUC-Ribo vector which previously had been digested with SmaI and EcoRI. The resulting plasmids were used as template in an in vitro transcription-translation reaction (TnT-T7Quick, Promega). The autoradiogram of SDS-PAGE analyses of the translation products revealed three dominant bands pVP2 (48-49 kDa), VP3 (32-33 kDa), and VP4 (28-29 kDa) when pHB-36A,(A-segment of CEF94) or pHB-60 (A-segment of D6948) was used as template. One dominant band (VP1 (91 kDa)) was found when we used plasmid pHB-34Z (B-segment of CEF94) or pHB-55 (B-segment of D6948) as template (data not shown).

Introduction of a Genetic Tag

To distinguish infectious virus generated from cloned cDNA from wild-type virus, we introduced a genetic tag in the 3'-UTR of the A-segment of IBDV-A isolate. Two nucleotides of pHB-36A were mutated (C3172T and 3T173A), thereby introducing a unique KpnI restriction site (GGTAAC (SEQ ID NO:1)). These mutations were introduced by the method described by Higuchi (1990). A 383 bp fragment of the resulting PCR fragment was ligated (Rapid ligation kit, Boehringher Mannheim) into the full-length A-segment clone (pHB-36A) by using two unique restriction sites (BglII and BlpI). The resulting plasmid pHB-36W was amplified in E. coli. The genetic tag was present in this full-length CEF94 A-segment clone, as could be concluded from sequence analysis and digestion with restriction enzyme KpnI (data not shown). No difference was observed in the resulting protein pattern when either pHB-36A or pHB-36W was used as template in an in vitro transcription/translation reaction (data not shown).

Construction of Mosaic A-Segment cDNA

We constructed plasmids containing mosaic IBDV A-segments which partly consisted of cDNA of one isolate (CEF94) and partly of cDNA of another isolate (D6948). To construct these plasmids, we have amplified specific parts of cDNA using appropriate IBDV-specific or selective primers. The amplified PCR fragment of cDNA of D6948 was subsequently used to replace the corresponding part in plasmids pHB-36W, using restriction endonucleases and T4 DNA ligase (Rapid DNA Ligation, Boehringher Mannheim).

Figure 8A:
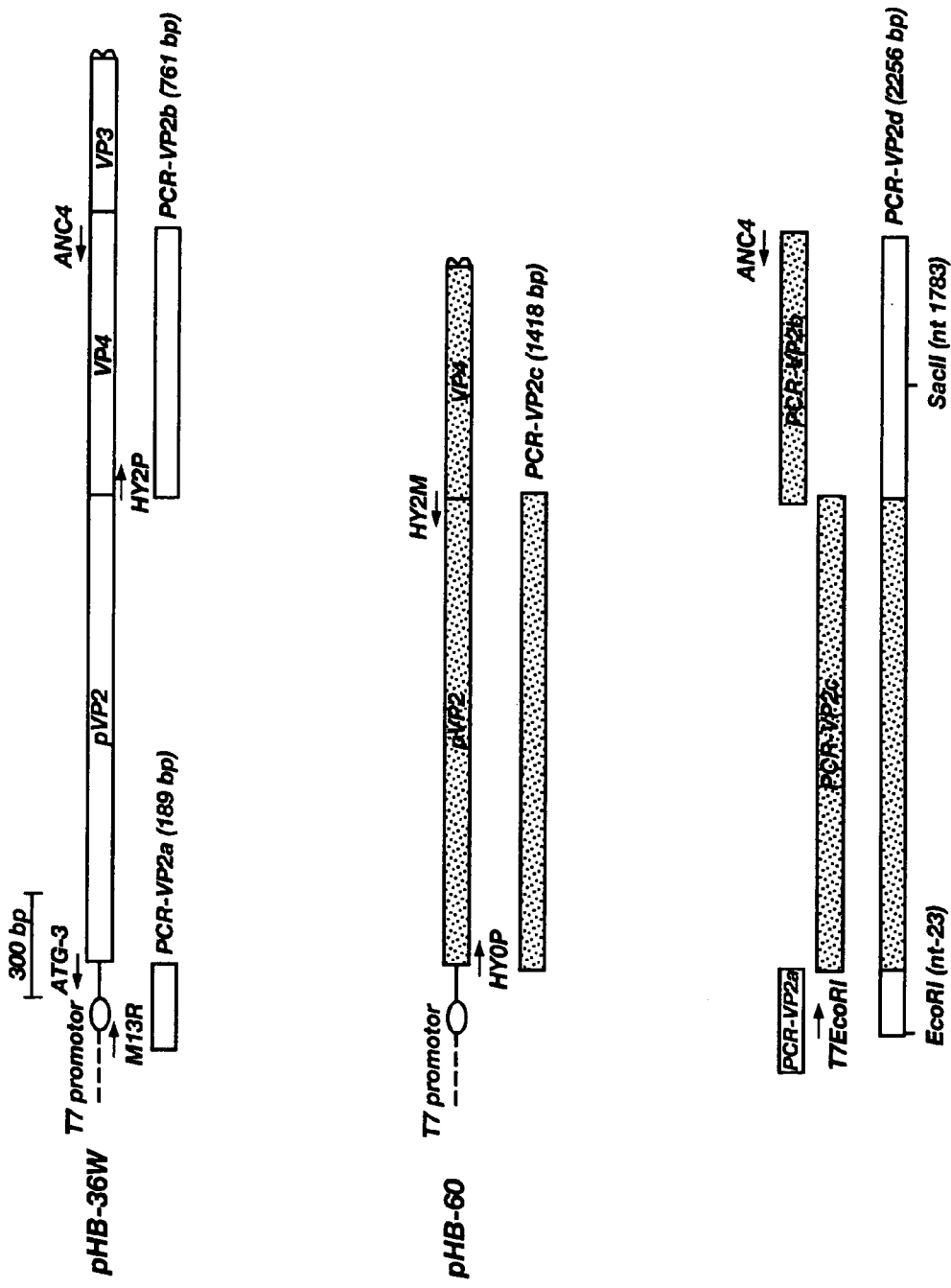
FIG. 8A: Construction of pHB36-vvP2.

For the construction of pHB36-vvVP2 (exchange of pVP2-encoding part, Table 4) we have used IBDV-specific primers to generate the mosaic PCR-VP2D fragment (2256 bp, see FIG. 8A). The internal part of this PCR fragment was used to exchange the corresponding part of pHB-36W, using unique sites for restriction enzymes EcoRI and SacII.

Figure 8B:
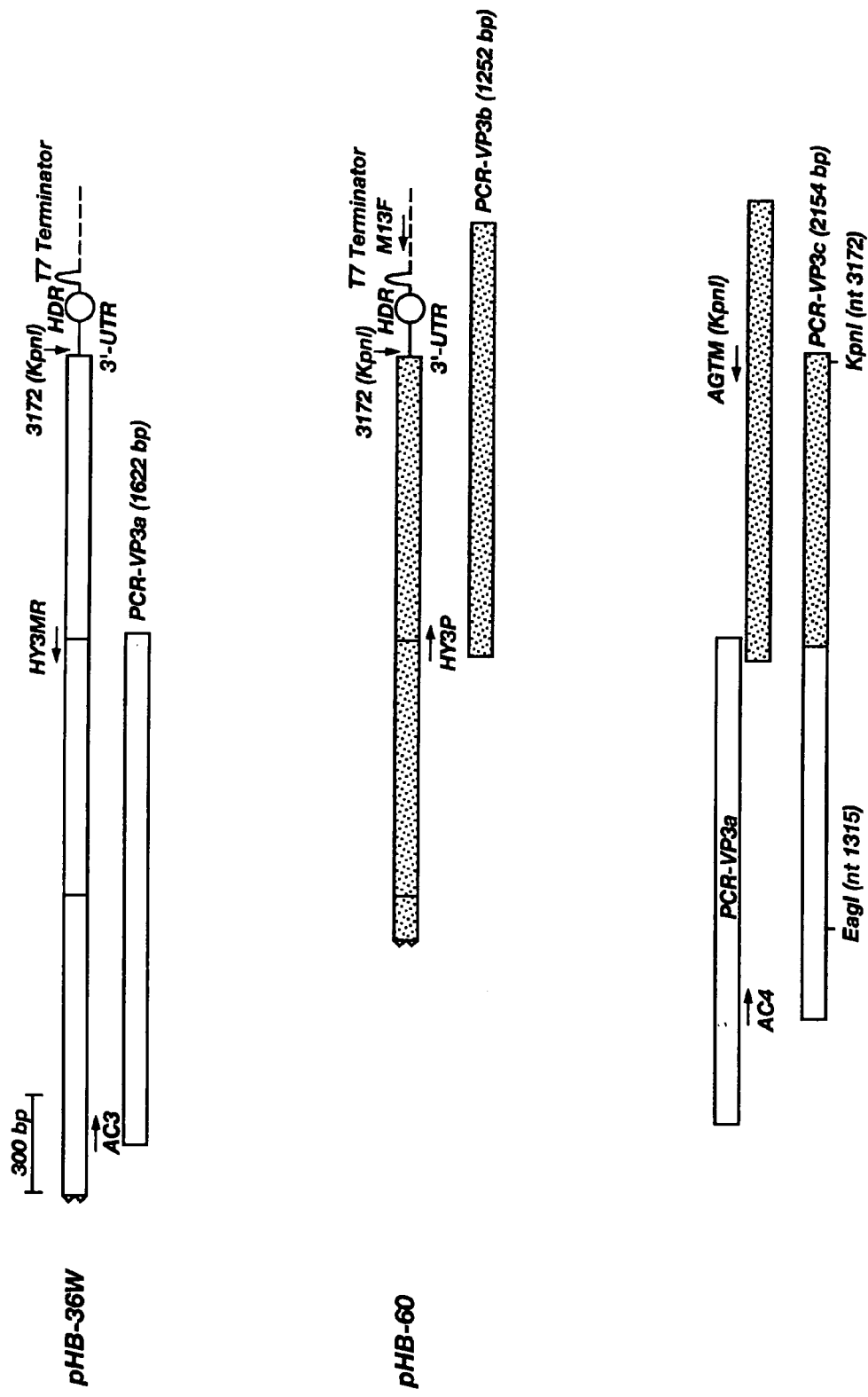
FIG. 8B: Construction of pHB36-vvVP3.

For the construction of plasmid pHB36-vvVP3 (Table 4) we used IBDV-specific primers to generate a mosaic PCR-VP3c fragment (2154 bp, see FIG. 8B. The internal part of this PCR fragment was used to exchange the corresponding part of pHB-36W, using unique sites for the EagI and KpnI (genetic tag site) restriction enzymes.

Figure 8C:
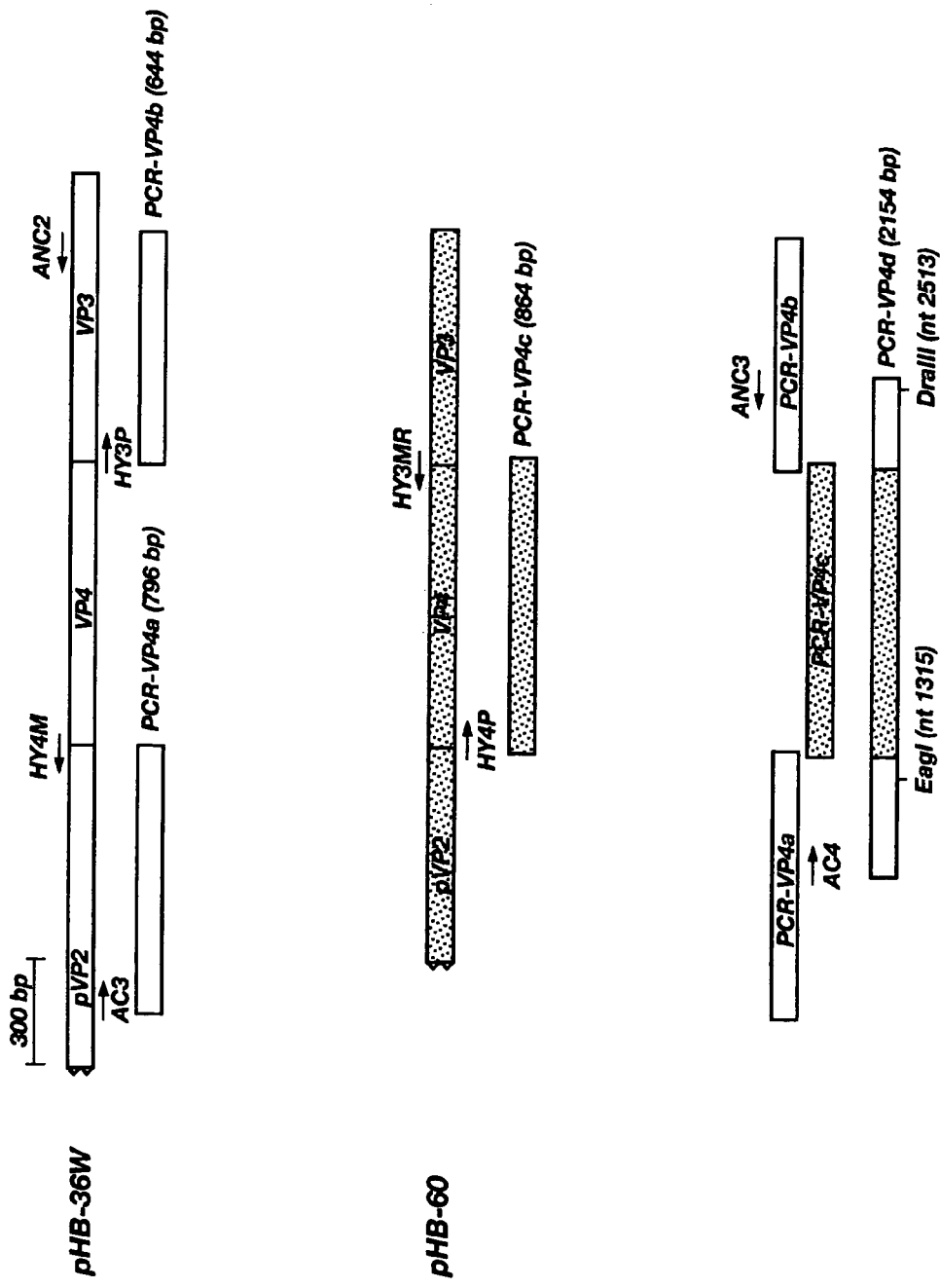
FIG. 8C: Construction of pHB36-vvVP4.

For the construction of plasmid pHB36-vvVP4 (Table 4) we used IBDV-specific primers to generate a mosaic PCR-VP4d fragment (2154 bp, see FIG. 8C. The internal part of this PCR fragment was used to exchange the corresponding part of pHB-36W, using the unique site for restriction enzymes for EagI and DraIII.

Plasmids pHB36-vvVP2, -vvVP3, and -vvVP4 were partly analyzed by nucleotide sequence determination to conform that no unintended mutations were introduced during the described manipulations.

Introduction of a Serological Marker

To obtain the cDNA of the A-segment of a serotype II IBDV isolate we generated single-stranded cDNA of TY89 as described above, by using the ANC1 primer. The coding region of the VP3 protein was subsequently independently amplified three times in a PCR by using 2 ml of RT-material, 1* Taq buffer, 50 μM of each dNTP, two IBDV serotype II-specific primers (0.2 pMol each), 1.5 units of enzyme, and 3.0 mM $MgCl_2$ in a 0.1 ml reaction volume. Amplification was performed by cycling 35 times between 94° C. (15 sec), 52° C. (15 sec) and 72° C. (1 min). The resulting 956 bp fragment was cloned in the pGEM-TEasy vector and the consensus nucleotide sequence was determined (FIGS. 2A–2G). One of the isolated plasmids contained the TY89 VP3 consensus sequence (pSV-VP3-TY89, FIG. 7) and was used as template to generate an 893 bp PCR fragment (see FIG. 8D). This PCR fragment was subsequently used to replace the corresponding part of plasmid pHB36W-vvVP3, by using the artificially introduced KpnI (nt 3175) and SacII (nt 1760) restriction sites in both plasmid pSV-VP3-TY89 and pHB36W-vvVP3. The resulting plasmid (pHB36-vvVP3, see FIG. 8D) encodes the N-terminal 722 amino acids of the CEF94 polyprotein and the 290 C-terminal amino acids of the TY89 polyprotein. The intended exchange was confirmed by nucleotide sequence analysis.

The same approach was used to exchange the C-terminal half of the coding sequence of the VP3 protein. Instead of the artificially introduced SacII site, we made use of the ScaI (nt 2799) site which is naturally present both in the TY89 and in the CEF94 cDNA of the A-segment, in combination with the artificially introduced KpnI site (nt 3172). The resulting plasmid (pHB36-s2VP3C, Table 4) encodes a polyprotein consisting of the N-terminal 890 amino acid of the CEF94 polyprotein, in combination with the C-terminal 122 amino acids of the TY89 polyprotein.

For the construction of plasmid pHB36-s2VP3N (see Table 4), we have replaced the ScaI (nt 2799)-KpnI (nt 3172) part of plasmid pHB36-s2VP3 with the corresponding part of plasmid pHB-36W. Using the specific restriction endonucleases ScaI and KpnI, and T4 ligase, the nucleotide sequence of plasmid pHB36-s2VP3N was conformed by sequence analysis.

For the introduction of the C-terminal-encoding part of the VP3 protein of IBDV isolate TY89 into the cDNA of isolate D6948, we have exchanged part of plasmid pHB-60 (nt 1760→nt 3260) with the corresponding part of plasmid pHB36-s2VP3C. Plasmid pHB36-s2VP3C was digested with restriction enzymes SacII and XbaI and a 1735 bp fragment was recovered from an agarose gel by Qiaex gel extraction kit (Qiaex). This DNA fragment was ligated in the 4440 bp vector fragment of pHB-60 which had previously been digested with the same restriction enzymes. The resulting plasmid (pHB60-s2VP3C1, Table 4) contains cDNA derived from IBDV isolates D6948 (nt 1 to 1760), CEF94 (nt 1760 to 2799 and nt 3175 to 3260), and TY89 (nt 2799 to 3175).

Transfection of QM5 Cells

QM5 cells, grown to 80% confluency in 60 mm dishes, were infected with Fowl Pox T7 (FPT7) (Britton et al., 1996) one hour prior to transfection. FPT7-infected QM5 cells were subsequently washed once with 5 ml QT-35 medium and incubated with 2 ml fresh Optimem 1 (Gibco/BRL) two times during 15 min. In the meantime, DNA (2.0 to 4.0 μg) was incubated in 0.5 ml Optimem 1 supplemented with 25 μl Lipofectamine (Gibco/BRL) and kept at room temperature for at least 30 min. The washed QM5 cells were covered with 4 ml of Optimem 1, the DNA/Lipofectamine transfection mixture was added and the cells were stored for 18 h in a 5.0% $CO_2$ incubator at 37° C.

Detection of Recombinant IBDV after Transfection of QM5 Cells

Transfected QM5 cells were washed once with PBS after the transfection. Infectious recombinant IBDV (rIBDV) was recovered from transfected QM5 cells by covering them with 4 ml of QT-35 medium supplemented with 5% fetal calf serum and 2% of an antibiotic mix (1000 U/ml Penicillin, 1000 µg/ml Streptomycin, 20 µg/ml Fungizone, 500 µg/ml Polymixin B, and 10 mg/ml Kanamycin) and incubated for 24 h at 37° C. (5.0% $CO_2$). The supernatant was filtered through a 200 mM filter (Acrodisc) to remove FPT7 virus and was subsequently stored at −70° C. or used directly for quantitation of rIBDV. Recombinant mosaic IBDV (mIBDV) which contains at least the pVP2 from vvIBDV isolate D6948 is unable to re-infect QM5 cells (see Table 5). Therefore, the supernatant of transfection experiments which contained D6948 pVP2-encoding cDNA was used to infect 11-day-old embryonated eggs via the chorioallantoic membrane (CAM) route. To determine the presence of infectious IBDV, the embryos were collected five days post-infection, homogenized by using a Sorval Omnimixer (3*10 sec, max. speed) and assayed for the presence of IBDV proteins in an IBDV protein-specific Elisa.

Serological Differentiation of Recombinant Mosaic IBDV (mIBDV)

Different monoclonal antibodies were used to detect recombinant mosaic IBDV (mIBDV) that contained part of the TY89 VP3 or the complete TY89 VP3. The mIBDVs were used to infect QM5 or primary bursa cells and incubated for 24 h (QM5 cells) or 48 h (primary bursa cells) in a 5% $CO_2$ incubator at 37° C. or 39° C., respectively. The infected cells were subsequently fixed and an immunoperoxidase monolayer assay (IPMA) was performed by using monoclonal antibodies which are either specific for VP2 of serotype I IBDV (Mab 1.4), or specific for VP3 of serotype II (Mab T75), or specific for VP3 of serotype I (Mab B-10 or C-3).

Virulence of rIBDV in Young SPF Chickens

To evaluate the degree of virulence of the generated rIBDV, srIBDV, and mIBDV isolates, we have inoculated 12 groups (10 21-day-old SPF chickens) with these viruses. Each chicken received nasally and by eye-drop 1000 ELD50 IBDV, with the exception of the negative control group, which received only PBS. The animals were monitored for clinical signs and dead chicks were removed each day. At 9 days post-infection, all the chicks from the negative control groups and all the surviving chicks from groups in which mortality had occurred were bled (5 ml) and euthanized for necropsy. From the other groups, 6 chicks were bled (5 ml) and taken for necropsy at day 9 post-infection, whereas the remaining 4 were bled (5 ml) and taken for necropsy at day 15 post-infection. Bursa and body weight were determined of all chicks which had been euthanized at day 9 post-infection.

Results

Nucleotide Sequence Determination of the 5'-Termini.

One group has reported the 5'- and 3'-terminal sequences of the segmented dsRNA genome of IBDV (Mundt and Muller, 1995). To verify the terminal sequence of the genome of IBDV and to be able to produce the exact cDNA sequence of a single IBDV isolate, we have determined the 5' terminal sequences of both the coding and non-coding strands of the two genomic segments of CEF94, a Chicken Embryo Fibroblast (CEF) adapted, classical isolate of IBDV, by using the RACE (Rapid Amplification of cDNA Ends) technique (Frohman et al., 1988). The RACE analysis was performed in duplicate on each of the four 5'-termini of the CEF94 genome. The resulting sequence data (Table 3) show that the lengths of the 5'-termini of the coding strands were the same in all cases. Furthermore, we found that the nucleotide sequence was identical, except for the last nucleotide, which varied in a few clones. This is in contrast to the sequence data of the 5'-termini of the non-coding strands, which varied in length considerably. We also found that the last nucleotide, although preferably a cytosine, varied in some clones similarly to what we found for the 5'-termini of the coding strands. The consensus sequence for the 3'-terminal nucleotide of the A-segment coding strand of CEF94 differs from the nucleotide sequence reported by Mundt and Muller (Mundt and Muller, 1995), i.e., being a cytosine instead of a thymine.

Generation of Plasmids Containing Full-Length IBDV cDNA

Using the sequence data of the 5'-termini, we cloned the entire coding and non-coding cDNA sequences of the A-segment and B-segment of classical isolate CEF94 by means of RT-PCR. Using the same procedure and using the same primers, we also generated the entire coding and non-coding cDNA of the A- and B-segments of a non-CEF-adapted, very virulent IBDV isolate D6948. The nucleotide sequence of the entire genome of both isolates was determined three times independently. This sequence information enabled us to generate a consensus nucleotide sequence of both the A- and B-segments of IBDV isolates CEF94 and D6948 (FIGS. 2A–2G).

Fowlpox T7 Polymerase Expression System

One system for generating infectious IBDV virus using in vitro synthesized mRNA derived from cDNA of a CEF-adapted IBDV isolate has previously been described (Mundt and Vakharia, 1996). This system is based upon in vitro run-off transcription from the T7 promoter which was artificially introduced in front of the cDNA sequences of the A- and B-segments. This RNA is subsequently transfected into VERO cells, after which infectious IBDV virus could be harvested from these cells. One of the drawbacks of this system is that the in vitro-generated RNA has to contain a 3'-G-ppp5'-(cap structure) on it's 5'-end in order to get translation of the introduced RNA into the viral proteins and, hence, replication of viral RNA. The in vitro production of high-quality mRNA is both inefficient and expensive as a cap structure has to be present at the 5'-end. Furthermore, expression levels from transfected RNA are generally low due to the short half-life of RNA. To circumvent the drawbacks of generating in vitro capped RNA and low expression levels, we have explored the possibility of using an in vivo-based T7-expression system (Fowlpox T7 polymerase expression system (Britton et al., 1996)) for generation of viral RNA from plasmids containing full-length IBDV cDNA.

Generating of Infectious IBDV Using Fowlpox-Infected Cells

Figure 7:
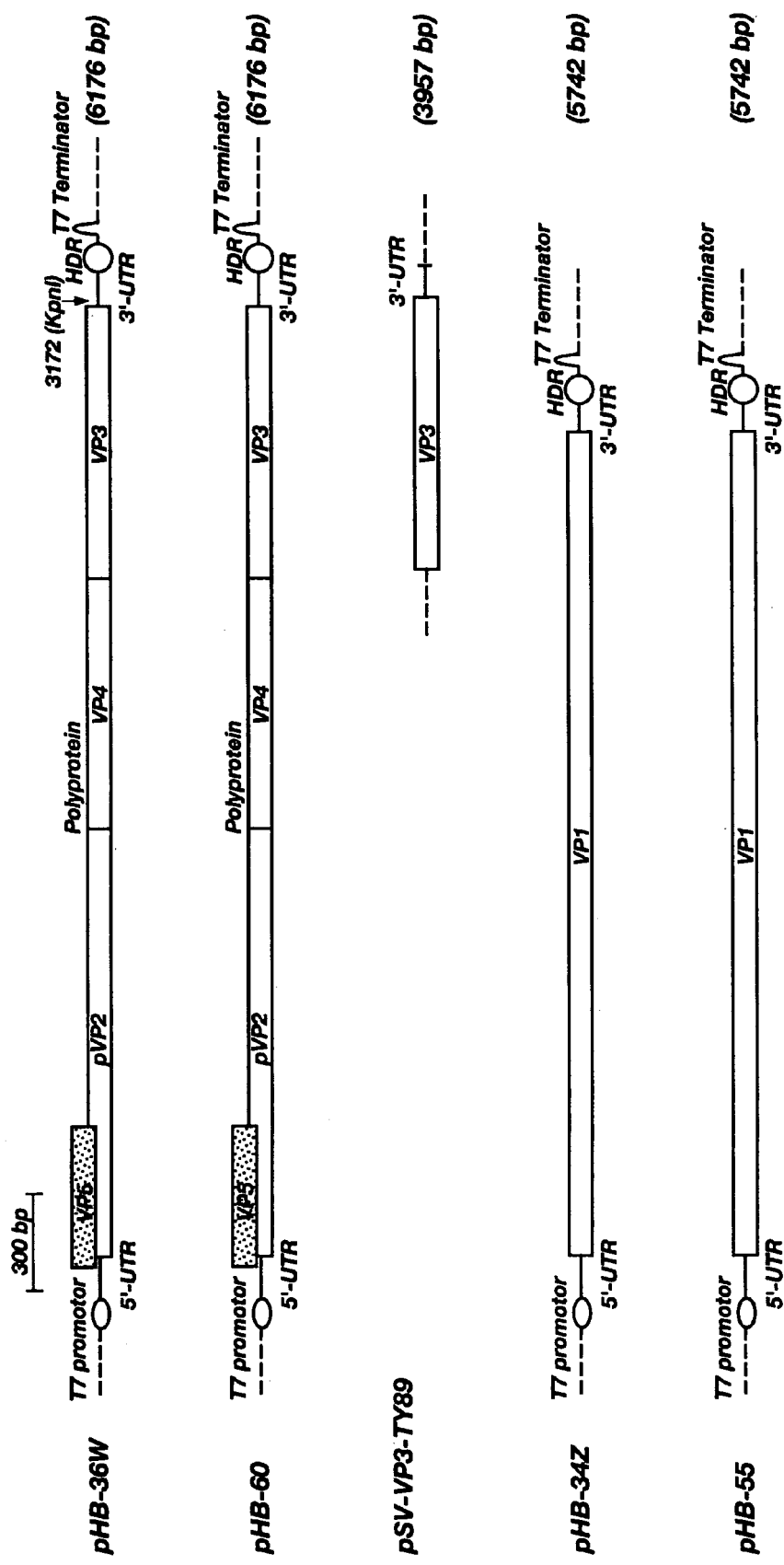
FIG. 7: Plasmid drawings.
Figure 8D:
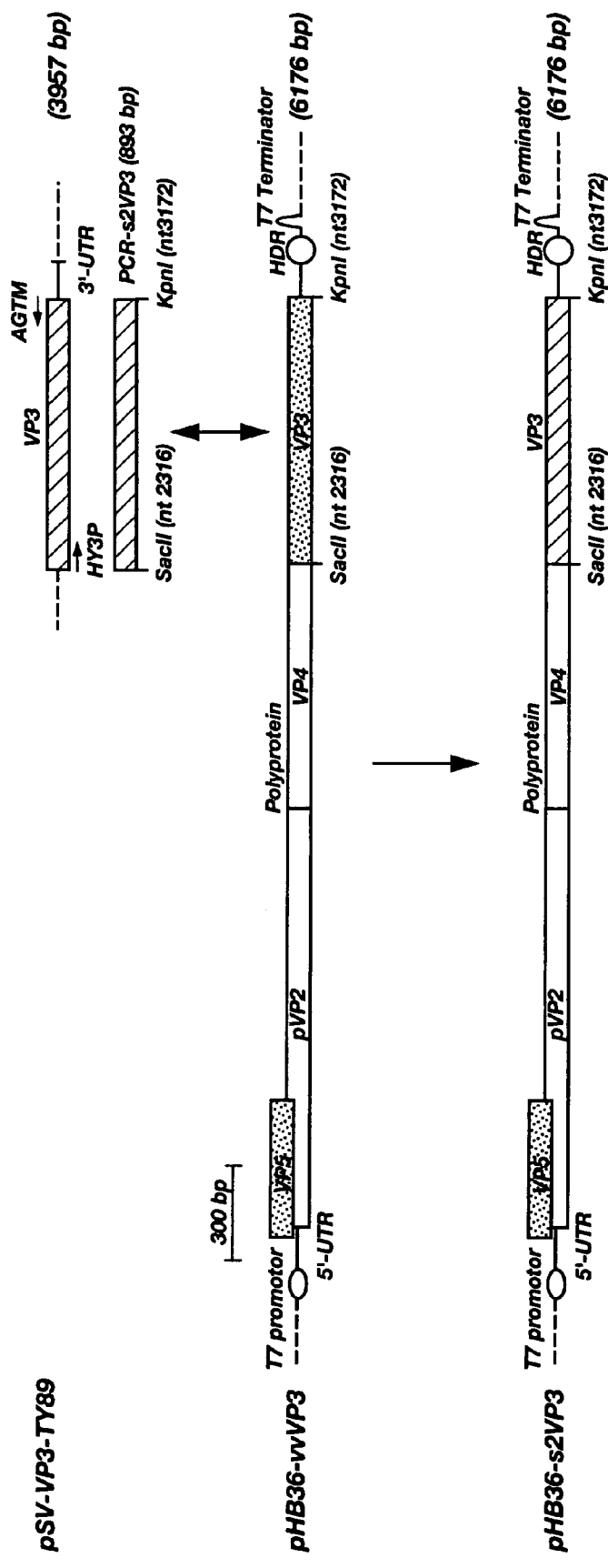
FIG. 8D: Construction of pHB36-s2VP3.
Figure 8E:
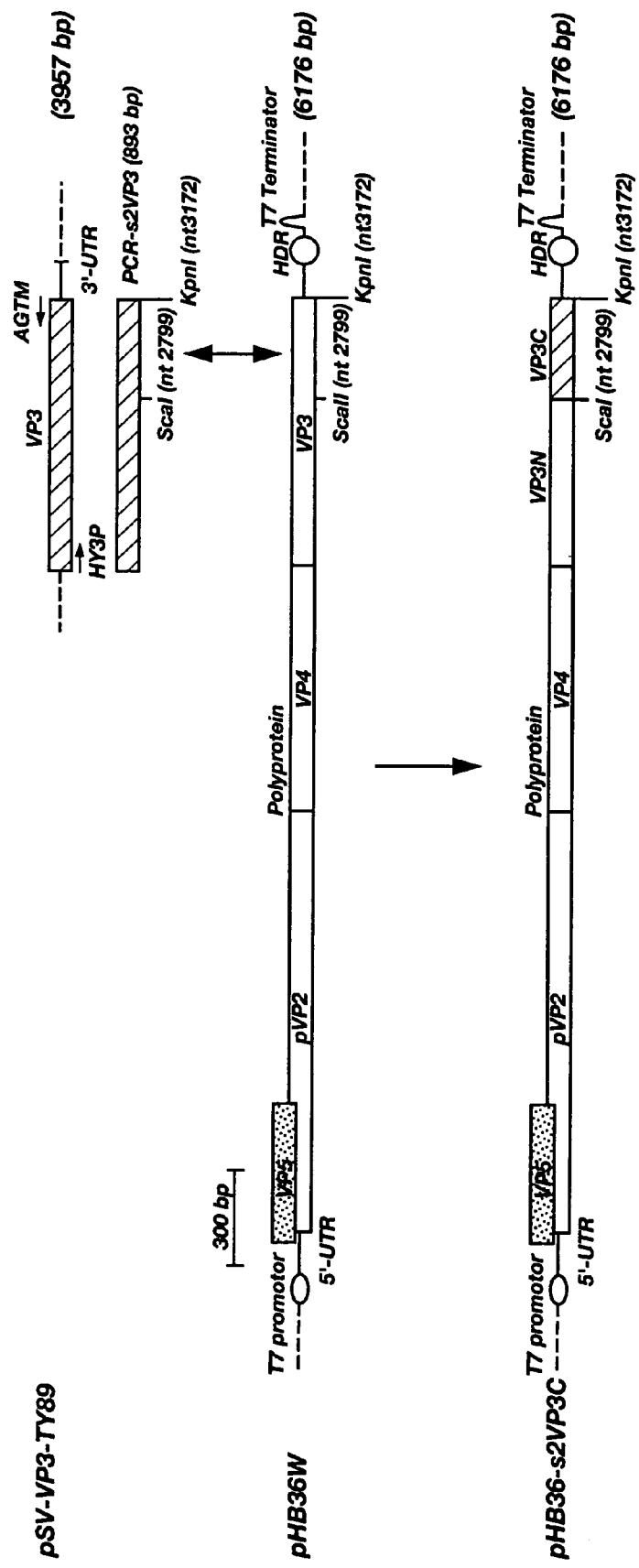
FIG. 8E: Construction of pHB36-s2VP3C.
Figure 8F:
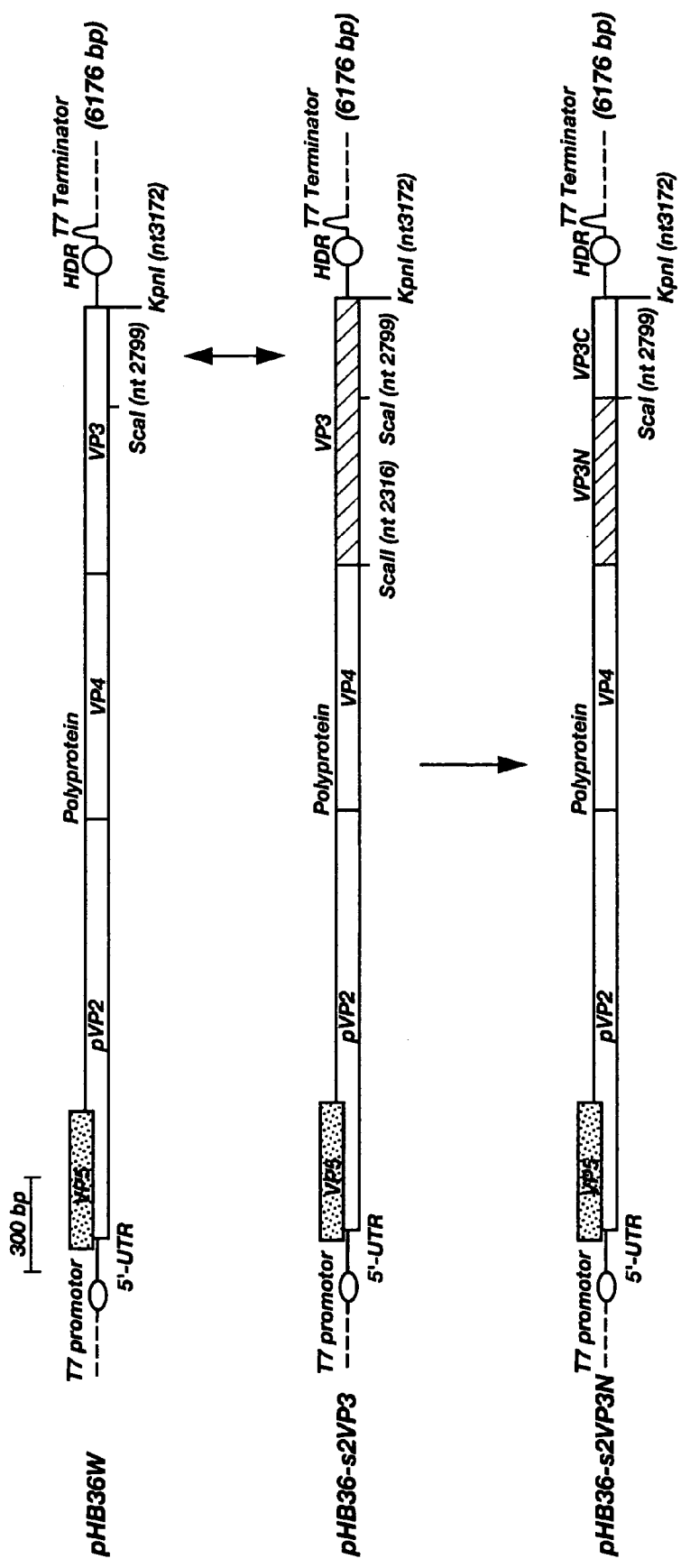
FIG. 8F: Construction of pHB36-s2VP3N.

To be able to generate IBDV from cloned cDNA which has the authentic terminal sequences, we introduced the cis-acting Hepatitis Delta Virus (HDV) ribozyme (Chowrira et al., 1994) downstream of the cDNA sequence of the A- and B-segments (FIG. 7). Furthermore, we introduced an additional modification in the 3' untranslated region of the CEF94 A-segment. By exchanging 2 nucleotides, we introduced a unique KpnI endonuclease restriction site in this cDNA. The introduction of this unique restriction site enables us to distinguish between wild-type IBDV and infectious IBDV virus generated from cloned cDNA (genetically tagged rIBDV). As expected, this plasmid yields the same viral proteins in an in vitro transcription-translation reaction as the A-segment clone without the genetic tag (data not shown).

Plasmid pHB-36W (A-segment CEF94), pHB-60 (A-segment D6948), pHB-34Z (B-segment CEF94), and pHB-55

(B-segment D6948) were used individually to transfect FPT7-infected QM5 cells as described in the Materials and Method section. To analyze whether the transfected QM5 cells expressed IBDV proteins, we performed an IPMA, 24 h after transfection. We used polyclonal antiserum directed either against VP3 (pHB-36W and pHB-60 transfections) or VP1 (pHB-34Z and pHB-55 transfections) in this analysis. About 10 to 50% of the QM5 cells expressed VP3 after transfection with pHB-36W or pHB-60 (data not shown). When B-segment-encoding plasmids were used (pHB-34Z or pHB-55), we found that the same percentage of cells (about 10 to 50%) were expressing VP1 (data not shown).

Subsequently, we co-transfected combinations of plasmids containing the A- and B-segment cDNAs into FPT7-infected QM5 cells. To screen for infectious recombinant IBDV (rIBDV) in the supernatant of the transfected QM5 cells, we transferred part of the supernatant (10% of the volume) after 18 h onto fresh QM5 cells or onto primary bursa cells. We only could detect rIBDV when A-segments plasmids in combination with B-segment plasmids were used to transfect the QM5 cells. rIBDV could not be detected when the supernatant of the cells transfected with A-segment (pHB-60) and B-segment (pHB-55) of D6948 (rD6948) was transferred onto QM5 cells. However, when the co-transfection supernatant of pHB-60 and pHB-55 was transferred onto primary bursa cells or embryonated eggs, we were able to show the presence of infectious IBDV (rD6948) in primary bursa cells (after 48 h) and in embryonated eggs (after five days). The presence of rIBDV in the first passage was established by using either an IPMA (QM5 cells or primary bursa cells) or an IBDV-specific Elisa (embryonated eggs). The generated rCEF94 and rD6948 isolates were amplified in 10-day-old embryonated SPF eggs and subsequently used to infect 21-day-old SPF chickens (10 chickens per IBDV isolate). The resulting data of the animal experiment (Table 6) shows that the mortality, body weight, bursa weight, and bursa-body weight ratio caused by rD6948 are the same as the parent very virulent D6948 isolate. Also, at necropsy, gross lesions of bursa were as severe for rD6948 as for the parental D6948 isolate (data not shown). From this chicken experiment it is concluded that rD6948 has retained the properties of a very virulent IBDV isolate, and is truly a very virulent rIBDV.

Detection of the Genetic Tag

Supernatant of rCEF94-infected QM5 cells was harvested and IBDV was isolated by centrifugation as described in the material section. The dsRNA genome was extracted and an A-segment-specific primer was used to generate single-stranded cDNA, by using reverse transcriptase. The cDNA was subsequently amplified by PCR. The generated PCR fragment was cloned into a high copy number *E. coli* plasmid (pGEM-Teasy, Promega) and was either digested which KpnI or used for nucleotide sequence determination. The presence of the genetic tag in rCEF94 was confirmed in both analyses.

Identification of a Lethal Amino Acid Mutation in VP4

Plasmid pHB-36 (A-segment CEF94, Table 4) contained a single nucleotide substitution at position 1875 (thymine instead of a cytosine) compared to the consensus CEF94 A-segment sequence (FIGS. 2A–2G). This nucleotide substitution leads to a valine at position 582 of the polyprotein instead of an alanine, which is encoded by the consensus sequence (V582A, FIGS. 4A–4C). As this amino acid mutation is present in the viral protease (VP4), we subsequently checked whether this protease was still able to autocatalytically liberate the viral proteins (pVP2, VP3 and VP4) from the polyprotein. When plasmid pHB-36 was used as template in a coupled in vitro transcription/translation reaction in the presence of $^{35}$S-labeled methionine, we found a delayed splicing of the polyprotein (data not shown). Apart from the viral proteins which are found in the case of normally spliced polyprotein (pVP2, VP3 and VP4), we found intermediate spliced products (60 kDa: VP4+VP3) and non-spliced polyprotein (data not shown). Although the viral protease (VP4) of clone pHB-36 is able to liberate the structural viral proteins (pVP2 and VP3) from the polyprotein, this clone did not yield rIBDV when using the FPT7-based transfection protocol as described above. Rapid autocatalytic cleavage of the polyprotein is apparently necessary for the generation of infectious rIBDV. We expect that other mutations within VP4 which alter the rate or specificity of the autocatalytic cleavage of the polyprotein will also have a negative effect on viability of the generated rIBDV. Furthermore, mutations in the region of the cleavage sites (pVP2-VP4 and VP4-VP3) may also have a negative effect on replication of rIBDV. Any mutation, introduced by modern molecular biological techniques into the cDNA of a very virulent IBDV may enable us to generate rIBDV which has a reduced viability and which can be used as a live or killed IBDV vaccine.

Generation of Segment-Reassorted IBDV

Transfection of CEF94 A-segment cDNA (pHB-36W) in combination with D6948 B-segment cDNA (pHB-55) yielded segment-reassorted IBDV (srIBDV-CADB) when supernatant of QM5 transfected cells was transferred onto fresh QM5 cells (Table 5). When D6948 A-segment cDNA (pHB-60) was used in combination with CEF94 B-segment cDNA (pHB-34Z), no infectious srIBDV (srIBDV-DACB) could be detected on QM5 cells (Table 5). However, when primary bursa cells were used to assay for the presence of infectious IBDV, we found in both cases (srIBDV-CADB and srIBDV-DACB) infected cells after 24 h of incubation. Out of the population of primary bursa cells, only lymphoid cells were infected with srIBDV-DACB, while both lymphoid and fibroblast cells were infected in the case of srIBDV-CADB. The srIBDV-DACB isolate induces the same clinical signs as D6948, while the srIBDV-CADB isolate has virulence comparable to CEF94 (Table 6).

Construction of Mosaic IBDV

By using modern molecular biological techniques such as those described above, we have created mosaic recombinant IBDV (mIBDV) which consists partly of cDNA derived from CEF94 and partly from D6948 (vvIBDV) or TY89 (a serotype II IBDV isolate). Replacement of the pVP2 protein-encoding sequence of CEF94 by the corresponding part of the D6948 yielded only virus (mCEF94-vvVP2) when the supernatant of transfected cells was transferred to cells which are normally susceptible for non-CEF-adapted vvIBDV, i.e., primary bursa cells or embryonated eggs (Table 5). Replacement of the VP3 or VP4 protein-encoding sequence of CEF94 with the corresponding part of D6948 yielded mIBDV by using QM5 cells as recipient in the first passage (mCEF-vvVP3 and mCEF-vvVP4, respectively).

Replacement of the complete VP3 cDNA (290 amino acids) of CEF94 by the corresponding part of the TY89 cDNA yielded a plasmid which encoded a polyprotein consisting of pVP2 and VP4 derived from CEF94 and of VP3 derived from TY89. When this plasmid (pHB36-s2VP3) was used in an in vitro transcription-translation reaction, all the expected proteins, pVP2, VP4 and VP3, were present (data not shown). Transfection of this plasmid in combination with a plasmid (pHB-34Z) containing the B-segment cDNA of CEF94 yielded a mosaic IBDV (mCEF94-s2VP3). Two monoclonal antibodies which are specific for serotype I VP3 (Mab B10 and C3) were unable to recognize this mCEF94-s2VP3, while an antibody which is specific for the serotype II VP3 (Mab T75) did recognize this mosaic virus (Table 5). As expected, the mCEF94-s2VP3 was also recognized by a serotype I-specific, neutralizing monoclonal antibody directed against VP2 of the CEF94 isolate (Mab 1.4). The TCID50 on QM5 cells, which was determined 18 hours after transfection, was considerably lower (3 logs) in the case of mCEF94-s2VP3 compared to rCEF94. Furthermore, we found that only single QM5 cells were infected by mCEF94-s2VP3 after 24 h. This is in contrast to the plaque-forming phenotype of CEF94 and rCEF94 on QM5 cells after 24 h of infection. To generate mIBDV which has the same replication and plaque-forming characteristics as rCEF94, but which is still antigenetically different from rCEF94, we subsequently exchanged only the N-terminal part (168 amino acids) or C-terminal part (122 amino acids) of the VP3 of CEF94 by the corresponding sequence of TY89. When these mosaic A-segment plasmids (pHB36-s2VP3N or pHB36-s2VP3C) were transfected in combination with pHB-34Z (CEF94 B-segment), we obtained mosaic IBDVs (mCEF94-s2VP3N or mCEF94-s2VP3C) with replication capabilities in QM5 cells that are equal (mCEF94-s2VP3C) or slightly reduced (mCEF94-s2VP3N) to those of rCEF94 IBDV (data not shown).

Subsequently, we checked the recognition of mCEF94-s2VP3N and mCEF94-s2VP3C virus by several Mabs in an IPMA on QM5-infected cells (Table 5). Mab T75, which is specific for VP3 of serotype II, also recognized mCEF94-s2VP3C, while the recognition of mCEF94-s2VP3N was slightly reduced. Mab B10, which is specific for VP3 of serotype I, did not recognize rCEF94-s2VP3C, while it still recognized mCEF94-s2VP3N. Another Mab (C3) which did not react with mCEF94-s2VP3-infected cells did react with mCEF94-s2VP3C-infected cells; although the reaction was reduced compared to QM5 cells infected with rCEF94 (Table 5), mCEF94-s2VP3N was not recognized by Mab C3. The serotype I-specific, neutralizing antibody Mab 1.4 which recognizes VP2 recognized, as expected, both mCEF94-s2VP3N and mCEF94-s2VP3C.

Figure 8G:
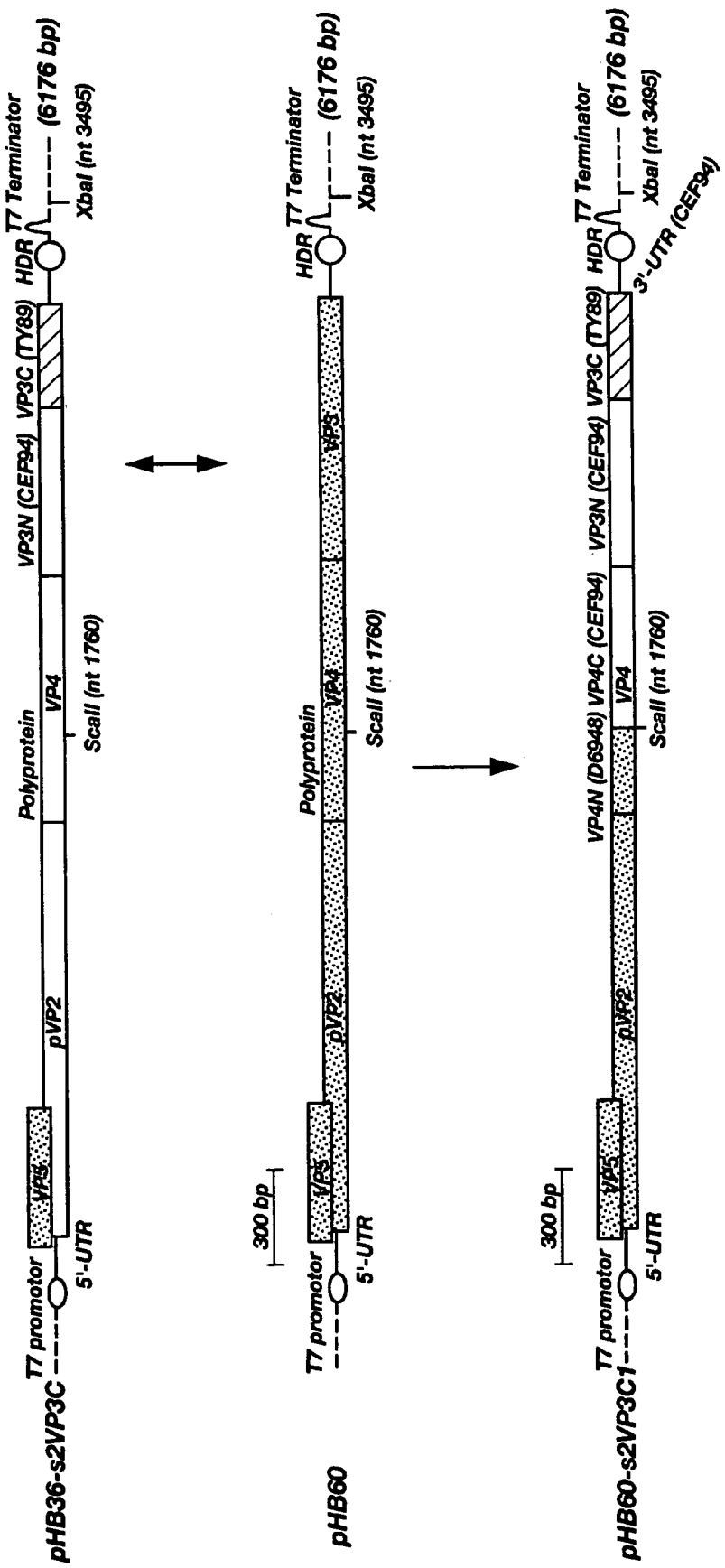
FIG. 8G: Construction of pHB60-s2VP3C1.

The coding sequence of the C-terminal part of serotype II VP3 (122 amino acids) was also used to replace the corresponding part of the cDNA of D6948. During the exchange, we have replaced some D6948 cDNA sequence (encoding for the C-terminal part of VP4 and the N-terminal part of VP3, and the 3'-UTR) with the corresponding sequence of CEF-94 (see FIG. 8G). The resulting plasmid (pHB60-s2VP3C1) was, together with pHB-55 (B-segment D6948), transfected into FPT7-infected QM5 cells. Supernatant of these transfected QM5 cells was collected after 24 h and was transferred to embryonated eggs and primary bursa cells. By using monoclonal antibodies, we were able to detect infected cells in the monolayer of primary bursa-derived cells (see Table 5). mD6948-s2VP3C1 gave the same reaction pattern with the monoclonal antibodies as mCEF-s2VP3C did. Isolate mD6948-s2VP3C1 (1000 ELD50/chicken) was also used to infect 10 SPF chickens (21 days old) to evaluate its virulence. This mIBDV isolate did not cause any mortality in a 9-day course, opposite to the D6948, rD6948 and srIBDV-DACB isolates (Table 6). However, the bursa is severely damaged by this mIBDV, as the bursa-body weight ratio of this group is the same as found in the groups which received D6948 or rD6948. This indicates that mD6948-s2VP3C1 is still able to replicate and induce apoptosis in the bursa of Fabricius.

EXAMPLE 1

Infectious Bursal Disease Virus is the causative agent of one of the most important and widespread infectious diseases among commercial chicken flocks. IBDV causes a depletion of B-lymphoid cells in the bursa of Fabricius, inducing immunosuppression, morbidity, or even acute mortality. Because currently used live IBDV vaccines are derivatives from field isolates, no serologic discrimination between field isolates and live vaccines can be made. The recently developed reverse genetics techniques for IBDV allow one to generating genetically modified IBDVs which might have altered biological and antigenic properties. Here, we describe the rescue of mosaic serotype I IBDVs, where the polyprotein encoding region was partly replaced by the corresponding region of a serotype II strain. A mosaic virus, containing the C-terminal part of serotype II VP3 showed only a slightly delayed release of progeny virus compared to unmodified serotype I virus, while maximum viral titers at 25 h post-infection were equal. Since serotype-specific epitope(s) are present in the C-terminal part of VP3, we were able to discriminate this rescued virus from serotype I and II IBDV strains. These findings make the use of a chimeric VP3 a promising approach to develop an IBDV marker vaccine.

Infectious Bursal Disease Virus (IBDV), a member of the Birnaviridae, is the causative agent of a highly contagious disease of chickens. This disease is also known as Gumboro, named after the place where the first outbreak of IBDV was reported (Cosgrove, 1962). The double-stranded RNA (dsRNA) genome, which is divided over two segments (Dobos et al., 1979), is packed within a capsid, consisting of two viral proteins (VP2 and VP3). The resulting single-shelled naked virus particle has a diameter of 60 nm and an icosahedral (T=13) symmetry (Bottcher et al., 1997).

The largest dsRNA segment (A-segment, 3260 bp) contains two partly overlapping open reading frames (ORFs). The first, smallest ORF encodes the non-structural viral protein VP5 (145–149 amino acids, 17 kDa). The second ORF encodes a polyprotein (1012 amino acids, 110 kDa), which is rapidly cleaved into three proteins: pVP2 (48 kDa), VP4 (29 kDa) and VP3 (33 kDa) by the autocatalytic activity of VP4, both in vivo (Dobos et al., 1979) and in vitro (Hudson et al., 1986). During virus maturation, pVP2 is further processed into VP2 (41–38 kDa), probably resulting from site-specific cleavage of pVP2 by a host cell-encoded protease (Kibenge et al., 1997). The B-segment (2827 bp) contains one large ORF, encoding VP1 (877–881 amino acids, 91 kDa). This RNA-dependent RNA polymerase is also a structural protein since it is found within the viral particle both as a free protein and covalently linked to the 5'-ends of the genomic RNA strands (genome-linked protein, VPg) (Dobos, 1993; Spies and Muller, 1990).

Two different serotypes of IBDV have been described (serotype I and II) (McFerran et al., 1980). Wild-type serotype I IBDV strains have a specific tropism for developing B-lymphoid cells in the bursa of Fabricius. Serotype I viruses are subdivided into classical strains, antigenic variant strains, and very virulent strains. Antigenic variant IBDV strains have only been reported in the USA (since 1985 (Snyder, 1990)) and were found to have a different pathologic phenotype. These antigenic variants appeared to have single amino acid changes in a specific region of the VP2 protein (the hypervariable region) that are probably responsible for the difference in phenotype. From 1988 on, European IBDV isolates were described that had an enhanced virulence (very virulent IBDV, vvIBDV), while having the same antigenic structure as classical isolates (Chettle, Stuart, and Wyeth, 1989). Although most nucleotide differences between classical and very virulent IBDV strains are found in the B-segment, we recently showed that the determinant(s) responsible for the enhanced virulence of a vvIBDV strain are located on the A-segment.

Unlike serotype I strains, wild-type serotype II strains do not have a specific tropism for B-lymphoid cells. Serotype II strains are naturally able to replicate in different tissues and can even be propagated on cell lines. Serotype II strains are usually recovered from turkeys and are neither pathogenic for turkeys (Jackwood et al., 1984) nor for chickens (Ismail, Saif, and Moorhead, 1988). Conformation-dependent, neutralizing epitopes are found within the hypervariable region of the capsid protein VP2 of both serotype I and II strains. Apart from VP2, the virion contains another abundant capsid protein, VP3. This protein does not contain virus-neutralizing epitopes, although a fast immune response is found against linear VP3 epitopes both after vaccination and infection (Fahey, IJ, and Bagust, 1985). It has been shown that some of the epitopes present in VP3 of serotype I and II strains are recognized by the same monoclonal antibody (group-specific epitopes) while other VP3 epitopes are serotype-specific (Mahardika and Becht, 1995; Oppling, Muller, and Brecht, 1991; Reddy, Silim, and Ratcliffe, 1992).

Differentiation between live serotype I IBDV vaccines and field isolates recovered during field outbreaks is difficult and laborious, as the genetic structure of the isolate in question has to be determined. Usually an RT-PCR is performed on the A-segment dsRNA, followed by sequence analysis (Eterradossi et al., 1999) or RFLP (Jackwood and Sommer, 1999). In search for an IBDV vaccine that can easily be distinguished from IBDV field isolates by means of a serologic test, we set out to alter the antigenic structure of a serotype I IBDV strain. During the last few years, several reports on the rescue of IBDV from cloned cDNA have been published (Boot et al., 1999; Lim et al., 1999; Mundt and Vakharia, 1996). Using our reverse genetics system, we have shown that we are able to generate virus from A-segment cDNA clones that are derived from dsRNA of different strains (i.e., classical, adapted and a very virulent). In this report, we describe the rescue of a mosaic IBDV in which VP3 of a serotype I strain (CEF94) was (partly) replaced by the corresponding part of a serotype II strain (TY89). Furthermore, we show that we are able to discriminate two of the rescued mosaic IBDVs from serotype I and II IBDV strains by using a set of serotype-specific monoclonal antibodies.

Methods

Viruses, Cells, and Antibodies.

The classical IBDV serotype I strain CEF94 is a derivative of PV1 which has been adapted for growth on cell cultures. (Boot et al., 1999; Petek, D'Aprile, and Cancellotti, 1973). IBDV strain TY89 is the prototype serotype II IBDV strain (McFerran et al., 1980) and is naturally able to grow on cell lines. Recombinant Fowlpox virus containing the T7 polymerase gene (FPV-T7) (Britton et al., 1996) was received from the laboratory of M. Skinner (Compton Laboratory, Berks, United Kingdom). QM5 cells, which are susceptible for both TY89 and CEF94 and for FPV-T7, were grown in QT35 medium (Gibco/BRL), supplemented with 5% Fetal Calf Serum (FCS) and 2% antibiotics solution ABII (1000 U/ml Penicillin, 1000 mg/ml Streptomycin, 20 mg/ml Fungizone, 500 mg/ml Polymixin B, and 10 mg/ml Kanamycin), in a $CO_2$ (5%) incubator at 37° C. Polyclonal antiserum against VP3/4 was produced by injecting rabbits with purified protein originating from bacteria transformed with an expression plasmid containing amino acids 722 to 1018 of the CEF94 polyprotein. Monoclonal antibodies IV, VII (Mahardika and Becht, 1995), and I/G4 (Oppling, Muller, and Brecht, 1991) were a kind gift of Dr. Müller, University of Leipzig (Germany). Mab 17/80 (Azad et al., 1986) was a kind gift of Dr. Lehrbach, Fort Dodge (Castle Hill, Australia). Monoclonal antibodies 1.4, 9.7, and 9.8 were prepared in our laboratory using standard procedures and using purified serotype I (CEF94) IBDV as antigen.

Generation and Cloning of IBDV cDNA Sequences.

The generation of pUC19-based plasmids containing the full-length cDNA of the two genomic dsRNA segments of CEF94 has been described before. The cDNA in these plasmids is preceded by a T7-promoter sequence and followed by the antigenomic Hepatitis Delta Virus ribozyme (Been, Perrotta, and Rosenstein, 1992) and a T7 terminator sequence. The entire VP3-encoding part of the serotype II strain TY89 was cloned by performing an RT-PCR on the dsRNA of TY89. The reverse transcription was performed with primer ANC1 (GGGGACCCGCGAACGG (SEQ ID NO:2)). Three independent PCRs were performed using primers RTAM (AATTGGTGTCCACACCTG (SEQ ID NO:3)) and RTAP (ATACAGGACCTAACTGGG (SEQ ID NO:4)) and 35 amplification cycles (annealing temperature of 52° C., and Taq polymerase). The resulting fragments (956 bp) were separately cloned into the pGEM-T Easy vector (Promega). The nucleotide sequence was determined on both strands using specific primers in a cycle sequencing reaction (BigDye terminator kit, PE Applied Biosystems) and an ABI310 DNA sequencer (PE Applied Biosystems). The consensus nucleotide sequence of the VP3 cDNA of TY89 was determined and the amino acid sequence (FIG. 9) was deduced. One of the clones, pSV-VP3-TY89(1), contained the consensus sequence and was used to generate the mosaic A-segment cDNA clones (see below).

Construction of the Mosaic A-Segment Plasmid pHB36-s2VP3.

To replace VP3 of CEF94 with VP3 of TY89 in the full-length A-segment clone of CEF94, we amplified the TY89 VP3-encoding part by PCR using primers HY3P (AACGTTTTCCTCACAA TCCgCGgGACTGGG (SEQ ID NO:5), non-hybridizing nucleotides are given as lower-case letters) and AGTM (GAGACTCCCAGGtaCCT-CACTC (SEQ ID NO:6)) (annealing temperature is 58° C., Pwo polymerase, and 30 cycles). This PCR fragment (893 bp) was digested with SacII (2316) and KpnI (nt 3172), resulting in a 856 bp fragment, which was agarose gel purified (Qiaex gel extraction kit, Qiagen). The fragment was subsequently used to replace the corresponding part of plasmid pHB36-vvVP3, which had been digested with SacII (partially, nt 2316) and KpnI (nt 3172). After ligation of the PCR fragment into the vector. (Rapid ligation Kit, Roche Molecular Biochemicals), we transformed *E. coli* DH5a cells with this mixture. Plasmids obtained from several independent colonies were analyzed and one plasmid having the intended sequence as determined by sequencing analysis was selected (pHB36-s2VP3, see FIG. 10).

Construction of Mosaic VP3 cDNAs.

To replace the N-terminal part of serotype I VP3, we used the same PCR as mentioned above (pHB36-s2VP3), only this time we used pHB-36W (A-segment CEF94) as a template, yielding a PCR fragment encoding the VP3 sequence of CEF94. This PCR fragment was digested with ScaI (nt 2799) and KpnI (nt 3172) to yield a 373 bp fragment. The agarose gel-purified fragment was subsequently used to replace the corresponding part of pHB36-s2VP3, which had been digested partially with ScaI (nt 2799) and KpnI (nt 3172), yielding pHB36-s2VP3N (see Table 9).

To replace the C-terminal part of serotype I VP3 we used the same approach as for generating pHB36-s2VP3N, only this time we used TY89 cDNA as template in the PCR and used pHB-36W as recipient for the 373 bp PCR fragment, yielding pHB36-s2VP3C (see Table 9).

Protein Analysis.

For western blotting, we purified CEF94 and TY89 IBDV from infected QM5 cells by differential centrifugation as described before (Boot et al., 1999). Viral proteins were separated in a 12% SDS-PAGE gel and blotted onto nitrocellulose (Protean BA85, Schleicher and Schuell). For detection of VP3 we used the ECL detection method (Amersham), using a VP3-specific monoclonal antibody and peroxidase conjugated rabbit anti-mouse serum (Dako) as the second antibody.

For in vitro transcription and translation, we used circular plasmids (0.4 μg) containing full-length A- or B-segments (see FIG. 10) in a 2.5 ml TnT-T7Quick reaction (Promega) in the presence of $^{35}$S-methionine. The resulting viral proteins were separated either directly or after immunoprecipitation in an SDS-PAGE gel (12%) and detected by autoradiography. For immunoprecipitation of in vitro-produced proteins, we used either polyclonal (PaVP3/4) or monoclonal antibodies directed against VP3 of serotype I IBDV (Mab IV$^{SI}$) or serotype II (Mab VII$^{SII}$). RIPA buffer (Sambrook, Fritsch, and Maniatis, 1989) was used during all incubations and washing steps. Antigen-antibody complexes were purified from the mixture by addition of Protein A Sepharose CL-4B (Amersham Pharmacia, Sweden), and three washing steps were performed.

Infection and Transfection of QM5 Cells.

QM5 cells were grown to 80% confluence in a 35 mm culture dish and infected with FPV-T7 (m.o.i.=3). After one hour, the cells were washed twice with 3 ml of QT-35 medium and covered with 3 ml Optimem 1 (Gibco/BRL). In the meantime, DNA (1.0 μg) was mixed with 12.5 μl Lipofectamine (Gibco/BRL) in 250 μl Optimem 1 and kept at room temperature for at least 30 min. The QM5 cells were subsequently covered with 2 ml of fresh Optimem 1 and the DNA/Lipofectamine mixture was added. After overnight incubation (18 h, at 37° C. in 5.0% $CO_2$), the transfected monolayer was rinsed once with PBS, fresh QM5 medium (supplemented with 5% FCS and 2% ABII) was added, and the plates were further incubated at 37° C. (5.0% $CO_2$). After 24 h of incubation, the plates were freeze/thawed once and the supernatant was filtered through a 200 nm filter (Acrodisc, GelmanSciences) to remove the Fowlpox virus (FPV-T7) and cellular debris. The cleared supernatant was either stored at −70° C. or used directly for detection of rIBDV by inoculating a near confluent monolayer of QM5 cells with part of the cleared transfection supernatant. IBDV-specific proteins were visualized after 24 or 48 h in an immunoperoxidase monolayer assay (IPMA) using polyclonal VP3/4 or monoclonal VP3-specific antibodies as the first antibody, and horseradish peroxidase conjugated goat anti rabbit or anti mouse as the second antibody.

Maximum Titers and Single-Step Growth Curves.

To determine maximum virus titers, we used the initially rescued virus to infect fresh QM5 cells. Cells were incubated in complete medium (37° C., 5.0% $CO_2$) for five days (or until complete CPE was visible), freeze-thawed once, and filtered through a 200 nm filter (Acrodisc). This procedure was repeated three times (3 serial passages). The amount of IBDV ($TCID_{50}$) after the final filtration was determined by infecting 96-well tissue culture plates, containing near confluent QM5 cells, with 10-fold dilutions of the IBDV samples. The 96-well plates were incubated for 48 hours, and wells in which IBDV antigen was present were detected by an IPMA.

For comparison of the replication ability of mCEF94-s2VP3C with unmodified serotype I IBDV, we determined single-step growth curves of rCEF94 and mCEF94-s2VP3C. QM5 cells ($2*10^6$) were grown overnight (16 h) in a 60 mm cell culture dish. The medium was subsequently removed and 1 ml PBS containing IBDV ($TCID_{50}$=7.0) was used to cover the cells. After one hour, the supernatant was removed, the cells were rinsed four times with 8 ml of PBS, and 5 ml of complete medium were added. At different time points (1 h, 5 h, 10 h, 15 h, 25 h, and 50 h post-infection), samples were taken from the supernatant and stored at −20° C. The viral titer in each sample ($TCID_{50}$) was determined in an IPMA (see above). Independent growth curves were performed two (mCEF94-s2VP3C) or three (rCEF94) times, and standard deviations between the titers at each time point were determined.

Results

Cloning and Analysis of the VP3-Encoding Region of a Serotype II Strain.

Figure 10:
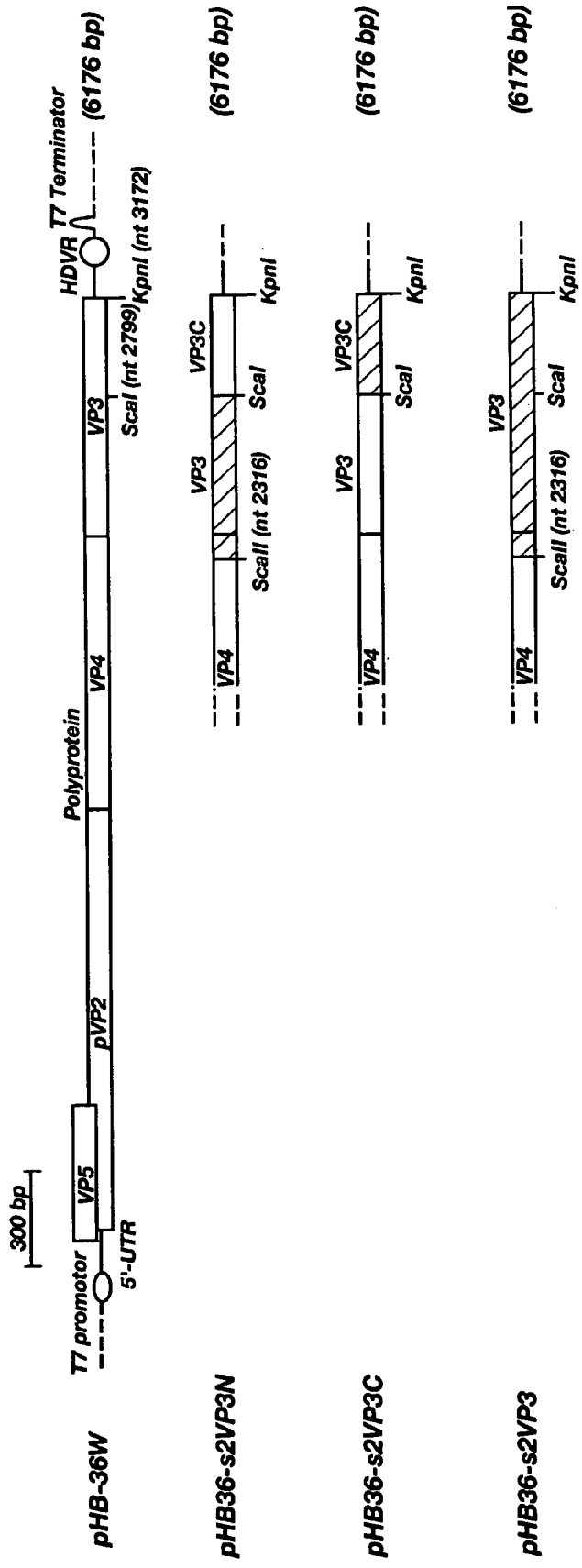
FIG. 10: Schematic representation of plasmids containing the full-length serotype I (CEF94) IBDV A-segment cDNA (pHB-36W), and mosaic full-length A-segment cDNAs (pHB36-s2VP3N, -s2VP3C and -s2VP3) based upon the genome of serotype I (CEF94) and serotype II (TY89) IBDV strains. Open boxes represent open reading frames based upon serotype I cDNA, while shaded boxes represent serotype II cDNA. Several genetic elements such as the remaining part of the polyprotein, the VP5 ORF, T7 RNA polymerase promoter and terminator sequences and the Hepatitis Delta Virus Ribozyme (HDVR) are only shown for pHB-36W but these are also present at the same positions in the other plasmids.

To construct serotype I recombinant IBDV viruses containing the VP3 protein of serotype II, we had to clone the corresponding cDNA of a serotype II strain. First, we attempted to clone the full-length A- and B-segment cDNAs of TY89, the prototype serotype II IBDV strain McFerran et al., 1980). To generate these cDNAs, we followed the full-length RT-PCR protocol that we used to clone the A-segment of serotype I strains. Although we succeeded repeatedly in cloning the full-length B-segment cDNA of TY89 (data not shown), we were unable to obtain the full-length cDNA of the A-segment using this protocol. Therefore, we only amplified the VP3-encoding part of the TY89 A-segment. An RT-PCR fragment containing VP3 of TY89 was obtained three times independently and cloned in the pGEM-T Easy vector. The consensus sequence for this part of the TY89 genome was determined and the deduced amino acid sequence was compared with the corresponding sequence of CEF94, a cell culture adapted serotype I strain (FIG. 9). The cDNA encoding the TY89 VP3 was subsequently used to generate mosaic A-segment cDNA plasmids which encode either the complete VP3 of TY89 (pHB36-s2VP3) or the N-terminal part (101 amino acids, pHB36-s2VP3N) or the C-terminal part (155 amino acids, pHB36-s2VP3C) (FIG. 10).

Figures 11A, 11B, 11C:
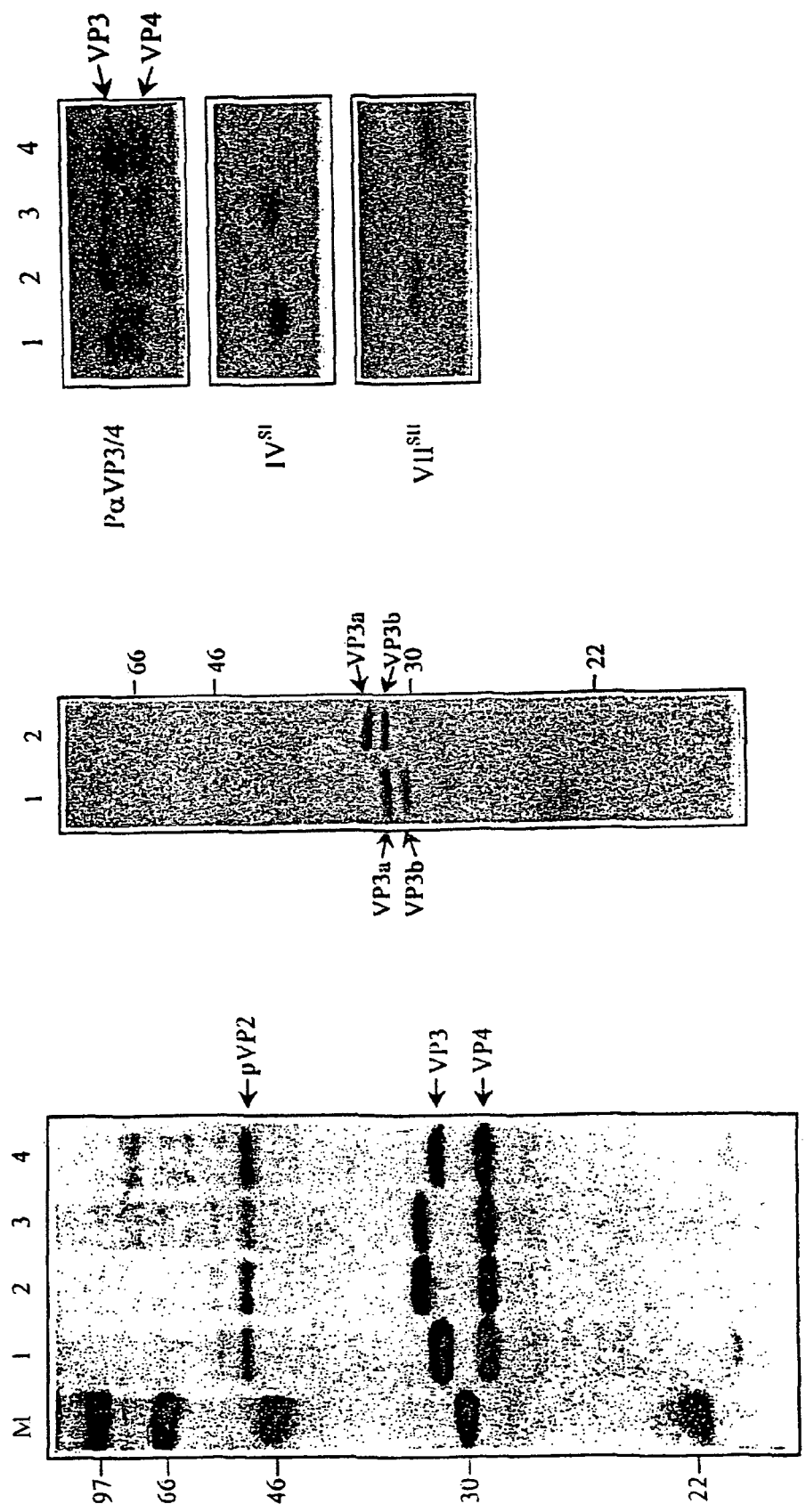
FIGS. 11A, 11B, and 11C: SDS-PAGE analysis of IBDV proteins. A) Autoradiogram of a coupled in vitro transcription/translation reaction using plasmids containing either the full-length A-segment sequence of CEF94 (lane 1: pHB-36W) or mosaic full-length A-segment sequences (lane 2: pHB36-s2VP3, lane 3: pHB36-s2VP3N, or lane 4: pHB36-s2VP3C). The positions of the viral (precursor) proteins are indicated on the right-hand side, while the position of marker proteins ($^{14}$C-labelled Amersham Rainbow marker) and their sizes (kDa) are indicated on the left hand side. B) Western blot analysis of purified IBDV of serotype I (lane 1: CEF94) and serotype II (lane 2: TY89). VP3 proteins (indicated by arrows) were visualized using a VP3-specific monoclonal antibody. The position of marker proteins (prestained Amersham Rainbow marker) and their sizes (kDa) are indicated on the right-hand side. C) Autoradiogram of immunoprecipitated $^{35}$S-methionine-labeled IBDV proteins. In vitro synthesized viral proteins originating from pHB-36W (lane 1), pHB36-s2VP3 (lane 2), pHB36-s2VP3N (lane 3), or pHB36-s2VP3C (lane 4) were immunoprecipitated using either a polyclonal antibody directed against serotype I VP3 and VP4 (PaVP3/4), or monoclonal antibodies specific for VP3 of either serotype I (Mab IV$^{SI}$) or serotype II (Mab VII$^{SII}$).

After having verified that the obtained plasmids had the correct sequence, they were used as templates in an in vitro transcription/translation reaction, followed by SDS-PAGE and autoradiography (FIG. 11A). The three proteins, pVP2, VP3 and VP4, which result from autocatalytic cleavage of the polyprotein, were present in all cases. The positions of the VP3 proteins derived from plasmids pHB36-s2VP3 and pHB36-s2VP3N were found at a higher position in the SDS-PAGE gel than VP3 of pHB-36W and pHB36-s2VP3C. A difference in migration during SDS-PAGE separation was also found between viral VP3 obtained from purified CEF94 and TY89 virus in a western blot analysis (FIG. 11B). This indicates that the observed difference in migration of VP3 from the mosaic full-length A-segment plasmids is not an experimental artifact, but due to amino acid differences in the N-terminal part of VP3.

Three amino acid changes are present in the viral protease (VP4) of pHB-36W-s2VP3 and -s2VP3N (FIG. 9), which is due to the fact that the suggested cleavage site of the polyprotein (Hudson et al., 1986) appeared not to be the genuine cleavage site as recently has been shown (Sanchez and Rodriguez, 1999). These differences apparently do not alter the migration behavior of VP4 in an SDS-PAGE analysis, as this VP4 is found at the same position as wild-type serotype I VP4 (FIG. 11A). Also, no influence of these amino acid changes was found on the in vitro cleavage of the polyprotein, as no uncleaved or partially cleaved polyprotein was present (FIG. 11A).

Localization of a Serotype-Specific Epitope on VP3.

Immunodominant epitopes, recognized by non-neutralizing antibodies, are present on VP3. At least one of these epitopes is serotype specific as has been reported by several researchers (Mahardika and Becht, 1995; Oppling, Muller, and Brecht, 1991; Reddy, Silim, and Ratcliffe, 1992). To map the position of serotype-specific epitopes and to assess their usefulness for discriminating virus rescued from mosaic A-segment cDNAs, we performed a radio-immune-precipitation (RIP) of the in vitro-translated and $\{^{35}S\}$-Met-labeled VP3 proteins, and used either a polyclonal (PaVP3/4) or monoclonal (Mab IV$^{SI}$ or Mab VII$^{SII}$) antibody in the RIP. We analyzed the precipitated proteins by SDS-PAGE, followed by autoradiography (FIG. 11C). As expected from the high level of homology, VP3 derived from both serotypes I and II was precipitated by polyclonal PaVP3/4 serum. However, monoclonal antibody IV$^{SI}$ only precipitated VP3 that contained the C-terminal part of serotype I VP3, while Mab VII$^{SII}$ precipitated solely VP3 that contained the C-terminal part of serotype II VP3. These results indicate that a serotype-specific epitope is present in the C-terminal 155 amino acids of VP3.

Rescue of Mosaic IBDV.

The full-length mosaic A-segment cDNA plasmids were used to rescue mosaic IBDV (mCEF94) by co-transfecting these plasmids with a plasmid containing the B-segment cDNA of CEF94 (pHB-52, (Boot et al., 1999)) into QM5 cells. To direct viral RNA synthesis through the use of a T7-promoter, we infected the QM5 cells with a recombinant Fowlpox virus that carries the T7 polymerase gene (FPV-T7, m.o.i.=3), prior to transfection. Expression of the polyprotein was examined in an IPMA 24 h after transfection and was found to be similar for all the used A-segment plasmids (about 30% of the cells expressed IBDV antigens, data not shown). The cleared supernatant of the transfected QM5 cells was used to determine the IBDV titer using fresh QM5 cells. Despite similar levels of expression of viral proteins after transfection, the resulting $TCID_{50}$ differed largely (Table 10). Recovery of mosaic virus having the C-terminal part of serotype II VP3 was as efficient as wild-type (Average $TCID_{50}$=4.8 compared to 5.1). However, the efficiency of recovering mosaic virus from plasmid pHB36-s2VP3 was strongly reduced (average $TCID_{50}$=1.1) compared to unmodified rCEF94 (average $TCID_{50}$=5.1). The same was found for the rescue of mosaic virus from pHB60-s2VP3N (average $TCID_{50}$=3.1), of which the titer was about 100-fold lower than unmodified rCEF94 after rescue (Table 10).

Replication of Mosaic IBDV.

Figure 12:
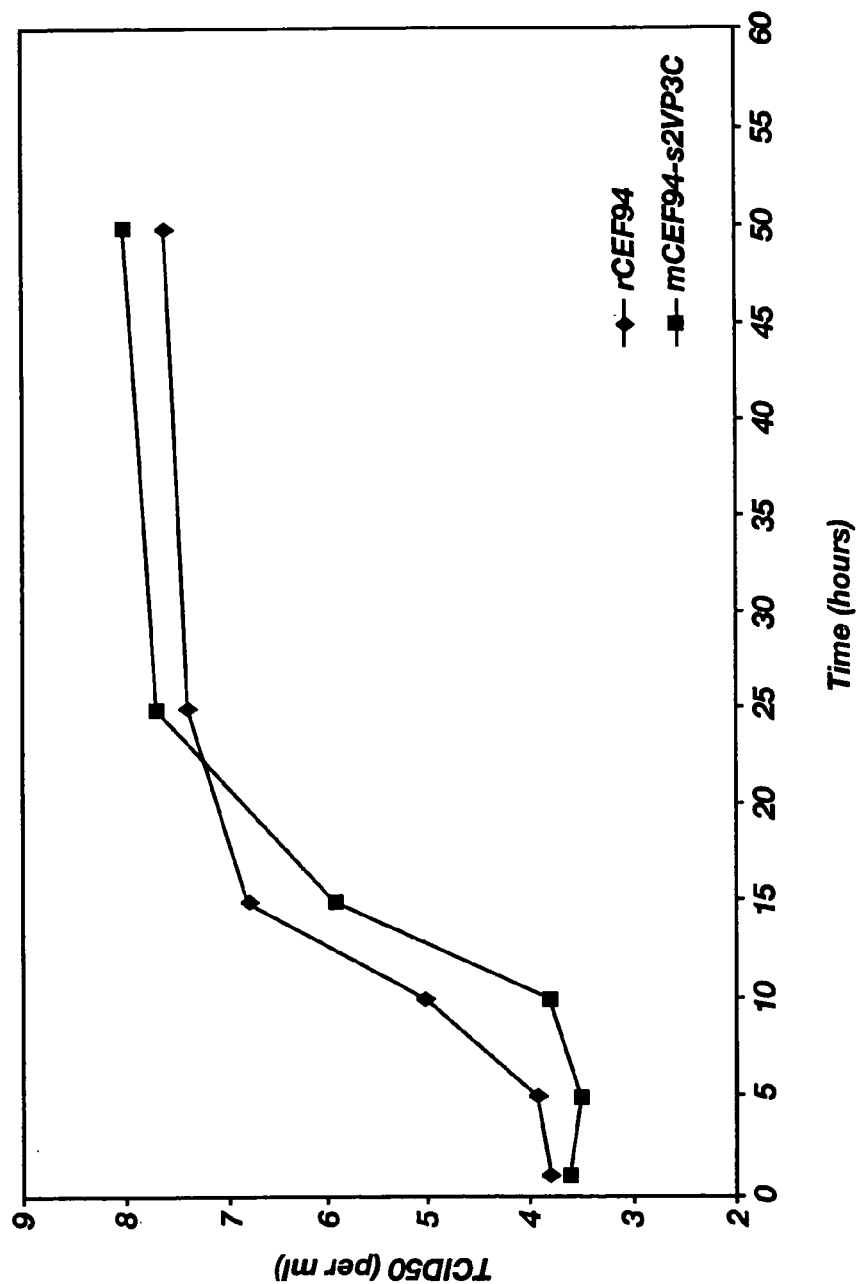
FIG. 12: Single-step growth curves of rCEF94 and mCFE94-s2VP3C. QM5 cells were infected with IBDV (m.o.i.=5, T=0 h) for one hour, washed four times, and covered with fresh medium. Samples were taken from the supernatant at different time points and the amount of IBDV (TCID$_{50}$ per ml) was determined. Error bars represent standard deviations.

To determine the effect of the exchange of parts of the polyprotein on replication, we determined the maximum titers of each virus after three serial passages. Although the mosaic virus which contained 3 amino acid changes in VP4, in combination with the N-terminal part of the serotype II VP3, did show an increase in viral titers after three serial passages, the maximum $TCID_{50}$ values (6.0) obtained were about 10-fold lower than those of unmodified rCEF94 and of mosaic virus containing the C-terminal part of serotype II VP3 (Table 10). To investigate whether rCEF94 and mCEF94-s2VP3C, which were rescued with the same efficiency, had the same replication kinetics in cell culture, we performed a single-step growth curve with both viruses using QM5 cells. Although the maximum titers obtained were the same at 25 h post-infection (p.i.), there was a delay in virus release in the case of mCEF94-s2VP3C in comparison to unmodified rCFE94 (FIG. 12). The first virus release after infection with unmodified rCEF94 was found at 10 h p.i., while at that time point, no release of virus was found after infection with mCEF94-s2VP3C.

Antigen Detection after Infection with Mosaic CEF94 Viruses.

Figure 13:
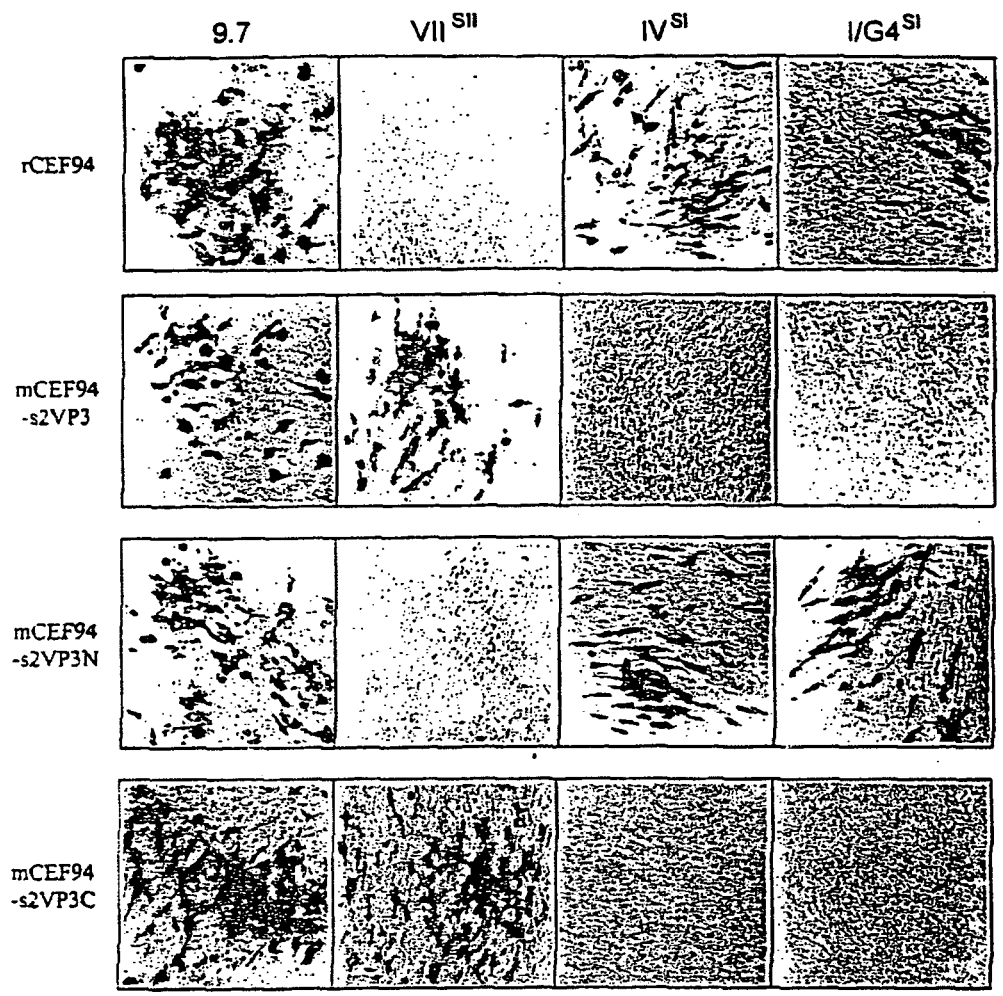
FIG. 13: Detection of VP3 antigen in (m)IBDV-infected QM5 cells using different monoclonal antibodies. Fresh monolayers of QM5 cells were infected with either rCEF94, mCEF94-s2VP3, -s2VP3N, or -s2VP3C and incubated during 48 h. Different monoclonal antibodies specific for VP3 of IBDV were used to assess the reactivity with the different mosaic viruses in an IPMA. An overview of the IPMA results of all used monoclonal antibodies is given in Table 11.

After rescue of the mosaic IBDV, we assessed the possibility of discriminating between these IBDVs by using a set of VP3-specific monoclonal antibodies. Fresh QM5 cells were infected with the rescued viruses rCEF94, mCEF94-s2VP3, -s2VP3N, and -s2VP3C, and viral antigens were detected at 48 h p.i., by using IBDV-specific monoclonal antibodies. Viral antigen originating from all the four different rescued viruses was detected in infected QM5 cells when serotype I-specific neutralizing VP2 antibodies (1.4 or 9.8, see Table 11) or non-neutralizing non-serotype-specific VP3 antibodies (9.7 or 17/80, see Table 11) were used. On the other hand, VP3 monoclonal antibodies which are serotype specific reacted differently with the four rescued viruses. Serotype I-specific antibodies (IV$^{SI}$ or I/G4$^{SI}$, see FIG. 13) reacted only with rCEF94 and mCEF94-s2VP3N while the serotype II-specific antibody (VII$^{SII}$, see FIG. 13) reacted only with mCEF94-s2VP3 and mCEF94-s2VP3C. The reaction pattern of the monoclonal antibodies used was the same when tested in an RIP on in vitro synthesized IBDV proteins (FIG. 11C) and by an IPMA on infected QM5 monolayers (FIG. 9).

Vaccination with so-called deletion (or marker) vaccines has been shown to be a very powerful tool for control and eradication of several viral animal diseases (van Oirschot, 1999). These vaccines are based on live (attenuated) virus strains which lack a non-essential, structural protein, allowing serologic discrimination of vaccinated and field virus-infected animals. Serologic discrimination between chickens vaccinated with a live IBDV vaccine strain and chickens infected with a wild-type IBDV field isolate is currently impossible, because all live IBDV vaccines are derived directly, or after serial passages, from IBDV field isolates. IBDV is a non-enveloped virus containing only three structural proteins (VP1, VP2 and VP3), which are all essential. Because it is not feasible to knock out one of the structural proteins of IBDV, we have used an alternative approach to introduce a serologic marker. Instead of deleting a viral protein, we have exchanged part of a structural protein by the corresponding part of a serotype II protein.

Several IBDV serotype-specific properties, like neutralizing epitopes and receptor recognition, are located within the hypervariable region of VP2. This difference in serotype-specific properties of VP2 is reflected by the difference of the primary sequence of a hypervariable region present within VP2. The identity between the VP2 hypervariable region of the two serotypes is only 67%, while the remaining parts of VP2 are identical for 93%. The other viral proteins also have an identity of over 90% (VP1=99%, VP3=95%, and VP4=92%), with the exception of VP5, which is only identical for 80%. Viral protein 3 is, just like VP2, a major constituent of the viral capsid. Based upon the fact that the VP3 has a basic C-terminal tail, which can interact with the packaged dsRNA, it has been proposed that VP3 constitutes the inner part of the virion (Bottcher et al., 1997). This hypothesis is further supported by the fact that VP2 but not VP3 is involved in receptor recognition, which implicates that at least part of VP2 has to be present at the surface of the virion. Furthermore, neutralizing antibodies are elicited only by VP2 and not by VP3, which is also indicative for surface exposure of VP2. The fact that no serotype-specific properties are known for VP3, and the fact that at least one linear, serotype-specific, non-neutralizing epitope is present within this protein (see Introduction), make the exchange of (part of) VP3 in our view the most promising approach to develop an IBDV marker vaccine.

First, the VP3-encoding cDNA of TY89 was cloned by means of RT-PCR and its nucleotide sequence was determined (see FIG. 9 for the deduced TY89 amino acid sequence). This cDNA was subsequently used to generate mosaic full-length A-segment cDNA plasmids (see FIG. 10). These full-length plasmids were analyzed for the production of viral proteins in a combined in vitro transcription/translation reaction in the presence of {$^{35}$S}-labeled methionine. Autocatalytic cleavage of the polyprotein by VP4 was not affected by the (partial) exchange of VP3. Also, the exchange of three amino acids of serotype I VP4, just in front of the VP4-VP3 cleavage site of the polyprotein in plasmids pHB36-s2VP3 and -s2VP3N (see FIG. 9), did not influence the autocatalytic cleavage. On the other hand, a quite remarkable difference in migration in SDS-PAGE between the in vitro synthesized VP3 originating from either serotype I or serotype II cDNA (FIG. 11A). The same difference in electrophoretic mobility was found for VP3 of purified TY89 and CEF94 (FIG. 11B), although the predicted sizes of these proteins are similar (28.8 kDA). A similar difference in migration behavior between VP3 derived from serotype I and II IBDV has also been noted by others (Oppling, Muller, and Brecht, 1991; Reddy, Silim, and Ratcliffe, 1992). Furthermore, we observed two VP3 bands (VP3a and VP3b) in the Western blot analysis of purified CEF94 and TY89 (FIG. 11B). Whether these two VP3 bands both represent functional proteins, or whether the smaller band (VP3b) is just a specific degradation product of the larger band (VP3a), is unclear. We have observed the presence of two VP3 bands for cell culture amplified CEF94 previously. Fahey et al. (Fahey, Erny, and Crooks, 1989) have made a similar observation for the Australian IBDV isolate 002/73, while also the presence of two VP3 bands for IPNV has been reported (Dobos, 1977) (Hjalmarsson and Everitt, 1999).

After in vitro characterization of viral proteins encoded by the full-length mosaic A-segments, we subsequently used these plasmids to rescue mosaic IBDV. The plasmid encoding the wild-type serotype I polyprotein (pHB-36W) and the three plasmids encoding a chimeric polyprotein (pHB36-s2VP3, -s2VP3N, and -s2VPC) were each co-transfected with the serotype I B-segment plasmid (pHB-52). We found that all transfections with full-length mosaic A-segment plasmids resulted in the appearance of infectious mIBDV. The rescue titers of mosaic viruses which carried the complete or the N-terminal part of serotype II VP3, in combination with three amino acid differences in VP4, were, however, considerably lower than those of unmodified rCEF94 or mCEF94 containing the C-terminal part of serotype II VP3. The difference in rescuing efficiency correlates with the maximum TCID$_{50}$ values obtained after 3 serial passages (Table 10). The introduction of the five amino acid differences in the N-terminal part of VP3 alone or in combination with the three amino acid differences in VP4 leads apparently to a reduction in replication efficiency. Based upon the fact the polyprotein cleavage is not affected by the amino acid changes in VP4, and the fact serotype II VP3 behaves differently in an SDS-PAGE analysis, we think that the observed reduction in replication efficiency of mCEF94-s2VP3 and -s2VP3N is largely due to a different folding of the N-terminal part of VP3.

The first reports of a potential IBDV marker vaccine virus concerned a VP5 knock-out mutant of the attenuated, cell culture adapted rD78 vaccine strain (Mundt, Kollner, and Kretzschmar, 1997; Yao, Goodwin, and Vakharia, 1998). Although a VP5-minus rIBDV might yield a good serological marker, its efficacy as a vaccine has not been proven yet. Replication of VP5-minus rIBDV is severely affected both in vitro and in vivo. Mundt et al. (Mundt, Kollner, and Kretzschmar, 1997) reported that VP5-minus rD78 had a highly reduced virus release (>200-fold lower titer after 24 h p.i. in a single-step growth curve), while Yao et al. (Yao, Goodwin, and Vakharia, 1998) reported a large reduction in virus yield and a much higher survival rate of CEF cells (8 days p.i., multi-step growth curve), in comparison to unmodified rD78. Although mCEF94-s2VP3C has a slightly retarded release of virus FIG. 12), replication in cell culture is much less affected than that of the VP5 knock-out mutant. The finding that mCEF94-s2VP3C virus replicates almost as efficiently as an unmodified serotype I strain, in combination with the possibility to discriminate this virus from both serotype I and II wild-type field isolates, makes the use of the C-terminal part of serotype II VP3 a very promising approach to develop an IBDV marker vaccine.

EXAMPLE 2

Exchange of the C-terminal part of VP3 results in an attenuated very virulent IBDV vaccine strain that induces a unique serologic response in chicken In this example, we describe the replacement of the cDNA encoding the C-terminal part of VP3 of the very virulent IBDV isolate (D6948) with the corresponding part of serotype II (TY89) cDNA. We were able to rescue the recombinant virus containing the serotype II C-terminal half of VP3 after transfection of QM5 cells and passage of the transfection supernatant either onto primary bursa cells or embryonated eggs. Infection of SPF-chickens with such a modified vvIBDV (mD6948-s21VP3C3) shows a significant reduction in virulence compared to unmodified very virulent IBDV. As expected, we found that the distinct bursa tropism of serotype I IBDV strains was not affected by the introduction of the serotype II C-terminal part VP3. Oral administration of mD6948-s2VP3C3 to 18-day-old broiler-type chickens showed that this virus is able to infect chickens, despite the presence of low, intermediate, or high levels of maternally-derived neutralizing IBDV antibodies.

Furthermore, we show that the antibody response of chickens challenged with modified virus can be discriminated from the unmodified virus, using a competition Elisa test. The fact that the modified very virulent D6948 isolate has a slightly reduced virulence, combined with the ability to discriminate chickens infected with mD6948-s2VP3C3 from chickens infected with wild-type (very virulent) IBDV field viruses, makes this mosaic IBDV isolate a valuable IBDV marker vaccine candidate.

Introduction

Infectious Bursal Disease Virus (IBDV) is the causative agent of a highly contagious disease among chickens known as Gumboro disease (Cosgrove, 1962). IBDV is a member of the family of Birnaviridae, having a double-stranded RNA (dsRNA) genome divided over two segments (Dobos et al., 1979). The largest dsRNA segment (A-segment, about 3260 bp) contains two partly overlapping open reading frames (ORFs). The first, smallest ORF encodes the non-structural Viral Protein 5 (VP5, 145–149 amino acids, 17 kDa). The second ORF encodes a polyprotein (1012 amino acids, 110 kDa), which is autocatalytically cleaved to yield the viral proteins pVP2 (also known as VPX, 48 kDa), VP4 (29 kDa) and VP3 (33 kDa). During in vivo virus maturation, pVP2 is processed into VP2 (41–38 kDa), probably resulting from site-specific cleavage of the pVP2 by a host cell-encoded protease (Kibenge et al., 1997). The smaller B-segment (about 2827 bp) contains one large ORF, encoding VP1 (877–881 amino acids, 91 kDa). Viral protein 1 is, next to being the RNA-dependent RNA polymerase, covalently linked to the 5'-ends of the genomic RNA segments (Viral Protein genome-linked, VPg) (Dobos, 1993). In vivo expression of the polyprotein (VP2-VP4-VP3) already results in the formation of virus-like particles, consisting of VP2 and VP3, which have the same dimensions as mature virions (60 nm). This indicates that neither the free VP1 nor viral dsRNA is essential for the formation of the viral capsid (Fernandez-Arias et al., 1998).

Two different serotypes of IBDV have been described (serotype I and II) (McFerran et al., 1980). The pathogenic wild-type serotype I IBDV isolates have a specific tropism for lymphoid cells in the bursa of Fabricius. Serotype I isolates are subdivided into classical, antigenic variant, and very virulent isolates. Antigenic variant IBDV isolates appeared to have single amino acid changes in a specific region of the VP2 protein (the hypervariable region) leading to a partial change of protein antigenicity (Snyder, 1990). Very virulent IBDV isolates, which were first isolated in Europe, have the same antigenic structure as classical strains, but have an enhanced virulence (Chettle, Stuart, and Wyeth, 1989). Amino acid differences between viral proteins of vvIBDV and classical IBDV isolates are scattered throughout all viral proteins, although most of them are found in the hypervariable region of VP2 (Brown and Skinner, 1996). Specific mutations in VP2 result both in a change of cell tropism (Mundt, 1999) and attenuation (Yamaguchi et al., 1996c). Although VP2 is a key factor for virulence, we showed recently that VP2 is not the sole determinant for the very virulent phenotype.

Unlike serotype I isolates, wild-type serotype II isolates do not have a specific B-lymphoid cell tropism. Serotype II isolates are naturally able to replicate in different tissues of the birds and can even be propagated on cell lines. Serotype II isolates are usually recovered from turkey and are neither pathogenic for turkey (Jackwood et al., 1984) nor chickens (Ismail, Saif, and Moorhead, 1988). Conformation-dependent, virus-neutralizing epitopes of both serotype I and II isolates are present on the capsid protein VP2. The other abundant viral capsid protein (VP3) does not contain virus-neutralizing epitopes, although a fast immune response is found against linear VP3 epitopes both after vaccination and infection (Fahey, IJ, and Bagust, 1985). Both serotype-specific and non-serotype-specific epitopes have been described for VP3 (Mahardika and Becht, 1995; Oppling, Muller, and Brecht, 1991; Yamaguchi et al., 1996a).

A common way of producing IBDV vaccines is the adaptation of wild-type virus by propagation in chicken embryos or in cell culture using primary chicken embryo cells or cell lines of either avian or mammalian origin. Adaptation of wild-type IBDV correlates always with a reduced virulence (attenuation) (Yamaguchi et al., 1996b; Yehuda et al., 1999). Differentiation between the used live IBDV vaccines and field IBDV isolates recovered during field outbreaks is currently difficult and laborious as the genetic structure of the IBDV isolate in question has to be determined. In search for an IBDV vaccine which can easily be distinguished from IBDV field isolates, we recently have replaced the complete or the N- or C-terminal half of the VP3 protein of an attenuated IBDV (CFE94) isolate by the corresponding part of a serotype II (TY89) isolate. Analysis of the rescued recombinant serotype I IBDV showed that virus containing the C-terminal part of serotype II VP3 has a slightly reduced virus release when propagated in cell culture, while the final titer is equal to unmodified serotype I IBDV. The mosaic virus in which either the complete or the N-terminal half of VP3 was replaced has a reduced yield (final titers are 10-fold lower) compared to unmodified CEF94, indicating a more severe interference in replication.

Material and Method

Viruses, Cells, and Antibodies.

The classical IBDV isolate CEF94 is a derivative of PV1 (Italy, 1973 (Petek, D'Aprile, and Cancellotti, 1973)), which is able to replicate on non-B-lymphoid cells (Boot et al., 1999). The D6948 strain is a very virulent field isolate (Poultry Health Service, The Netherlands, 1989), which is only able to grow on B-lymphoid cells. Recombinant Fowlpox virus containing the T7 polymerase gene (FP-T7) (Britton et al., 1996) was a kind gift of M. Skinner (Compton Laboratory, Berks, United Kingdom). QM5 cells (a quail cell line (Antin and Ordahl, 1991) were maintained by using QT35 medium (Gibco-BRL), supplemented with 5% Fetal Calf Serum (FCS) and 2% antibiotic solution (QT35$^{FA}$ medium). Primary bursa cells were isolated from 14-day-old SPF embryos and were maintained in Eagle's modified Minimal Essential Medium (EMEM) supplemented with 15% FCS, 0.125% Lacto Albumin Hydrolysate, and 1000 Units Penicillin and 1 mg Streptomycin per ml. The VP3-specific monoclonal antibodies B10A, IV, VII (Mahardika and Becht, 1995) and I/G4 (Oppling, Muller, and Brecht, 1991) were a kind gift of Dr. Müller, University of Leipzig (Germany), while VP3 monoclonal antibody 9.7 was prepared in our laboratory.

Construction of Chimeric VP3 cDNAs.

Figure 1:
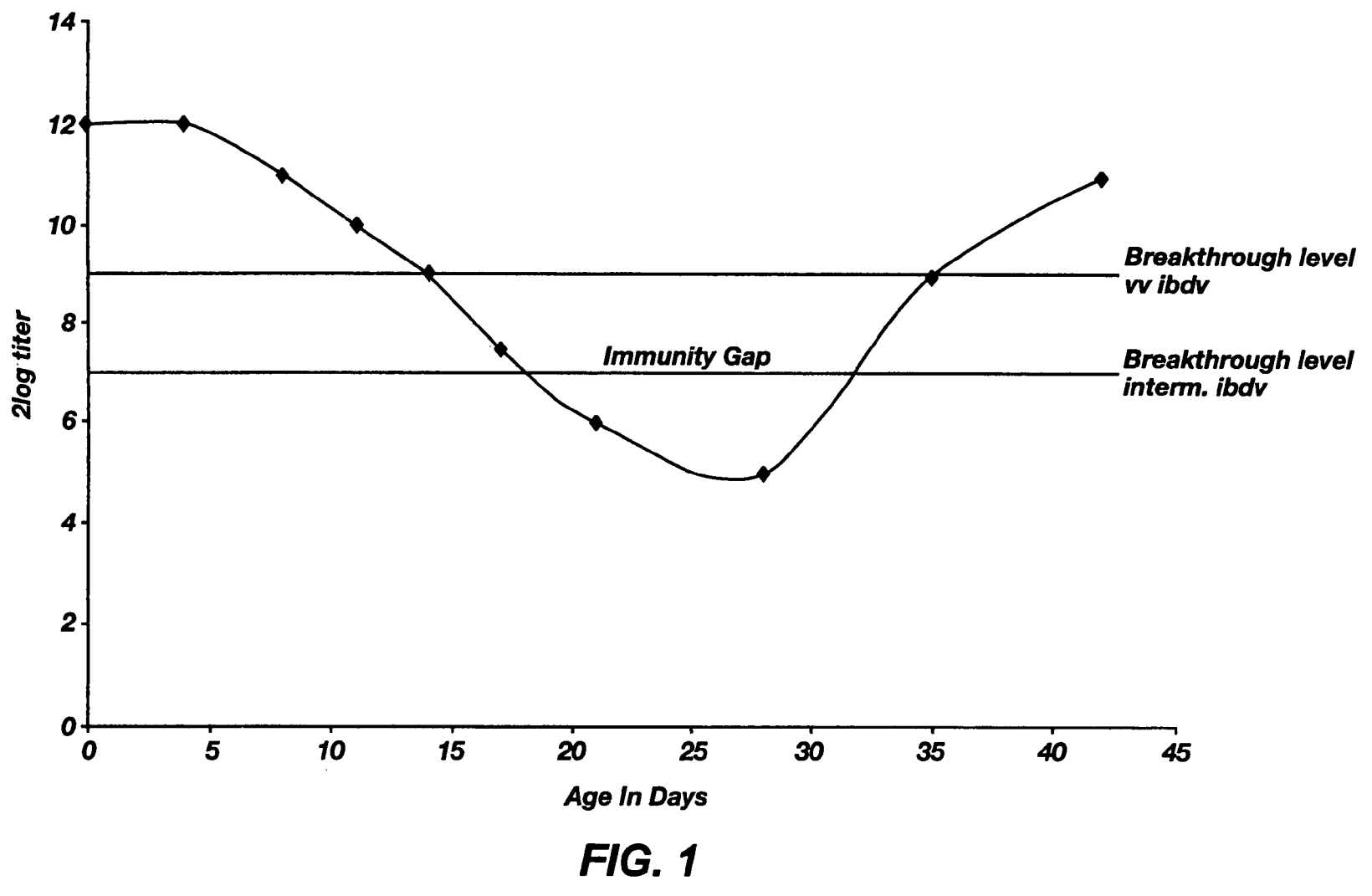

The construction of hybrid CEF94 and TY89 plasmids have been described before. For the construction of plasmid pHB60-s2VP3N, we generated 5 different PCR fragments. In all PCRs we have used Pwo polymerase during 20 reaction cycles. PCR-1N was made using pHB-60 as template and primers AC3 (GGTAGCCACA TGTGACAG (SEQ ID NO:7)) and HY3MR (CCAGTCCCGC GGAT-TGTGAGG (SEQ ID NO:8)) at 56° C., yielding a 1614 bp fragment (nt 731-2346). PCR-2N was made using pHB36-s2VPN as template and primers HY3P (AACGTTTTCC TCACAATCCG CGGGACTGGG (SEQ ID NO:5)) and M13F-17 (GTAAAACGAC GGCCAGT (SEQ ID NO:9)) at 56° C., yielding a 1251 bp fragment (nt 2318-3566). PCR-3N was made using gel-purified PCR-1N and PCR-2N fragments as template and primers AC4 (ACCCAGCCAA TCACATCC (SEQ ID NO:10)) and AGTM (GAGACTC-CCA GGTACCTCAC TC (SEQ ID NO:6)) at 54° C., yielding a 2151 bp fragment (nt 1057-3208), which was subsequently digested with ScaI (nt 2799), yielding PCR-3sN. PCR-4N was made using pHB-60 as template and primers AC9 (CTCAAAGAAG ATGGAGACC (SEQ ID NO:11)) and M13F-24 (CGCCAGGGTT TTCCCAGTCA CGAC (SEQ ID NO:12)) at 54° C., yielding a 869 bp fragment (nt 2727-3593). PCR-5 was made using gel-purified PCR-3sN and PCR-4 fragments as template and primers AC5 (AAGGCCTTCATGGAGGTGGC CG (SEQ ID NO:13)) and M13F-17 (GTAAAACGAC GGCCAGT.(SEQ ID NO:9)) at 54° C., yielding a 2143 bp fragment (nt 1423-3566), which was subsequently digested with XhoI and XbaI, yielding a 1889 bp PCR-5xxN fragment (nt 1606-3495). The PCR-5xxN fragment was subsequently used to replace the corresponding part of pHB-60 using the rapid DNA ligation kit and transformation of E. coli cells. The DNA sequence of the selected plasmid clone of pHB60-s2VP3N was determined (nt 1600-3325), and appeared to have the intended mosaic D6948-TY89 cDNA sequence as shown in FIG. 1.

For the construction of pHB60-s2VP3C3, we first transferred a 1735 bp fragment of pHB36-s2VP3C into pHB-60 using the unique SacII (1670) and XbaI (3495) sites, yielding pHB60-s2VP3C1. The 3'-UTR region of CEF94 was subsequently replaced by the corresponding cDNA sequence of D6948. A PCR fragment (385 bp, nt 3184-3566) was generated by using primers AGTP (CTTGAGTGAG GTAC-CTGGGAG (SEQ ID NO:14)) and M13F-17 (GTAAAAC-GAC GGCCAGT (SEQ ID NO:9)), using pHB-60 as template, with a hybridization temperature of 52° C., Pwo polymerase, and 20 reaction cycles. This PCR fragment was purified, and digested with KpnI and XbaI. The resulting fragment 315 bp, nt 3198-3519) was gel purified and used to replace the corresponding part of pHB60-s2VP3C1 (digested with KpnI and XbaI), by using rapid ligation and transformation of E. coli cells, yielding pHB60-s2VP3C2. Next, a PCR fragment (1187 bp, nt 1423-2607) was generated by using primers AC5 (AAGGCCTTCA TGGAG-GTGGC CG (SEQ ID NO:13)) and vvVP3CM (GAGAAAATTT CGCATCCGATG (SEQ ID NO:15)) using pHB-60 as template, with a hybridization temperature of 54° C., Pwo polymerase, and 20 reaction cycles. This PCR fragment was purified (High Pure PCR purification, Boehringer Mannheim), digested with SacII (nt 1760) and ApoI (nt 2576). The resulting 816 bp fragment was used to replace the corresponding part of pHB60-s2VP3C2 (digested with ApoI (nt 2576, partially) and SacII (nt 1760)), by using rapid ligation and transformation of E. coli cells, yielding pHB60-s2VP3C3. The DNA sequence of the selected plasmid clone of pHB60-s2VP3C3 was determined (nt 1600-3275), and appeared to have the intended mosaic D6948-TY89 cDNA sequence as shown in FIG. 1.

Infection and Transfection of QM5 Cells.

QM5 cells were grown to 80% confluency in a 35 mm culture dish (M-6, 9.6 $cm^2$/well) and infected with either Fowlpox virus-T7 (FP-T7) (Britton et al., 1996) or Modified Vaccinia Ankara (MVA-T7) (Wyatt, Moss, and Rozenblatt, 1995) with an multiplicity of infection (m.o.i.) of 3. After one hour, the cells were washed twice with 3 ml of QT-35 medium and covered with 3 ml Optimem 1 (Gibco/BRL). In the meantime, DNA (1.0 mg) was mixed with 12.5 ml Lipofectamine (Gibco/BRL) in 250 ml Optimem 1 and kept at room temperature for at least 30 min. The QM5 cells were subsequently covered with 2 ml of fresh Optimem 1 and the DNA/Lipofectamine mixture was added. The transfection was performed overnight (18 h) in a 37° C. incubator (5.0% $CO_2$). The transfected monolayer was rinsed once with PBS, and fresh QM5$^{FA}$ medium (2.5 ml) was added and the plates were further incubated in the 37° C. (5.0% $CO_2$) incubator. After 24 h of incubation, the plates were freeze/thawed once and the supernatant was filtered through a 200 nm pore-size filter (Acrodisc, Gelman Sciences) to remove Fowlpox virus and cellular debris. The cleared supernatant was either stored at −70° C. or used directly for further analysis.

Detection of Infectious rIBDV.

After transfection, cell culture-adapted rIBDV was detected by inoculating a near confluent monolayer of QM5 cells with 10-fold dilutions of the cleared transfection supernatant. IBDV-specific proteins were visualized after 24 h in an immunoperoxidase Monolayer Assay (IPMA) (Boot et al., 1999). Rescued IBDV (e.g., rD6948), which is unable to replicate on QM5 cells, was used to inoculate a monolayer of primary bursa cells which had been grown in vitro for 24 h in a 35 mm tissue culture dish (10 $cm^2$) in a $CO_2$ incubator (5%) at 39° C. IBDV-specific proteins in infected B-lymphoid cells were detected in an IPMA after 48 h using Mab 9.7, which is a non-serotype-specific VP3 antibody.

Virulence of rIBDV in Young SPF Chickens.

The virulence of the rescued IBDV isolates was evaluated in SPF layer-type chickens. The IBDV isolates were first propagated on embryonated eggs, by inoculating the QM5 cell supernatant of a transfection experiment into 11-day-old embryonated eggs via the chorioallantoic membrane route. After five days of incubation, the embryos (dead or alive) were recovered, homogenized in a Sorval Omni-mixer (3*10 sec, max. speed) and subsequently clarified by centrifugation (6000 g, 10 min.), and stored in aliquots at −70° C. The virus titers (50% embryo lethal dose, $ELD_{50}$) in these samples were determined using 11-day-old embryonated eggs. The groups of (21-day-old) chickens were housed separately in isolators and inoculated intranasally and by eye-drop with 1000 $ELD_{50}$ IBDV in PBS, or only PBS (negative control group). The animals were monitored for clinical signs daily and dead chicks were removed and necropsied. In experiment 1, most surviving birds were bled (5 ml) and euthanized for necropsy at 9 days post-infection (p.i.), while some birds were left until day 15 p.i. to be bled and euthanized (see Table 13). In experiment 2, all surviving birds were bled and euthanized for necropsy at 13 days p.i. Bursa and body weights were determined of all chicks euthanized, and viral-neutralizing antibody titers in sera were determined using 100 $TCID_{50}$ of CEF94 and a confluent monolayer of QM5 cells. Samples from the bursa of Fabricius taken at necropsy were fixed in 10% neutral-buffered formalin for histopathology, and samples were also snap frozen in liquid nitrogen and preserved at −70° C. for immunohistochemistry (only Exp. 1).

Histopathology and Immunohistochemistry.

Formalin-fixed bursa samples were dehydrated, embedded in paraffin wax, sectioned and stained with Hematoxylin-Eosin (H & E). Histopathologic bursal lesion score (HBLS) was determined by microscopic analysis of the bursa. HBLS was determined on a scale of 1 to 5 according to (Bayyari et al., 1996): 1=normal bursa; 2=scattered or partial follicle damage; 3=50% or less follicle damage; 4=50–75% follicle damage; 5=75–100% follicle damage. Frozen bursa samples were sectioned for immunohistology on a cryostat at 8 μm thickness and taken up on glass slides (Superfrost®). The sections were fixed with acetone for 10 min, air-dried and stored at −20° C. until used. An immunoperoxidase staining was performed as described (Pol, Gielkens, and Van Oirschot, 1989). Briefly, endogenous peroxidase in sections was eliminated by 0.01% $H_2O_2$. Non-specific reactions were blocked by 0.2% bovine serum albumin. Mab B10A or IV$^{SI}$ was used as the primary antibody, whereas goat-anti-rabbit or rabbit-anti-mouse antibody conjugated to peroxidase (Dako) was used as the secondary antibody, and Diamino-benzidine (DAB) as substrate.

Infection of Young Broilers which Possess Maternally-Derived IBDV Antibodies.

Serum of young broilers derived from breeders, which had been vaccinated with both live and killed IBDV vaccines, were assessed for the presence of maternally-derived antibodies at 7 and 15 days post-hatch (p.h.). The level of IBDV-specific antibodies were determined both by using the IBDV-specific Elisa of Idexx (Idexx, Westbrook, USA) and by using a virus neutralization test. In the virus neutralization test, we used 100 $TCID_{50}$ of CEF94 and a confluent monolayer of QM5 cells. Based upon the results of the IBDV Idexx Elisa at 15 days p.h., we grouped the animals in five different groups of at least 14 animals (see Table 14) and housed the groups separately in isolators. At 18 days p.h., each individual chicken received 1000 $ELD_{50}$ of mD6948-s2VP3C3 orally in the crop. Blood samples were taken of each chicken at 22, 25, 32, and 42 days p.h. and the levels of IBDV antibodies were determined in each sample in the IBDV Idexx Elisa and in the virus neutralization test. Five birds of each group were euthanized after the blood sample of 22 days p.h., while the remaining birds were euthanized after the blood sample of 42 days p.h. The bursa/body weight ratio was determined for each bird which was euthanized at 41 days p.h.

Results

Construction and Analysis of Chimeric A-Segment Plasmids.

Figure 14:
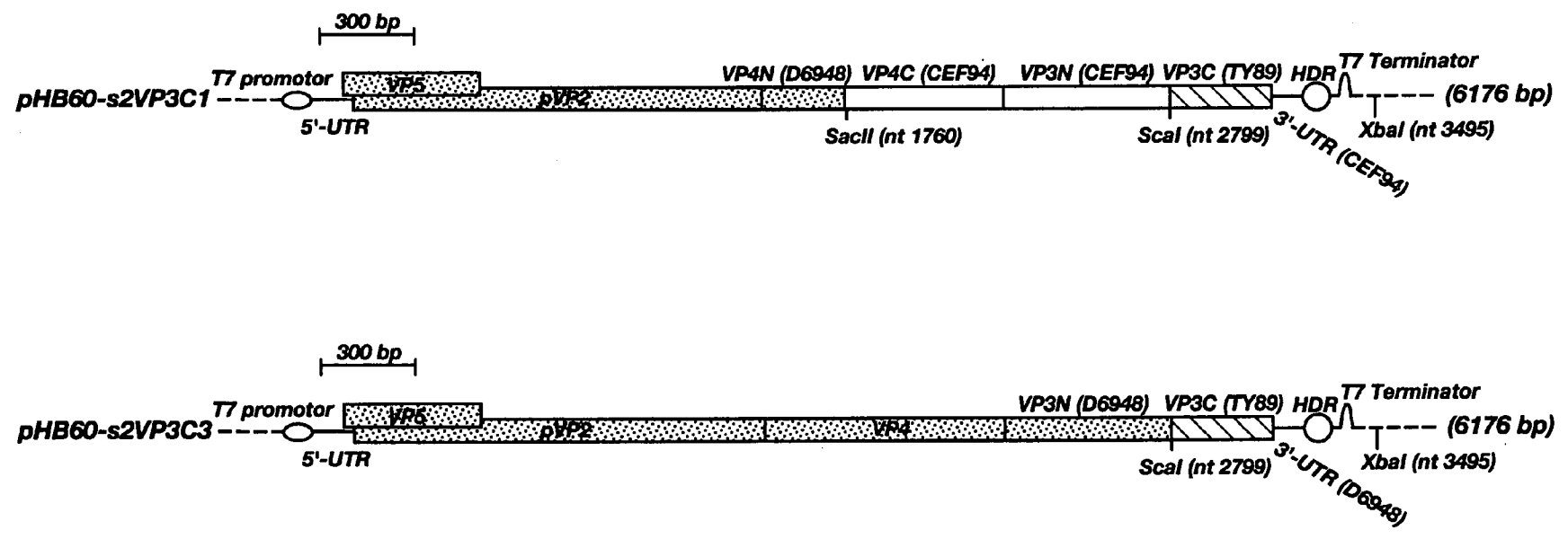

To assess the viability, virulence and antigenic properties of IBD viruses containing a chimeric A-segment dsRNA, we have made several plasmids which contain a full-length A-segment cDNA encoding a hybrid polyprotein. Next to A-segment plasmids based upon CEF94 cDNA, and encoding a VP3 which is (partially) derived from the TY89 serotype II isolate, we constructed three chimeric plasmids which are based upon A-segment plasmid of D6948, a very virulent IBDV isolate. Two of these plasmids (pHB60-s2VP3C1-s2VP3C3, see FIG. 14 and Table 12) encoded a polyprotein in which the C-terminal part of the VP3 is derived from serotype II, while the other (pHB60-s2VP3N, FIG. 14 and Table 12) encodes a polyprotein in which the N-terminal part of VP3 originates from serotype II IBDV. All plasmids encoding the hybrid VP3 proteins possess a T7 promoter and the hepatitis delta virus ribozyme. T7 RNA polymerase-driven transcription of these plasmids leads to positive stranded A-segment IBDV RNA which exactly mimics the nucleotide sequence of the viral positive stranded RNA. A difference is, however, present between native viral RNA and artificially produced viral-like RNA, because a viral protein genome-linked molecule (VP1) is present at the 5'-end of native RNA which lacks in the artificially produced RNA.

Figure 15:
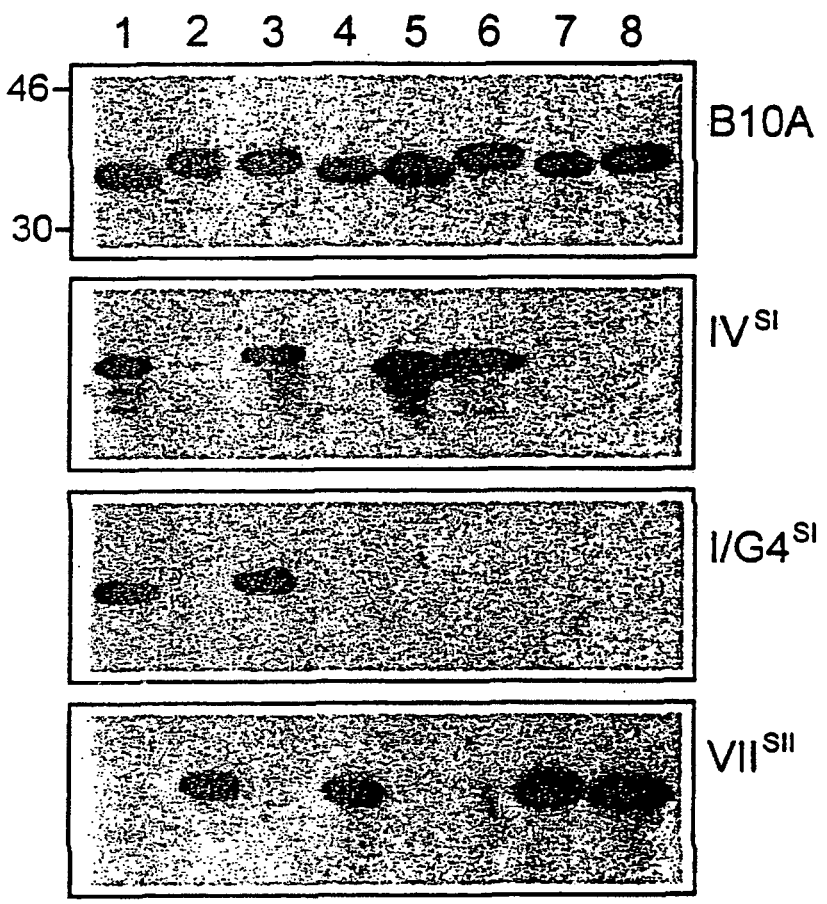
FIG. 15: Western blot analysis of protein samples isolated 24 h after transfection of FPT7-infected QM-5 cells with either pHB-36W (1), pHB36-s2VP3 (2), pHB36-s2VP3N (3), pHB36-s2VP3C (4), pHB-60 (5), pHB60-s2VP3N (6), pHB60-s2VP3C1 (7), pHB60-s2VP3C3 (8). Four SDS-PAGE gels, containing equal amounts of cell extracts, were blotted onto nitrocellulose, and VP3 was detected using the four indicated Mabs. Size markers (Rainbow marker, Amersham) are indicated in kDa on the left.

The constructed plasmids were subsequently used to transfect QM5 cells, which were infected prior to transfection with a recombinant poxvirus (either Fowlpox (FP-T7 or vaccinia MVA-T7) which expresses T7 polymerase cytoplasmatically after infection. No replication of the resulting A-segment RNA can occur as the RNA-dependent RNA polymerase (VP1), encoded by the B-segment, is absent. After transfection, the cells were washed and the total cell extract was assessed for the presence of the (recombinant) VP3 by Western blot analysis (FIG. 15). Four different monoclonal antibodies known to react (serotype-specific) with VP3 were used. Monoclonal B10A is a non-serotype-specific monoclonal antibody and reacted with VP3 encoded by all the used plasmids. The serotype I-specific monoclonal IV$^{SI}$ reacts only with those VP3's which possess the C-terminal part of serotype I, while monoclonal I/G4$^{SI}$ only recognizes the VP3 C-terminal part of the cell culture adapted classical serotype I isolate (CEF94), and not with the very virulent serotype I-(D6948-) derived VP3. The recognition pattern of the serotype II-specific monoclonal T75$^{SI}$ is just the opposite of monoclonal IV$^{SI}$; it recognizes exclusively those VP3's which possess the serotype II C-terminal part.

Amino Acid Sequence Comparison.

Based upon the Western blot analysis, we concluded that the VP3 epitopes, which are recognized by the three serotype-specific Mabs, are linear and present in the C-terminal part (amino acid. 850–1012) of this protein. An alignment of the deduced amino acid sequences of the VP3 part of the polyprotein reveals that only two amino acids are different between the two serotype I isolates CEF94 and D6948 (i.e., amino acid 981 and 1005; see FIG. 16). The fact that monoclonal I/G4$^{SI}$ only recognizes CEF94 and not D6948 is apparently due to one of these amino acid differences. Furthermore, I/G4$^{SI}$ is also unable to react with TY89. Several differences are present between the VP3 of the serotype II and serotype I strains. Because the epitope for I/G4$^{SI}$ is present either around amino acid 981 or 1005 (see above), we concluded that the amino acid difference at position 981 or 992 (see FIG. 16) is responsible for the difference in reactivity of I/G4$^{SI}$.

Rescue of Infectious Mosaic IBDV.

The full-length hybrid A-segment plasmids were subsequently transfected into FP-T7- or MVA-T7-infected QM5 cells, in combination with a full-length B-segment plasmid (either pHB-34Z or pHB-55). Infectious mosaic IBDV could be rescued 24 h after transfection, either using fresh QM5 (for all mCEF94 derivatives) or primary bursa cells (for mD6948-s2VP3C1 and -s2VP3C3) (Table 12). No virus could be rescued when plasmid pHB60-S2VP3N was transfected in combination with plasmid pHB-55. This means that either this mosaic virus is not viable or that our method to rescue this virus is not efficient enough. The rescued viruses and the parental wild-type strains were all amplified on embryonated SPF eggs and harvested. The viral titer (50% embryo lethal dosis ($ELD_{50}$)) for each virus stock was subsequently determined using embryonated SPF eggs.

Infection of SPF Chickens with Mosaic IBDV.

To assess the virulence of rescued mosaic IBDV strains, we inoculated (internasally and intraocularly) groups of SPF chickens with 1000 $ELD_{50}$ of wild-type or mosaic virus strains and determined several relevant parameters, both during the living phase and post-mortem (Table 13). In the first animal experiment (Exp. 1), we observed mortality only in groups which received D6948 (either wild-type or rescued) during the first five days after inoculation. No mortality occurred in this experiment when the D6948 derivative mD6948-s2VP3C1 was used to inoculate the chickens. This is in contrast to the second animal experiment (Exp. 2) in which one chicken (out of 15) of this group died within 5 days p.i. In Exp. 2 we found no mortality after infection with mD6948-S2VP3C3, a derivative of D6849 which is closer to the wild-type D6948 than mD6948-s2VP3C1 (see FIG. 14 and Table 13). The bursa and body weights of each chicken were determined after euthanization (Table 13). The group average of the ratio between the bursa weight and body weight is a good indication of the damage of the bursa of the SPF chickens, due to the IBDV infection. Cell culture adapted IBDV strains (e.g., CEF94), which no longer possess a specific tropism for developing B-lymphoid cells in the bursa of Fabricius, induced only a minor reduction of this ratio (Table 13), while non-cell culture adapted IBDV strains (e.g., the very virulent D6948 and derivatives thereof), which possess the specific bursa tropism, induced a large reduction of the bursa/body weight ratio. The introduction of the C-terminal part encoding part of the serotype II VP3 into the genome of vvIBDV (mD6948-s2VP3C3) did not alter this ratio, consistent with the fact that tropism for the bursa correlates with the sequence of VP2. Despite the fact that the very virulent VP2 sequence is present in mD6948-s2VP3C1, a difference is found for the bursa/body weight ratio of mD6948-s2VP3C1 in comparison to wild-type or rescued D6948. This specific combination of the D6948, CEF94 and TY89 genomes apparently influences viral replication and hence bursa damage in this animal experiment (Exp. 2).

Immunohistochemistry of infected bursa of Fabricius.

Sections of the bursa of Fabricius of IBDV-infected chickens (rD6948 or mD6948-s2VP3C1, Exp. 1) were used to show the presence of viral antigen after infection. Monoclonal antibodies, either non-serotype-specific (B10A) or serotype I-specific ($IV^{SI}$), were used to show the distribution of viral antigen throughout the infected bursa. Using Mab B10A, we were able to detect viral antigen in the bursas of both rD6948- and mD6948-s2VP3C3-infected chickens. When Mab $IV^{SI}$ was used, no viral antigen could be detected in bursas from mD6948-s2VP3C3-infected chickens, while viral antigen was clearly detected in bursas of rD6948-infected chickens (data not shown).

Histopathology of Infected Bursa.

Figure 17:
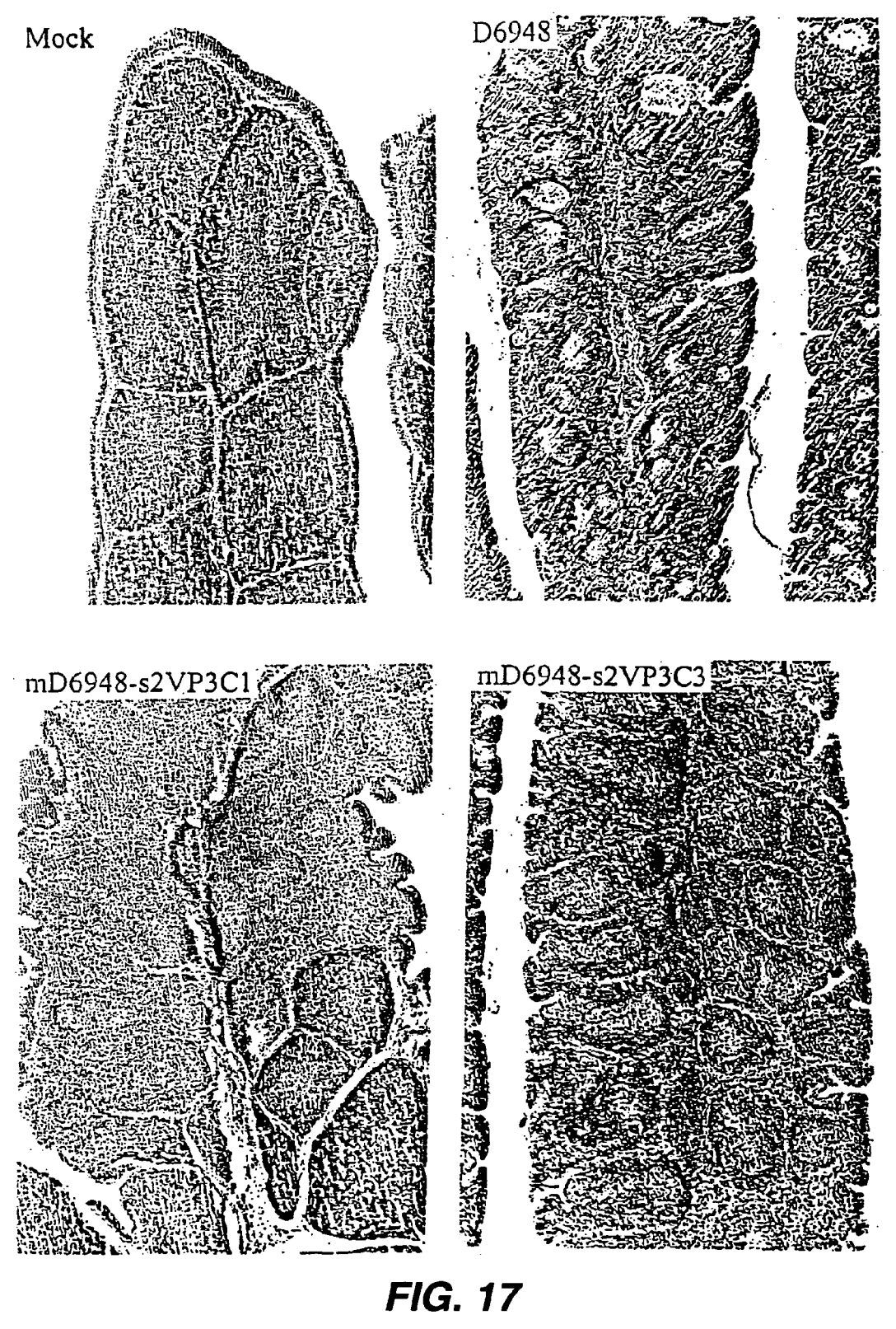

Sections of the bursa of Fabricius of IBDV-infected chickens (Exp. 2) were examined after euthanization to determine the severity of bursa damage (Histopathological Bursa Lesions Score, HBLS). Bursae were classified according to Bayyari (Bayyari et al., 1996) from 1 for a normal bursa to 5 for 75–100% follicle damage (see Material and Methods). All viruses having the VP2 of CEF94 induced only minor bursa damage (<2.0), while all viruses having a VP2 of D6948 induced severe bursa damage (4.7–5.0) (Table 13). Based upon the HBLS, it seems that bursa damage is almost identical after mD6948-s2VP3C1 and -s2VP3C3 infection, in comparison to unmodified D6948. However, careful examination reveals some clear differences between the induced damage of the bursa follicles by the different D6948-based viruses (FIG. 17). Both D6948 and rD6948 completely destroyed the follicular structure in the bursa and induced necrosis and cystic formation. The overall follicular structure of the bursas of mD6948-s2VP3C1- and -s2VP3C3-infected chickens is, however, still present. Some follicles of the mD6948-s2VP3C1-infected bursa have the same appearance as found in control bursas (PBS group), although the diameter of these follicles is generally reduced in comparison to wild-type follicles (see FIG. 17). We also found that the length of the bursa villi is reduced in (m)D6948-infected chickens, in comparison to mock-infected chickens. The reduction in the length of the villi in (m)D6948-infected bursas correlates with the reduced weight (and volume) of these bursas.

Infection of Young Broilers which Possess Maternally-Derived IBDV Antibodies.

After having verified that mD6948-s2VP3C3 has a reduced virulence (attenuation) in comparison to wild-type D6948, we assessed whether this virus is able to infect and induce IBDV-neutralizing antibodies in young chickens which possess maternally-derived IBDV antibodies (animal Exp. 3). Five groups of at least 14 young chickens were formed on the basis of the IBDV-specific antibody levels (IBDV Idexx Elisa) in the blood serum samples taken 15 days post-hatch (p.h.) (see Table 14). At day 18 p.i., each chicken was infected with mD6948-s2VP3C3 (1000 $ELD_{50}$) and the level of IBDV-specific antibodies was determined both by Elisa (Idexx, see Table 14) and by virus neutralization (see Table 15). The level of IBDV antibodies as determined by the Idexx Elisa correlated overall quite well with the level of virus-neutralizing antibodies as determined with the virus-neutralizing assay (Tables 14 and 15). When the $^2$log virus-neutralizing antibody titers are below 8.0, the Idexx Elisa gives a negative score (taken as 0).

In this animal experiment (Exp. 3), we found that mD6948-s2VP3C3 is able to infect birds which possess no (group 1, average Idexx value at 3 days pre-infection is 18), intermediate (group 2, average IBDV Idexx at 3 days pre-infection is 361) or high (group 5, average IBDV Idexx value at 3 days pre-infection is 1283) average level of maternally-derived antibodies (Table 14). That the chickens in groups 1, 2 and 5 had indeed been infected is also clear from the average of the calculated bursa/body weight ratio (BBR) of the chickens euthanized at 42 days p.h. For groups 1 (BBR=0.57; SD=0.21), 2 (BBR=0.69; SD=0.25) and 5 (BBR=0.70; SD=0.16), these values are reduced compared to the non-infected groups 3 (BBR=2.22; SD=0.42) and 4 (BBR=2.17; SD=0.68). Although mD6948-s2VP3C3 was apparently able to infect the birds of group 5, which had the highest average level of maternally-derived antibodies, no infection had taken place in groups 3 and 4, which have an intermediate-to-high average level of maternally-derived antibodies (average IBDV Idexx value at 3 days pre-infection is 576 and 899 for groups 3 and 4, respectively). Apparently there is no strict correlation between the levels of maternally-derived (neutralizing) antibodies and the ability of mD6948-s2VP3C3 to infect the chick.

Outbreaks of very virulent IBDV (vvIBDV) among commercial chicken flocks were first reported in Europe, but are now found worldwide. Very virulent IBDV strains are able to infect young chicks despite a relatively high titer of maternally-derived IBDV antibodies (MDIA) which are protective for infection with classical IBDV isolates. To prevent vvIBDV outbreaks, vaccines based upon wild-type (vv)IBDV isolates (hot vaccines) are being administered when the young chicks still have high levels of MDIA. In flocks with a high variation coefficient of MDIA, vaccination with a hot vaccine may lead to severe bursa damage in chicks with low levels of MDIA.

Furthermore, the introduction of live, wild-type vvIBDV as vaccine into the field is unwanted by the animal health authorities, as transmission cannot be prevented and no discriminating test is available to distinguish between vaccine and field virus.

In this example, we described the rescue of very virulent derived mosaic IBDV (mD6948-s2VP3C3), which has a VP3 that is based partly (the C-terminal 155 amino acids)

upon the VP3 sequence of the serotype II TY89 strain. Earlier we described the generation and in vitro analysis of a mosaic virus (mCEF94-s2VP3C), based upon the classical attenuated serotype I strain CEF94, which has the same C-terminal exchange of the VP3 coding sequence (the C-terminal 155 amino acids) as mD6948-s2VP3C3. Replication of this virus appeared to be slightly reduced, as no virus release was found at 10 h post-infection of a monolayer of QM5 cells. This is in contrast to wild-type CEF94, which showed a virus release at 10 h p.i. Equal final IBDV titers ($>10^7$) were reached both for wild-type CEF94 and mCEF94-s2VP3C between 25 and 50 h p.i., indicating that replication of mCEF94-s2VP3C is only minorly affected by the exchange of the C-terminal 155 amino acids of VP3 for those of TY89. Here we show that mD6948-s2VP3C3 has a reduced virulence in comparison to wild-type D6948. This conclusion is based upon the fact that i) it does not induce any mortality when administered to 21-day-old layer-type SPF chicks, while wild-type D6948 induced mortality in about 50% of the birds (Table 13), ii) the induced bursa damage after infection of 21-day-old SPF-chickens with mD6948-s2VP3C3 is reduced in comparison to infection with D6948 (FIG. 17). The introduction of the C-terminal part of VP3 serotype II in the background of a serotype I isolate leads apparently both in vivo and in vitro small but distinct phenotype.

In this example, we furthermore show that mD6948-s2VP3C3 is able to infect young chicks which possess maternally-derived, IBDV-specific neutralizing antibodies. This particular mosaic virus infected all broiler-type non-SPF chicks in three groups which possessed either an average Idexx IBDV antibody titer of 18 (group 1, Table 14), 361 (group 2, Table 14) or 1283 (group 5, Table 14), at 3 days pre-infection. A distinct raise in the IBDV-specific antibody levels is present between 4 and 7 days post-infection in some of the animals belonging to groups 1 and 2, while all animals of these groups have high IBDV antibody levels between 7 and 14 days post-infection. The IBDV-specific antibody titer was found to raise between 14 and 24 days post-infection in group 5, indicating that infection proceeded at a slower rate in this group than in groups 1 and 2. The average IBDV Idexx value of group 5 is far higher (1283 at 3 days pre-infection) than found for groups 1 (18 at 3 days pre-infection) and 2 (361 at 3 days pre-infection). The difference in level of the maternally-derived antibody titers results most likely in the observed delay in the rise of active (neutralizing) IBDV antibody levels in group 5 in comparison with groups 1 and 2.

Sera of animals of experiment 2 were used in a competition Elisa, in which we used prokaryotically expressed C-terminal 290 amino acids of the CEF94 polyprotein as the coated antigen. Sera chickens infected with D6948 and mD6948-s2VP3C1 were used to compete with either monoclonal antibodies IV or I/G4. At a dilution of 1:500 of the chicken sera, we found that sera from chickens infected with mD6948-s2VP3C1 were not able to compete with of Mab IV and I/G4 in the interaction with the coated antigen, while sera of D6948-infected chickens were able to compete with this interacting (FIG. 18). This indicates that the introduction of the serotype II sequences into the cDNA of D6948 leads to a mosaic virus which induces a unique antibody response. Using the described competition Elisa, we are able to distinguish between chickens infected with the wild-type serotype I vvIBDV virus (strain D6948) and the mosaic serotype I–II, attenuated vvIBDV virus (strain mD6948-s2VP3C1). Despite the fact that the I/G4 did not react in the Western blot analysis with VP3 derived from pHB60 (FIG. 15), we found that antibodies induced by the derived virus of pHB60 (rD6948) were able to compete for the CEF94 antigen. The fact that the mosaic very virulent D6948 isolate (mD6948-s2VP3C3) has a reduced virulence (attenuated), combined with the ability of this virus to infect young chicks which have low, intermediate, or high levels of maternally-derived IBDV-neutralizing antibodies makes this virus a prime candidate for an efficacious vaccine to prevent outbreaks of vvIBDV. The ability to discriminate between chickens vaccinated (infected) with this virus from chickens infected with wild-type (very virulent) viruses makes this mosaic (vv)IBDV virus even more valuable, as it can be used to detect and follow (sub)-clinical (vv)IBDV infections in vaccinated flocks using our described competition Elisa. This (vv)IBDV marker vaccine also enables Gumboro eradication programs.

EXAMPLE 3

Many recent outbreaks of infectious bursal disease in commercial chicken flocks worldwide are due to the spread of very virulent strains of infectious bursal disease virus (vvIBDV). The molecular determinants for the enhanced virulence of vvIBDV compared to classical IBDV are unknown. The lack of a reverse genetics system to rescue vvIBDV from its cloned cDNA hampers the identification and study of these determinants. In this report we describe, for the first time, the rescue of vvIBDV from its cloned cDNA. Two plasmids containing a T7 promoter and either the full-length A- or B-segment cDNA of vvIBDV (D6948) were co-transfected into QM5 cells expressing T7 polymerase. The presence of vvIBDV could be detected after passage of the transfection supernatant to either primary bursa cells (in vitro) or embryonated eggs (in vivo), but not QM5 cells. Rescued vvIBDV (rD6948) appeared to have the same virulence as the parental isolate D6948. Segment-reassorted IBDV, in which one of the two genomic segments originated from cDNA of classical attenuated IBDV CEF94 and the other from D6948, could also be rescued by using this system. Segment-reassorted virus containing the A-segment of the classical attenuated isolate (CEF94) and the B-segment of the very virulent isolate (D6948) is only released after 15 h after an in vitro infection. This indicates a slightly retarded replication, as the first release of CEF94 is already found at 10 h after infection. Next to segment reassortants, we generated and analyzed mosaic IBDV. In these mosaic IBDVs, we replaced the region of CEF94 encoding one of the viral proteins (pVP2, VP3, or VP4) by the corresponding region of D6948. Analysis of these mIBDV isolates showed that tropism for non-B-lymphoid cells was exclusively determined by the viral capsid protein VP2. However, the very virulent phenotype was not solely determined by this protein, since mosaic virus containing VP2 of vvIBDV neither induced morbidity nor mortality in young chickens.

Introduction

Infectious Bursal Disease Virus (IBDV) is the causative agent of a highly contagious disease among chickens known as Gumboro disease (11). IBDV is a member of the family of Birnaviridae, having a double-stranded RNA (dsRNA) genome divided over two segments (14). The dsRNA genome is covered by a capsid of two viral proteins, which results in a single-shelled naked virus particle (60 nm) with an icosahedral (T=13) symmetry (5). The largest dsRNA segment (A-segment, about 3260 bp) contains two partly overlapping open reading frames (ORFs). The first, smallest ORF encodes the non-structural Viral Protein 5 (VP5, +/−145 amino acids, 17 kDa, see FIG. 19). The second ORF encodes a polyprotein (1012 amino acids, 110 kDa, see FIGS. 20A and 20B), which is autocatalytically cleaved to yield the viral proteins pVP2 (also known as VPX, 48 kDa), VP4 (29 kDa) and VP3 (33 kDa) VP2, VP3, and VP4. During in vivo virus maturation, pVP2 is processed into VP2 (41–38 kDa), probably resulting from site-specific cleavage of the pVP2 by a host cell-encoded protease (19). VP2 and VP3 are the two proteins that constitute the shell of the virion. Neutralizing antibodies are only known for VP2, and these antibodies are conformation dependent. The B-segment (about 2827 bp) contains one large ORF, encoding the 91 kDa VP1 protein (see FIGS. 21A and 21B). This protein contains a consensus RNA-dependent RNA polymerase motif (8). Furthermore, this protein has been reported to be linked to the 5'-ends of the genomic RNA segments (Viral Protein genome-linked, VPg) (12, 29).

The pathogenic serotype I IBDV isolates are subdivided into classical, antigenic variant, and very virulent isolates. Antigenic variant IBDVs have only been reported in the USA (since 1985) and were found to have single amino acid changes in a specific region of the VP2 protein (the hypervariable region), leading to a different pathologic phenotype (28). Later on in Europe (since 1988 (9)), reports appeared describing IBDV isolates that had an enhanced virulence (very virulent IBDV, vvIBDV), while having the same antigenic structure as classical isolates. Amino acid differences between viral proteins of vvIBDV and classical IBDV isolates were found scattered throughout all viral proteins, although most of them were found in the hypervariable region of VP2 (7, 24). It is currently unknown whether all, or only a few of these amino acid mutations, contribute to the enhanced virulence of the vvIBDV isolates.

Wild-type IBDV replicates specifically in developing B-lymphoid cells in the bursa of Fabricius. During this replication, viral proteins induce apoptosis resulting in a rapid depletion of B-cells (31). A common way of producing IBDV vaccines is the adaptation of wild-type virus by propagation in chicken embryos or in cell culture using primary chicken embryo cells (CEC), primary chicken embryo fibroblast cells (CEF), or cell lines such as quail-derived cells (QT35, QM5, or QM7) or mammalian cells (Vero cells). Adaptation of wild-type IBDV is always reported to correlate with attenuation (32, 34). Adapted IBDV is able to infect non-B-lymphoid chicken cells, resulting most likely in a reduced viral load in the B-lymphoid cells in the bursa of infected chickens. Several reports have appeared which described amino acid mutations resulting from adaptation of wild-type IBDV during propagation on non-B-lymphoid cells (20, 33, 34). Furthermore, two studies have been published in which amino acid mutations have been introduced, using a reverse genetics system, in the VP2 region of IBDV (20, 22). These analyses show that important amino acids for propagation on non-B-lymphoid cells are found within the hypervariable region of VP2 (i.e., amino acids at position 253, 279, and 284). The influence of mutations found in other parts of the genome (e.g., in VP1 (7, 34)) is unclear at the moment. Studies focussed at determining the influence of site-directed single or multiple amino acid mutations are hampered by the lack of a reverse genetics system which can generate very virulent IBDV. In this report we describe such a system. Using the full-length cDNA of a wild-type very virulent IBDV isolate (D6948) we have successfully rescued recombinant D6948 (rD6948). Furthermore, we rescued mosaic IBDV after transfection of plasmids which contained largely cDNA originating from an attenuated classical isolate (CEF94) and partly of cDNA originating from wild-type vvIBDV (D6948).

Material and Method

Viruses, Cells, and Antibodies.

The classical IBDV isolate CEF94 is a derivative of PV1 which has been adapted for growth on cell cultures (3, 23). The wild-type vvIBDV isolate D6948 was originally isolated by the Poultry Health Service of the Netherlands (PHD, Doorn, 1989) and was purified by repeated limited dilution passages in embryonated eggs (5 times). It was subsequently passed twice in SPF chickens in our laboratory. Recombinant Fowlpox virus containing the T7 polymerase gene (FPV-T7) (6) was received from the laboratory of M. Skinner (Compton Laboratory, Berks, United Kingdom). QM5 cells (1) were maintained by using QT35 medium (Gibco-BRL), supplemented with 5% Fetal Calf Serum (FCS) and 2% antibiotics solution ABII (1000 U/ml Penicillin (Yamanouchi), 1 mg/ml Streptomycin (Radiumfarma, Italy), 20 mg/ml Fungizone, 500 mg/ml Polymixin B, and 10 mg/ml Kanamycin), in a $CO_2$ (5%) incubator at 37° C. Primary bursa cells were isolated from 14-day-old SPF embryos and were maintained in Eagle's modified Minimal Essential Medium (EMEM) supplemented with 15% FCS, 0.125% Lacto Albumine Hydrolysate (Oxiod), 1000 Units Penicillin/ml (Yamanouchi) and 1 mg/ml Streptomycin (Radiumfarma, Italy). Polyclonal rabbit antiserum against VP1 was produced by injecting rabbits with purified recombinant VP1 (30). A Polyclonal rabbit serum against VP3 and VP4 of IBDV was produced as follows: A PCR fragment containing nt 2297 to nt 3192 of the A-segment cDNA (amino acids 722→1018 of the polyprotein) of CEF94 was fused to a his (6*) tag, using *E. coli* expression plasmid pQE-30 (Qiagen). The expressed fusion protein was purified using Ni-NTA resin (Qiagen) according to the supplier's instruction. The purified proteins were separated in an SDS-PAGE gel and full-length fusion product (+/−35 kDa) was isolated from the gel according to Hardy et al. (16). The recovered protein was subsequently used to immunize rabbits. The specificity (both VP4 and VP3 are recognized) and reactivity of the rabbit serum (PaVP3/4) was confirmed in Elisa, Radio-Immune-Precipitation, and IPMA analysis (data not shown).

Generation of Full-Length A- and B-Segment Clones.

To produce full-length single-stranded cDNA of both the A- and B-segments of the two IBDV isolates (CEF94 and D6948), we used primers specific for the 3'-end of the coding strand for reverse transcription (4). Two primers specific for the 3'-end of both the coding and non-coding strand were subsequently used to amplify the full-length A- and B-segment cDNAs in a PCR amplification using a mixture of Taq and Pwo enzymes (Expand, Boehringer Mannheim) (4). The two primers which hybridize with the 3'-terminus of the non-coding strand contained a 5' extension encoding the T7 promoter (4). Three independent RT-PCR reactions were performed for each segment and the resulting PCR fragments were cloned into the pGEM-T vector (Promega) (A-segment) or in a pUC19 derivative which contained the antigenomic cis-acting Hepatitis Delta Virus (HDV) ribozyme (10) and a T7 polymerase terminator (see FIG. 22 and (3) (B-segment). Sequence analysis was performed on both strands using sequence-specific primers in a cycle sequencing reaction (BigDye terminator kit, PE Applied Biosystems) and an ABI310 apparatus (PE Applied Biosystems). An unintended mutation in one of the A-segment of D6948 clones (pHB-22) was restored by exchanging a restriction enzyme fragment from an independent clone (data not shown), yielding pHB-22R. pHB-22R contains the consensus cDNA of the A-segment of the D6948 vvIBDV isolate. We subsequently transferred this full-length A-segment sequence into a pUC18-based vector, which contained the Hepatitis Delta Virus (HDV) ribozyme and a T7 polymerase terminator (see above) by PCR amplification using the same primers as used in the RT-PCR protocol (4). During this transfer, an unintended mutation was introduced in the VP4-encoding part of the polyprotein (A1817G). This mutation was subsequently used as a genetic tag for virus rescued from this D6948 A-segment plasmid. The A-segment cDNA clone of CEF94 (pHB-36W) contains a two-nucleotide genetic tag ($3172_{C \to T}$ and $3173_{T \to A}$), thereby introducing a unique KpnI restriction site GGTAAC (SEQ ID NO:1) in the 3'-UTR of the A-segment (3).

Protein Sequence Comparisons.

Amino acid sequences used for sequence alignments were retrieved from the GenBank database (accession numbers are given between parentheses). For the alignment of VP5 and polyprotein (A-segment) of the vvIBDV, we used the predicted amino acid sequence of isolates D6948 (AF240686), HK46 (AF092944), UK661 (X92760), and OKYM (D49707). For the alignment of the vvIBDV VP1 sequences (B-segment), we used the predicted amino acid sequence of D6948 (AF240687), HK46 (AF092944), UK661, (X92761), OKYM (D49707), IL3 (AF083093), and LA (AF083092).

In Vitro Transcription and Translation.

Circular plasmids (0.4 mg) containing full-length A- or B-segments preceded by a T7-promotor were used as template in a 2.5 ml in vitro transcription-translation reaction (TnT-T7Quick, Promega) in the presence of $^{35}$S-Methionine. The resulting viral proteins were separated in an SDS-PAGE gel (12%) and visualized by autoradiography.

Infection and Transfection of QM5 Cells.

QM5 cells were grown to 80% confluency in a 35 mm culture dish (M-6, 9.6 cm$^2$/well) and infected with Fowlpox virus-T7 (FPV-T7, m.o.i.=3). After one hour, the cells were washed twice with 3 ml of QT-35 medium and covered with 3 ml of Optimem 1 (Gibco/BRL). In the meantime, DNA (1.0 mg) was mixed with 12.5 ml of Lipofectamine (Gibco/BRL) in 250 ml of Optimem 1 and kept at room temperature for at least 30 min. The QM5 cells were subsequently covered with 2 ml of fresh Optimem 1 and the DNA/Lipofectamine mixture was added. The transfection was performed overnight (18 h) in a 37° C. incubator (5.0% CO$_2$). The transfected monolayer was rinsed once with PBS, and fresh QM5 medium (supplemented with 5% FCS and 2% ABII) was added and the plates were further incubated in the 37° C. (5.0% CO$_2$) incubator. After 24 h of incubation the plates were freeze/thawed once and the supernatant was filtered through a 200 nm filter (Acrodisc, GelmanSciences) to remove the Fowlpox virus (FP-T7) and cellular debris. The cleared supernatant was either stored at −70° C. or used directly for further analysis.

Detection of Infectious rIBDV.

After transfection, infectious rIBDV was detected by inoculating a near-confluent monolayer of QM5 cells with part of the cleared transfection supernatant. IBDV-specific proteins were visualized after 24 h in an Immunoperoxidase Monolayer Assay (IPMA) (3). Rescued IBDV (e.g., rD6948) which is unable to replicate on QM5 cells was also used to inoculate a monolayer of primary bursa cells which had been grown in vitro for 24 h in a 35 mm tissue culture dish (10 cm$^2$) in a CO$_2$ incubator (5%) at 39° C. IBDV-specific proteins in infected B-lymphoid cells were detected in an IPMA after 48 h.

Single-Step IBDV Growth Curves.

To assess the replication ability of the rCEF94 and srIBDV-CADB isolates (see Table 16), we determined single-step growth curves. QM5 cells (2*10$^6$) were grown overnight (16 h) in a 60 mm cell culture dish. The medium was subsequently removed and 1 ml of medium containing IBDV (TCID$_{50}$=10$^{7.0}$; m.o.i.=5) was used to cover the cells. After one hour, the medium was removed, the cells were rinsed three times with PBS, and 5 ml fresh medium was added. At different time points (5 h, 10 h, 15 h, and 25 h post-infection), samples were taken from the medium and stored at −20° C. The amount of IBDV (TCID$_{50}$) in each sample was determined by infecting 96-well tissue culture plates, containing near confluent QM5 cells, with 10-fold dilutions of the IBDV samples. The 96-well plates were incubated for 48 hours, and infective centers of IBDV (IBDV-antigen positive areas) were detected by an IPMA (see Detection of infectious rIBDV).

Construction of Mosaic A-Segment Plasmids pHB36-vvVP2.

To replace the coding sequence of the pVP2 part of the CEF94 polyprotein with the corresponding part of the D6948 polyprotein, we generated three PCR fragments (i.e., VP2a, VP2b and VP2c, see FIG. 26). PCR fragment VP2a (189 bp) was generated using primers M13R (TCACACAG-GAAACAG CTATGAC (SEQ ID NO:16)) and ATG3 (CATCGCTGCGATCGTTTGTCTGATCTCTAC (SEQ ID NO:17)), and pHB-36W as template. PCR fragment VP2b (761 bp) was generated by using primers (ATCCGGGC-CCTAAGGAGG (SEQ ID NO:18)) and ANC4 (GC-CAAGTCGGTGTGCAG (SEQ ID NO:19)), and pHB-36W as template. PCR fragment VP2c (1418 bp) was generated using primers HY0P (TATCATTGATGGTCAGTAGAG (SEQ ID NO:20)) and HY2M (CACCGGCACAGCTATCC (SEQ ID NO:21)), and pHB-22R as template. These three PCR fragments were agarose gel purified using a Qiaex gel extraction kit (Qiagen, Germany) and used as template (50 ng of each fragment) in a fusion PCR using primers T7EcoRI (GG<u>AATTC</u>TAATACGACTCACTATAGG (SEQ ID NO:22)) and ANC4 (SEQ ID NO:19). This PCR fragment (2256 bp) was subsequently digested with EcoRI and SacII (resulting in a 1806 bp fragment), agarose gel purified (Qiaex gel extraction kit, Qiagen) and ligated into pHB-36W, which had been digested with the same restriction enzymes, and was then used to transform *E. coli* DH5a cells. Several plasmids were analyzed and one plasmid having the intended sequence was selected (pHB36-vvVP2).

Construction of Mosaic A-Segment Plasmids pHB36-vvVP3.

To replace the coding sequence of the VP3 part of the CEF94 polyprotein with the corresponding part of the D6948 polyprotein, we generated two PCR fragments. PCR fragment VP3a (1622 bp) was generated using primers AC3 (GGTAGCCACATGTGACAG (SEQ ID NO:7)) and HY3M (CCAGTC<u>cCGcGG</u>ATTGTGAGG (SEQ ID NO:23)), and pHB-36W as template. PCR fragment VP3b (1252 bp) was generated by using primers HY3P (AACGTTTTCCTCACAAT<u>CCgCGg</u>GACTGGG (SEQ ID NO:5)) and M13F (GTAAAACGACGGCCAGT (SEQ ID NO:24)) and pHB-22R as template. These two PCR fragments were agarose gel purified and used as template (50 ng of each fragment) in a fusion PCR using primers AC4

(ACCCAGCCAATCACATCC (SEQ ID NO: 10)) and AGTM (GAGACTCCCAGGtaCCTCACTC (SEQ ID NO:6)). This PCR fragment (2154 bp) was subsequently digested with EagI and KpnI (resulting in a 1857 bp fragment), and used to exchange the corresponding part of pHB-36W in the same way as described for pHB36-vvVP2, yielding pHB36-vvVP3.

Construction of Mosaic A-Segment Plasmids pHB36-vvVP4.

To replace the coding sequence of the VP4 part of the CEF94 polyprotein with the corresponding part of the D6948 polyprotein, we generated three PCR fragments. PCR fragment VP4a (796 bp) was generated using primers AC3 (SEQ ID NO:7) and HY4M (CCGGCACAGC-TATCCT (SEQ ID NO:25)), and pHB-36W as template. PCR fragment VP4b (644 bp) was generated by using primers HY3P (SEQ ID NO:5) and ANC2 (CTGCCTGTC-CTGGAGCC (SEQ ID NO:26)), and pHB-36W as template. PCR fragment VP4c (864 bp) was generated using primers HY4P (ACATAATCCGGGCCATAAGG (SEQ ID NO:27)) and HY3M (SEQ ID NO:23), and pHB-22R as template. These three PCR fragments were agarose gel purified and used as template (50 ng of each fragment) in a fusion PCR using primers AC4 (SEQ ID NO: 10) and ANC3 (CGATGGGCGTTCGGGTC (SEQ ID NO:28)). This PCR fragment (2154 bp) was subsequently digested with EagI and DraIII (resulting in a 1189 bp fragment), and used to exchange the corresponding part of pHB-36W in the same way as described for pHB36-vvVP2, yielding pHB36-vvVP4.

Virulence of rIBDV in Young SPF Chickens.

The virulence of the rescued rIBDV, srIBDV, and mIBDV (see Table 16) isolates was evaluated in SPF layer-type chickens. The IBDV isolates were first propagated on embryonated eggs, by inoculating the QM5 cell supernatant of a transfection experiment into 11-day-old embryonated eggs via the chorioallantoic membrane route. After five days of incubation, the embryos (dead or alive) were recovered, homogenized in a Sorval Omni-mixer (3*10 sec, max. speed) and subsequently clarified by centrifugation (6000 g, 10 min.), and stored in aliquots at −70° C. The virus titers (50% embryo lethal dose, $ELD_{50}$) in these samples were determined using 11-day-old embryonated eggs. In the virulence test, 9 groups of chickens (21 days old) were inoculated intranasally and by eye-drop with 1000 $ELD_{50}$ IBDV in PBS. In addition, one group of 10 chickens received PBS only (negative control group). The groups of chickens were housed separately in isolators. The animals were monitored for clinical signs daily and dead chicks were removed and necropsied. At 9 days post-infection (p.i.), all chicks from the negative control groups and all remaining chicks from groups in which mortality had occurred were bled (5 ml) and euthanized for necropsy. From the other groups, 6 chicks were bled (5 ml) and taken for necropsy at day 9 p.i., whereas the remaining 4 were bled (5 ml) and taken for necropsy at day 15 p.i. Bursa and body weight were determined of all chicks that had been euthanized at day 9 p.i. The bursa/body weight ratios were analyzed by a one-way analysis of variance with a factor for groups. Ratios were log-transformed prior to analysis. Pairwise comparisons between groups were based on Fisher's LSD method (pairwise t-tests with a pooled variance estimator). At necropsy at day 9 and 15 p.i., samples from the bursa of Fabricius were fixed in 10% neutral-buffered formalin for histopathology. Bursa samples were snap frozen in liquid nitrogen and preserved at −70° C. for immunohistochemical examination.

IBDV antibody titers in serum, taken just before euthanasia, were determined using the Infectious Bursal Disease Antibody detection kit (Idexx, Westbrook, USA).

Histopathology and Immunohistochemistry.

Formalin-fixed bursa samples were dehydrated, embedded in paraffin wax, sectioned and stained with Hematoxylin-Eosin (H & E). Histopathologic bursal lesion score (HBLS) was determined by microscopic analysis of the bursa. HBLS was determined on a scale of 1 to 5 according to (2): 1=normal bursa; 2=scattered or partial follicle damage; 3=50% or less follicle damage; 4=50–75% follicle damage; 5=75–100% follicle damage. Frozen bursa samples were sectioned for immunohistology on a cryostat at 8 μm thickness and taken up on glass slides (Superfrost®). The sections were fixed with acetone for 10 min, air-dried and stored at −20° C. until used. An immunoperoxidase staining was performed as described (25). Briefly, endogenous peroxidase in sections was eliminated by 0.01% $H_2O_2$. Non-specific reactions were blocked by 0.2% bovine serum albumin. A 1:100 dilution of PaVP3/4 was used as the primary antibody, whereas a 1:100 dilution of goat anti-rabbit IgG antibody conjugated to peroxidase (Dako) was used as the secondary antibody, and Diamino-benzidine (DAB) as substrate.

Detection of Genetic Tag.

Bursae of chickens originating from the groups in which mortality had occurred during the animal experiment (see above) were homogenized and viral dsRNA was extracted using a QiaAmp Tissue Kit (Qiagen, Germany). The dsRNA was concentrated by standard ethanol precipitation and subsequently used as template in a reverse transcription reaction using primer ANC1 (GGGGACCCGCGAACGG (SEQ ID NO:2)). A PCR (Taq polymerase) was performed on this template using primers AC3 (SEQ ID NO:7) and ANC5 (CCCATCTGGAGCATATCC (SEQ ID NO:29)) and cycling 35 times between 94° C. (15 s), 55° C. (15 s), and 72° C. (90 s). The obtained PCR products (1266 bp) were gel purified (Qiaex gel extraction kit, Qiagen), and used as template for sequence analysis, by using primer AC6 (TTCACCTGGGGTACTCCG (SEQ ID NO:30)).

Results

Cloning of Full-Length cDNA of vvIBDV.

To study molecular determinants that are responsible for the very virulent phenotype of vvIBDV isolates, we cloned and sequenced the full-length A- and B-segments of the very virulent IBDV isolate D6948 three times independently. The cDNA of the D6948 A-segment (3260 bp) differs at 122 positions from the sequence of the classical, attenuated CEF94 IBDV isolate (data not shown). These nucleotide differences result in an N-terminal extension of 4 amino acids (MLSL) for the predicted VP5 of D6948, and 5 additional amino acid differences between the two VP5 proteins (FIG. 19). Furthermore, 18 amino acid differences are present between the two polyproteins, of which 11 are located in the pVP2 part, 5 in the VP4 part, and 2 in the VP3 part of the polyprotein (FIGS. 20A and 20B). Between the two B-segments (2827 bp), we found 288 nucleotide differences (data not shown), resulting in 17 amino acid differences between the two VP1's (FIGS. 21A and 21B), the only protein encoded on the B-segment.

By combining sequences of different full-length cDNA clones, we constructed plasmids which contained the consensus cDNA sequence of the D6948 A- and B-segments. The A- and B-segment cDNAs, including an artificially introduced T7 promoter sequence, were subsequently transferred to a pUC19-based vector which contained a cis-acting hepatitis delta virus ribozyme (10), yielding pHB-60 (A-segment) and pHB-55 (B-segment) (Table 16 and FIG. 22). These pUC19-based transcription plasmids are the basis for rescuing rIBDV from cloned cDNA, using a recombinant helper virus (Fowlpox) that expresses T7 polymerase (6). We have used this in vivo T7 expression system previously to rescue infectious IBDV from cloned cDNA of the cell culture adapted, classical IBDV isolate CEF94 (3).

In Vitro Transcription/Translation.

The A- and B-segment cDNA clones of vvIBDV isolate D6948 were used as templates in an in vitro transcription/translation reaction (TnT-T7Quick, Promega). The protein products of these cDNA clones appeared to be identical to those of the classical attenuated CEF94 cDNA plasmids (i.e., pVP2, VP3, and VP4 in case of the A-segment and VP1 in case of the B-segment) in an SDS-PAGE analysis (FIGS. 23A and 23B). The pVP2 from D6948 is found at a slightly higher position than the pVP2 protein from CEF94. Plasmid pHB-60 (D6948 A-segment) contains a single nucleotide substitution at position 1817 nt (A1817G), resulting from the PCR-based cloning strategy. This mutation leads to a conserved amino acid substitution in VP4 (I563V). As this mutation did not affect the processing of the polyprotein (FIG. 23A and unpublished results), we have subsequently used this mutation as a tag for virus rescued from this D6948 A-segment plasmid.

Transfection of QM5 Cells.

Plasmids containing the A- and B-segment cDNA of either CEF94 or D6948 were used to co-transfect QM5 cells. Transient expression of the viral proteins originating from both the A- or B-segments was observed in all examined cases in an immunoperoxidase monolayer assay (IPMA), by using antibodies specific for either VP3/4 (A-segment) or VP1 (B-segment) (data not shown). To assess the production of infectious IBDV originating from cloned cDNA (referred hereafter as rescued IBDV; rIBDV), we transferred part of the supernatant onto a fresh monolayer of QM5 cells (first passage) and analyzed the expression of viral proteins in these cells after 24 h in an IPMA. This analysis showed that no infectious rIBDV could be detected in QM5 cells treated with the supernatant of a co-transfection of the A- and B-segment plasmids of vvIBDV isolate D6948 (see FIG. 24). In contrast, infectious rIBDV was present in QM5 cells treated with supernatant of the co-transfection with plasmids containing the A- and B-segments of the attenuated CEF94 isolate (FIG. 24). The co-transfection of the A-segment plasmid of D6948 with the B-segment plasmid of CEF94 yielded no infectious segment-reassorted IBDV (srIBDV-DACB, Table 16). However, the reciprocal combination srIBDV-CADB (Table 16) did yield infectious segment-reassorted IBDV (FIG. 24). Wild-type IBDV isolates such as D6948 are unable to grow on fibroblast cells like QM5 (see Introduction). Therefore, we assessed the presence of infectious rD6948 originating from cloned cDNA by transferring supernatants of transfected QM5 cells onto primary bursa cells which had been grown in vitro for 24 h. Similar to wild-type D6948, which can infect only the lymphoid cells present in this monolayer (data not shown), we were able to detect rD6948 in several lymphoid cells after two days of incubation with the transfection supernatant (FIG. 24, lower panel). Incubation of primary bursa cells with the transfection supernatant of A- and B-segment cDNAs from CEF94 showed that not only lymphoid cells but also fibroblast cells were infected, leading to a destruction of the monolayer within 48 h of incubation. Virus present in the supernatant of a transfection with the A-segment cDNA of D6948 and B-segment cDNA of CEF94 was only able to infect lymphoid cells, and no destruction of the monolayer was observed after 48 h. Similar to rD6948, srIBDV-DACB is apparently unable to infect fibroblast cells. Again, infection of fibroblast cells was found with virus originating from transfection of the A-segment cDNA of CEF94 and B-segment cDNA of D6948, although the monolayer appeared to be less destructed after 48 h in comparison with rCEF94 (FIG. 24).

Single-Step Growth Curves.

To determine whether the rescued rCEF94 and srIBDV-CADB had the same replication properties on QM5 cells as wild-type CEF94, we performed single-step growth curves (in triplicate) for each of these viruses. QM5 cells were infected during one hour with IBDV (m.o.i.=5), after which time the cells were rinsed three times and incubated in complete medium. Part of the supernatant of the infected QM5 cultures was removed at different time points. The amount of IBDV ($TCID_{50}$ per ml) was determined in each sample (FIG. 25). Release of infectious IBDV was found at 10 h p.i. for both wild-type CEF94 and rCEF94, while the first release of srIBDV-CADB was only found at 15 h p.i. Final titers (24 h p.i.) were about the same for wild-type CEF94, rCEF94, and the rescued segment-reassorted IBDV containing the A-segment of CEF94.

Construction of Mosaic A-Segment Plasmids.

To analyze the viral determinants responsible for the very virulent phenotype of isolate D6948, we constructed three different plasmids containing full-length mosaic IBDV A-segment cDNA. Using a PCR-based method (see FIG. 26), we constructed DNA fragments of which the middle part consisted of cDNA originating from D6948 (i.e., the pVP2-, VP3- or VP4-encoding part), while the flanking cDNA originated from CEF94. The transition positions between the different cDNAs are at the putative cleavage sites between the pVP2-VP4 and VP4-VP3 parts of the polyprotein (i.e., behind amino acids 453 and 723, respectively (18), see FIGS. 20A and 20B). The mosaic PCR fragments were subsequently used to replace the corresponding part of CEF94 A-segment cDNA in plasmid pHB-36W, using specific restriction endonucleases. The exchanged parts of the generated plasmids, named pHB36-vvVP2, -vvVP3, and -vvVP4, were sequenced and plasmids containing the intended mosaic cDNA sequence were subsequently used for in vitro transcription/translation and analyzed for the production of viral proteins by means of SDS-PAGE (FIG. 23C). No apparent difference in the autocatalytic cleavage was observed in the polyproteins encoded by these mosaic cDNA A-segments.

Rescue of IBDV from Mosaic A-Segment cDNA.

The plasmids pHB36-vvVP2, -vvVP3, and -vvVP4 were used to transfect QM5 cells together with the B-segment cDNA of CEF94 (pHB-34Z). The presence of infectious IBDV (hereafter referred to as mIBDV, see also Table 16) was analyzed by transferring aliquots of the transfection supernatant to a fresh monolayer of QM5 cells. After 1 day of incubation, we fixed the cells and used an IBDV-specific antibody assay (IPMA) to test for the presence of mIBDV. No mIBDV could be detected in the QM5 monolayer when supernatant of the pHB36-vvVP2 plasmid was used, while in the case of pHB36-vvVP3 and pHB36-vvVP4, mIBDV was clearly present (FIG. 27). The fact that we did not detect mCEF94-vvVP2 in the QM5 monolayer could result from the difference in cell tropism between the rCEF94 and mCEF94-vvVP2. To check for this possibility, we transferred part of the supernatant of the transfection with pHB36-vvVP2 onto a monolayer of primary bursa cells. After two days, we were able to show the presence of mCEF94-vvVP2 virus in some of the B-lymphoid cells (FIG. 27, lower panel). Apparently, mCEF94-vvVP2 had the same cell-tropism as D6948, rD6948, and srIBDV-DACB, since it was only able to grow on B-lymphoid cells and not on fibroblast cells.

Animal Experiment.

To compare the virulence of rIBDV, srIBDV and mIBDV isolates with the parent isolates, we inoculated 21-day-old SPF chickens (10 chickens per virus) intranasally and by eye-drop in one eye with 1000 $ELD_{50}$ each. Clinical signs occurred only in the groups that had received D6948, rD6948 and srIBDV-DACB (data not shown). In these groups, the mortality was 3 out of 10 (D6948), 5 out of 10 (rD6948), and 2 out of 10 (srIBDV-DACB) (Table 17). Neither morbidity nor mortality was found in the other groups. At day 9 p.i., all remaining chickens of the groups in which mortality had occurred (D6948 (n=7), rD6948 (n=5) and srIBDV-DACB (n=8)) and all chickens from the control group were bled and necropsied. From the remaining groups, 6 chickens were bled and necropsied, while the remaining 4 were left until 15 days p.i. to determine the IBDV antibody levels. The bursa/body weight ratio in all groups in which mortality occurred was very much reduced (<2.0). Fisher's LDS test showed that the bursa/body weight ratios of D6948, rD6948, srIBDV-DACB, and mCEF94-vvVP2 are indeed significantly lower ($P<0.01$) than the values of the control group and of the groups which received the other viruses. That reduction in bursa/body weight ratio does not always correlate with the occurrence of mortality is clear from inoculation with mCEF-vvVP2. Although the bursa/body weight ratio is severely reduced (<2.0), no morbidity (data not shown) or mortality (Table 17) occurred in this group. The mCEF94-vvVP3 and -vvVP4 isolates induced neither mortality nor morbidity nor a large reduction in the bursa/body weight ratio. Only in those groups where the bursa/body weight ratio was severely reduced, we found that all chicks possessed antibodies against IBDV 9 days p.i., while several chickens possessed no IBDV antibodies in the groups where no mortality had occurred (Table 17). All birds which were examined at 15 days p.i. possessed IBDV antibodies, except for 3 chickens (of the 4 examined) which had received wild-type CEF94 virus (data not shown).

Detection of Genetic Tag.

The bursae of several chickens of the groups in which mortality had occurred (D6948, rD6948, and srIBDV-DACB) were recovered. Viral RNA derived from the homogenized bursae was used as template in an RT-PCR (see Materials and Methods section). The resulting PCR fragments, spanning the A-segment from nt 709 to nt 1975, were used for the nucleotide sequence determination. The PCR fragments derived from the groups inoculated with rD6948 and srIBDV-DACB contained the genetic tag (A1817G), which was present in the A-segment cDNA plasmid (pHB-60) (data not shown). The PCR-fragment originating from dsRNA of bursae infected with wild-type D6948 did not contain this genetic tag (data not shown).

Several studies have been published in which amino acid changes of (very) virulent IBDV isolates, resulting from adaptation to non-B-lymphoid cell cultures, have been mapped (20, 22, 33). The reverse genetic IBDV systems described so far (3, 20, 22) are only capable of rescuing IBDV from cloned cDNA originating from adapted (i.e., being able to grow on non-B-lymphoid cell) IBDV isolates. As a result of this limitation no mutagenesis studies can be performed in rescued IBDV possessing the original B-lymphoid cell tropism. To overcome this limitation, we have modified our method of rescuing IBDV from cloned cDNA.

The possibility was explored of using primary bursa cells for rescuing vvIBDV. Therefore, we first transfected primary bursa cells with the A- and B-segment cDNA-containing plasmids. We found that transfection of B-lymphoid bursa cells was very inefficient. The cells are very fragile and both the isolation and maintenance of these B-lymphoid cells are laborious. Furthermore, fibroblast cells, isolated from the bursa along with the B-lymphoid cells, grow rapidly in vitro, in contrast to the lymphoid cells. This difference in growth rate results in a monolayer consisting mostly of non-B-lymphoid cells after 42 h of incubation, the time required for transfection using the Fowlpox T7 in vivo expression system.

In search for a more efficient system of rescuing vvIBDV, we modified subsequently our method of rescuing cell culture adapted IBDV (CEF94, (3)) from transfected QM5 cells by harvesting supernatant of transfected QM5 cells (non-permissive for propagation of wild-type IBDV), and transferring this to a monolayer of primary bursa cells (containing B-lymphoid cells which are permissive for propagation of wild-type IBDV). This method allowed us to rescue vvIBDV from its cloned cDNA (rD6948). Rescued D6948 was subsequently used in an animal experiment, along with wild-type D6948 to assess its virulence. Chicks (21-day-old, SPF) were infected with different IBDV isolates. Comparison of all analyzed parameters (mortality, bursa/body weight ratio, histopathologic bursa lesion score, immunohistochemistry, antibody titers (Table 17), and morbidity (data not shown)) collected during 9 days p.i. showed an identical virulence for wild-type and rescued D6948. This showed that the rescued D6948 is indeed very virulent. The dsRNA of both D6948 and rD6948 was isolated from the bursa of infected chickens and used in an RT-PCR, followed by direct sequence determination. The genetic tag in the VP4 part of the polyprotein encoded by the D6948 A-segment cDNA plasmid was, as expected, present in rD6948-derived dsRNA (data not shown). The single mutation in VP4 (1563V), which results from the genetic tag in the A-segment cDNA, does not result in a difference in phenotype (in vitro and in vivo) of rD6948, compared to D6948. This is the first report describing the rescue of a wild-type vvIBDV isolate from cloned cDNA.

After having verified that the deduced cDNA sequence of D6948 represents indeed a true vvIBDV sequence, we compared the deduced amino acid sequence of D6948 proteins with those of other (vv)IBVD isolates. One striking difference between the VP5 sequences of the classical attenuated isolate CEF94 and the vvIBDV isolate D6948 is that the vvIBDV VP5 has an N-terminal extension of 4 amino acids (see FIG. 19). This extension is also predicted for the two other vvIBDV isolates of which the sequences of this region have been published (HK46 (20) and UK661 (7). All classical isolates lack this N-terminal extension, while the only antigenic variant (GLS) of which the cDNA sequence in this region is available has the same extension. Whether the AUG-codon at position 85 is indeed used as a start codon for the production of VP5 of the very virulent and the GLS isolate remains to be determined. It would be interesting to see if the N-terminal extended VP5 results in a different phenotype. Of the other amino acid differences in VP5 (FIG. 19), only R49G and W137R are found for all known vvIBDV VP5 sequences (UK661, OKYM (33), and HK46). Several reports have focused on differences between the pVP2 sequences of IBDV isolates of different origin (e.g., (15)). The amino acid difference at positions 253, 279, 284, and 330 (FIGS. 20A and 20B) are most likely the result of adaptation of CEF94 on CEF cells (20, 22, 33). Of the remaining amino acid differences, only 8 are conserved (see amino acid residues in bold face, FIGS. 20A and 20B) among all the four vvIBDV isolates (D6948, UK661, OKYM, and HK46), compared with the published sequences of classical and antigenic variant isolates.

The length of the ORF for VP1/VPg of CEF94 is two amino acids longer than the same ORF of D6948. Heterogeneity in the length of the VP1/VPg ORF has also been found by others (34). All VP1/VPg's of vvIBDV isolates appear to have a size of 879 amino acids, while some of the VP1's of classical isolates have a size of only 877 amino acids. The 881 amino acids found for the VP1/VPg of CEF94 is the largest VP1 published so far. Furthermore, we identified 17 amino acid differences between the VP1/VPg sequences of CEF94 and D6948 (FIGS. 21A and 21B). Although it has been found that attenuation of IBDV results in amino acid changes in the VP1 sequence (34), no direct correlation between the three changes identified by Yehuda et al. and attenuation has been proven. In fact, we show that segment-reassorted IBDV (srIBDV-DACB, see Table 16), which contains the B-segment of a classical, attenuated IBDV isolate, induces the same mortality and histopathologic lesions as wild-type very virulent IBDV. This indicates that the amino acid changes found in VP1 after adaptation are not related to the attenuation of the virus. Six of the 17 amino acid differences are found in all of the vvIBDV isolates of which the cDNA sequence has been published (see amino acid residues in bold face in FIGS. 21A and 21B).

To assess the influence of the amino acid differences between the viral proteins from different isolates, we constructed plasmids which contained cDNA from both CEF94 and D6948. A small difference in molecular weight between the pVP2 proteins encoded by the cDNA of CEF94 and D6948 was found in an SDS-PAGE analysis (FIG. 23A). The difference in position in the SDS-PAGE gel is also found for the pVP2 proteins encoded by pHB36W and pHB36-vvVP2 (FIG. 23C). A small difference is present between the position of VP4 encoded by pHB36-vvVP3 and pHB-36-vvVP4, in comparison with VP4 encoded by pHB-36W. The first amino acid difference between the two VP3 proteins of CEF94 and D6948 (H751D, FIGS. 20A and 20B) is found 28 amino acids downstream of the proposed cleavage site (behind amino acid 722 (18), see FIGS. 20A and 20B). The difference in the molecular weight of VP4 can be explained if the actual cleavage site of VP4-VP3 is not behind the two basic amino acid residues, but at least >28 amino acids more downstream. Alternative cleavage sites between VP4/VP3 have been proposed to be located behind amino acid 736 (after Tyr-Leu (13) or in the region 752–756 (A-X-A-A-S, (18)). Recently it was indeed shown, using a site-directed mutagenesis approach, that the cleavage site between VP4 and VP3 is most likely located between amino acid residues 755 and 756 (27). We observed that polyclonal antibodies raised against part of the polyprotein starting at position 722 is also able to react strongly with VP4, adding further proof to the assumption that the actual cleavage site is located downstream of amino acid 722 (Boot unpublished data).

The viruses derived from the mosaic A-segment plasmids were checked for growth on either QM5 cells and/or primary bursa cells and used to challenge SPF chickens. Segment-reassorted virus containing the A-segment of D6948 and the B-segment of CEF94 (srIBDV-DACB, Table 16) induced the same signs and lesions as wild-type and recombinant D6948 (Table 17). The differences found within the VP1/VPg proteins of classical (adapted) and very virulent (non-adapted) isolates have apparently no major influence on virulence. The reciprocal combination (srIBDV-DACB, Table 16) induced less CPE in the monolayer of primary bursa cells in comparison to rCEF94 (FIG. 24). We also found a delay in release of new viral particles by srIBDV-CADB in comparison with CEF94 and rCEF94 (FIG. 25). Despite the difference in in vitro virus release between these isolates, we found no difference in the in vivo challenge using SPF chickens. IBDV antibody titers of rCEF94 and srIBDV-CADB are comparable both at 9 days p.i. (Table 17) and 15 days p.i. (data not shown). It has been suggested that segment reassortment between B-segments of serotype I and II isolates occurs in the field (7). Naturally occurring segment reassorting is frequently found for highly segmented dsRNA viruses (Reo- and Rotavirus, (26)). We did not find any phylogenetic evidence for a natural reassortment of IBDV segments. All VP1 proteins of vvIBDV have distinct amino acid changes when compared to classical serotype I isolates and serotype II isolates (FIGS. 21A and 21B, and data not shown). Although no proof exists for IBDV reassortments in the field, Müller has succeeded in producing segment-reassorted virus in the laboratory by co-cultivation of strains belonging to the different serotypes (21).

Exchange of either pVP2 (including a large part of VP5), VP3 or VP4 of CEF94 with the corresponding proteins of D6948 yielded in all cases viable virus. Both the mCEF94-vvVP3 and mCEF94-vvVP4 are able to replicate on QM5 cells, while mCEF94-vvVP2 is only able to replicate on B-lymphoid cells. No differences were found in the single-step growth curves of mCEF94-vvVP3, mCEF94-vvVP4, CEF94 and rCEF94 on QM5 cells (data not shown). It has been shown previously that the factor responsible for propagation in non-B-lymphoid cells is located on VP2 (20, 22, 32). In this study, we show that wild-type vvIBDV is able to replicate in QM5 cells once it is artificially (transfection of cDNA) introduced in these cells. Thus, the inability to replicate on non-B-lymphoid cells is apparently located in the inability to recognize the receptor and/or the inability to enter the cell. Two possible explanations for this change in cell tropism, resulting from mutations in wild-type VP2, exist: 1) These mutations lead to a (conformational) change in VP2, resulting in recognition of a receptor present on a wide range of cells (general IBDV receptor) and, at the same time, loss of recognition of the specific B-lymphoid cell receptor (B-lymphoid IBDV receptor). The domain responsible for interacting with the general IBDV receptor and with the B-lymphoid IBDV receptor is, in this case, located in the same region of VP2 (e.g., the hypervariable region). 2) These mutations lead to a (conformational) change in VP2, resulting in recognition of the general IBDV receptor, but leaves the recognition of the B-lymphoid IDBV receptor (either by VP2, VP3, or a combination of both) intact. The phenomenon that cell culture adapted IBDV is still able to enter and replicate in B-lymphoid cells is explained by the assumption that the general IBDV receptor is also present on B-lymphoid cells (entry model 1 and 2). Entry model 2 even predicts replication of cell culture adapted isolates in B-lymphoid cells when the general IBDV receptor is missing on B-lymphoid cells, by usage of the genuine B-lymphoid IBDV receptor.

It has been found that two specific amino acid mutations (Aspartic acid$^{279}$ to Asparagine$^{279}$, and Alanine$^{284}$ to Threonine$^{284}$) alone, or in combination with a third mutation (Glumatine$^{253}$ to Histidine$^{253}$), might be enough to alter the tropism of a wild-type IBDV strain from an exclusive B-lymphoid cell tropism into a more general tropism (e.g., VERO, QM7, QM5 or CEF cells). Only limited data (20, 22, 33) has been published supporting this. It might be possible that an IBDV strain which possess all these three adaptation mutations (Histidine at position 253, Asparagine at position 279 and Threonine at position 284) is able to grow on B-lymphoid cells, but is still unable to grow on non-B-lymphoid cells, due to a specific amino acid sequence somewhere else in VP2 or in one of the other viral proteins.

TABLE 1

Classification of live IBDV vaccines used to induce active protection in young chickens which are passively protected by maternal IBDV antibodies.

| Type of vaccine (live IBD virus) | Ability to induce an immune response when IBDV antibody titers are equal or below | Immunosuppressive |
|---|---|---|
| Mild | 50–100 | No |
| Intermediate | 100–200* | No |
| Strong | 500* | Yes |

*The Animal Health Service (Deventer, The Netherlands) uses an Idexx Elisa value of 128 (2log7) as the maximum titer for the use of live intermediate vaccines and a value of 512 (2log9) for strong vaccines.

TABLE 2

Primers (oligonucleotides) used for sequence determination, in RT-PCR or PCR reactions. Nucleotides which are unable to hybridize with wild-type IBDV genomes are given in small face. Primers which are specific either for the serotype II (s2) or very virulent (vv) genome are indicated.

| Name | Sequence | Position |
|---|---|---|
| Anchor (SEQ ID NO:31) | cacgaattcactatcgattctggatccttc | — |
| Anchor Primer (SEQ ID NO:32) | gaaggatccagaatcgatag | — |
| ANC0 (SEQ ID NO:33) | GGGGACCCGCGAACGGATC | A: -1/-18 |
| ANC1 (SEQ ID NO:34) | GGGGACCCGCGAACGG | A: -1/-16 |
| T7AC0 (SEQ ID NO:35) | ggaattctaatacgactcactataGGATACGATCGGTCTGACCCCGG | A: 1/23 |
| BNC1 (SEQ ID NO:36) | GGGGGCCCCCGCAGG | B: -1/-15 |
| T7BC1 (SEQ ID NO:37) | ggaattctaatacgactcactataGGATACGATGGGTCTGACCCT | B: 1/21 |

TABLE 3

Nucleotide sequence corresponding to the 5'- and 3'-termini of the coding strands of the two genomic segments of IBDV (CEF94). Numbers behind specific sequences indicate the number of times each sequence was obtained.

| 5'-terminus of the A-segment coding strand | Complementary sequence of the 5'-terminus of the A-segment non-coding strand | 5'-terminus of the B-segment coding strand | Complementary sequence of-terminus of the B-segment non-coding strand |
|---|---|---|---|
| 5'UGAUACGAUC>>> (SEQ ID NO:38) | >>>CGGG$^{3'}$ (SEQ ID NO:42) | 5'UGAUACGAUG>>> (2x) (SEQ ID NO:50) | >>>GGGGGCCA$^{3'}$ (SEQ ID NO:53) |
| 5'AGAUACGAUC>>> (SEQ ID NO:39) | >>>CGGGUCCC$^{3'}$ (SEQ ID NO:43) | 5'GGAUACGAUG>>> (5x) (SEQ ID NO:51) | >>>GGGGGCCU$^{3'}$ (SEQ ID NO:54) |
| 5'GGAUACGAUC>>> (7x) (SEQ ID NO:40) | >>>CGGGUCCCU$^{3'}$ (SEQ ID NO:44) | | >>>GGGGGCCC$^{3'}$ (2x) (SEQ ID NO:55) |
| | >>>CGGGUCCCC$^{3'}$ (6x) (SEQ ID NO:45) | | >>>GGGGGCCCC$^{3'}$ (2x) (SEQ ID NO:56) |
| | >>>CGGGUCCCCC$^{3'}$ (SEQ ID NO:46) | | >>>GGUGGCCCC$^{3'}$ (SEQ ID NO:57) |

TABLE 3-continued

Nucleotide sequence corresponding to the 5'- and 3'-termini of the coding strands of the two genomic segments of IBDV (CEF94). Numbers behind specific sequences indicate the number of times each sequence was obtained.

| 5'-terminus of the A-segment coding strand | Complementary sequence of the 5'-terminus of the A-segment non-coding strand | 5'-terminus of the B-segment coding strand | Complementary sequence of-terminus of the B-segment non-coding strand |
|---|---|---|---|
| | >>>CGGGUCCCCCCU3' [3] (SEQ ID NO:47) | | >>>GGGGGCCCCCC3' [3] (SEQ ID NO:58) |
| | >>>CGGGUCCCCCCC3' (SEQ ID NO:48) | | >>>GGGGGCCCCCG3' (SEQ ID NO:59) |
| Consensus 5'GGAUACGAUC>>> (SEQ ID NO:41) | >>>CGGGUCCCC3' (nt 3260) (SEQ ID NO:49) | 5'GGAUACGAUG>>> (SEQ ID NO:52) | >>>GGGGGCCCCC3' (nt 2827) (SEQ ID NO:60) |

TABLE 4

Description of the used plasmids

| Name | Based on plasmid | Description |
|---|---|---|
| pUC18-Ribo | pUC18 | Contains the SmaI-XbaI fragment of pTV-2A |
| pHB-36A | pUC18-Ribo | Contains the consensus cDNA sequence of the A-segment of CEF94 (see FIGS. 2A–2G) |
| pHB-36W | pHB-36A | An artificially introduced KpnI-site (genetic tag) in the 3'-UTR of the CEF94 A-segment-encoding cDNA (see FIGS. 2A–2G and 3A–3F) |
| pHB-36 | pHB-36A | Contains a lethal amino acid substitution in the VP4 part of the polyprotein (V582A) |
| pHB-60 | pUC18-Ribo | Contains the consensus cDNA sequence of the D6948 A-segment (see FIGS. 2A–2G) |
| pHB-34Z | pUC18-Ribo | Contains the consensus cDNA sequence of the CEF94 B-segment (see FIGS. 3A–3F) |
| pHB-55 | pUC18-Ribo | Contains the consensus cDNA sequence of the D6948 B-segment (see FIGS. 3A–3F) |
| pSV-TY89-VP3 | pGEM-Teasy | Contains the consensus cDNA of TY89 encoding the entire VP3 (A-segment, see FIGS. 2A–2G and 3A–3F) |
| pHB36-vvVP2 | pHB-36W | Contains D6948 A-segment cDNA which encodes the entire VP2 (453 amino acids) |
| pHB36-vvVP3 | pHB-36W | Contains D6948 A-segment cDNA which encodes the entire VP3 (289 amino acids) |
| pHB36-vvVP4 | pHB-36W | Contains D6948 A-segment cDNA which encodes the entire VP4 (270 amino acids) |
| pHB36-s2VP3 | pHB-36W | Contains TY89 A-segment cDNA which encodes the entire VP3 (289 amino acids) |
| pHB36-s2VP3C | pHB-36W | Contains TY89 A-segment cDNA which encodes the C-terminal part (122 amino acids) of VP3 |
| pHB36-s2VP3N | pHB-36W | Contains TY89 A-segment cDNA which encodes the N-terminal part (168 amino acids) of VP3 |
| pHB60-s2VP3C1 | pHB-60 | Contains cDNA encoding a mosaic polyprotein (D6948 (1–543 AA), CEF94 (544–889 AA), and TY89 (890–1012 AA). The 5'-UTR is derived from D6948, while the 3'-UTR is derived from CEF94. An unique KpnI-site (genetic tag) is furthermore present in the 3'-UTR |

TABLE 5

Description of the generated rIBDV, srIBDV, and mIBDV.
The ability of these viruses to
infect QM5 or primary bursa cells was examined in an
immuno peroxidase monolayer assay (IPMA)
using either polyclonal serum directed against VP3 or
monoclonal antibodies directed against
VP2 of IBDV serotype I (1.4), VP3 of serotype II (T-75), or VP3 of serotype I
(B10 and C3); nd means not determined.

| | Derived from plasmids | | Replication on | | Mab's | | | |
|---|---|---|---|---|---|---|---|---|
| IBDV virus | A-segment | B-segment | QM5 cells | Bursa cells | 1.4 | T75 | B10 | C3 |
| rCEF94 | pHB-36W | pHB-34Z | + | + | + | − | + | + |
| rD6948 | pHB-60 | pHB-55 | − | + | + | − | + | + |
| srIBDV-DACB | pHB-60 | pHB-34Z | − | + | nd | nd | nd | nd |
| srIBDV-CADB | pHB-36W | pHB-55 | + | nd | nd | nd | nd | nd |

TABLE 5-continued

Description of the generated rIBDV, srIBDV, and mIBDV.
The ability of these viruses to
infect QM5 or primary bursa cells was examined in an
immuno peroxidase monolayer assay (IPMA)
using either polyclonal serum directed against VP3 or
monoclonal antibodies directed against
VP2 of IBDV serotype I (1.4), VP3 of serotype II (T-75), or VP3 of serotype I
(B10 and C3); nd means not determined.

| IBDV virus | Derived from plasmids | | Replication on | | Mab's | | | |
| --- | --- | --- | --- | --- | --- | --- | --- | --- |
| | A-segment | B-segment | QM5 cells | Bursa cells | 1.4 | T75 | B10 | C3 |
| mCEF94-vvVP2 | pHB3E-vvVP2 | pHB-34Z | − | + | nd | nd | nd | nd |
| mCEF94-vvVP3 | pHB36-vvVP3 | pHB-34Z | + | nd | nd | nd | nd | nd |
| mCEF94-vvVP4 | pHB36-vvVP4 | pHB-34Z | + | nd | nd | nd | nd | nd |
| mCEF94-s2VP3 | pHB3E-s2VP3 | pHB-34Z | + | nd | + | + | − | +/− |
| mCEF94-s2VP3C | pHB36-s2VP3C | pHB-34Z | + | nd | + | + | − | +/− |
| mCEF94-s2VP3N | pHB36-s2VP3N | pHB-34Z | + | nd | + | +/− | + | − |
| mD6948-s2VP3C1 | pHB60-s2VP3C1 | pHB-55 | − | + | + | + | − | +/− |

TABLE 6

Clinical data of 21-day old chickens infected with wild-type, rIBDV, srIBDV or mIBDV isolates (12 groups of 10 chickens). Each chicken was inoculated with 1000 ELD$_{50}$ IBDV, expect for the negative control group (PBS), and each group was kept in a separate isolator. The bursa and body weight of euthanized chickens was determined at nine days post infection. Standard deviation is given between brackets, together with the number of animals (n) used for determination of the given numbers. The bursa/body weight ratio for each animal was calculated and mean values (standard deviation) per group are given.

| IBDV virus | Number of deads (after 9 days) | Body weight (grams) | Bursa weight (grams) | Bursa/Body weight (*1000) |
| --- | --- | --- | --- | --- |
| PBS | 0 | 305 (29, n = 10) | 1.9 (0.4, n = 10) | 6.1 (1.2) |
| CEF94 | 0 | 341 (16, n = 6) | 2.0 (0.6, n = 6) | 6.0 (1.8) |
| D6948 | 3 | 245 (56, n = 7) | 0.4 (0.1, n = 7) | 1.7 (0.6) |
| rCEF94 | 0 | 317 (15, n = 6) | 1.3 (0.5, n = 6) | 4.2 (1.3) |
| rD6948 | 5 | 261 (24, n = 5) | 0.4 (0.1, n = 5) | 1.7 (0.2) |
| srIBDV-DACB | 2 | 263 (35, n = 8) | 0.4 (0.1, n = 8) | 1.5 (0.3) |
| srIBDV-CADB | 0 | 314 (13, n = 6) | 1.8 (0.8, n = 6) | 5.7 (2.7) |
| mCEF94-vvVP2 | 0 | 309 (27, n = 6) | 0.6 (0.2, n = 6) | 1.9 (0.4) |
| mCEF94-vvVP3 | 0 | 325 (33, n = 6) | 2.0 (0.3, n = 6) | 6.2 (0.7) |
| mCEF94-vvVP4 | 0 | 330 (23, n = 6) | 1.5 (0.5, n = 6) | 4.4 (1.3) |
| mCEF94-s2VP3C | 0 | 320 (11, n = 6) | 1.3 (0.4, n = 6) | 4.1 (1.3) |
| mD6948-s2VP3C1 | 0 | 315 (26, n = 6) | 0.6 (0.2, n = 6) | 1.9 (0.6) |

TABLE 7

Origin and phenotype of the IBDV isolates

| Isolate | Reference | Virulence |
| --- | --- | --- |
| D6948 | Boot et al, unpublished | Very virulent |
| rD6948 | Boot et al, unpublished | Very virulent |
| UK661 | Brown and Skinner, 1996 | Very virulent |
| 5123 | Ter Huurne et al., unpublished | Very virulent |
| 96-B4 | Ter Huurne et al., unpublished | Avirulent |
| 96-C4 | Ter Huurne et al., unpublished | Avirulent |
| 96-C5 | Ter Huurne et al., unpublished | Avirulent |
| 96-C6 | Ter Huurne et al., unpublished | Very virulent |
| 97-B3 | Ter Huurne et al., unpublished | Avirulent |
| 97-B4 | Ter Huurne et al., unpublished | Very virulent |
| 97-B5 | Ter Huurne et al., unpublished | Very virulent |
| 97-B6 | Ter Huurne et al., unpublished | Very virulent |
| Zoontjes | Ter Huurne et al., unpublished | Very virulent |
| Hungary | Ter Huurne et al., unpublished | Very virulent |
| OKYM | Yamaguchi et al., 1996 | Very virulent |
| OKYMT | Yamaguchi et al., 1996 | Avirulent |
| TKSM | Yamaguchi et al., 1996 | Very virulent |
| TKSMT | Yamaguchi et al., 1996 | Avirulent |
| HK46 | Lim et al., 1999 | Very virulent |
| HK46-NT | Lim et al., 1999 | Not determined |

TABLE 8

Amino acid sequence of the hypervariable region of VP2 of different IBDV isolates. The sequence of the hydrophilic regions (underlined) and the hydrophobic region of very virulent isolate D6948 (amino acid 214 to 328) is used as parental isolate for alignment of the other sequences. Identical amino acid are represented by a dash.

```
D6949        214 AADDYQFSSQYQAGGVTITLFSANIDAITSLSIGGELVFQTSVQGLILGATIYLIGFDGTAVITRAVAADNGLTAGTDNLMPFNIV  328
(SEQ ID                                                                        IPTSEITPQITSIKLEIVTSKSGGQAGDQMSWS
NO:61)

rD6948           ----------------------------------------------------------------------------------------
(SEQ ID                                                                        --------------------------------
NO:61)

UK661            ----------------------------------------------------------------------------------------
(SEQ ID                                                                        --------------------------------
NO:61)

5123             ----------------------------------------------------------------------------------------
(SEQ ID                                                                        --------------------------------
NO:61)

96-B4            -------------P--------------------V--------------V--------------T--------N----T-----L----
(SEQ ID                                                                        ----N---------------------------
NO:62)

96-C4            -------------L--------------------N------A-N-----------T-------S-----T-I----------
(SEQ ID                                                                        ---N----------------------------
NO:63)

96-C5            -------------P--------------------V--------------V----------------------Y----T-----L----
(SEQ ID                                                                        ---N----------------------------
NO:64)

96-C6            ----------------------------------------------------------------------------------------
(SEQ ID                                                                        --------------------------------
NO:61)

97-B3            ------------------------------------------------------------------------N---------------
(SEQ ID                                                                        --------------------------------
NO:65)

97-B4            ----------------------------------------------------------------------------------------
(SEQ ID                                                                        --------------------------------
NO:61)

97-B5            ----------------------------------------------------------------------------------------
(SEQ ID                                                                        --------------------------------
NO:61)

97-B6            ----------------------------------------------------------------------------------------
(SEQ ID                                                                        --------------------------------
NO:61)

Zoontjes         ----------------------------------------------------------------------------------------
(SEQ ID                                                                        -----T----------V---------------
NO:66)

Hungary          ----------------------------------------------------------------------------------------
(SEQ ID                                                                        --------------------------------
NO:61)

OKYM             ----------------------------------------------------------------------------------------
(SEQ ID                                                                        --------------------------------
NO:61)

OKYMT            -----------------------------------------T---------------------N----T-----------
(SEQ ID                                                                        ------------------F-------------
NO:67)

TKSM             ----------------------------------------------------------------------------------------
(SEQ ID                                                                        --------------------------------
NO:61)

TKSMT            -----------------------------------H--------D-------------T------N----T-----------
(SEQ ID                                                                        --------------------------------
NO:68)

HK46             ----------------------------------------------------------------------------------------
(SEQ ID                                                                        --------------------------------
NO:61)
```

TABLE 8-continued

Amino acid sequence of the hypervariable region of VP2 of different IBDV isolates. The sequence of the hydrophilic regions (underlined) and the hydrophobic region of very virulent isolate D6948 (amino acid 214 to 328) is used as parental isolate for alignment of the other sequences. Identical amino acid are represented by a dash.

```
HK46-NT        ------------------------------------------------------------------N----T-----------
(SEQ ID                                                                                    -------------------------------
NO:69)
```

TABLE 9

| Virus | A-segment plasmid | B-segment plasmid | Feature |
|---|---|---|---|
| rCEF94 | pHB-36W | pHB-52 | Rescued CEF94 |
| mCEF94-s2VP3 | pHB36-s2VP3 | pHB-52 | Rescued mosaic IBDV, which encodes a polyprotein consisting of amino acid 1–723 originating from CEF94 and amino acids 724–1012 originating from TY89; 760 nucleotides have been exchanged of which 102 are different (13%). |
| mCEF94-s2VP3N | pHB36-s2VP3N | pHB-52 | Rescued mosaic IBDV, which encodes a polyprotein consisting of amino acid 1–723 and 857–1012 originating from CEF94 and amino acids 724–856 originating from TY89; 398 nucleotides have been exchanged of which 65 are different (16%). |
| mCEF94-s2VP3C | pHB36-s2VP3C | pHB-52 | Rescued mosaic IBDV, which encodes a polyprotein consisting of amino acid 1–856 originating from CEF94 and amino acids 857–1012 originating from TY89; 371 nucleotides have been exchanged, of which 37 are different (10%) |

TABLE 10

| Virus | TCID$_{50}$ after transfection | | | | Maximum* TCID$_{50}$ |
|---|---|---|---|---|---|
| | Exp. 1 | Exp. 2 | Exp. 3 | Average | |
| rCEF94 | 4.9 | 5.6 | 4.7 | 5.1 | 7.0 |
| mCEF94-s2VP3 | 2.0 | 0.3 | 1.0 | 1.1 | 6.0 |
| mCEF94-s2VP3N | 3.0 | 3.5 | 2.9 | 3.1 | 6.1 |
| mCEF94-s2VP3C | 5.0 | 5.0 | 4.3 | 4.8 | 6.9 |

*Determined after 3 passages of initially rescued virus

TABLE 12

Description of the used viruses

| Name | Based on plasmid[2] | Main features |
|---|---|---|
| CEF94 | n.r. | Serotype I, classical, cell culture adapted IBDV strain |
| D6948 | n.r. | Serotype I, very virulent IBDV field isolate |
| TY89 | n.r. | Prototype serotype II IBDV field isolate |
| rCEF94 | pHB-36W + pHB-34Z | Rescued CEF94: classical, cell culture adapted IBDV |
| rD6948 | pHB-60 + pHB-55 | Rescued D6948: very virulent IBDV |
| mCEF94-s2VP3 | pHB36-s2VP3 + pHB-34Z | Rescued mosaic IBDV having a hybrid polyprotein; amino acid 1–723 of CEF94 and 723–1012 of TY89 |
| mCEF94-s2VP3N | pHB36-s2VP3N + pHB-34Z | Rescued mosaic IBDV having a hybrid polyprotein; amino acid 1–723 and 857–1012 of CEF94 and 723–856 of TY89 |
| mCEF94-s2VP3C | pHB36-s2VP3C + pHB-34Z | Rescued mosaic IBDV having a hybrid polyprotein; amino acid 1–856 of CEF94 and 857–1012 of TY89 |
| mD6948-s2VP3N[1] | pHB60-s2VPN + pHB-55 | mosaic IBDV cDNA encoding a hybrid polyprotein; amino acid 1–723 and 857–1012 of D6948 and 723–856 of TY89 |
| mD6948-s2VP3C1 | pHB60-s2VP3C1 + pHB-55 | Rescued mosaic IBDV having a hybrid polyprotein; amino acid 1–543 of D6948, 544–856 of CEF94, and 857–1012 of TY89 |
| mD6948-s2VP3C3 | pHB60-s2VP3C3 + pHB-55 | Rescued mosaic IBDV having a hybrid polyprotein; amino acid 1–856 of D6948 and 857–1012 of TY89) |

[1]this virus could not be rescued
[2]n.r: not relevant

TABLE 11

| Monoclonal antibody | Directed against | Reaction of IBDV proteins in an immuno peroxidase monolayer assay | | | | | |
|---|---|---|---|---|---|---|---|
| | | CEF94 | TY89 | rCEF94 | mCEF94-s2VP3 | mCEF94-s2VP3N | mCEF94-s2VP3C |
| 1.4 | VP2, serotype I | + | − | + | + | + | + |
| 9.8 | VP2, serotype I | + | − | + | + | + | + |
| 9.7 | VP3, serotype I | + | + | + | + | + | + |
| IV | VP3, serotype I | + | − | + | − | + | − |
| I/G4 | VP3, serotype I | + | − | + | − | + | − |
| VII | VP3, serotype II | − | + | − | + | − | + |
| 17/80 | VP3, serotype I | + | + | + | + | + | + |

TABLE 13

Experimental data of the chicken infection experiments 1 and 2

| Virus | CODE | Mortality[1] | Idexx Antibody titers[2] | VN titers[3] | Bursa weight (gr)[4] | Bursa/Body weight[5] | HBLS[6] |
|---|---|---|---|---|---|---|---|
| Exp. 1 | 99.16 | | | | | | |
| PBS | Gr. 1 | 0/10 | 0 (0, 10, 0) | 0.0 (0.0) | 1.9 (0.4, 10) | 6.1 (1.2) | 1.0 (0.0, 9) |
| CEF94 | Gr. 2 | 0/10 | 207 (507, 6, 1) | 6.5 (1.2) | 2.0 (0.6, 6) | 6.0 (1.8) | 1.6 (1.1, 10) |
| rCEF94 | Gr. 4 | 0/10 | 260 (290, 6, 3) | 9.7 (1.8) | 1.3 (0.5, 6) | 4.2 (1.3) | 1.9 (0.7, 10) |
| mCEF94-s2VP3C | Gr. 11 | 0/10 | 824 (433, 6, 6) | 10.8 (1.5) | 1.3 (0.4, 6) | 4.1 (1.3) | 1.1 (0.3, 10) |
| D6948 | Gr. 3 | 3/10 | 1626 (690, 7, 7) | 10.3 (1.4) | 0.4 (0.1, 7) | 1.7 (0.6) | 5.0 (0.0, 7) |
| rD6948 | Gr. 5 | 5/10 | 1549 (791, 4, 4) | 10.3 (1.5) | 0.4 (0.1, 5) | 1.7 (0.2) | 5.0 (0.0, 4) |
| mD6948-s2VP3C1 | Gr. 12 | 0/10 | 956 (326, 6, 6) | 10.8 (1.2) | 0.6 (0.2, 6) | 1.9 (0.6) | 5.0 (0.0, 8) |
| Exp. 2 | 99.18 | | | | | | |
| PBS | Gr. 1 | 0/15 | 0 (0, 15, 0) | 0.0 (0.0) | 2.3 (0.7, 15) | 6.1 (1.8) | 1.4 (1.3, 10) |
| D6948 | Gr. 2 | 8/15 | 2489 (948, 7, 7) | 11.7 (1.6) | 0.3 (0.2, 7) | 0.8 (0.7) | 5.0 (0.0, 8) |
| rD6948 | Gr. 3 + 6 | 7/30 | 2308 (905, 23, 23) | 10.0 (1.5) | 0.3 (0.1, 23) | 1.0 (0.4) | 5.0 (0.0, 20) |
| mD6948-s2VP3C1 | Gr. 4 | 1/15 | 2122 (1300, 14, 14) | 9.0 (1.8) | 0.9 (0.2, 14) | 2.7 (0.7) | 4.7 (0.7, 10) |
| mD6948-s2VP3C3 | Gr. 5 | 0/15 | 1760 (880, 15, 15) | 8.8 (1.6) | 0.5 (0.1, 15) | 1.6 (0.4) | 5.0 (0.0, 10) |

[1]Accumulated number of mortalities during the first 5 days p.i./total number of challenged birds
[2]Average value (standard deviation, number of chicken samples used, number of positive samples)
[3]The presence of neutralizing antibodies was determined using the CEF94 IBDV strain; titers are given as 2Log values (standard deviation)
[4]Average bursa weight (*1000) of chickens in each group is given (standard deviation, number of animals)
[5]The bursa weight / body weight ratio for each animal was calculated and the average value (standard deviation) per group is given
[6]Average histopathologic bursal lesion score (HBLS) according to Bayyari et al (1996) of birds who survived the infection is given (standard deviation, number of bursae scored)

TABLE 14

IBDV specific antibody titers (Idexx) before and after infection with mD6948-s2VP3C3

| Days p.h.[1] | Group 1[2] | Group 2 | Group 3 | Group 4 | Group 5 |
|---|---|---|---|---|---|
| 7 | 1997 (300, 17, 17) | 2991 (543, 17, 17) | 3332 (691, 18, 18) | 3657 (676, 17, 17) | 3970 (446, 14, 14) |
| 15 | 18 (75, 17, 1) | 361 (101, 17, 16) | 576 (65, 18, 18) | 899 (150, 17, 17) | 1283 (154, 14, 14) |
| 18 | infection | infection | infection | infection | infection |
| 22 | 0 (0, 17, 0) | 0 (0, 17, 0) | 0 (0, 17, 0) | 0 (0, 17, 0) | 95 (261, 14, 2) |
| 25 | 391 (600, 12, 4) | 822 (1261, 12, 5) | 477 (1166, 13, 2) | 479 (750, 12, 4) | 516 (1084, 9, 3) |
| 32 | 1587 (852, 12, 11) | 1468 (746, 12, 12) | 367 (882, 12, 2) | 0 (0, 11, 0) | 0 (0, 9, 0) |
| 42 | 3241 (905, 11, 11) | 2877 (1177, 10, 10) | 149 (227, 11, 4) | 132 (234, 11, 2) | 2809 (633, 9, 9) |

[1]p.h. = post hatch
[2]The given antibody titers are the average of the positive animals with the standard deviation (first value between brackets), number of animal samples used (second value between brackets) and number of samples positive (third value between brackets) of values determined in duplo for each chicken in the group at a given day post hatch (p.h.)

TABLE 15

IBDV neutralizing antibody titers determined before and after infection with mD6948-s2VP3C3

| Days p.h.[1] | Group 1[2] | Group 2 | Group 3 | Group 4 | Group 5 |
|---|---|---|---|---|---|
| 15 | 7.2 (0.8, 17) | 8.8 (1.0, 17) | 9.3 (1.4, 15) | 9.9 (1.4, 17) | 9.9 (1.2, 14) |
| 18 | Infection | Infection | Infection | Infection | Infection |
| 25 | 5.8 (1.9, 12) | 4.8 (1.6, 12) | 6.4 (1.5, 8) | 7.6 (1.6, 7) | 7.3 (0.9, 9) |
| 32 | 10.9 (1.1, 12) | 10.8 (1.4, 12) | 5.3 (1.2, 12) | 5.4 (0.7, 11) | 5.6 (0.7, 9) |
| 42 | 9.8 (1.6, 11) | 10.0 (1.3, 10) | 3.6 (0.9, 11) | 3.7 (0.7, 11) | 9.3 (1.3, 9) |

[1]p.h. = post hatch
[2]The given values are the average of the individual $^2$Log virus neutralizing antibody titers of animals belonging to the same groups. Between brackets is the standard deviation and number of sera used, respectively.

TABLE 16

Description of plasmids and viruses

| Name | Based on plasmid* | Main feature |
|---|---|---|
| Plasmids | | |
| pUC18-Ribo | pUC18 | Contains the hepatitis delta virus ribozym |
| pHB-22R | pGEM-T | A-segment cDNA of D6948 (consensus sequence) |
| pHB-60 | pUC18-Ribo | A-segment cDNA of D6948, including a genetic tag |
| pHB-36W | pUC18-Ribo | A-segment cDNA of CEF94, including a genetic tag |
| pHB-34Z | pUC18-Ribo | B-segment cDNA of CEF94 (consensus sequence) |
| pHB-55 | pUC18-Ribo | B-segment cDNA of D6948 (consensus sequence) |
| pHB36-vvVP2 | pHB-36W | pVP2 of CEF94 cDNA is replaced by pVP2 of D6948 (453 amino acids) |
| pHB36-vvVP3 | pHB-36W | VP3 of CEF94 cDNA is replaced by VP3 of D6948 cDNA (289 amino acids) |
| pHB36-vvVP4 | pHB-36W | VP4 of CEF94 cDNA is replaced by VP4 of D6948 cDNA (270 amino acids) |
| Viruses | | |
| CEF94 | n.r. | Classical, cell culture adapted IBDV isolate (derivative of PVI) |
| D6948 | n.r. | Very virulent IBDV field isolate (The Netherlands, 1989) |
| rCEF94 | pHB-36W + pHB-34Z | Rescued IBDV: classical, cell culture adapted IBDV |
| rD6948 | pHB-60 + pHB-55 | Rescued IBDV: very virulent IBDV |
| srIBDV-CADB | pHB-36W + pHB-55 | Rescued segment reassorted IBDV: (A-segment = CEF94, B-segment = D6948) |
| srIBDV-DACB | pHB-60 + pHB-34Z | Rescued segment reassorted IBDV: (A-segment = D6948, B-segment CEF94) |
| mCEF94-vvVP2 | pHB36-vvVP2 + pHB-34Z | Rescued mosaic IBDV, pVP2 originates from D6948, the remaining parts from CEF94 |
| mCEF94-vvVP3 | pHB36-vvVP3 + pHB-34Z | Rescued mosaic IBDV, VP3 originates from D6948, the remaining parts from CEF94 |
| mCEF94-vvVP4 | pHB36-vvVP4 + pHB-34Z | Rescued mosaic IBDV, VP4 originates from D6948, the remaining parts from CEF94 |

*n.r: not relevant

TABLE 17

Experimental data of 21-day-old chickens challenged with 1000 $ELD_{50}$ of wild-type, rIBDV, srIBDV, or mIBDV isolates.

| Virus* | Mortality[1] | Bursa weight (gr)[2] | Bursa/Body weight[3] (*1000) | HBLS[4] | IBDV antigens[5] | Antibody titers[6] (Idexx) |
|---|---|---|---|---|---|---|
| PBS | 0/10 | 1.9 (0.4, 10) | 6.1 (1.2) | 1.0 (0.0, 9) | − | 0 (0, 10, 0) |
| CEF94 | 0/10 | 2.0 (0.6, 6) | 6.0 (1.8) | 1.6 (1.1, 10) | + | 207 (507, 6, 1) |
| D6948 | 3/10 | 0.4 (0.1, 7) | 1.7 (0.6) | 5.0 (0.0, 7) | nd | 1626 (690, 7, 7) |
| rCEF94 | 0/10 | 1.3 (0.5, 6) | 4.2 (1.3) | 1.9 (0.7, 10) | + | 260 (290, 6, 3) |
| rD6948 | 5/10 | 0.4 (0.1, 5) | 1.7 (0.2) | 5.0 (0.0, 4) | + | 1549 (791, 4, 4) |
| srIBDV-DACB | 2/10 | 0.4 (0.1, 8) | 1.5 (0.3) | 5.0 (0.0, 6) | + | 833 (415, 8, 8) |
| srIBDV-CADB† | 0/10 | 1.5 (0.4, 5) | 4.7 (1.0) | 1.9 (1.3, 10) | + | 400 (619, 6, 2) |
| mCEF94-vvVP2 | 0/10 | 0.6 (0.2, 6) | 1.9 (0.4) | 5.0 (0.0, 10) | + | 953 (186, 6, 6) |
| mCEF94-vvVP3 | 0/10 | 2.0 (0.3, 6) | 6.2 (0.7) | 1.4 (0.5, 10) | nd | 454 (399, 6, 4) |
| mCEF94-vvVP4 | 0/10 | 1.5 (0.5, 6) | 4.4 (1.3) | 1.5 (0.5, 10) | + | 431 (356, 6, 4) |

[1] Accumulated number of mortalities during the first 9 days p.i/total number of challenged birds
[2] Average bursa weight (9 days p.i.) of chickens is given (standard deviation, number of animals)
[3] The bursa/body weight ratio for each animal was calculated and the mean value (standard deviation) per group is given
[4] Average histopathologic bursal lesion score (HBLS) of birds who survived the challenge is given (standard deviation, number of bursae scored)
[5] Presence of VP4/VP3 antigens in bursa coupes was determined (nd = not done)
[6] IBDV Antibody titers (Idexx) of the chickens euthanised at day 9 p.i. (standard deviation, number of chickens used, number positive chickens).
*Viruses given in bold-face are unable to grow on QM5 cells
†The values of one chick of this group have been left out, as this chick had an unusually large bursa (3.4 gr)

REFERENCES

Antin, P. B. and Ordahl, C. P. (1991) Isolation and characterization of an avian myogenic cell line. Dev Biol 143(1), 111–21.

Berg, T. P. v. d., Gonze, M. and Meulemans, G. (1991) Acute infectious bursal disease in poultry: isolation and characterisation of a highly virulent strain. Avian Pathology 20(1), 133–143.

Bernard, J. (1980) *Drosophila* X virus RNA polymerase: tentative model for in vitro replication of the double-stranded virion RNA. J. Virol. 33, 717–723.

Britton, P., Green, P., Kottier, S., Mawditt, K. L., Penzes, Z., Cavanagh, D. and Skinner, M. A. (1996) Expression of bacteriophage T7 RNA polymerase in avian and mammalian cells by a recombinant fowlpox virus. J Gen Virol 77(Pt 5), 963–7.

Brown, M. D. and Skinner, M. A. (1996) Coding sequences of both genome segments of a European 'very virulent' infectious bursal disease virus. Virus Res. 40, 1–15.

Bruenn, J. A. (1991) Relationships among the positive strand and double-strand RNA viruses as viewed through their RNA-dependent RNA polymerases. Nucleic Acids Res 19(2), 217–26.

Chettle, N. J., Stuart, J. C. and Wyeth, P. J. (1989) Outbreak of virulent infectious bursal disease in East Anglia. Veterinary Record 125(10), 271–272.

Chowrira, B. M., Pavco, P. A. and McSwiggen, J. A. (1994) In vitro and in vivo comparison of hammerhead, hairpin, and hepatitis delta virus self-processing ribozyme cassettes. J Biol Chem 269(41), 25856–64.

Cosgrove, A. S. (1962) An apparently new disease of chickens: avian nephrosis. Avian Diseases 6, 385–389.

De Wit, J. J. and Van Loon, A. A. W. M. (1998) Gumboro-vaccinatie. Tijdschrift voor Diergeneeskunde 123, 7–10.

Diaz-Ruiz, J. R. and Kaper, J. M. (1978) Isolation of viral Double-stranded RNAs using a LiCl fractionation procedure. Preparatieve Biochemistery 8, 1–17.

Dobos, P., Hill, B. J., Hallett, R., Kells, D. T. C., Becht, H. and Teninges, D. (1979) Biophysical and biochemical characterization of five animal viruses with bisegmented double-stranded RNA genomes. J. Virol. 32, 593–605.

Ducatelle, R. V. A., Uyttebroek, E., De Ruyne, L., Mast, J., Goddeeris, B., Desmidt, M. and Deherdt, P. (1995) Infectious Bursal Disease in Europe, Consequences of changing epidemiological conditions. Summit on Infectious Bursal Disease, 10–14.

Eterradossi, N., Rivallan, G., Toquin, D. and Guittet, M. (1997) Limited antigenic variation among recent infectious bursal disease virus isolates from France. Arch Virol 142(10), 2079–87.

Frohman, M. A., Dush, M. K. and Martin, G. R. (1988) Rapid production of full-length cDNAs from rare transcripts: amplification using a single gene-specific oligonucleotide primer. Proc Natl Acad Sci USA 85(23), 8998–9002.

Gardner, H., Kerry, K., Riddle, M., Brouwer, S. and Gleeson, L. (1997) Poultry virus infection in Antarctic penguins [letter]. Nature 387(6630), 245.

Heine, H. G., Haritou, M., Failla, P., Fahey, K. and Azad, A. (1991) Sequence analysis and expression of the host-protective immunogen VP2 of a variant strain of infectious bursal disease virus which can circumvent vaccination with standard type I strains. Journal of General Virology 72(8), 1835–1843.

Ismail, Y. M., Saif, Y. M. and Moorhead, P. D. (1988) Lack of pathogenicity of five serotype 2 infectious bursal disease viruses in chickens. Avian Diseases 32(4), 757–759.

Jackwood, D. J., Saif, Y. M. and Hughes, J. H. (1982) Characteristics and serologic studies of two serotypes of infectious bursal disease virus in turkeys. Avian Dis 26(4), 871–82.

Kibenge, F. S., Qian, B., Cleghorn, J. R. and Martin, C. K. (1997) Infectious bursal disease virus polyprotein processing does not involve cellular proteases [In Process Citation]. Arch Virol 142(12), 2401–19.

Kouwenhoven, B. and Van den Bos, J. (1995) Control of Very virulent Infectious Bursal Disease (Gumboro Disease) in the Netherlands with more virulent vaccines. Summit on Infectious Bursal Disease, 29–32.

Lasher, H. N. and Shane, S. M. (1994) Infectious bursal disease. World's Poultry Science Journal 50(2), 133–166.

Lim, B. L., Cao, Y., Yu, T. and Mo, C. W. (1999) Adaptation of very virulent infectious bursal disease virus to chicken embryonic fibroblasts by site-directed mutagenesis of residues 279 and 284 of viral coat protein VP2. J Virol 73(4), 2854–62.

McFerran, J. B., McNulty, M. S., McKillop, T. J., McCracken, R. M., Collins, D. S. and Allan, G. M. (1980) Isolation and serological studies with infectious bursal disease viruses from fowl, turkey and ducks: demonstation of a second serotype. Avain Pathology 9, 395–404.

Mertens, P. P. C., Jamieson, P. B. and Dobos, P. (1982) In vitro RNA synthesis by infectious pancreatic necrosis virus-associated RNA polymerase. J. Gen. Virol. 59, 47–56.

Muller, H. (1991) Effect of viral structure and replication characteristics on the pathogenesis of infectious bursal disease. Berl. Munch. Tierartzl. Wochenschrift 104(4), 113–117.

Mundt, E. and Muller, H. (1995) Complete nucleotide sequences of 5'- and 3'-noncoding regions of both genome segments of different strains of infectious bursal disease virus. Virology 209(1), 10–8.

Mundt, E. and Vakharia, V. N. (1996) Synthetic transcripts of double-stranded Birnavirus genome are infectious. PNAS 93, 11131–11136.

Pattnaik, A. K., Ball, L. A., LeGrone, A. W. and Wertz, G. W. (1992) Infectious defective interfering particles of VSV from transcripts of a cDNA clone. Cell 69(6), 1011–20.

Petek, M., D'Aprile, P. N. and Cancellotti, F. (1973) Biological and phyco-chemical properties of the infectious bursal disease virus (IBDV). Avian Pathology 2, 135–152.

Snyder, D. B. (1990) Changes in the field status of infectious bursal disease virus. Avian Pathology 19(3), 419–423.

Snyder, D. B., Lana, D. P., Savage, P. K., Yancey, F. S., Mengel, S. A. and Marquardt, W. W. (1988a) Differentiation of infectious bursal disease viruses directly from infected tissues with neutralizing monoclonal antibodies: evidence of a major antigenic shift in recent field isolates. Avian Diseases 32(3), 535–539.

Snyder, D. B., Lutticken, D., Savage, P. K., Yancey, F. S., Van der Marel, P., Mengel, S. A., Russek-Cohen, E. and Marquardt, W. W. (1988b) Differentiation of infectious bursal disease virus (IBDV) directly from infected tissues: isolation and geographic distribution of a novel antigenic variant of IBDV. Proceedings of the 23rd National Meeting on Poultry Health and Condemnations. Vol. October 20–21, 119–128.

Vakharia, V. and Mundt, E. (1996) A method for generating Birnavirus from synthetic RNA transcripts.

Vakharia, V. N., He, J., Ahamed, B. and Snyder, D. b. (1994) Molecular basis of antigenic variation in infectious bursal disease virus. Virus Research 31, 265–273.

Weiland, J. J. and Dreher, T. W. (1989) Infectious TYMV RNA from cloned cDNA: effects in vitro and in vivo of point substitutions in the initiation codons of two extensively overlapping ORFs. Nucleic Acids Res 17(12), 4675–87.

Yamaguchi, T., Ogawa, M., Inoshima, Y., Miyoshi, M., Fukushi, H. and Hirai, K. (1996) Identification of sequence changes responsible for the attenuation of highly virulent infectious bursal disease virus. Virology 223, 219–223.

Higuchi. (1990) Recombinant PCR. In: M. A. Innis, D. H. Gelfnad, J. J. Sninsky and T. J. White (Eds), PCR protocols, Acedemic Press, San Diego, pp. 177–183.

Muller, H. (1987) Structural and pathogenic qualities of two serotypes as well as reassortant of the infectious virus bursitis (IBDV), Thesis, Justus Liebig-Universitat Giessen.

Mundt, E., B. Kollner, and D. Kretzschmar. (1997) VP5 of infectious bursal disease virus is not essential for viral replication in cell culture. J. Virol. 71(7), 5647–51.

Yao, K., Goodwin, M. A. and Vakharia, V. N. (1998) Generation of a mutant infectious bursal disease virus that does not cause bursal lesions. J Virol 72(4), 2647–54.

Higuchi. (1990) Recombinant PCR. In: M. A. Innis, D. H. Gelfnad, J. J. Sninsky and T. J. White (Eds), PCR protocols, Acedemic Press, San Diego, pp. 177–183.

Muller, H. (1987) Structural and pathogenic qualities of two serotypes as well as reassortant of the infectious virus bursitis (IBDV), Thesis, Justus Liebig-Universitat Giessen.

Mundt, E., B. Kollner, and D. Kretzschmar. (1997) VP5 of infectious bursal disease virus is not essential for viral replication in cell culture. J. Virol. 71(7), 5647–51.

Yao, K., Goodwin, M. A. and Vakharia, V. N. (1998) Generation of a mutant infectious bursal disease virus that does not cause bursal lesions. J Virol 72(4), 2647–54.

References Belonging to Example 1

Azad, A. A., Fahey, K. J., Barrett, S. A., Erny, K. M., and Hudson, P. J. (1986). Expression in *Escherichia coli* of cDNA fragments encoding the gene for the host-protective antigen of infectious bursal disease virus. *Virology* 149(2), 190–198.

Been, M. D., Perrotta, A. T., and Rosenstein, S. P. (1992). Secondary structure of the self-cleaving RNA of hepatitis delta virus: applications to catalytic RNA design. *Biochemistry* 31(47), 11843–52.

Boot, H. J., ter Huurne, A. A., Peeters, B. P., and Gielkens, A. L. (1999). Efficient rescue of infectious bursal disease virus from cloned cDNA: evidence for involvement of the 3'-terminal sequence in genome replication. *Virology* 265(2), 330–41.

Bottcher, B., Kiselev, N. A., Stel'Mashchuk, V. Y., Perevozchikova, N. A., Borisov, A. V., and Crowther, R. A. (1997). Three-dimensional structure of infectious bursal disease virus determined by electron cryomicroscopy. *J. Virol.* 71(1), 325–30.

Britton, P., Green, P., Kottier, S., Mawditt, K. L., Penzes, Z., Cavanagh, D., and Skinner, M. A. (1996). Expression of bacteriophage T7 RNA polymerase in avian and mammalian cells by a recombinant fowlpox virus. *Journal of General Virology* 77(Pt 5), 963–7.

Chettle, N. J., Stuart, J. C., and Wyeth, P. J. (1989). Outbreak of virulent infectious bursal disease in East Anglia. *Veterinary Record* 125(10), 271–272.

Cosgrove, A. S. (1962). An apparently new disease of chickens: avian nephrosis. *Avian Diseases* 6, 385–389.

Dobos, P. (1993). In vitro guanylylation of infectious pancreatic necrosis virus polypeptide VP1. *Virology* 193(1), 403–13.

Dobos, P. (1995). The molecular biology of infectious pancreatic necrosis virus (IPNV). *Annual Review of Fish Diseases* 5, 25–54.

Dobos, P., Hill, B. J., Hallett, R., Kells, D. T. C., Becht, H., and Teninges, D. (1979). Biophysical and biochemical characterization of five animal viruses with bisegmented double-stranded RNA genomes. *Journal of Virology* 32, 593–605.

Eterradossi, N., Arnauld, C., Tekaia, F., Toquin, D., Le Coq, H., Rivallan, G., Guitet, M., Domenech, J., Van den Berg, T. P., and Skinner, M. A. (1999). Antigenic and genetic relationships between European very virulent infectious bursal disease viruses and an early West African isolate. *Avian Pathology* 28, 36–46.

Fahey, K. J., Erny, K., and Crooks, J. (1989). A conformational immunogen on VP-2 of infectious bursal disease virus that induces virus-neutralizing antibodies that passively protect chickens. *Journal of General Virology* 70(6), 1473–1481.

Fahey, K. J., IJ, O. D., and Bagust, T. J. (1985). Antibody to the 32K structural protein of infectious bursal disease virus neutralizes viral infectivity in vitro and confers protection on young chickens. *Journal of General Virology* 66(12), 2693–2702. Hjalmarsson, A., and Everitt, E. (1999). Identification of IPNV-specified components released from productively infected RTG-2 cells following massive cytopathic effect. *Arch Virol* 144(8), 1487–501.

Hudson, P. J., McKern, N. M., Power, B. E., and Azad, A. A. (1986). Genomic structure of the large RNA segment of infectious bursal disease virus. *Nucleic Acid Research* 14, 5001–5012.

Ismail, Y. M., Saif, Y. M., and Moorhead, P. D. (1988). Lack of pathogenicity of five serotype 2 infectious bursal disease viruses in chickens. *Avian Diseases* 32(4), 757–759.

Jackwood, D. J., Saif, Y. M., Moorhead, P. D., and Bishop, G. (1984). Failure of two serotype II infectious bursal disease viruses to affect the humoral immune response of turkeys. *Avian Diseases* 28(1), 100–116.

Jackwood, D. J., and Sommer, S. E. (1999). Restriction fragment length polymorphisms in the VP2 gene of infectious bursal disease viruses from outside the United States. *Avian Diseases* 43(2), 310–4.

Kibenge, F. S., Qian, B., Cleghorn, J. R., and Martin, C. K. (1997). Infectious bursal disease virus polyprotein processing does not involve cellular proteases. *Archives of Virology* 142(12), 2401–19.

Lim, B. L., Cao, Y., Yu, T., and Mo, C. W. (1999). Adaptation of very virulent infectious bursal disease virus to chicken embryonic fibroblasts by site-directed mutagenesis of residues 279 and 284 of viral coat protein VP2. *Journal of Virology* 73(4), 2854–62.

Mahardika, G. N. K., and Becht, H. (1995). Mapping of cross-reacting and serotype-specific epitopes on the VP3 structural protein of the infectious bursal disease virus (IBDV). *Archives of Virology* 140(4), 765–774.

McFerran, J. B., McNulty, M. S., McKillop, T. J., McCracken, R. M., Collins, D. S., and Allan, G. M. (1980). Isolation and serological studies with infectious bursal disease viruses from fowl, turkey and ducks: demonstation of a second serotype. *Avain Pathology* 9, 395–404.

Mundt, E., Kollner, B., and Kretzschmar, D. (1997). VP5 of infectious bursal disease virus is not essential for viral replication in cell culture. *Journal of Virology* 71(7), 5647–5651. Mundt, E., and Vakharia, V. N. (1996). Synthetic transcripts of double-stranded Birnavirus genome are infectious. *Proceedings of the National Academy of Science USA* 93, 11131–11136.

Oppling, V., Muller, H., and Brecht, H. (1991). The structural polypeptide VP3 of infectious bursal disease virus carries group- and sertopy-specific epitopes. *Journal of General Virology* 72, 2275–2278.

Petek, M., D'Aprile, P. N., and Cancellotti, F. (1973). Biological and physico-chemical properties of the infectious bursal disease virus (IBDV). *Avian Pathology* 2, 135–152.

Reddy, S. K., Silim, A., and Ratcliffe, M. J. H. (1992). Biological roles of the major capsid proteins and relationships between the two existing serotypes of infectious bursal disease virus. *Archives of Virology* 127, 1–4.

Sambrook, J., Fritsch, E. F., and Maniatis, T. (1989). "Molecular Cloning: A Laboratory Manual." 2nd ed., Cold Spring Harbor Laboratory Press, Cold Spring Harbor, N.Y.

Sanchez, A. B., and Rodriguez, J. F. (1999). Proteolytic Processing in Infectious Bursal Disease Virus: Identification of the Polyprotein Cleavage Sites by Site-Directed Mutagenesis. *Virology* 262(1), 190–199.

Snyder, D. B. (1990). Changes in the field status of infectious bursal disease virus. *Avian Pathology* 19(3), 419–423.

Spies, U., and Muller, H. (1990). Demonstration of enzyme activities required for cap structure formation in infectious bursal disease virus, a member of the birnavirus group. *Journal of General Virology* 71(4), 977–981 van Oirschot, J. T. (1999). Diva vaccines that reduce virus transmission. *Journal of Biotechnology* 73(2–3), 195–205.

Yao, K., Goodwin, M. A., and Vakharia, V. N. (1998). Generation of a mutant infectious bursal disease virus that does not cause bursal lesions. *Journal of Virology* 72(4), 2647–54.

References Belonging to Example 2

Antin, P. B., and Ordahl, C. P. (1991). Isolation and characterization of an avian myogenic cell line. *Dev Biol* 143(1), 111–21.

Bayyari, G. R., Story, J. D., Beasley, J. N., and Skeeles, J. K. (1996). Pathogenicity studies of an Arkansas variant infectious bursal disease virus. *Avian Dis* 40(3), 516–32.

Boot, H. J., ter Huurne, A. A., Peeters, B. P., and Gielkens, A. L. (1999). Efficient rescue of infectious bursal disease virus from cloned cDNA: evidence for involvement of the 3'-terminal sequence in genome replication. *Virology* 265(2), 330–41.

Britton, P., Green, P., Kottier, S., Mawditt, K. L., Penzes, Z., Cavanagh, D., and Skinner, M. A. (1996). Expression of bacteriophage T7 RNA polymerase in avian and mammalian cells by a recombinant fowlpox virus. *Journal of General Virology* 77(Pt 5), 963–7.

Brown, M. D., and Skinner, M. A. (1996). Coding sequences of both genome segments of a European 'very virulent' infectious bursal disease virus. *Virus Res.* 40, 1–15.

Chettle, N. J., Stuart, J. C., and Wyeth, P. J. (1989). Outbreak of virulent infectious bursal disease in East Anglia. *Veterinary Record* 125(10), 271–272.

Cosgrove, A. S. (1962). An apparently new disease of chickens: avian nephrosis. *Avian Diseases* 6, 385–389.

Dobos, P. (1993). In vitro guanylylation of infectious pancreatic necrosis virus polypeptide VP1. *Virology* 193(1), 403–13.

Dobos, P., Hill, B. J., Hallett, R., Kells, D. T. C., Becht, H., and Teninges, D. (1979). Biophysical and biochemical characterization of five animal viruses with bisegmented double-stranded RNA genomes. *Journal of Virology* 32, 593–605.

Fahey, K. J., IJ, O. D., and Bagust, T. J. (1985). Antibody to the 32K structural protein of infectious bursal disease virus neutralizes viral infectivity in vitro and confers protection on young chickens. *Journal of General Virology* 66(12), 2693–2702.

Fernandez-Arias, A., Risco, C., Martinez, S., Albar, J. P., and Rodriguez, J. F. (1998). Expression of ORF A1 of infectious bursal disease virus results in the formation of virus-like particles. *J Gen Virol* 79(Pt 5), 1047–54.

Ismail, Y. M., Saif, Y. M., and Moorhead, P. D. (1988). Lack of pathogenicity of five serotype 2 infectious bursal disease viruses in chickens. *Avian Diseases* 32(4), 757–759.

Jackwood, D. J., Saif, Y. M., Moorhead, P. D., and Bishop, G. (1984). Failure of two serotype II infectious bursal disease viruses to affect the humoral immune response of turkeys. *Avian Diseases* 28(1), 100–116.

Kibenge, F. S., Qian, B., Cleghorn, J. R., and Martin, C. K. (1997). Infectious bursal disease virus polyprotein processing does not involve cellular proteases. *Archives of Virology* 142(12), 2401–19.

Mahardika, G. N. K., and Becht, H. (1995). Mapping of cross-reacting and serotype-specific epitopes on the VP3 structural protein of the infectious bursal disease virus (IBDV). *Archives of Virology* 140(4), 765–774.

McFerran, J. B., McNulty, M. S., McKillop, T. J., McCracken, R. M., Collins, D. S., and Allan, G. M. (1980). Isolation and serological studies with infectious bursal disease viruses from fowl, turkey and ducks: demonstation of a second serotype. *Avain Pathology* 9, 395–404.

Mundt, E. (1999). Tissue culture infectivity of different strains of infectious bursal disease virus is determined by distinct amino acids in VP2. *J Gen Virol* 80(Pt 8), 2067–76.

Oppling, V., Muller, H., and Brecht, H. (1991). The structural polypeptide VP3 of infectious bursal disease virus carries group- and sertopy-specific epitopes. *Journal of General Virology* 72, 2275–2278.

Petek, M., D'Aprile, P. N., and Cancellotti, F. (1973). Biological and physico-chemical properties of the infectious bursal disease virus (IBDV). *Avian Pathology* 2, 135–152.

Pol, J. M. A., Gielkens, A. L. J., and Van Oirschot, J. T. (1989). Comparative pathogenesis of three strains of pseudorabies virus in pigs. *Microbial Pathogenesis* 7, 361–371.

Snyder, D. B. (1990). Changes in the field status of infectious bursal disease virus. *Avian Pathology* 19(3), 419–423.

Wyatt, L. S., Moss, B., and Rozenblatt, S. (1995). Replication-deficient vaccinia virus encoding bacteriophage T7 RNA polymerase for transient gene expression in mammalian cells. *Virology* 210(1), 202–5.

Yamaguchi, T., Iwata, K., Kobayashi, M., Ogawa, M., Fukushi, H., and Hirai, K. (1996a). Epitope mapping of capsid proteins VP2 and VP3 of infectious bursal disease virus. *Archives of Virology* 141(8), 1493–507.

Yamaguchi, T., Kondo, T., Inoshima, Y., Ogawa, M., Miyoshi, M., Yanai, T., Masegi, T., Fukushi, H., and Hirai, K. (1996b). In vitro attenuation of highly virulent infectious bursal disease virus: some characteristics of attenuated strains. *Avian Dis* 40(3), 501–9.

Yamaguchi, T., Ogawa, M., Inoshima, Y., Miyoshi, M., Fukushi, H., and Hirai, K. (1996c). Identification of sequence changes responsible for the attenuation of highly virulent infectious bursal disease virus. *Virology* 223, 219–223.

Yehuda, H., Pitcovski, J., Michael, A., Gutter, B., and Goldway, M. (1999). Viral protein 1 sequence analysis of three infectious bursal disease virus strains: a very virulent virus, its attenuated form, and an attenuated vaccine. *Avian Dis* 43(1), 55–64.

References Belonging to Example 3

Antin, P. B., and C. P. Ordahl. 1991. Isolation and characterization of an avian myogenic cell line. Dev Biol. 143:111–21.

Bayyari, G. R., J. D. Story, J. N. Beasley, and J. K. Skeeles. 1996. Pathogenicity studies of an Arkansas variant infectious bursal disease virus. Avian Dis. 40:516–32.

Boot, H. J., A. A. ter Huurne, B. P. Peeters, and A. L. Gielkens. 1999. Efficient rescue of infectious bursal disease virus from cloned cDNA: evidence for involvement of the 3'-terminal sequence in genome replication. Virology. 265:330–41.

Bottcher, B., N. A. Kiselev, V. Y. Stel'Mashchuk, N. A. Perevozchikova, A. V. Borisov, and R. A. Crowther. 1997. Three-dimensional structure of infectious bursal disease virus determined by electron cryomicroscopy. J. Virol. 71:325–30.

Britton, P., P. Green, S. Kottier, K. L. Mawditt, Z. Penzes, D. Cavanagh, and M. A. Skinner. 1996. Expression of bacteriophage T7 RNA polymerase in avian and mammalian cells by a recombinant fowlpox virus. J Gen Virol. 77:963–7.

Brown, M. D., and M. A. Skinner. 1996. Coding sequences of both genome segments of a European 'very virulent' infectious bursal disease virus. Virus Res. 40:1–15.

Bruenn, J. A. 1991. Relationships among the positive strand and double-strand RNA viruses as viewed through their RNA-dependent RNA polymerases. Nucleic Acids Res. 19:217–26.

Chettle, N. J., J. C. Stuart, and P. J. Wyeth. 1989. Outbreak of virulent infectious bursal disease in East Anglia. Veterinary Record. 125:271–272.

Chowrira, B. M., P. A. Pavco, and J. A. McSwiggen. 1994. In vitro and in vivo comparison of hammerhead, hairpin, and hepatitis delta virus self-processing ribozyme cassettes. J Biol. Chem. 269:25856–64.

Cosgrove, A. S. 1962. An apparently new disease of chickens: avian nephrosis. Avian Diseases. 6:385–389.

Dobos, P. 1993. In vitro guanylylation of infectious pancreatic necrosis virus polypeptide VP1. Virology. 193:403–13.

Dobos, P. 1995. The molecular biology of infectious pancreatic necrosis virus (IPNV). Annual review of fish diseases. 5:25–54.

Dobos, P., B. J. Hill, R. Hallett, D. T. C. Kells, H. Becht, and D. Teninges. 1979. Biophysical and biochemical characterization of five animal viruses with bisegmented double-stranded RNA genomes. J. Virol. 32:593–605.

Eterradossi, N., and e. al. 1999. Antigenic and genetic relationships between European very virulent infectious bursal disease viruses and an early West african isolate. Avian Pathology. 28:36–46.

Hardy, E., H. Santana, A. Sosa, L. Hernandez, C. Fernandez-Patron, and L. Castellanos-Serra. 1996. Recovery of biologically active proteins detected with imidazole-sodium dodecyl sulfate-zinc (reverse stain) on sodium dodecyl sulfate gels. Anal Biochem. 240:150–2.

Higuchi. 1990. Recombinant PCR, p. 177–183. In M. A. Innis and D. H. Gelfnad and J. J. Sninsky and T. J. White (ed.), PCR protocols. Acedemic Press, San Diego.

Hudson, P. J., N. M. McKern, B. E. Power, and A. A. Azad. 1986. Genomic structure of the large RNA segment of infectious bursal disease virus. NAR. 14:5001–5012.

Kibenge, F. S., B. Qian, J. R. Cleghorn, and C. K. Martin. 1997. Infectious bursal disease virus polyprotein processing does not involve cellular proteases. Arch Virol. 142: 2401–19.

Lim, B. L., Y. Cao, T. Yu, and C. W. Mo. 1999. Adaptation of very virulent infectious bursal disease virus to chicken embryonic fibroblasts by site-directed mutagenesis of residues 279 and 284 of viral coat protein VP2. J. Virol. 73:2854–62.

Muller, H. 1991. Effect of viral structure and replication characteristics on the pathogenesis of infectious bursal disease. Berl Munch Tierarztl Wochenschr. 104:113–7.

Mundt, E. 1999. Tissue culture infectivity of different strains of infectious bursal disease virus is determined by distinct amino acids in VP2. J Gen Virol. 80:2067–76.

Petek, M., P. N. D'Aprile, and F. Cancellotti. 1973. Biological and physico-chemical properties of the infectious bursal disease virus (IBDV). Avian Pathology. 2:135–152.

Pitcovski, J., D. Goldberg, B. Z. Levi, D. Di-Castro, A. Azriel, S. Krispel, T. Maray, and Y. Shaaltiel. 1998. Coding region of segment A sequence of a very virulent isolate of IBDV-comparison with isolates from different countries and virulence. Avian Dis. 42:497–506.

Pol, J. M. A., A. L. J. Gielkens, and J. T. Van Oirschot. 1989. Comparative pathogenesis of three strains of pseudorabies virus in pigs. Microbial Pathogenesis. 7:361–371.

Ramig, R. F. 1997. Genetics of the rotaviruses. Annu Rev Microbiol. 51:225–55.

Sanchez, A. B., and J. F. Rodriguez. 1999. Proteolytic Processing in Infectious Bursal Disease Virus: Identification of the Polyprotein Cleavage Sites by Site-Directed Mutagenesis. Virology. 262:190–199.

Snyder, D. B. 1990. Changes in the field status of infectious bursal disease virus. Avian Pathology. 19:419–423.

Spies, U., and H. Muller. 1990. Demonstration of enzyme activities required for cap structure formation in infectious bursal disease virus, a member of the birnavirus group. J Gen Virol. 71:977–981.

Vasconcelos, A. C., and K. M. Lam. 1995. Apoptosis in chicken embryos induced by the infectious bursal disease virus. J Comp Pathol. 112:327–38.

Yamaguchi, T., T. Kondo, Y. Inoshima, M. Ogawa, M. Miyoshi, T. Yanai, T. Masegi, H. Fukushi, and K. Hirai. 1996. In vitro attenuation of highly virulent infectious bursal disease virus: some characteristics of attenuated strains. Avian Dis. 40:501–9.

Yamaguchi, T., M. Ogawa, Y. Inoshima, M. Miyoshi, H. Fukushi, and K. Hirai. 1996. Identification of sequence changes responsible for the attenuation of highly virulent infectious bursal disease virus. Virology. 223:219–223.

Yehuda, H., J. Pitcovski, A. Michael, B. Gutter, and M. Goldway. 1999. Viral protein 1 sequence analysis of three infectious bursal disease virus strains: a very virulent virus, its attenuated form, and an attenuated vaccine. Avian Dis. 43:55–64.

What is claimed is:

1. A method for obtaining an infectious recombinant very virulent Infectious Bursal Disease Virus (vvIBDV), said method comprising:
   transfecting at least one first cell, which cell is non-permissive for vvIBDV, with a recombinant nucleic acid comprising a vvIBDV genome;
   incubating said at least one first cell in a culture medium, so as to produce recombinant vvIBDV which recombinant vvIBDV does not infect said at least one first cell, and which further retains its vvIBDV character;
   rescuing said recombinant vvIBDV from said at least one transfected first cell or said culture medium; and
   propagating said recovered rescued recombinant vvIBDV in at least one second cell which is permissive for said vvIBDV.

2. The method according to claim 1 wherein said at least one first cell is a non-bursa cell-derived cell.

3. The method according to claim 2 wherein said at least one second cell is a bursa cell-derived cell.

4. The method according to claim 2 wherein said at least one first cell is a CEF cell, a VERO cell or a QM5 cell.

5. The method according to claim 4 wherein said at least one first cell has additionally been provided with a helper virus or a viral protein derived from a helper virus.

6. The method according to claim 5 wherein said viral protein comprises T7-polymerase.

7. The method according to claim 6 wherein said vvIBDV has at least retained the incapacity to be propagated on a vvIBDV non-permissive cell selected from the group consisting of a VERO, a QM5 and a CEF cell.

8. The method according to claim 3 wherein said at least one second cell is a primary bursa cell.

9. The method according to claim 1 wherein said vvIBDV comprises a serotype II IBDV nucleic acid.

10. The method according to claim 9 wherein said vvIBDV is lacking at least one immunodominant epitope specific for a serotype I IBDV.

11. The method according to claim 1 wherein said at least one second cell is a bursa cell-derived cell.

4. The method according to claim 2 wherein said at least one first cell is a CEF cell, a VERO cell or a QM5 cell.

* * * * *

UNITED STATES PATENT AND TRADEMARK OFFICE
CERTIFICATE OF CORRECTION

PATENT NO. : 7,294,500 B2
APPLICATION NO. : 10/046671
DATED : November 13, 2007
INVENTOR(S) : Hendrik Johannis Boot, Anna Agnes H. M. ter Huurne and Bernardus Petrus H. Peeters It is certified that error appears in the above-identified patent and that said Letters Patent is hereby corrected as shown below:

|  | COLUMN 76, | LINE 34, | create a new paragraph starting at "Hjalmarsson, A.," and ending at "1487–501." |
|---|---|---|---|
|  | COLUMN 77, | LINE 10, | create a new paragraph starting at "Mundt," and ending at "11131–11136." |
|  | COLUMN 80, | LINE 49, | create a new paragraph starting at "Ramig," and ending at "51:225-55." |
| CLAIM 4, | COLUMN 168, | LINE 65, | (duplicate) delete "4. The method according to claim 2 wherein said at least one first cell is a CEF cell, a VERO cell or a QM5 cell." |

Signed and Sealed this
Nineteenth Day of March, 2013

Teresa Stanek Rea
*Acting Director of the United States Patent and Trademark Office*

SEQUENCE LISTING

<160> NUMBER OF SEQ ID NOS: 87

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: KpnI
      restriction site

<400> SEQUENCE: 1 ggtaac                                                                6

<210> SEQ ID NO 2
<211> LENGTH: 16
<212> TYPE: DNA
<213> ORGANISM: Infectious bursal disease virus
<220> FEATURE:
<221> NAME/KEY: misc_feature
<223> OTHER INFORMATION: Primer ANC1

<400> SEQUENCE: 2
ggggacccgc gaacgg                                                    16

<210> SEQ ID NO 3
<211> LENGTH: 18
<212> TYPE: DNA
<213> ORGANISM: Infectious bursal disease virus
<220> FEATURE:
<221> NAME/KEY: misc_feature
<223> OTHER INFORMATION: Primer RTAM

<400> SEQUENCE: 3
aattggtgtc cacacctg                                                  18

<210> SEQ ID NO 4
<211> LENGTH: 18
<212> TYPE: DNA
<213> ORGANISM: Infectious bursal disease virus
<220> FEATURE:
<221> NAME/KEY: misc_feature
<223> OTHER INFORMATION: Primer RTAP

<400> SEQUENCE: 4
atacaggacc taactggg                                                  18

<210> SEQ ID NO 5
<211> LENGTH: 30
<212> TYPE: DNA
<213> ORGANISM: Infectious bursal disease virus
<220> FEATURE:
<221> NAME/KEY: misc_feature
<223> OTHER INFORMATION: Primer HY3P

<400> SEQUENCE: 5
aacgttttcc tcacaatccg cgggactggg                                     30

```
<210> SEQ ID NO 6
<211> LENGTH: 22
<212> TYPE: DNA
<213> ORGANISM: Infectious bursal disease virus
<220> FEATURE:
<221> NAME/KEY: misc_feature
<223> OTHER INFORMATION: Primer AGTM

<400> SEQUENCE: 6
gagactccca ggtacctcac tc                                          22

<210> SEQ ID NO 7
<211> LENGTH: 18
<212> TYPE: DNA
<213> ORGANISM: Infectious bursal disease virus
<220> FEATURE:
<221> NAME/KEY: misc_feature
<223> OTHER INFORMATION: Primer AC3

<400> SEQUENCE: 7
ggtagccaca tgtgacag                                               18

<210> SEQ ID NO 8
<211> LENGTH: 21
<212> TYPE: DNA
<213> ORGANISM: Infectious bursal disease virus
<220> FEATURE:
<221> NAME/KEY: misc_feature
<223> OTHER INFORMATION: Primer HY3MR

<400> SEQUENCE: 8
ccagtcccgc ggattgtgag g                                           21

<210> SEQ ID NO 9
<211> LENGTH: 17
<212> TYPE: DNA
<213> ORGANISM: Infectious bursal disease virus
<220> FEATURE:
<221> NAME/KEY: misc_feature
<223> OTHER INFORMATION: Primer M13F-17

<400> SEQUENCE: 9
gtaaaacgac ggccagt                                                17

<210> SEQ ID NO 10
<211> LENGTH: 18
<212> TYPE: DNA
<213> ORGANISM: Infectious bursal disease virus
<220> FEATURE:
<221> NAME/KEY: misc_feature
<223> OTHER INFORMATION: Primer AC4

<400> SEQUENCE: 10
acccagccaa tcacatcc                                               18

<210> SEQ ID NO 11
<211> LENGTH: 19
<212> TYPE: DNA
<213> ORGANISM: Infectious bursal disease virus
<220> FEATURE:
<221> NAME/KEY: misc_feature
<223> OTHER INFORMATION: Primer AC9

<400> SEQUENCE: 11
ctcaaagaag atggagacc                                              19

<210> SEQ ID NO 12
```

<211> LENGTH: 24
<212> TYPE: DNA
<213> ORGANISM: Infectious bursal disease virus
<220> FEATURE:
<221> NAME/KEY: misc_feature
<223> OTHER INFORMATION: Primer M13F-24

<400> SEQUENCE: 12
cgccagggtt tcccagtca cgac                                    24

<210> SEQ ID NO 13
<211> LENGTH: 22
<212> TYPE: DNA
<213> ORGANISM: Infectious bursal disease virus
<220> FEATURE:
<221> NAME/KEY: misc_feature
<223> OTHER INFORMATION: Primer AC5

<400> SEQUENCE: 13
aaggccttca tggaggtggc cg                                     22

<210> SEQ ID NO 14
<211> LENGTH: 21
<212> TYPE: DNA
<213> ORGANISM: Infectious bursal disease virus
<220> FEATURE:
<221> NAME/KEY: misc_feature
<223> OTHER INFORMATION: Primer AGTP

<400> SEQUENCE: 14
cttgagtgag gtacctggga g                                      21

<210> SEQ ID NO 15
<211> LENGTH: 21
<212> TYPE: DNA
<213> ORGANISM: Infectious bursal disease virus
<220> FEATURE:
<221> NAME/KEY: misc_feature
<223> OTHER INFORMATION: Primer vvVP3CM

<400> SEQUENCE: 15
gagaaaattt cgcatccgat g                                      21

<210> SEQ ID NO 16
<211> LENGTH: 22
<212> TYPE: DNA
<213> ORGANISM: Infectious bursal disease virus
<220> FEATURE:
<221> NAME/KEY: misc_feature
<223> OTHER INFORMATION: Primer M13R

<400> SEQUENCE: 16
tcacacagga aacagctatg ac                                     22

<210> SEQ ID NO 17
<211> LENGTH: 30
<212> TYPE: DNA
<213> ORGANISM: Infectious bursal disease virus
<220> FEATURE:
<221> NAME/KEY: misc_feature
<223> OTHER INFORMATION: Primer ATG3

<400> SEQUENCE: 17
catcgctgcg atcgtttgtc tgatctctac                             30

<210> SEQ ID NO 18
<211> LENGTH: 18

```
<212> TYPE: DNA
<213> ORGANISM: Infectious bursal disease virus
<220> FEATURE:
<221> NAME/KEY: misc_feature
<223> OTHER INFORMATION: Primer

<400> SEQUENCE: 18
atccgggccc taaggagg                                                18

<210> SEQ ID NO 19
<211> LENGTH: 17
<212> TYPE: DNA
<213> ORGANISM: Infectious bursal disease virus
<220> FEATURE:
<221> NAME/KEY: misc_feature
<223> OTHER INFORMATION: Primer ANC4"

<400> SEQUENCE: 19
gccaagtcgg tgtgcag                                                 17

<210> SEQ ID NO 20
<211> LENGTH: 21
<212> TYPE: DNA
<213> ORGANISM: Infectious bursal disease virus
<220> FEATURE:
<221> NAME/KEY: misc_feature
<223> OTHER INFORMATION: Primer HY0P

<400> SEQUENCE: 20
tatcattgat ggtcagtaga g                                            21

<210> SEQ ID NO 21
<211> LENGTH: 17
<212> TYPE: DNA
<213> ORGANISM: Infectious bursal disease virus
<220> FEATURE:
<221> NAME/KEY: misc_feature
<223> OTHER INFORMATION: Primer HY2M

<400> SEQUENCE: 21
caccggcaca gctatcc                                                 17

<210> SEQ ID NO 22
<211> LENGTH: 26
<212> TYPE: DNA
<213> ORGANISM: Infectious bursal disease virus
<220> FEATURE:
<221> NAME/KEY: misc_feature
<223> OTHER INFORMATION: Primer T7EcoRI

<400> SEQUENCE: 22
ggaattctaa tacgactcac tatagg                                       26

<210> SEQ ID NO 23
<211> LENGTH: 21
<212> TYPE: DNA
<213> ORGANISM: Infectious bursal disease virus
<220> FEATURE:
<221> NAME/KEY: misc_feature
<223> OTHER INFORMATION: Primer HY3M

<400> SEQUENCE: 23
ccagtcccgc ggattgtgag g                                            21

<210> SEQ ID NO 24
<211> LENGTH: 17
<212> TYPE: DNA
```

<213> ORGANISM: Infectious bursal disease virus
<220> FEATURE:
<221> NAME/KEY: misc_feature
<223> OTHER INFORMATION: Primer M13F

<400> SEQUENCE: 24
gtaaaacgac ggccagt                                                    17

<210> SEQ ID NO 25
<211> LENGTH: 16
<212> TYPE: DNA
<213> ORGANISM: Infectious bursal disease virus
<220> FEATURE:
<221> NAME/KEY: misc_feature
<223> OTHER INFORMATION: Primer HY4M

<400> SEQUENCE: 25
ccggcacagc tatcct                                                     16

<210> SEQ ID NO 26
<211> LENGTH: 17
<212> TYPE: DNA
<213> ORGANISM: Infectious bursal disease virus
<220> FEATURE:
<221> NAME/KEY: misc_feature
<223> OTHER INFORMATION: Primer ANC2

<400> SEQUENCE: 26
ctgcctgtcc tggagcc                                                    17

<210> SEQ ID NO 27
<211> LENGTH: 20
<212> TYPE: DNA
<213> ORGANISM: Infectious bursal disease virus
<220> FEATURE:
<221> NAME/KEY: misc_feature
<223> OTHER INFORMATION: Primer HY4P

<400> SEQUENCE: 27
acataatccg ggccataagg                                                 20

<210> SEQ ID NO 28
<211> LENGTH: 17
<212> TYPE: DNA
<213> ORGANISM: Infectious bursal disease virus
<220> FEATURE:
<221> NAME/KEY: misc_feature
<223> OTHER INFORMATION: Primer ANC3

<400> SEQUENCE: 28
cgatgggcgt tcgggtc                                                    17

<210> SEQ ID NO 29
<211> LENGTH: 18
<212> TYPE: DNA
<213> ORGANISM: Infectious bursal disease virus
<220> FEATURE:
<221> NAME/KEY: misc_feature
<223> OTHER INFORMATION: Primer ANC5

<400> SEQUENCE: 29
cccatctgga gcatatcc                                                   18

<210> SEQ ID NO 30
<211> LENGTH: 18
<212> TYPE: DNA
<213> ORGANISM: Infectious bursal disease virus

```
<220> FEATURE:
<221> NAME/KEY: misc_feature
<223> OTHER INFORMATION: Primer AC6

<400> SEQUENCE: 30
ttcacctggg gtactccg                                                        18

<210> SEQ ID NO 31
<211> LENGTH: 30
<212> TYPE: DNA
<213> ORGANISM: Infectious bursal disease virus
<220> FEATURE:
<221> NAME/KEY: primer_bind
<222> LOCATION: (1)..(30)
<223> OTHER INFORMATION: Anchor

<400> SEQUENCE: 31
cacgaattca ctatcgattc tggatccttc                                           30

<210> SEQ ID NO 32
<211> LENGTH: 20
<212> TYPE: DNA
<213> ORGANISM: Infectious bursal disease virus
<220> FEATURE:
<221> NAME/KEY: primer_bind
<222> LOCATION: (1)..(20)
<223> OTHER INFORMATION: Anchor primer

<400> SEQUENCE: 32
gaaggatcca gaatcgatag                                                      20

<210> SEQ ID NO 33
<211> LENGTH: 19
<212> TYPE: DNA
<213> ORGANISM: Infectious bursal disease virus
<220> FEATURE:
<221> NAME/KEY: primer_bind
<222> LOCATION: (1)..(19)
<223> OTHER INFORMATION: Primer ANC0

<400> SEQUENCE: 33
ggggacccgc gaacggatc                                                       19

<210> SEQ ID NO 34
<211> LENGTH: 16
<212> TYPE: DNA
<213> ORGANISM: Infectious bursal disease virus
<220> FEATURE:
<221> NAME/KEY: primer_bind
<222> LOCATION: (1)..(16)
<223> OTHER INFORMATION: Primer ANC1

<400> SEQUENCE: 34
ggggacccgc gaacgg                                                          16

<210> SEQ ID NO 35
<211> LENGTH: 47
<212> TYPE: DNA
<213> ORGANISM: Infectious bursal disease virus
<220> FEATURE:
<221> NAME/KEY: primer_bind
<222> LOCATION: (1)..(47)
<223> OTHER INFORMATION: Primer T7AC0

<400> SEQUENCE: 35
ggaattctaa tacgactcac tataggatac gatcggtctg accccgg                        47
```

```
<210> SEQ ID NO 36
<211> LENGTH: 15
<212> TYPE: DNA
<213> ORGANISM: Infectious bursal disease virus
<220> FEATURE:
<221> NAME/KEY: primer_bind
<222> LOCATION: (1)..(15)
<223> OTHER INFORMATION: Primer BNC1

<400> SEQUENCE: 36
gggggccccc gcagg                                                    15

<210> SEQ ID NO 37
<211> LENGTH: 45
<212> TYPE: DNA
<213> ORGANISM: Infectious bursal disease virus
<220> FEATURE:
<221> NAME/KEY: primer_bind
<222> LOCATION: (1)..(45)
<223> OTHER INFORMATION: Primer T7BC1"

<400> SEQUENCE: 37
ggaattctaa tacgactcac tataggatac gatgggtctg accct                   45

<210> SEQ ID NO 38
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: 5'-Terminus of the A-segment coding strand
      of IBDV

<400> SEQUENCE: 38
ugauacgauc                                                          10

<210> SEQ ID NO 39
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: 5'-Terminus of the A-segment coding strand
      of IBDV

<400> SEQUENCE: 39
agauacgauc                                                          10

<210> SEQ ID NO 40
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: 5'-Terminus of the A-segment coding strand
      of IBDV

<400> SEQUENCE: 40
ggauacgauc                                                          10

<210> SEQ ID NO 41
<211> LENGTH: 10
<212> TYPE: RNA
<213> ORGANISM: Infectious bursal disease virus
<220> FEATURE:
<221> NAME/KEY: misc_RNA
```

```
<222> LOCATION: (1)..(10)
<223> OTHER INFORMATION: Consensus sequence corresponding to the
      5'-terminus of the A-segment coding strand of
      IBDV

<400> SEQUENCE: 41
ggauacgauc                                                              10

<210> SEQ ID NO 42
<211> LENGTH: 4
<212> TYPE: RNA
<213> ORGANISM: Infectious bursal disease virus
<220> FEATURE:
<221> NAME/KEY: misc_RNA
<222> LOCATION: (1)..(4)
<223> OTHER INFORMATION: Complementary sequence of the 5'-terminus
      of the A-segment non-coding strand of IBDV

<400> SEQUENCE: 42 cggg                                                                     4

<210> SEQ ID NO 43
<211> LENGTH: 8
<212> TYPE: RNA
<213> ORGANISM: Infectious bursal disease virus
<220> FEATURE:
<221> NAME/KEY: misc_RNA
<222> LOCATION: (1)..(8)
<223> OTHER INFORMATION: Complementary sequence of the 5'-terminus
      of the A-segment non-coding strand of IBDV

<400> SEQUENCE: 43 cggguccc                                                                 8

<210> SEQ ID NO 44
<211> LENGTH: 9
<212> TYPE: RNA
<213> ORGANISM: Infectious bursal disease virus
<220> FEATURE:
<221> NAME/KEY: misc_RNA
<222> LOCATION: (1)..(9)
<223> OTHER INFORMATION: Complementary sequence of the 5'-terminus
      of the A-segment non-coding strand of IBDV

<400> SEQUENCE: 44 cgggucccu                                                                9

<210> SEQ ID NO 45
<211> LENGTH: 9
<212> TYPE: RNA
<213> ORGANISM: Infectious bursal disease virus
<220> FEATURE:
<221> NAME/KEY: misc_RNA
<222> LOCATION: (1)..(9)
<223> OTHER INFORMATION: Complementary sequence of the 5'-terminus
      of the A-segment non-coding strand of IBDV

<400> SEQUENCE: 45 cggguccccc                                                               9

<210> SEQ ID NO 46
<211> LENGTH: 11
<212> TYPE: RNA
<213> ORGANISM: Infectious bursal disease virus
<220> FEATURE:
<221> NAME/KEY: misc_RNA
<222> LOCATION: (1)..(11)
<223> OTHER INFORMATION: Complementary sequence of the 5'-terminus
      of the A-segment non-coding strand of IBDV
```

<400> SEQUENCE: 46
cggguccccc c					11

<210> SEQ ID NO 47
<211> LENGTH: 12
<212> TYPE: RNA
<213> ORGANISM: Infectious bursal disease virus
<220> FEATURE:
<221> NAME/KEY: misc_RNA
<222> LOCATION: (1)..(12)
<223> OTHER INFORMATION: Complementary sequence of the 5'-terminus
      of the A-segment non-coding strand of IBDV

<400> SEQUENCE: 47
cggguccccc cu					12

<210> SEQ ID NO 48
<211> LENGTH: 12
<212> TYPE: RNA
<213> ORGANISM: Infectious bursal disease virus
<220> FEATURE:
<221> NAME/KEY: misc_RNA
<222> LOCATION: (1)..(12)
<223> OTHER INFORMATION: Complementary sequence of the 5'-terminus
      of the A-segment non-coding strand of IBDV

<400> SEQUENCE: 48
cggguccccc cc					12

<210> SEQ ID NO 49
<211> LENGTH: 9
<212> TYPE: RNA
<213> ORGANISM: Infectious bursal disease virus
<220> FEATURE:
<221> NAME/KEY: misc_RNA
<222> LOCATION: (1)..(9)
<223> OTHER INFORMATION: Consensus complementary sequence of the
      5'-terminus of the A-segment non-coding strand of
      IBDV

<400> SEQUENCE: 49 cgggucccc					9

<210> SEQ ID NO 50
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: 5'-Terminus of the B-segment coding strand
      of IBDV

<400> SEQUENCE: 50 ugauacgaug					10

<210> SEQ ID NO 51
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: 5'-Terminus of the B-segment coding strand
      of IBDV

<400> SEQUENCE: 51

-continued ggauacgaug                                                            10

<210> SEQ ID NO 52
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: Consensus sequence of the 5'-terminus of
      the B-segment coding strand of IBDV

<400> SEQUENCE: 52
ggauacgaug                                                            10

<210> SEQ ID NO 53
<211> LENGTH: 8
<212> TYPE: RNA
<213> ORGANISM: Infectious bursal disease virus
<220> FEATURE:
<221> NAME/KEY: misc_RNA
<222> LOCATION: (1)..(8)
<223> OTHER INFORMATION: Complementary sequence of the 5'-terminus
      of the B-segment non-coding strand of IBDV

<400> SEQUENCE: 53 gggggcca                                                               8

<210> SEQ ID NO 54
<211> LENGTH: 8
<212> TYPE: RNA
<213> ORGANISM: Infectious bursal disease virus
<220> FEATURE:
<221> NAME/KEY: misc_RNA
<222> LOCATION: (1)..(8)
<223> OTHER INFORMATION: Complementary sequence of the 5'-terminus
      of the B-segment non-coding strand of IBDV

<400> SEQUENCE: 54 gggggccu                                                               8

<210> SEQ ID NO 55
<211> LENGTH: 8
<212> TYPE: RNA
<213> ORGANISM: Infectious bursal disease virus
<220> FEATURE:
<221> NAME/KEY: misc_RNA
<222> LOCATION: (1)..(8)
<223> OTHER INFORMATION: Complementary sequence of the 5'-terminus
      of the B-segment non-coding strand of IBDV

<400> SEQUENCE: 55 gggggccc                                                               8

<210> SEQ ID NO 56
<211> LENGTH: 9
<212> TYPE: RNA
<213> ORGANISM: Infectious bursal disease virus
<220> FEATURE:
<221> NAME/KEY: misc_RNA
<222> LOCATION: (1)..(9)
<223> OTHER INFORMATION: Complementary sequence of the 5'-terminus
      of the B-segment non-coding strand of IBDV

<400> SEQUENCE: 56 gggggcccc                                                              9

<210> SEQ ID NO 57

```
<211> LENGTH: 10
<212> TYPE: RNA
<213> ORGANISM: Infectious bursal disease virus
<220> FEATURE:
<221> NAME/KEY: misc_RNA
<222> LOCATION: (1)..(10)
<223> OTHER INFORMATION: Complementary sequence of the 5'-terminus
      of the B-segment non-coding strand of IBDV

<400> SEQUENCE: 57
gguggccccc                                                            10

<210> SEQ ID NO 58
<211> LENGTH: 11
<212> TYPE: RNA
<213> ORGANISM: Infectious bursal disease virus
<220> FEATURE:
<221> NAME/KEY: misc_RNA
<222> LOCATION: (1)..(11)
<223> OTHER INFORMATION: Complementary sequence of the 5'-terminus
      of the B-segment non-coding strand of IBDV

<400> SEQUENCE: 58
gggggccccc c                                                          11

<210> SEQ ID NO 59
<211> LENGTH: 11
<212> TYPE: RNA
<213> ORGANISM: Infectious bursal disease virus
<220> FEATURE:
<221> NAME/KEY: misc_RNA
<222> LOCATION: (1)..(11)
<223> OTHER INFORMATION: Complementary sequence of the 5'-terminus
      of the B-segment non-coding strand of IBDV

<400> SEQUENCE: 59
gggggccccc g                                                          11

<210> SEQ ID NO 60
<211> LENGTH: 10
<212> TYPE: DNA
<213> ORGANISM: Infectious bursal disease virus
<220> FEATURE:
<221> NAME/KEY: misc_RNA
<222> LOCATION: (1)..(10)
<223> OTHER INFORMATION: Consensus complementary sequence of the
      5'-terminus of the B-segment non-coding strand of
      IBDV

<400> SEQUENCE: 60
gggggccccc                                                            10

<210> SEQ ID NO 61
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolates D6948, rD6948, UK661
      5123, 96-C6, 97-B4, 97-B5, 97-B6, Hungary, OKYM,
      TKSM and HK46

<400> SEQUENCE: 61

Ala Ala Asp Asp Tyr Gln Phe Ser Ser Gln Tyr Gln Ala Gly Gly Val
 1               5                  10                  15

Thr Ile Thr Leu Phe Ser Ala Asn Ile Asp Ala Ile Thr Ser Leu Ser
            20                  25                  30
```

```
Ile Gly Gly Glu Leu Val Phe Gln Thr Ser Val Gln Gly Leu Ile Leu
            35                  40                  45

Gly Ala Thr Ile Tyr Leu Ile Gly Phe Asp Gly Thr Ala Val Ile Thr
        50                  55                  60

Arg Ala Val Ala Ala Asp Asn Gly Leu Thr Ala Gly Thr Asp Asn Leu
65                  70                  75                  80

Met Pro Phe Asn Ile Val Ile Pro Thr Ser Glu Ile Thr Gln Pro Ile
                85                  90                  95

Thr Ser Ile Lys Leu Glu Ile Val Thr Ser Lys Ser Gly Gly Gln Ala
                100                 105                 110

Gly Asp Gln Met Ser Trp Ser
            115

<210> SEQ ID NO 62
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate 96-B4

<400> SEQUENCE: 62

Ala Ala Asp Asp Tyr Gln Phe Ser Ser Gln Tyr Gln Pro Gly Gly Val
1               5                   10                  15

Thr Ile Thr Leu Phe Ser Ala Asn Ile Asp Ala Ile Thr Ser Leu Ser
            20                  25                  30

Val Gly Gly Glu Leu Val Phe Gln Thr Ser Val Gln Gly Leu Val Leu
            35                  40                  45

Gly Ala Thr Ile Tyr Leu Ile Gly Phe Asp Gly Thr Thr Val Ile Thr
        50                  55                  60

Arg Ala Val Ala Ala Asn Asn Gly Leu Thr Thr Gly Thr Asp Asn Leu
65                  70                  75                  80

Leu Pro Phe Asn Ile Val Ile Pro Thr Asn Glu Ile Thr Gln Pro Ile
                85                  90                  95

Thr Ser Ile Lys Leu Glu Ile Val Thr Ser Lys Ser Gly Gly Gln Ala
                100                 105                 110

Gly Asp Gln Met Ser Trp Ser
            115

<210> SEQ ID NO 63
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate 96-C4

<400> SEQUENCE: 63

Ala Ala Asp Asp Tyr Gln Phe Ser Ser Gln Tyr Gln Leu Gly Gly Val
1               5                   10                  15

Thr Ile Thr Leu Phe Ser Ala Asn Ile Asp Ala Ile Thr Ser Leu Ser
            20                  25                  30

Ile Gly Gly Glu Leu Val Phe Asn Thr Ser Val Gln Gly Leu Ala Leu
            35                  40                  45

Asn Ala Thr Ile Tyr Leu Ile Gly Phe Asp Gly Thr Thr Val Ile Thr
```

```
                50                  55                  60
Arg Ala Val Ala Ser Asp Asn Gly Leu Thr Thr Gly Ile Asp Asn Leu
 65                  70                  75                  80

Met Pro Phe Asn Ile Val Ile Pro Thr Asn Glu Ile Thr Gln Pro Ile
                 85                  90                  95

Thr Ser Ile Lys Leu Glu Ile Val Thr Ser Lys Ser Gly Gly Gln Ala
                100                 105                 110

Gly Asp Gln Met Ser Trp Ser
            115

<210> SEQ ID NO 64
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of a IBDV isolate 96-C5

<400> SEQUENCE: 64

Ala Ala Asp Asp Tyr Gln Phe Ser Ser Gln Tyr Gln Pro Gly Gly Val
  1               5                  10                  15

Thr Ile Thr Leu Phe Ser Ala Asn Ile Asp Ala Ile Thr Ser Leu Ser
                 20                  25                  30

Val Gly Gly Glu Leu Val Phe Gln Thr Ser Val Gln Gly Leu Val Leu
             35                  40                  45

Gly Ala Thr Ile Tyr Leu Ile Gly Phe Asp Gly Thr Ala Val Ile Thr
     50                  55                  60

Arg Ala Val Ala Ala Tyr Asn Gly Leu Thr Thr Gly Thr Asp Asn Leu
 65                  70                  75                  80

Leu Pro Phe Asn Ile Val Ile Pro Thr Asn Glu Ile Thr Gln Pro Ile
                 85                  90                  95

Thr Ser Ile Lys Leu Glu Ile Val Thr Ser Lys Ser Gly Gly Gln Ala
                100                 105                 110

Gly Asp Gln Met Ser Trp Ser
            115

<210> SEQ ID NO 65
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate 97-B3

<400> SEQUENCE: 65

Ala Ala Asp Asp Tyr Gln Phe Ser Ser Gln Tyr Gln Ala Gly Gly Val
  1               5                  10                  15

Thr Ile Thr Leu Phe Ser Ala Asn Ile Asp Ala Ile Thr Ser Leu Ser
                 20                  25                  30

Ile Gly Gly Glu Leu Val Phe Gln Thr Ser Val Gln Gly Leu Ile Leu
             35                  40                  45

Gly Ala Thr Ile Tyr Leu Ile Gly Phe Asp Gly Thr Ala Val Ile Thr
     50                  55                  60

Arg Ala Val Ala Ala Asn Asn Gly Leu Thr Ala Gly Thr Asp Asn Leu
 65                  70                  75                  80
```

```
Met Pro Phe Asn Ile Val Ile Pro Thr Ser Glu Ile Thr Gln Pro Ile
                85                  90                  95

Thr Ser Ile Lys Leu Glu Ile Val Thr Ser Lys Ser Gly Gly Gln Ala
            100                 105                 110

Gly Asp Gln Met Ser Trp Ser
        115

<210> SEQ ID NO 66
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate Zoontjes

<400> SEQUENCE: 66

Ala Ala Asp Asp Tyr Gln Phe Ser Ser Gln Tyr Gln Ala Gly Gly Val
  1               5                  10                  15

Thr Ile Thr Leu Phe Ser Ala Asn Ile Asp Ala Ile Thr Ser Leu Ser
             20                  25                  30

Ile Gly Gly Glu Leu Val Phe Gln Thr Ser Val Gln Gly Leu Ile Leu
         35                  40                  45

Gly Ala Thr Ile Tyr Leu Ile Gly Phe Asp Gly Thr Ala Val Ile Thr
     50                  55                  60

Arg Ala Val Ala Ala Asp Asn Gly Leu Thr Ala Gly Thr Asp Asn Leu
 65                  70                  75                  80

Met Pro Phe Asn Ile Val Ile Pro Thr Ser Glu Thr Thr Gln Pro Ile
                85                  90                  95

Thr Ser Ile Lys Leu Val Ile Val Thr Ser Lys Ser Gly Gly Gln Ala
            100                 105                 110

Gly Asp Gln Met Ser Trp Ser
        115

<210> SEQ ID NO 67
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate OKYMT

<400> SEQUENCE: 67

Ala Ala Asp Asp Tyr Gln Phe Ser Ser Gln Tyr Gln Ala Gly Gly Val
  1               5                  10                  15

Thr Ile Thr Leu Phe Ser Ala Asn Ile Asp Ala Ile Thr Ser Leu Ser
             20                  25                  30

Ile Gly Gly Glu Leu Val Phe Gln Thr Ser Val Gln Gly Leu Thr Leu
         35                  40                  45

Gly Ala Thr Ile Tyr Leu Ile Gly Phe Asp Gly Thr Ala Val Ile Thr
     50                  55                  60

Arg Ala Val Ala Ala Asn Asn Gly Leu Thr Thr Gly Thr Asp Asn Leu
 65                  70                  75                  80

Met Pro Phe Asn Ile Val Ile Pro Thr Ser Glu Ile Thr Gln Pro Ile
                85                  90                  95

Thr Ser Ile Lys Leu Glu Ile Val Thr Phe Lys Ser Gly Gly Gln Ala
            100                 105                 110
```

Gly Asp Gln Met Ser Trp Ser
        115

<210> SEQ ID NO 68
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate TKSMT

<400> SEQUENCE: 68

Ala Ala Asp Asp Tyr Gln Phe Ser Ser Gln Tyr Gln Ala Gly Gly Val
 1               5                  10                  15

Thr Ile Thr Leu Phe Ser Ala Asn Ile Asp Ala Ile Thr Ser Leu Ser
            20                  25                  30

Ile Gly Gly Glu Leu Val Phe His Thr Ser Val Gln Gly Leu Ile Leu
        35                  40                  45

Asp Ala Thr Ile Tyr Leu Ile Gly Phe Asp Gly Thr Ala Val Thr Thr
    50                  55                  60

Arg Ala Val Ala Ala Asn Asn Gly Leu Thr Thr Gly Thr Asp Asn Leu
65                  70                  75                  80

Met Pro Phe Asn Ile Val Ile Pro Thr Ser Glu Ile Thr Gln Pro Ile
                85                  90                  95

Thr Ser Ile Lys Leu Glu Ile Val Thr Ser Lys Ser Gly Gly Gln Ala
            100                 105                 110

Gly Asp Gln Met Ser Trp Ser
        115

<210> SEQ ID NO 69
<211> LENGTH: 119
<212> TYPE: PRT
<213> ORGANISM: Infectious bursal disease virus
<220> FEATURE:
<221> NAME/KEY: DOMAIN
<222> LOCATION: (1)..(119)
<223> OTHER INFORMATION: Amino acid sequence of the hypervariable
      region of VP2 of IBDV isolate HK46-NT

<400> SEQUENCE: 69

Ala Ala Asp Asp Tyr Gln Phe Ser Ser Gln Tyr Gln Ala Gly Gly Val
 1               5                  10                  15

Thr Ile Thr Leu Phe Ser Ala Asn Ile Asp Ala Ile Thr Ser Leu Ser
            20                  25                  30

Ile Gly Gly Glu Leu Val Phe Gln Thr Ser Val Gln Gly Leu Ile Leu
        35                  40                  45

Gly Ala Thr Ile Tyr Leu Ile Gly Phe Asp Gly Thr Ala Val Ile Thr
    50                  55                  60

Arg Ala Val Ala Ala Asn Asn Gly Leu Thr Thr Gly Thr Asp Asn Leu
65                  70                  75                  80

Met Pro Phe Asn Ile Val Ile Pro Thr Ser Glu Ile Thr Gln Pro Ile
                85                  90                  95

Thr Ser Ile Lys Leu Glu Ile Val Thr Ser Lys Ser Gly Gly Gln Ala
            100                 105                 110

Gly Asp Gln Met Ser Trp Ser
        115

<210> SEQ ID NO 70
<211> LENGTH: 3260
<212> TYPE: DNA
<213> ORGANISM: Infectious bursal disease virus
<220> FEATURE:
<221> NAME/KEY: misc_feature
<222> LOCATION: (1)..(3260)
<223> OTHER INFORMATION: Consensus cDNA sequence of IBDV A-segment

<400> SEQUENCE: 70

```
ggatacgatc ggtctgaccc cgggggagtc acccgggggac aggcygwcaa ggycttgttc      60
caggatggaa ctcctccttc tacaaygcta tcattgatgg tyagtagaga tcagacaaac     120
gatcgcagcg atgacraacc tgcaagatca aacccaacag attgttccgt tcatacggag     180
ccttctgatg ccaacaaccg gaccggcgtc cattccggac gacaccctrg agaagcacac     240
tctcaggtca gagacctcga cctacaattt gactgtgggg gacacaggt cagggctaat      300
tgtcttttc cctggwttcc ctggctcaat tgtgggtgct cactacacac tgcagagcaa      360
tgggaactac aagttcgatc agatgctcct gactgcccag aacctaccgg ccagytacaa     420
ctactgcagg ctagtgagtc ggagtctcac agtgaggtca agcacactyc ctggtggcgt     480
ttatgcacta aayggcacca taaacgccgt gaccttccaa ggaagcctga gtgaactgac     540
agatgttagc tacaatgggt tgatgtctgc aacagccaac atcaacgaca aaatygggaa     600
cgtcctagta ggggaagggg tmaccgtcct cagcttaccc acatcatatg atcttgggta     660
tgtgagrcty ggtgacccca ttcccgcwat agggctygac ccaaaaatgg tagcmacatg     720
tgacagcagt gacaggccca gagtctacac cataactgca gccgatgatt accaattctc     780
atcacagtac caascaggtg gggtaacaat cacactgttc tcagcyaaya tygatgccat     840
cacaagcctc agcrtygggg gagarctcgt gtttcaaaca agcgtccamg gccttrtact     900
gggygcyacc atctacctya taggctttga tgggacwgcg gtaatcacca grgctgtggc     960
cgcaracaat gggctracgr ccggcacyga caaccttwtg ccattcaatm ttgtgattcc    1020
aacmarcgag ataacccagc caatcacatc catcaaactg gagatagtga cctccaaaag    1080
tggtggtcag gcrggggatc agatgtcrtg gtcrgcaagw gggagcctag cagtgacgat    1140
ccayggtggc aactatccag ggccctccg tcccgtcacr ctagtrgcct acgaaagagt    1200
ggcaacagga tcygtcgtta cggtcgcygg ggtgagcaac ttcgagctga tcccaaatcc    1260
tgaactagca agaacctggt tyacagaata cggccgattt gacccaggag ccatgaacta    1320
cacaaaattg atactgagtg agagggaccg tcttggcatc aagaccgtmt ggccaacaag    1380
ggagtacact gactttcgyg artacttcat ggaggtggcc gacctcaact ctcccctgaa    1440
gattgcagga gcattyggct tcaaagacat aatccgggcc mtaaggagga tagctgtgcc    1500
ggtggtctcy acaytgttcc caccygccgc tcccctagcc catgcaattg gggaaggtgt    1560
agactacctg ctgggcgatg aggcacaggc tgcttcagga actgctcgag ccgcgtcagg    1620
aaaagcaaga gctgcctcag gccgcataag gcagctract ctcgccgccg acaagggta    1680
cgaggtagtc gcgaatctrt tycaggtgcc ccagaatccy gtagtcgacg ggattctygc    1740
ttcacctggg rtactccgcg gygcacacaa cctcgactgc gtgttragag agggtgccac    1800
gctattccct gtggtyatya cgacagtgga agaygccatg acacccaaag caytgaacag    1860
caaaatgttt gctgtcattg aaggcgtgcg agaagayctc caacctccwt ctcaaagagg    1920
atccttcata cgaactctct cyggacayag agtctatgga tatgctccag atgggggact    1980
tccactggag actgggagag aytacaccgt kgtcccaata gatgatgtct gggacgacag    2040
```

-continued

| | | | | |
|---|---|---|---|---|
| cattatgctg | tccaaagayc | ccatacctcc | tattgtggga | aacagyggaa ayctagccat | 2100 |
| agcttacatg | gatgtgtttc | gacccaaagt | cccmatccat | gtggcyatga cgggagccct | 2160 |
| caaygcytrt | ggcgagattg | agaamgtrag | ctttagaagc | accaagctcg ccactgcaca | 2220 |
| ccgacttggc | ctyaagttgg | ctggtcccgg | wgcattygay | gtraacaccg ggyccaactg | 2280 |
| ggcracgtty | atcaaacgtt | tycctcacaa | tccmcgmgac | tggacaggy tmccytacct | 2340 |
| caacctwccm | tayctyccac | cmamwgcwgg | acgycagtwc | sayctkgccm tggchgchtc | 2400 |
| mgagttcaaa | gagaccccmg | aactcgarrr | ygcygtsmgw | gcmatggamg cwgcwgcmaa | 2460 |
| cgtsgaccca | ytrttccrmt | cwgcdctcmr | bgtsttcatg | tggytggaag araaygggat | 2520 |
| tgtracygay | atggcyaact | tcgcmctcag | cgacccgaac | gcmcaymgga tgmrmaattt | 2580 |
| ycthgcaaay | gcwccmcarg | cmggmagcaa | gtcgcaragr | gccaagtayg gsacrgcwgg | 2640 |
| ctacggagtg | gaggcymgrg | gccccacdcc | agargargca | cagagggara aagacacacg | 2700 |
| gatctcmaag | aagatggara | cbatgggcat | ctacttygca | acaccrgaat gggtagcact | 2760 |
| caayggggcac | cgrggsccaa | gccccggcca | gctvaagtac | tggcaraaca camgagaaat | 2820 |
| accdgahccm | aacgaggact | aycyagacta | ygtgcaygcr | gagaagagcc ggttggcrtc | 2880 |
| agaagaacar | rtcytaaggg | cagcyacgtc | gatctacggg | gctccaggac aggcwgarcc | 2940 |
| accccaagcy | ttcatagacg | aagtygccar | rgtctatgaa | atcaaccatg grcgtggycc | 3000 |
| maaccargar | cagatgaarg | ayctgctcyt | gactgcgatg | gagatgaagc atcgcaatcc | 3060 |
| caggcgggct | cyaccaaagc | cmaagccaaa | acccaatgct | ccawcacaga gaccccctgg | 3120 |
| wcggctgggc | cgctggatca | ggrcbgtctc | tgaygaggac | ytkgagtgag gywcctggga | 3180 |
| gtctcccgac | accaccccgcg | caggygtgga | caccaattmr | kmmhtaswrm atycsaaatt | 3240 |
| ggatccgttc | gcgggtcccc | | | | 3260 |

<210> SEQ ID NO 71
<211> LENGTH: 3260
<212> TYPE: DNA
<213> ORGANISM: Infectious bursal disease virus
<220> FEATURE:
<221> NAME/KEY: misc_feature
<222> LOCATION: (1)..(3260)
<223> OTHER INFORMATION: cDNA sequence CEF94-A of IBDV A-segment

<400> SEQUENCE: 71

| | | | | |
|---|---|---|---|---|
| ggatacgatc | ggtctgaccc | cggggagtc | acccggggac | aggccgtcaa ggtcttgttc | 60 |
| caggatggaa | ctcctccttc | tacaacgcta | tcattgatgg | tcagtagaga tcagacaaac | 120 |
| gatcgcagcg | atgacaaacc | tgcaagatca | aacccaacag | attgttccgt tcatacggag | 180 |
| ccttctgatg | ccaacaaccg | gaccggcgtc | cattccggac | gacaccctgg agaagcacac | 240 |
| tctcaggtca | gagacctcga | cctacaattt | gactgtgggg | gacacagggt cagggctaat | 300 |
| tgtcttttc | cctggattcc | ctggctcaat | tgtgggtgct | cactacacac tgcagagcaa | 360 |
| tgggaactac | aagttcgatc | agatgctcct | gactgcccag | aacctaccgg ccagttacaa | 420 |
| ctactgcagg | ctagtgagtc | ggagtctcac | agtgaggtca | agcacacttc ctggtggcgt | 480 |
| ttatgcacta | aacggcacca | taaacgccgt | gaccttccaa | ggaagcctga gtgaactgac | 540 |
| agatgttagc | tacaatgggt | tgatgtctgc | aacagccaac | atcaacgaca aaattgggaa | 600 |
| cgtcctagta | ggggaagggg | tcaccgtcct | cagcttaccc | acatcatatg atcttgggta | 660 |
| tgtgaggctt | ggtgaccca | ttcccgcaat | agggcttgac | ccaaaaatgg tagccacatg | 720 |
| tgacagcagt | gacaggccca | gagtctacac | cataactgca | gccgatgatt accaattctc | 780 |

-continued

```
atcacagtac caaccaggtg gggtaacaat cacactgttc tcagccaaca ttgatgccat    840
cacaagcctc agcgttgggg gagagctcgt gtttcaaaca agcgtccacg gccttgtact    900
gggcgccacc atctacctca taggctttga tgggacagcg gtaatcacca gggctgtggc    960
cgcaaacaat gggctgacga ccggcaccga caaccttttg ccattcaatc ttgtgattcc    1020
aacmarcgag ataacccagc caatcacatc catcaaactg gagatagtga cctccaaaag    1080
tggtggtcag gcagggggatc agatgtcgtg gtcggcaaga gggagcctag cagtgacgat    1140
ccatggtggc aactatccag gggccctccg tcccgtcacg ctagtgggcct acgaaagagt    1200
ggcaacagga tccgtcgtta cggtcgctgg ggtgagcaac ttcgagctga tcccaaatcc    1260
tgaactagca aagaacctgg ttacagaata cggccgattt gacccaggag ccatgaacta    1320
cacaaaattg atactgagtg agagggaccg tcttggcatc aagaccgtct ggccaacaag    1380
ggagtacact gactttcgtg aatacttcat ggaggtggcc gacctcaact ctcccctgaa    1440
gattgcagga gcattcggct tcaaagacat aatccgggcc ataaggagga tagctgtgcc    1500
ggtggtctcc acattgttcc cacctgccgc tcccctagcc catgcaattg ggaaggtgt    1560
agactacctg ctgggcgatg aggcacaggc tgcttcagga actgctcgag ccgcgtcagg    1620
aaaagcaaga gctgcctcag gccgcataag gcagctgact ctcgccgccg acaaggggta    1680
cgaggtagtc gcgaatctat tccaggtgcc ccagaatccc gtagtcgacg ggattcttgc    1740
ttcacctggg gtactccgcg gtgcacacaa cctcgactgc gtgttaagag agggtgccac    1800
gctattccct gtggttatta cgacagtgga agacgccatg acacccaaag cattgaacag    1860
caaaatgttt gctgtcattg aaggcgtgcg agaagacctc caacctcctt ctcaaagagg    1920
atccttcata cgaactctct ctggacacag agtctatgga tatgctccag atggggtact    1980
tccactggag actgggagag actacaccgt tgtcccaata gatgatgtct gggacgacag    2040
cattatgctg tccaaagatc ccatacctcc tattgtggga aacagtggaa atctagccat    2100
agcttacatg gatgtgttc gacccaaagt cccaatccat gtggctatga cgggagccct    2160
caatgcttgt ggcgagattg agaaagtaag ctttagaagc accaagctcg ccactgcaca    2220
ccgacttggc cttaagttgg ctggtcccgg agcattcgat gtaaacaccg ggcccaactg    2280
ggcaacgttc atcaaacgtt tccctcacaa tccacgcgac tgggacaggc tcccctacct    2340
caacctacca taccttccac ccaatgcagg acgccagtac caccttgcca tggctgchtc    2400
agagttcaaa gagacccccg aactcgagag tgccgtcaga gcaatggaag cagcagccaa    2460
cgtggaccca ctattccaat ctgcactcag tgtgttcatg tggctggaag agaatgggat    2520
tgtgactgac atggccaact tcgcactcag cgacccgaac gcccatcgga tgcgaaattt    2580
tcttgcaaac gcaccacaag caggcagcaa gtcgcaaagg gccaagtacg ggacagcagg    2640
ctacggagtg gaggctcggg gccccacacc agaggaagca cagagggaaa agacacacg    2700
gatctcaaag aagatggaga ccatgggcat ctactttgca acaccagaat gggtagcact    2760
caatgggcac cgagggccaa gccccggcca gctaaagtac tggcagaaca cacgagaaat    2820
accggaccca aacgaggact atctagacta cgtgcatgca gagaagagcc ggttggcatc    2880
agaagaacaa atcctaaggg cagctacgtc gatctacggg gctccaggac aggcagagcc    2940
accccaagct ttcatagacg aagttgccaa agtctatgaa atcaaccatg acgtggccc    3000
aaaccaagaa cagatgaaag atctgctctt gactgcgatg gagatgaagc atcgcaatcc    3060
caggcgggct ctaccaaagc ccaagccaaa acccaatgct ccaacacaga gaccccctgg    3120
```

-continued

| tcggctgggc cgctggatca ggaccgtctc tgatgaggac cttgagtgag gtacctggga | 3180 |
| gtctcccgac accacccgcg caggtgtgga caccaattcg gacttacaac atcccaaatt | 3240 |
| ggatccgttc gcgggtcccc | 3260 |

<210> SEQ ID NO 72
<211> LENGTH: 3260
<212> TYPE: DNA
<213> ORGANISM: Infectious bursal disease virus
<220> FEATURE:
<221> NAME/KEY: misc_feature
<222> LOCATION: (1)..(3260)
<223> OTHER INFORMATION: cDNA sequence D6948-A of IBDV A-segment

<400> SEQUENCE: 72

| ggatacgatc ggtctgaccc cggggagtc acccgggac aggctgacaa ggccttgttc | 60 |
| caggatggaa ctcctccttc tacaatgcta tcattgatgg ttagtagaga tcagacaaac | 120 |
| gatcgcagcg atgacgaacc tgcaagatca aacccaacag attgttccgt tcatacggag | 180 |
| ccttctgatg ccaacaaccg gaccggcgtc cattccggac gacaccctag agaagcacac | 240 |
| tctcaggtca gagacctcga cctacaattt gactgtgggg gacacagggt cagggctaat | 300 |
| tgtcttttc cctggtttcc ctggctcaat tgtgggtgct cactacacac tgcagagcaa | 360 |
| tgggaactac aagttcgatc agatgctcct gactgcccag aacctaccgg ccagctacaa | 420 |
| ctactgcagg ctagtgagtc ggagtctcac agtgaggtca agcacactcc tggtggcgt | 480 |
| ttatgcacta aatggcacca taaacgccgt gaccttccaa ggaagcctga gtgaactgac | 540 |
| agatgttagc tacaatgggt tgatgtctgc aacagccaac atcaacgaca aaatcgggaa | 600 |
| cgtcctagta ggggaagggg taaccgtcct cagcttaccc acatcatatg atcttgggta | 660 |
| tgtgagactc ggtgacccca ttcccgctat agggctcgac caaaaatgg tagcaacatg | 720 |
| tgacagcagt gacaggccca gagtctacac cataactgca gccgatgatt accaattctc | 780 |
| atcacagtac caagcaggtg gggtaacaat cacactgttc tcagctaata tcgatgccat | 840 |
| cacaagcctc agcatcgggg gagaactcgt gtttcaaaca agcgtccaag gccttatact | 900 |
| gggtgctacc atctaccta taggctttga tgggactgcg gtaatcacca gagctgtggc | 960 |
| cgcaracaat gggctaacgg ccggcactga caaccttatg ccattcaata ttgtgattcc | 1020 |
| aaccagcgag ataacccagc caatcacatc catcaaactg gagatagtga cctccaaaag | 1080 |
| tggtggtcag gcgggggatc agatgtcatg gtcagcaagt gggagcctag cagtgacgat | 1140 |
| ccacggtggc aactatccag gggcccctcg tccccgtcaca ctagtagcct acgaaagagt | 1200 |
| ggcaacagga tctgtcgtta cggtcgccgg ggtgagcaac ttcgagctga tcccaaatcc | 1260 |
| tgaactagca aagaacctgg tcacagaata cggccgattt gacccaggag ccatgaacta | 1320 |
| cacaaaattg atactgagtg agagggaccg tcttggcatc aagaccgtat ggccaacaag | 1380 |
| ggagtacact gactttcgcg agtacttcat ggaggtggcg gacctcaact ctccctgaa | 1440 |
| gattgcagga gcatttggct tcaaagacat aatccgggcc ctaaggagga tagctgtgcc | 1500 |
| ggtggtctct acactgttcc cacccgccgc tcccctagcc catgcaattg gggaaggtgt | 1560 |
| agactacctg ctgggcgatg aggcacaggc tgcttcagga actgctcgag ccgcgtcagg | 1620 |
| aaaagcaaga gctgcctcag gccgcataag gcagctaact ctcgccgccg acaagggta | 1680 |
| cgaggtagtc gcgaatctgt ttcaggtgcc ccagaatcct gtagtcgacg ggattctcgc | 1740 |
| ttcacctggg atactccgcg cgcacacaa cctcgactgc gtgttgagag aggtgccac | 1800 |
| gctattccct gtggtcatca cgacagtgga agatgccatg acacccaaag cactgaacag | 1860 |

-continued

```
caaaatgttt gctgtcattg aaggcgtgcg agaagatctc caacctccat ctcaaagagg     1920
atccttcata cgaactctct ccggacatag agtctatgga tatgctccag atgggtact      1980 tccactggag actgggagag attacaccgt ggtcccaata gatgatgtct gggacgacag     2040
cattatgctg tccaaagacc ccatacctcc tattgtggga aacagcggaa acctagccat     2100
agcttacatg gatgtgtttc gacccaaagt ccccatccat gtggccatga cgggagccct     2160
caacgcctat ggcgagattg agaacgtgag ctttagaagc accaagctcg ccactgcaca     2220
ccgacttggc ctcaagttgg ctggtcccgg tgcatttgac gtgaacaccg ggtccaactg     2280
ggcgacgttt atcaaacgtt ttcctcacaa tccacgcgac tgggacaggc tcccttacct     2340
caaccttcca taccttccac ccaatgcagg acgccagtac gacctggcca tggccgcttc     2400
agagttcaaa gagaccccccg aactcgagag cgccgtcaga gccatggaag cagcagccaa     2460
cgtggaccca ctgttccaat ctgcgctcag cgtgttcatg tggctggaag agaatgggat     2520
tgtgactgat atggccaact tcgcactcag cgacccgaac gcccatcgga tgcgcaattt     2580
tctcgcaaac gcaccacaag caggcagcaa gtcgcaaaga gccaagtacg ggacagcagg     2640
ctacggagtg gaggcccggg gccccactcc agaggaagca cagagggaaa aagacacacg     2700
gatctcaaag aagatggaga ctatgggcat ctactttgca acaccagaat gggtagcact     2760
caatgggcac cggggggccaa gccccggcca gctgaagtac tggcagaaca cacgagaaat     2820
acctgatcca aacgaggact acctagacta cgtgcatgca gagaagagcc ggttggcatc     2880
agaagaacaa atcctaaggg cagctacgtc gatctacggg gctccaggac aggcagagcc     2940
accccaagcc ttcatagacg aagtcgccaa agtctatgaa atcaaccatg ggcgtggccc     3000
caaccaagaa cagatgaaag atctgctcct gactgcgatg gagatgaagc atcgcaatcc     3060
caggcgggct ccaccaaagc ccaagccaaa acccaatgct ccaacacaga gaccccctgg     3120
tcggctgggc cgctggatca gggctgtctc tgatgaggac cttgagtgag gtacctggga     3180
gtctcccgac accacccgcg caggtgtgga caccaattcg gccatacaac atcccaaatt     3240
ggatccgttc gcgggtcccc                                                 3260
```

<210> SEQ ID NO 73
<211> LENGTH: 964
<212> TYPE: DNA
<213> ORGANISM: Infectious bursal disease virus
<220> FEATURE:
<221> NAME/KEY: misc_feature
<222> LOCATION: (1)..(964)
<223> OTHER INFORMATION: cDNA sequence TY89-A of IBDV A-segment

<400> SEQUENCE: 73

```
cgtttccctc acaatccccg agactgggac aggttaccct acctcaacct tccctatctt      60
ccaccaacag ctggacgtca gttccatctg gccctggcag cctccgagtt caaagagacc     120
ccagaactcg aagacgctgt gcgtgcaatg gacgctgctg caaacgtcga cccattgttc     180
cgctcagctc tccaggtctt catgtggttg aagaaaacg ggattgtaac cgacatggct     240
aacttcgccc tcagcgaccc gaacgcacac aggatgaaaa atttcctagc aaatgctccc     300
caggccggaa gcaagtcgca gagggccaag tatggcacgg ctggctacgg agtggaggct     360
agaggcccca cgccagaaga ggcacagagg gagaaagaca cacggatctc caagaagatg     420
gaaacgatgg gcatctactt cgcaacaccg aatgggtag cactcaacgg gcaccgaggc     480
ccaagccccg gccagctcaa gtactggcaa aacacaagag aaataccaga acccaacgag     540
```

| | |
|---|---|
| gactacccag actatgtgca cgcggagaag agccggttgg cgtcagaaga acaggtctta | 600 |
| agggcagcca cgtcgatcta cggggctcca ggacaggctg aaccacccca agccttcata | 660 |
| gacgaagtcg ccagggtcta tgaaatcaac catgggcgtg gtccaaacca ggagcagatg | 720 |
| aaggacctgc tcctgactgc gatggagatg aagcatcgca atcccaggcg ggctccacca | 780 |
| aagccaaagc caaaacccaa tgctccatca cagagacccc ctggacggct gggccgctgg | 840 |
| atcaggacgg tctctgacga ggacttggag tgaggctcct gggagtctcc cgacaccacc | 900 |
| cgcgcaggtg tggacaccaa ttaatcacta gtgaattcga aattggatcc gttcgcgggt | 960 |
| cccc | 964 |

<210> SEQ ID NO 74
<211> LENGTH: 2827
<212> TYPE: DNA
<213> ORGANISM: Infectious bursal disease virus
<220> FEATURE:
<221> NAME/KEY: misc_feature
<222> LOCATION: (1)..(2827)
<223> OTHER INFORMATION: Consensus cDNA sequence of IBDV B-segment

<400> SEQUENCE: 74

| | |
|---|---|
| ggatacgatg ggtctgaccc tctgggagtc acgaattaac gtggctacta ggggygatrm | 60 |
| ccrccgctrg ctgccacgtt agtggctcct cttcttgatg attctrccac catgagtgac | 120 |
| rttttcaaya gtccacaggc gcgaagcamg atmtcagcag cgttcggcat aaagcctacw | 180 |
| gctggacarg aygtggaaga actcytgatc cctaargtyt gggtgccacc tgaggatccs | 240 |
| ytkgccagcc ctagtcgwct ggcmaagttc ctcagrgara acggctacaa rrttytgcag | 300 |
| ccacggtctc trccygagaa tgaggagtat gagaccgayc aaatactccc wgacytagcw | 360 |
| tggatgmgrc agatagargg rgctgttta aaaccmacyc tatctctccc yattggagay | 420 |
| caggagtact ccctgwaarta ctacccaaca caycgcccka gcaaggaraa gcccaatgcg | 480 |
| tacccgccmg ayatcgcayt actcaagcag atgatytacy tgtttctcca ggttccmgag | 540 |
| gccammgakr rcctwaarga tgargtmacc ctmytraccc aaaacatwag rgayaargcc | 600 |
| tayggragtg ggacctacat gggacargcm acymgacttg tkgcyatgaa rgaggtygcc | 660 |
| actggragaa acccaaacaa rgatcctcta aagcttgggt acacytttga gagcatgcs | 720 |
| cagctacttg acatcacwyt accggtaggc ccacccggtg aggatgacaa gccctgggtr | 780 |
| ccactcacaa grgtgccgtc amggatgttg gtwctgacgg gmgacgtaga tggsgamttt | 840 |
| gaggttgarg aytaccttcc caaaatcaac ctcaagtcat caagtggact rccmtatgtw | 900 |
| ggtcgcacca aggagagac wattggsgag atgatagcya tmtcraacca gtttctymga | 960 |
| gagctatcar crctgytgaa gcarggtgca gggacaaarg ggtcraacaa gaagaagctr | 1020 |
| ctcagcatgy taagtgacta ytggtactta tcatgyggc ttttgtttcc maaggctgar | 1080 |
| aggtacgaca aaagycatg gctcaccaag acccgkaaca tatggtcagc tccatcmcca | 1140 |
| acacacctca tgatctcwat gatmacctgg cccgtgatgt ccaayagccc aaayaacgtg | 1200 |
| ttgaacattg argggtgtcc rtcactctac aarttcaacc cgttyagagg wgggytraac | 1260 |
| aggatcgtsg agtggatawt ggcyccggaw gaacccaagg cyytwgtata tgckgacaac | 1320 |
| atatacattg tycactcmaa cacgtggtac tcaattgacc tagagaaggg tgaggcaaac | 1380 |
| tgcackcgyc aacacatgca rgccgcmatg tactacatmc tyaccagagg rtggtcmgay | 1440 |
| aacggygacc cmatgttcaa tcaracatgg gccacctttg csatgaacat tgccccwgct | 1500 |
| ctagtkgtgg actcatcrtg yctgatwatg aacctkcara tyaagacmta tggtcaaggc | 1560 |

```
agygggaatg cagccacstt catcaacaac cayctyytka gcacsctwgt gctwgaccag    1620
tggaacytga tgarrcarcc yagwccagac agcgargagt tcaartcaat tgargacaag    1680
ctrggyatca acttyaagat tgagaggtcc attgatgaya tyaggggcaa gctsagacag    1740
cttgtccycc ttgcacaacc agggtacctg agtggrgggg tygaaccaga rcaayccagc    1800
ccaactgtwg agctkgacct actmggrtgg tcwgcwacwt acagcaaaga tctygggatc    1860
tatgtgccgg tgcttgacaa ggaacgcyta ttttgytctg ctgcgtatcc caarggrgta    1920
gagaayaara gyctcaartc caargtyggg atcgagcarg catacaargt wgtcaggtay    1980
gaggcgttga ggttggtagg tggttggaac tacccactcc tgaacaaagc ytgcaagaay    2040
aaygcargyg cmgctcggcg gcatctggag gccaagggt tcccrctcga ygagttcctm    2100
gccgagtggt cwgagytgtc mgagttcggw gargcyttcg aaggcttcaa yatcaagctg    2160
acmgtaacay ckgagagcct mgccgaactk aacarrccag taccccccaa rccyccaaat    2220
gtcaacagac cagtcaacac yggkggrctm aaggcagtca gcaaygccct caagaccggy    2280
cggtayagra aygaagccgg actragtggy ctcgtcctyc tagccacmgc mmgmagccgw    2340
ctrcargayg cagtyaaggc caaggcagar gccgagaaac tccacaagtc yaagccmgay    2400
gaccccgatg cagactggtt ygaamgrtca gaaacyctgt cagacctkct ggagaaagcc    2460
gacatygcca gcaaggtcgc ycactcagca ctcgtggaaa caagcgacgc ycttgaagcr    2520
gtycagtcra cytcmgtgta cacyccaag tacccagarg tyaagaaccc acagaccgcc    2580
tccaaccccg ttgttgggct ccacctgccc gccaagagrg ccaccggtgt ccaggcmgct    2640
cttctcggag caggracgag cagaccaatg gggatggagg cyccaacacg gtccaagaac    2700
gccgtgaaaa tggccaaamg gcggcaacgc caaaargaga gccgccaaya gccatgatgg    2760
gaaccactca agaagaggac actaayccca gaccccgtat ccccggcctt cgcctgcggg    2820
ggccccc                                                              2827
```

<210> SEQ ID NO 75
<211> LENGTH: 2827
<212> TYPE: DNA
<213> ORGANISM: Infectious bursal disease virus
<220> FEATURE:
<221> NAME/KEY: misc_feature
<222> LOCATION: (1)..(2827)
<223> OTHER INFORMATION: cDNA sequence CEF94-B of IBDV B-segment

<400> SEQUENCE: 75

```
ggatacgatg ggtctgaccc tctgggagtc acgaattaac gtggctacta ggggcgataa     60
ccgccgctgg ctgccacgtt agtggctcct cttcttgatg attctgccac catgagtgac    120
attttcaaca gtccacaggc gcgaagcacg atctcagcag cgttcggcat aaagcctact    180
gctggacaag acgtggaaga actcttgatc cctaaagttt gggtgccacc tgaggatccg    240
cttgccagcc ctagtcgact ggcaaagttc ctcagagaga acggctacaa agttytgcag    300
ccacggtctc tgcccgagaa tgaggagtat gagaccgacc aaatactccc agacttagca    360
tggatgcgac agatagaagg ggctgtttta aaacccactc tatctctccc tattggagat    420
caggagtact tcccaaagta ctacccaaca catcgcccta gcaaggagaa gcccaatgcg    480
tacccgccag acatcgcact actcaagcag atgatttacc tgtttctcca ggttccagag    540
gccaacgagg gcctaaagga tgaagtaacc ctcttgaccc aaaacataag ggacaaggcc    600
tatggaagtg ggacctacat gggacaagca actcgacttg tggccatgaa ggaggtcgcc    660
```

```
actggaagaa acccaaacaa ggatcctcta aagcttgggt acactttga gagcatcgcg     720 cagctacttg acatcacact accggtaggc ccacccggtg aggatgacaa gccctgggtg     780
ccactcacaa gagtgccgtc acggatgttg gtactgacgg gagacgtaga tggcgacttt     840
gaggttgaag attaccttcc caaaatcaac ctcaagtcat caagtggact accatatgta     900
ggtcgcacca aggagagac aattggcgag atgatagcta tctcaaacca gtttctcaga     960
gagctatcaa cactgttgaa gcaaggtgca gggacaaagg ggtcaaacaa gaagaagcta    1020
ctcagcatgt taagtgacta ttggtactta tcatgcgggc ttttgtttcc aaaggctgaa    1080
aggtacgaca aaagtacatg gctcaccaag acccggaaca tatggtcagc tccatcccca    1140
acacacctca tgatctctat gatcacctgg cccgtgatgt ccaacagccc aataacgtg     1200 ttgaacattg aagggtgtcc atcactctac aaattcaacc cgttcagagg agggttgaac    1260
aggatcgtcg agtggatatt ggccccggaa gaacccaagg ctcttgtata tgcggacaac    1320
atatacattg tycactcaaa cacgtggtac tcaattgacc tagagaaggg tgaggcaaac    1380
tgcactcgcc aacacatgca agccgcaatg tactacatac tcaccagagg gtggtcagac    1440
aacggcgacc aatgttcaa tcaaacatgg gccacctttg ccatgaacat tgcccctgct    1500
ctagtggtgg actcatcgtg cctgataatg aacctgcaaa ttaagaccta tggtcaaggc    1560
agcgggaatg cagccacgtt catcaacaac cacctcttga gcacgctagt gcttgaccag    1620
tggaacctga tgagacagcc cagaccagac agcgaggagt tcaaatcaat tgaggacaag    1680
ctaggtatca actttaagat tgagaggtcc attgatgata tcaggggcaa gctgagacag    1740
cttgtcctcc ttgcacaacc agggtacctg agtgggggg ttgaaccaga acaatccagc    1800
ccaactgttg agcttgacct actagggtgg tcagctacat acagcaaaga tctcgggatc    1860
tatgtgccgg tgcttgacaa ggaacgccta ttttgttctg ctgcgtatcc caagggagta    1920
gagaacaaga gtctcaagtc caaagtcggg atcgagcagg catacaaggt agtcaggtat    1980
gaggcgttga ggttggtagg tggttggaac tacccactcc tgaacaaagc ctgcaagaat    2040
aatgcaggcc ccgctcggcg gcatctggag gccaaggggg tcccactcga cgagttccta    2100
gccgagtggt ctgagctgtc agagttcggt gaggccttcg aagcttcaa tatcaagctg    2160 accgtaacat ctgagagcct agccgaactg aacaagccag tacccccaa gcccccaaat    2220 gtcaacagac cagtcaacac tggggactc aaggcagtca gcaacgccct caagaccggt    2280
cggtacagga acgaagccgg actgagtggt ctcgtccttc tagccacagc aagaagccgt    2340
ctgcaagatg cagttaaggc caaggcagaa gccgagaaac tccacaagtc caagccagac    2400
gaccccgatg cagactggtt cgaaagatca gaaactctgt cagaccttct ggagaaagcc    2460
gacatcgcca gcaaggtcgc ccactcagca ctcgtggaaa caagcgacgc ccttgaagca    2520
gttcagtcga cttccgtgta cactcccaag tacccagaag tcaagaaccc acagaccgcc    2580 tccaacccg ttgttgggct ccacctgccc gccaagagag ccaccggtgt ccaggccgct    2640
cttctcggag caggaacgag cagaccaatg gggatggagg ccccaacacg gtccaagaac    2700
gccgtgaaaa tggccaaacg gcggcaacgc caaaaggaga gccgccaaca gccatgatgg    2760
gaaccactca agaagaggac actaatccca gaccccgtat ccccggcctt cgcctgcggg    2820
ggccccc                                                              2827
```

<210> SEQ ID NO 76
<211> LENGTH: 2827
<212> TYPE: DNA
<213> ORGANISM: Infectious bursal disease virus
<220> FEATURE:
<221> NAME/KEY: misc_feature
<222> LOCATION: (1)..(2827)
<223> OTHER INFORMATION: cDNA sequence D6948-B of IBDV B-segment

<400> SEQUENCE: 76

| | | | | | |
|---|---|---|---|---|---|
| ggatacgatg | ggtctgaccc | tctgggagtc | acgaattaac | gtggctacta | ggggtgatgc | 60 |
| ccaccgctag | ctgccacgtt | agtggctcct | cttcttgatg | attctaccac | catgagtgac | 120 |
| gttttcaata | gtccacaggc | gcgaagcaag | atatcagcag | cgttcggcat | aaagcctaca | 180 |
| gctggacagg | atgtggaaga | actcctgatc | cctaaggtct | gggtgccacc | tgaggatccc | 240 |
| ttggccagcc | ctagtcgtct | ggccaagttc | ctcagggaaa | acggctacaa | gattctgcag | 300 |
| ccacggtctc | tacctgagaa | tgaggagtat | gagaccgatc | aaatactccc | tgacctagct | 360 |
| tggatgaggc | agatagaggg | agctgtttta | aaaccaaccc | tatctctccc | cattggagac | 420 |
| caggagtact | tccctaaata | ctacccaaca | caccgcccga | gcaaggaaaa | agcccaatgcg | 480 |
| tacccgcccg | atatcgcatt | actcaagcag | atgatctact | tgtttctcca | ggttcccgag | 540 |
| gccacagata | accttaaaga | tgaggtcacc | ctactaaccc | aaaacattag | agataaagcc | 600 |
| tacgggagtg | ggacctacat | gggacaggcc | accagacttg | ttgctatgaa | agaggttgcc | 660 |
| actgggagaa | acccaaacaa | agatcctcta | aagcttgggt | acacctttga | gagcatagcc | 720 |
| cagctacttg | acatcacttt | accggtaggc | ccacccggtg | aggatgacaa | gccctgggta | 780 |
| ccactcacaa | gggtgccgtc | aaggatgttg | gttctgacgg | gcgacgtaga | tggggaattt | 840 |
| gaggttgagg | actaccttcc | caaaatcaac | ctcaagtcat | caagtggact | gccctatgtt | 900 |
| ggtcgcacca | aggagaaac | tattggggag | atgatagcca | tatcgaacca | gtttcttcga | 960 |
| gagctatcag | cgctgctgaa | gcagggtgca | gggacaaaag | ggtcgaacaa | gaagaagctg | 1020 |
| ctcagcatgc | taagtgacta | ctggtactta | tcatgtgggc | ttttgtttcc | caaggctgag | 1080 |
| aggtacgaca | aaagcacatg | gctcaccaag | acccgtaaca | tatggtcagc | tccatcacca | 1140 |
| acacacctca | tgatctcaat | gataacctgg | cccgtgatgt | ccaatagccc | aaacaacgtg | 1200 |
| ttgaacattg | aggggtgtcc | gtcactctac | aagttcaacc | cgtttagagg | tgggctaaac | 1260 |
| aggatcgtgg | agtggataat | ggctccggat | gaacccaagg | ccttagtata | tgctgacaac | 1320 |
| atatacattg | ttcactccaa | cacgtggtac | tcaattgacc | tagagaaggg | tgaggcaaac | 1380 |
| tgcacgcgtc | aacacatgca | ggccgccatg | tactacatcc | ttaccagagg | atggtccgat | 1440 |
| aacggtgacc | ccatgttcaa | tcagacatgg | gccacctttg | cgatgaacat | tgccccagct | 1500 |
| ctagttgtgg | actcatcatg | tctgattatg | aaccttcaga | tcaagacata | tggtcaaggc | 1560 |
| agtgggaatg | cagccacctt | catcaacaac | catcttctta | gcacccttgt | gctagaccag | 1620 |
| tggaacttga | tgaagcaacc | tagtccagac | agcgaagagt | tcaagtcaat | tgaagacaag | 1680 |
| ctgggcatca | acttcaagat | tgagaggtcc | attgatgaca | ttaggggcaa | gctcagacag | 1740 |
| cttgtccccc | ttgcacaacc | agggtacctg | agtggagggg | tcgaaccaga | gcaacccagc | 1800 |
| ccaactgtag | agctggacct | actcggatgg | tctgcaactt | acagcaaaga | tcttgggatc | 1860 |
| tatgtgccgg | tgcttgacaa | ggaacgctta | ttttgctctg | ctgcgtatcc | caagggggta | 1920 |
| gagaataaaa | gcctcaaatc | caaggttggg | atcgagcaag | catacaaagt | tgtcaggtac | 1980 |
| gaggcgttga | ggttggtagg | tggttggaac | tacccactcc | tgaacaaagc | ttgcaagaac | 2040 |
| aatgcaagtg | cagctcggcg | gcatctggag | gccaagggt | tcccgctcga | tgagttcctc | 2100 |
| gccgagtggt | cagagttgtc | cgagttcgga | gaagctttcg | aaggcttcaa | catcaagctg | 2160 |

-continued

```
acagtaacac cggagagcct cgccgaactt aacagaccag taccccccaa acctccaaat    2220
gtcaacagac cagtcaacac cggtgggcta aaggcagtca gcaatgccct caagaccggc    2280
cggtatagaa atgaagccgg actaagtggc ctcgtcctcc tagccaccgc ccgcagccga    2340
ctacaggacg cagtcaaggc caaggcagag gccgagaaac tccacaagtc taagcccgat    2400
gaccccgatg cagactggtt tgaacggtca gaaaccctgt cagacctgct ggagaaagcc    2460
gacattgcca gcaaggtcgc tcactcagca ctcgtggaaa caagcgacgc tcttgaagcg    2520
gtccagtcaa cctcagtgta cacccccaaag tacccagagg ttaagaaccc acagaccgcc    2580
tccaaccccg ttgttgggct ccacctgccc gccaagaggg ccaccggtgt ccaggcagct    2640
cttctcggag cagggacgag cagaccaatg gggatggagg ctccaacacg gtccaagaac    2700
gccgtgaaaa tggccaaaag gcggcaacgc caaaaagaga gccgccaata gccatgatgg    2760
gaaccactca agaagaggac actaaccccca gaccccgtat ccccggcctt cgcctgcggg    2820
ggcccc                                                                2827
```

<210> SEQ ID NO 77
<211> LENGTH: 1012
<212> TYPE: PRT
<213> ORGANISM: Infectious bursal disease virus
<220> FEATURE:
<221> NAME/KEY: DOMAIN
<222> LOCATION: (1)..(1012)
<223> OTHER INFORMATION: Consensus sequence of IBDV polyprotein
<220> FEATURE:
<221> NAME/KEY: MISC_FEATURE
<222> LOCATION: (222)
<223> OTHER INFORMATION: The 'Xaa' at position 222 may be any amino acid
<220> FEATURE:
<221> NAME/KEY: MISC_FEATURE
<222> LOCATION: (242)
<223> OTHER INFORMATION: The 'Xaa' at position 242 may be any amino acid
<220> FEATURE:
<221> NAME/KEY: MISC_FEATURE
<222> LOCATION: (253)
<223> OTHER INFORMATION: The 'Xaa' at position 253 may be any amino acid
<220> FEATURE:
<221> NAME/KEY: MISC_FEATURE
<222> LOCATION: (256)
<223> OTHER INFORMATION: The 'Xaa' at position 256 may be any amino acid
<220> FEATURE:
<221> NAME/KEY: MISC_FEATURE
<222> LOCATION: (279)
<223> OTHER INFORMATION: The 'Xaa' at position 279 may be any amino acid
<220> FEATURE:
<221> NAME/KEY: MISC_FEATURE
<222> LOCATION: (284)
<223> OTHER INFORMATION: The 'Xaa' at position 284 may be any amino acid
<220> FEATURE:
<221> NAME/KEY: MISC_FEATURE
<222> LOCATION: (290)
<223> OTHER INFORMATION: The 'Xaa' at position 290 may be any amino acid
<220> FEATURE:
<221> NAME/KEY: MISC_FEATURE
<222> LOCATION: (294)
<223> OTHER INFORMATION: The 'Xaa' at position 294 may be any amino acid
<220> FEATURE:
<221> NAME/KEY: MISC_FEATURE
<222> LOCATION: (299)
<223> OTHER INFORMATION: The 'Xaa' at position 299 may be any amino acid
<220> FEATURE:
<221> NAME/KEY: MISC_FEATURE
<222> LOCATION: (330)
<223> OTHER INFORMATION: The 'Xaa' at position 330 may be any amino acid
<220> FEATURE:
<221> NAME/KEY: MISC_FEATURE
<222> LOCATION: (451)
<223> OTHER INFORMATION: The 'Xaa' at position 451 may be any amino acid
<220> FEATURE:
<221> NAME/KEY: MISC_FEATURE

```
<222> LOCATION: (541)
<223> OTHER INFORMATION: The 'Xaa' at position 541 may be any amino acid
<220> FEATURE:
<221> NAME/KEY: MISC_FEATURE
<222> LOCATION: (680)
<223> OTHER INFORMATION: The 'Xaa' at position 680 may be any amino acid
<220> FEATURE:
<221> NAME/KEY: MISC_FEATURE
<222> LOCATION: (685)
<223> OTHER INFORMATION: The 'Xaa' at position 685 may be any amino acid
<220> FEATURE:
<221> NAME/KEY: MISC_FEATURE
<222> LOCATION: (715)
<223> OTHER INFORMATION: The 'Xaa' at position 715 may be any amino acid

<400> SEQUENCE: 77
```

Met Thr Asn Leu Gln Asp Gln Thr Gln Gln Ile Val Pro Phe Ile Arg
 1               5                  10                  15

Ser Leu Leu Met Pro Thr Thr Gly Pro Ala Ser Ile Pro Asp Asp Thr
             20                  25                  30

Leu Glu Lys His Thr Leu Arg Ser Glu Thr Ser Thr Tyr Asn Leu Thr
         35                  40                  45

Val Gly Asp Thr Gly Ser Gly Leu Ile Val Phe Phe Pro Gly Phe Pro
     50                  55                  60

Gly Ser Ile Val Gly Ala His Tyr Thr Leu Gln Ser Asn Gly Asn Tyr
 65                  70                  75                  80

Lys Phe Asp Gln Met Leu Leu Thr Ala Gln Asn Leu Pro Ala Ser Tyr
                 85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Xaa Gly Gly
    210                 215                 220

Val Thr Ile Thr Leu Phe Ser Ala Asn Ile Asp Ala Ile Thr Ser Leu
225                 230                 235                 240

Ser Xaa Gly Gly Glu Leu Val Phe Gln Thr Ser Val Xaa Gly Leu Xaa
                245                 250                 255

Leu Gly Ala Thr Ile Tyr Leu Ile Gly Phe Asp Gly Thr Ala Val Ile
            260                 265                 270

Thr Arg Ala Val Ala Ala Xaa Asn Gly Leu Thr Xaa Gly Thr Asp Asn
        275                 280                 285

Leu Xaa Pro Phe Asn Xaa Val Ile Pro Thr Xaa Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Xaa Gly Ser Leu Ala Val Thr
                325                 330                 335

```
Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
            355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
            435                 440                 445

Arg Ala Xaa Arg Arg Ile Ala Val Pro Val Val Ser Thr Leu Phe Pro
        450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
                485                 490                 495

Gly Lys Ala Arg Ala Ala Ser Gly Arg Ile Arg Gln Leu Thr Leu Ala
            500                 505                 510

Ala Asp Lys Gly Tyr Glu Val Val Ala Asn Leu Phe Gln Val Pro Gln
            515                 520                 525

Asn Pro Val Val Asp Gly Ile Leu Ala Ser Pro Gly Xaa Leu Arg Gly
    530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
        595                 600                 605

Tyr Gly Tyr Ala Pro Asp Gly Val Leu Pro Leu Glu Thr Gly Arg Asp
    610                 615                 620

Tyr Thr Val Val Pro Ile Asp Asp Val Trp Asp Asp Ser Ile Met Leu
625                 630                 635                 640

Ser Lys Asp Pro Ile Pro Pro Ile Val Gly Asn Ser Gly Asn Leu Ala
                645                 650                 655

Ile Ala Tyr Met Asp Val Phe Arg Pro Lys Val Pro Ile His Val Ala
            660                 665                 670

Met Thr Gly Ala Leu Asn Ala Xaa Gly Glu Ile Glu Xaa Val Ser Phe
            675                 680                 685

Arg Ser Thr Lys Leu Ala Thr Ala His Arg Leu Gly Leu Lys Leu Ala
        690                 695                 700

Gly Pro Gly Ala Phe Asp Val Asn Thr Gly Xaa Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
            740                 745                 750
```

```
Ala Met Ala Ala Ser Glu Phe Lys Glu Thr Pro Glu Leu Glu Ser Ala
            755                 760                 765

Val Arg Ala Met Glu Ala Ala Asn Val Asp Pro Leu Phe Gln Ser
    770                 775                 780

Ala Leu Ser Val Phe Met Trp Leu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
            835                 840                 845

Glu Ala Gln Arg Glu Lys Asp Thr Arg Ile Ser Lys Lys Met Glu Thr
    850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
            915                 920                 925

Tyr Gly Ala Pro Gly Gln Ala Glu Pro Pro Gln Ala Phe Ile Asp Glu
            930                 935                 940

Val Ala Lys Val Tyr Glu Ile Asn His Gly Arg Gly Pro Asn Gln Glu
945                 950                 955                 960

Gln Met Lys Asp Leu Leu Leu Thr Ala Met Glu Met Lys His Arg Asn
                965                 970                 975

Pro Arg Arg Ala Pro Pro Lys Pro Lys Pro Lys Pro Asn Ala Pro Thr
            980                 985                 990

Gln Arg Pro Pro Gly Arg Leu Gly Arg Trp Ile Arg Thr Val Ser Asp
            995                 1000                1005

Glu Asp Leu Glu
    1010

<210> SEQ ID NO 78
<211> LENGTH: 1012
<212> TYPE: PRT
<213> ORGANISM: Infectious bursal disease virus
<220> FEATURE:
<221> NAME/KEY: DOMAIN
<222> LOCATION: (1)..(1012)
<223> OTHER INFORMATION: Sequence of IBDV polyprotein CEF94-PP

<400> SEQUENCE: 78

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
```

-continued

```
                85                  90                  95
Asn Tyr Cys Arg Leu Val Ser Arg Ser Leu Thr Val Arg Ser Ser Thr
            100                 105                 110
Leu Pro Gly Gly Val Tyr Ala Leu Asn Gly Thr Ile Asn Ala Val Thr
            115                 120                 125
Phe Gln Gly Ser Leu Ser Glu Leu Thr Asp Val Ser Tyr Asn Gly Leu
            130                 135                 140
Met Ser Ala Thr Ala Asn Ile Asn Asp Lys Ile Gly Asn Val Leu Val
145                 150                 155                 160
Gly Glu Gly Val Thr Val Leu Ser Leu Pro Thr Ser Tyr Asp Leu Gly
                165                 170                 175
Tyr Val Arg Leu Gly Asp Pro Ile Pro Ala Ile Gly Leu Asp Pro Lys
            180                 185                 190
Met Val Ala Thr Cys Asp Ser Ser Asp Arg Pro Arg Val Tyr Thr Ile
            195                 200                 205
Thr Ala Ala Asp Asp Tyr Gln Phe Ser Ser Gln Tyr Gln Pro Gly Gly
            210                 215                 220
Val Thr Ile Thr Leu Phe Ser Ala Asn Ile Asp Ala Ile Thr Ser Leu
225                 230                 235                 240
Ser Val Gly Gly Glu Leu Val Phe Gln Thr Ser Val His Gly Leu Val
                245                 250                 255
Leu Gly Ala Thr Ile Tyr Leu Ile Gly Phe Asp Gly Thr Ala Val Ile
            260                 265                 270
Thr Arg Ala Val Ala Ala Asn Asn Gly Leu Thr Thr Gly Thr Asp Asn
            275                 280                 285
Leu Leu Pro Phe Asn Leu Val Ile Pro Thr Asn Glu Ile Thr Gln Pro
            290                 295                 300
Ile Thr Ser Ile Lys Leu Glu Ile Val Thr Ser Lys Ser Gly Gly Gln
305                 310                 315                 320
Ala Gly Asp Gln Met Ser Trp Ser Ala Arg Gly Ser Leu Ala Val Thr
                325                 330                 335
Ile His Gly Gly Asn Tyr Pro Gly Ala Leu Arg Pro Val Thr Leu Val
            340                 345                 350
Ala Tyr Glu Arg Val Ala Thr Gly Ser Val Val Thr Val Ala Gly Val
            355                 360                 365
Ser Asn Phe Glu Leu Ile Pro Asn Pro Glu Leu Ala Lys Asn Leu Val
            370                 375                 380
Thr Glu Tyr Gly Arg Phe Asp Pro Gly Ala Met Asn Tyr Thr Lys Leu
385                 390                 395                 400
Ile Leu Ser Glu Arg Asp Arg Leu Gly Ile Lys Thr Val Trp Pro Thr
                405                 410                 415
Arg Glu Tyr Thr Asp Phe Arg Glu Tyr Phe Met Glu Val Ala Asp Leu
            420                 425                 430
Asn Ser Pro Leu Lys Ile Ala Gly Ala Phe Gly Phe Lys Asp Ile Ile
            435                 440                 445
Arg Ala Ile Arg Arg Ile Ala Val Pro Val Val Ser Thr Leu Phe Pro
450                 455                 460
Pro Ala Ala Pro Leu Ala His Ala Ile Gly Glu Gly Val Asp Tyr Leu
465                 470                 475                 480
Leu Gly Asp Glu Ala Gln Ala Ala Ser Gly Thr Ala Arg Ala Ala Ser
                485                 490                 495
Gly Lys Ala Arg Ala Ala Ser Gly Arg Ile Arg Gln Leu Thr Leu Ala
            500                 505                 510
```

```
Ala Asp Lys Gly Tyr Glu Val Val Ala Asn Leu Phe Gln Val Pro Gln
        515                 520                 525

Asn Pro Val Val Asp Gly Ile Leu Ala Ser Pro Gly Val Leu Arg Gly
        530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
                565                 570                 575

Ser Lys Met Phe Ala Val Ile Glu Gly Val Arg Glu Asp Leu Gln Pro
            580                 585                 590

Pro Ser Gln Arg Gly Ser Phe Ile Arg Thr Leu Ser Gly His Arg Val
        595                 600                 605

Tyr Gly Tyr Ala Pro Asp Gly Val Leu Pro Leu Glu Thr Gly Arg Asp
        610                 615                 620

Tyr Thr Val Val Pro Ile Asp Asp Val Trp Asp Asp Ser Ile Met Leu
625                 630                 635                 640

Ser Lys Asp Pro Ile Pro Pro Ile Val Gly Asn Ser Gly Asn Leu Ala
                645                 650                 655

Ile Ala Tyr Met Asp Val Phe Arg Pro Lys Val Pro Ile His Val Ala
            660                 665                 670

Met Thr Gly Ala Leu Asn Ala Cys Gly Glu Ile Glu Lys Val Ser Phe
        675                 680                 685

Arg Ser Thr Lys Leu Ala Thr Ala His Arg Leu Gly Leu Lys Leu Ala
        690                 695                 700

Gly Pro Gly Ala Phe Asp Val Asn Thr Gly Pro Asn Trp Ala Thr Phe
705                 710                 715                 720

Ile Lys Arg Phe Pro His Asn Pro Arg Asp Trp Asp Arg Leu Pro Tyr
                725                 730                 735

Leu Asn Leu Pro Tyr Leu Pro Pro Asn Ala Gly Arg Gln Tyr His Leu
            740                 745                 750

Ala Met Ala Ala Ser Glu Phe Lys Glu Thr Pro Glu Leu Glu Ser Ala
        755                 760                 765

Val Arg Ala Met Glu Ala Ala Asn Val Asp Pro Leu Phe Gln Ser
770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
            820                 825                 830

Tyr Gly Thr Ala Gly Tyr Gly Val Glu Ala Arg Gly Pro Thr Pro Glu
        835                 840                 845

Glu Ala Gln Arg Glu Lys Asp Thr Arg Ile Ser Lys Lys Met Glu Thr
        850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Asp Pro Asn Glu Asp Tyr Leu Asp Tyr Val His Ala Glu Lys
            900                 905                 910

Ser Arg Leu Ala Ser Glu Glu Gln Ile Leu Arg Ala Ala Thr Ser Ile
        915                 920                 925
```

```
Tyr Gly Ala Pro Gly Gln Ala Glu Pro Pro Gln Ala Phe Ile Asp Glu
    930                 935                 940
Val Ala Lys Val Tyr Glu Ile Asn His Gly Arg Gly Pro Asn Gln Glu
945                 950                 955                 960
Gln Met Lys Asp Leu Leu Leu Thr Ala Met Glu Met Lys His Arg Asn
                965                 970                 975
Pro Arg Arg Ala Pro Pro Lys Pro Lys Pro Lys Pro Asn Ala Pro Thr
            980                 985                 990
Gln Arg Pro Pro Gly Arg Leu Gly Arg Trp Ile Arg Thr Val Ser Asp
        995                 1000                1005
Glu Asp Leu Glu
    1010

<210> SEQ ID NO 79
<211> LENGTH: 1012
<212> TYPE: PRT
<213> ORGANISM: Infectious bursal disease virus
<220> FEATURE:
<221> NAME/KEY: DOMAIN
<222> LOCATION: (1)..(1012)
<223> OTHER INFORMATION: Sequence of IBDV polyprotein D6948-PP

<400> SEQUENCE: 79

Met Thr Asn Leu Gln Asp Gln Thr Gln Gln Ile Val Pro Phe Ile Arg
  1               5                  10                  15
Ser Leu Leu Met Pro Thr Thr Gly Pro Ala Ser Ile Pro Asp Asp Thr
                 20                  25                  30
Leu Glu Lys His Thr Leu Arg Ser Glu Thr Ser Thr Tyr Asn Leu Thr
             35                  40                  45
Val Gly Asp Thr Gly Ser Gly Leu Ile Val Phe Phe Pro Gly Phe Pro
         50                  55                  60
Gly Ser Ile Val Gly Ala His Tyr Thr Leu Gln Ser Asn Gly Asn Tyr
 65                  70                  75                  80
Lys Phe Asp Gln Met Leu Leu Thr Ala Gln Asn Leu Pro Ala Ser Tyr
                 85                  90                  95
Asn Tyr Cys Arg Leu Val Ser Arg Ser Leu Thr Val Arg Ser Ser Thr
                100                 105                 110
Leu Pro Gly Gly Val Tyr Ala Leu Asn Gly Thr Ile Asn Ala Val Thr
            115                 120                 125
Phe Gln Gly Ser Leu Ser Glu Leu Thr Asp Val Ser Tyr Asn Gly Leu
        130                 135                 140
Met Ser Ala Thr Ala Asn Ile Asn Asp Lys Ile Gly Asn Val Leu Val
145                 150                 155                 160
Gly Glu Gly Val Thr Val Leu Ser Leu Pro Thr Ser Tyr Asp Leu Gly
                165                 170                 175
Tyr Val Arg Leu Gly Asp Pro Ile Pro Ala Ile Gly Leu Asp Pro Lys
            180                 185                 190
Met Val Ala Thr Cys Asp Ser Ser Asp Arg Pro Arg Val Tyr Thr Ile
        195                 200                 205
Thr Ala Ala Asp Asp Tyr Gln Phe Ser Ser Gln Tyr Gln Ala Gly Gly
    210                 215                 220
Val Thr Ile Thr Leu Phe Ser Ala Asn Ile Asp Ala Ile Thr Ser Leu
225                 230                 235                 240
Ser Ile Gly Gly Glu Leu Val Phe Gln Thr Ser Val Gln Gly Leu Ile
                245                 250                 255
Leu Gly Ala Thr Ile Tyr Leu Ile Gly Phe Asp Gly Thr Ala Val Ile
```

-continued

```
                260                 265                 270
Thr Arg Ala Val Ala Ala Asp Asn Gly Leu Thr Ala Gly Thr Asp Asn
            275                 280                 285
Leu Met Pro Phe Asn Ile Val Ile Pro Thr Ser Glu Ile Thr Gln Pro
        290                 295                 300
Ile Thr Ser Ile Lys Leu Glu Ile Val Thr Ser Lys Ser Gly Gly Gln
305                 310                 315                 320
Ala Gly Asp Gln Met Ser Trp Ser Ala Ser Gly Ser Leu Ala Val Thr
                325                 330                 335
Ile His Gly Gly Asn Tyr Pro Gly Ala Leu Arg Pro Val Thr Leu Val
            340                 345                 350
Ala Tyr Glu Arg Val Ala Thr Gly Ser Val Val Thr Val Ala Gly Val
        355                 360                 365
Ser Asn Phe Glu Leu Ile Pro Asn Pro Glu Leu Ala Lys Asn Leu Val
    370                 375                 380
Thr Glu Tyr Gly Arg Phe Asp Pro Gly Ala Met Asn Tyr Thr Lys Leu
385                 390                 395                 400
Ile Leu Ser Glu Arg Asp Arg Leu Gly Ile Lys Thr Val Trp Pro Thr
                405                 410                 415
Arg Glu Tyr Thr Asp Phe Arg Glu Tyr Phe Met Glu Val Ala Asp Leu
            420                 425                 430
Asn Ser Pro Leu Lys Ile Ala Gly Ala Phe Gly Phe Lys Asp Ile Ile
        435                 440                 445
Arg Ala Leu Arg Arg Ile Ala Val Pro Val Val Ser Thr Leu Phe Pro
    450                 455                 460
Pro Ala Pro Leu Ala His Ala Ile Gly Glu Gly Val Asp Tyr Leu
465                 470                 475                 480
Leu Gly Asp Glu Ala Gln Ala Ala Ser Gly Thr Ala Arg Ala Ala Ser
                485                 490                 495
Gly Lys Ala Arg Ala Ala Ser Gly Arg Ile Arg Gln Leu Thr Leu Ala
            500                 505                 510
Ala Asp Lys Gly Tyr Glu Val Val Ala Asn Leu Phe Gln Val Pro Gln
        515                 520                 525
Asn Pro Val Val Asp Gly Ile Leu Ala Ser Pro Gly Ile Leu Arg Gly
    530                 535                 540
Ala His Asn Leu Asp Cys Val Leu Arg Glu Gly Ala Thr Leu Phe Pro
545                 550                 555                 560
Val Val Ile Thr Thr Val Glu Asp Ala Met Thr Pro Lys Ala Leu Asn
                565                 570                 575
Ser Lys Met Phe Ala Val Ile Glu Gly Val Arg Glu Asp Leu Gln Pro
            580                 585                 590
Pro Ser Gln Arg Gly Ser Phe Ile Arg Thr Leu Ser Gly His Arg Val
        595                 600                 605
Tyr Gly Tyr Ala Pro Asp Gly Val Leu Pro Leu Glu Thr Gly Arg Asp
    610                 615                 620
Tyr Thr Val Val Pro Ile Asp Asp Val Trp Asp Ser Ile Met Leu
625                 630                 635                 640
Ser Lys Asp Pro Ile Pro Pro Ile Val Gly Asn Ser Gly Asn Leu Ala
                645                 650                 655
Ile Ala Tyr Met Asp Val Phe Arg Pro Lys Val Pro Ile His Val Ala
            660                 665                 670
Met Thr Gly Ala Leu Asn Ala Tyr Gly Glu Ile Glu Asn Val Ser Phe
        675                 680                 685
```

```
Arg Ser Thr Lys Leu Ala Thr Ala His Arg Leu Gly Leu Lys Leu Ala
    690                 695                 700

Gly Pro Gly Ala Phe Asp Val Asn Thr Gly Ser Asn Trp Ala Thr Phe
705                 710                 715                 720

Ile Lys Arg Phe Pro His Asn Pro Arg Asp Trp Asp Arg Leu Pro Tyr
                    725                 730                 735

Leu Asn Leu Pro Tyr Leu Pro Pro Asn Ala Gly Arg Gln Tyr Asp Leu
                740                 745                 750

Ala Met Ala Ala Ser Glu Phe Lys Glu Thr Pro Glu Leu Glu Ser Ala
            755                 760                 765

Val Arg Ala Met Glu Ala Ala Asn Val Asp Pro Leu Phe Gln Ser
770                 775                 780

Ala Leu Ser Val Phe Met Trp Leu Glu Glu Asn Gly Ile Val Thr Asp
785                 790                 795                 800

Met Ala Asn Phe Ala Leu Ser Asp Pro Asn Ala His Arg Met Arg Asn
                805                 810                 815

Phe Leu Ala Asn Ala Pro Gln Ala Gly Ser Lys Ser Gln Arg Ala Lys
                820                 825                 830

Tyr Gly Thr Ala Gly Tyr Gly Val Glu Ala Arg Gly Pro Thr Pro Glu
            835                 840                 845

Glu Ala Gln Arg Glu Lys Asp Thr Arg Ile Ser Lys Lys Met Glu Thr
850                 855                 860

Met Gly Ile Tyr Phe Ala Thr Pro Glu Trp Val Ala Leu Asn Gly His
865                 870                 875                 880

Arg Gly Pro Ser Pro Gly Gln Leu Lys Tyr Trp Gln Asn Thr Arg Glu
                885                 890                 895

Ile Pro Asp Pro Asn Glu Asp Tyr Leu Asp Tyr Val His Ala Glu Lys
                900                 905                 910

Ser Arg Leu Ala Ser Glu Glu Gln Ile Leu Arg Ala Ala Thr Ser Ile
            915                 920                 925

Tyr Gly Ala Pro Gly Gln Ala Glu Pro Pro Gln Ala Phe Ile Asp Glu
930                 935                 940

Val Ala Lys Val Tyr Glu Ile Asn His Gly Arg Gly Pro Asn Gln Glu
945                 950                 955                 960

Gln Met Lys Asp Leu Leu Leu Thr Ala Met Glu Met Lys His Arg Asn
                965                 970                 975

Pro Arg Arg Ala Pro Pro Lys Pro Lys Pro Lys Pro Asn Ala Pro Thr
            980                 985                 990

Gln Arg Pro Pro Gly Arg Leu Gly Arg Trp Ile Arg Ala Val Ser Asp
        995                 1000                1005

Glu Asp Leu Glu
    1010

<210> SEQ ID NO 80
<211> LENGTH: 290
<212> TYPE: PRT
<213> ORGANISM: Infectious bursal disease virus
<220> FEATURE:
<221> NAME/KEY: DOMAIN
<222> LOCATION: (1)..(290)
<223> OTHER INFORMATION: Sequence of IBDV polyprotein TY89-PP

<400> SEQUENCE: 80

Arg Phe Pro His Asn Pro Arg Asp Trp Asp Arg Leu Pro Tyr Leu Asn
1               5                   10                  15
```

```
Leu Pro Tyr Leu Pro Pro Thr Ala Gly Arg Gln Phe His Leu Ala Leu
            20                  25                  30

Ala Ala Ser Glu Phe Lys Glu Thr Pro Glu Leu Glu Asp Ala Val Arg
        35                  40                  45

Ala Met Asp Ala Ala Asn Val Asp Pro Leu Phe Arg Ser Ala Leu
 50                  55                  60

Gln Val Phe Met Trp Leu Glu Glu Asn Gly Ile Val Thr Asp Met Ala
65                  70                  75                  80

Asn Phe Ala Leu Ser Asp Pro Asn Ala His Arg Met Lys Asn Phe Leu
                85                  90                  95

Ala Asn Ala Pro Gln Ala Gly Ser Lys Ser Gln Arg Ala Lys Tyr Gly
            100                 105                 110

Thr Ala Gly Tyr Gly Val Glu Ala Arg Gly Pro Thr Pro Glu Glu Ala
        115                 120                 125

Gln Arg Glu Lys Asp Thr Arg Ile Ser Lys Lys Met Glu Thr Met Gly
130                 135                 140

Ile Tyr Phe Ala Thr Pro Glu Trp Val Ala Leu Asn Gly His Arg Gly
145                 150                 155                 160

Pro Ser Pro Gly Gln Leu Lys Tyr Trp Gln Asn Thr Arg Glu Ile Pro
                165                 170                 175

Glu Pro Asn Glu Asp Tyr Pro Asp Tyr Val His Ala Glu Lys Ser Arg
            180                 185                 190

Leu Ala Ser Glu Glu Gln Val Leu Arg Ala Ala Thr Ser Ile Tyr Gly
        195                 200                 205

Ala Pro Gly Gln Ala Glu Pro Pro Gln Ala Phe Ile Asp Glu Val Ala
    210                 215                 220

Arg Val Tyr Glu Ile Asn His Gly Arg Gly Pro Asn Gln Glu Gln Met
225                 230                 235                 240

Lys Asp Leu Leu Leu Thr Ala Met Glu Met Lys His Arg Asn Pro Arg
                245                 250                 255

Arg Ala Pro Pro Lys Pro Lys Pro Lys Pro Asn Ala Pro Ser Gln Arg
            260                 265                 270

Pro Pro Gly Arg Leu Gly Arg Trp Ile Arg Thr Val Ser Asp Glu Asp
        275                 280                 285

Leu Glu
    290

<210> SEQ ID NO 81
<211> LENGTH: 881
<212> TYPE: PRT
<213> ORGANISM: Infectious bursal disease virus
<220> FEATURE:
<221> NAME/KEY: DOMAIN
<222> LOCATION: (1)..(881)
<223> OTHER INFORMATION: Consensus sequence of IBDV VP1
<220> FEATURE:
<221> NAME/KEY: MISC_FEATURE
<222> LOCATION: (4)
<223> OTHER INFORMATION: The 'Xaa' at position 4 may be any amino acid
<220> FEATURE:
<221> NAME/KEY: MISC_FEATURE
<222> LOCATION: (13)
<223> OTHER INFORMATION: The 'Xaa' at position 13 may be any amino acid
<220> FEATURE:
<221> NAME/KEY: MISC_FEATURE
<222> LOCATION: (61)
<223> OTHER INFORMATION: The 'Xaa' at position 61 may be any amino acid
<220> FEATURE:
<221> NAME/KEY: MISC_FEATURE
<222> LOCATION: (145)...(147)
<223> OTHER INFORMATION: The 'Xaa' at positions 145-147 may be any amino
```

```
              acid
<220> FEATURE:
<221> NAME/KEY: MISC_FEATURE
<222> LOCATION: (242)
<223> OTHER INFORMATION: The 'Xaa' at position 242 may be any amino acid
<220> FEATURE:
<221> NAME/KEY: MISC_FEATURE
<222> LOCATION: (287)
<223> OTHER INFORMATION: The 'Xaa' at position 287 may be any amino acid
<220> FEATURE:
<221> NAME/KEY: MISC_FEATURE
<222> LOCATION: (390)
<223> OTHER INFORMATION: The 'Xaa' at position 390 may be any amino acid
<220> FEATURE:
<221> NAME/KEY: MISC_FEATURE
<222> LOCATION: (393)
<223> OTHER INFORMATION: The 'Xaa' at position 393 may be any amino acid
<220> FEATURE:
<221> NAME/KEY: MISC_FEATURE
<222> LOCATION: (508)
<223> OTHER INFORMATION: The 'Xaa' at position 508 may be any amino acid
<220> FEATURE:
<221> NAME/KEY: MISC_FEATURE
<222> LOCATION: (511)
<223> OTHER INFORMATION: The 'Xaa' at position 511 may be any amino acid
<220> FEATURE:
<221> NAME/KEY: MISC_FEATURE
<222> LOCATION: (546)
<223> OTHER INFORMATION: The 'Xaa' at position 546 may be any amino acid
<220> FEATURE:
<221> NAME/KEY: MISC_FEATURE
<222> LOCATION: (562)
<223> OTHER INFORMATION: The 'Xaa' at position 562 may be any amino acid
<220> FEATURE:
<221> NAME/KEY: MISC_FEATURE
<222> LOCATION: (646)
<223> OTHER INFORMATION: The 'Xaa' at position 646 may be any amino acid
<220> FEATURE:
<221> NAME/KEY: MISC_FEATURE
<222> LOCATION: (687)
<223> OTHER INFORMATION: The 'Xaa' at position 687 may be any amino acid
<220> FEATURE:
<221> NAME/KEY: MISC_FEATURE
<222> LOCATION: (695)
<223> OTHER INFORMATION: The 'Xaa' at position 695 may be any amino acid
<220> FEATURE:
<221> NAME/KEY: MISC_FEATURE
<222> LOCATION: (880)...(881)
<223> OTHER INFORMATION: The 'Xaa' at positions 880-881 may be any amino
      acid

<400> SEQUENCE: 81

Met Ser Asp Xaa Phe Asn Ser Pro Gln Ala Arg Ser Xaa Ile Ser Ala
  1               5                  10                  15

Ala Phe Gly Ile Lys Pro Thr Ala Gly Gln Asp Val Glu Glu Leu Leu
                 20                  25                  30

Ile Pro Lys Val Trp Val Pro Glu Asp Pro Leu Ala Ser Pro Ser
             35                  40                  45

Arg Leu Ala Lys Phe Leu Arg Glu Asn Gly Tyr Lys Xaa Leu Gln Pro
 50                  55                  60

Arg Ser Leu Pro Glu Asn Glu Tyr Glu Thr Asp Gln Ile Leu Pro
 65                  70                  75                  80

Asp Leu Ala Trp Met Arg Gln Ile Glu Gly Ala Val Leu Lys Pro Thr
                 85                  90                  95

Leu Ser Leu Pro Ile Gly Asp Gln Glu Tyr Phe Pro Lys Tyr Tyr Pro
                100                 105                 110

Thr His Arg Pro Ser Lys Glu Lys Pro Asn Ala Tyr Pro Pro Asp Ile
            115                 120                 125

Ala Leu Leu Lys Gln Met Ile Tyr Leu Phe Leu Gln Val Pro Glu Ala
        130                 135                 140
```

```
Xaa Xaa Xaa Leu Lys Asp Glu Val Thr Leu Leu Thr Gln Asn Ile Arg
145                 150                 155                 160

Asp Lys Ala Tyr Gly Ser Gly Thr Tyr Met Gly Gln Ala Thr Arg Leu
                165                 170                 175

Val Ala Met Lys Glu Val Ala Thr Gly Arg Asn Pro Asn Lys Asp Pro
            180                 185                 190

Leu Lys Leu Gly Tyr Thr Phe Glu Ser Ile Ala Gln Leu Leu Asp Ile
        195                 200                 205

Thr Leu Pro Val Gly Pro Pro Gly Asp Asp Lys Pro Trp Val Pro
210                 215                 220

Leu Thr Arg Val Pro Ser Arg Met Leu Val Leu Thr Gly Asp Val Asp
225                 230                 235                 240

Gly Xaa Phe Glu Val Glu Asp Tyr Leu Pro Lys Ile Asn Leu Lys Ser
            245                 250                 255

Ser Ser Gly Leu Pro Tyr Val Gly Arg Thr Lys Gly Glu Thr Ile Gly
                260                 265                 270

Glu Met Ile Ala Ile Ser Asn Gln Phe Leu Arg Glu Leu Ser Xaa Leu
            275                 280                 285

Leu Lys Gln Gly Ala Gly Thr Lys Gly Ser Asn Lys Lys Leu Leu
        290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335

Ile Trp Ser Ala Pro Ser Pro Thr His Leu Met Ile Ser Met Ile Thr
                340                 345                 350

Trp Pro Val Met Ser Asn Ser Pro Asn Asn Val Leu Asn Ile Glu Gly
            355                 360                 365

Cys Pro Ser Leu Tyr Lys Phe Asn Pro Phe Arg Gly Gly Leu Asn Arg
            370                 375                 380

Ile Val Glu Trp Ile Xaa Ala Pro Xaa Glu Pro Lys Ala Leu Val Tyr
385                 390                 395                 400

Ala Asp Asn Ile Tyr Ile Val His Ser Asn Thr Trp Tyr Ser Ile Asp
                405                 410                 415

Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
    435                 440                 445

Phe Asn Gln Thr Trp Ala Thr Phe Ala Met Asn Ile Ala Pro Ala Leu
450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Xaa Gln Pro Xaa Pro
                500                 505                 510

Asp Ser Glu Glu Phe Lys Ser Ile Glu Asp Lys Leu Gly Ile Asn Phe
            515                 520                 525

Lys Ile Glu Arg Ser Ile Asp Asp Ile Arg Gly Lys Leu Arg Gln Leu
            530                 535                 540

Val Xaa Leu Ala Gln Pro Gly Tyr Leu Ser Gly Gly Val Glu Pro Glu
545                 550                 555                 560
```

```
Gln Xaa Ser Pro Thr Val Glu Leu Asp Leu Leu Gly Trp Ser Ala Thr
        565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
        595                 600                 605

Lys Ser Lys Val Gly Ile Glu Gln Ala Tyr Lys Val Val Arg Tyr Glu
    610                 615                 620

Ala Leu Arg Leu Val Gly Gly Trp Asn Tyr Pro Leu Leu Asn Lys Ala
625                 630                 635                 640

Cys Lys Asn Asn Ala Xaa Ala Ala Arg Arg His Leu Glu Ala Lys Gly
                645                 650                 655

Phe Pro Leu Asp Glu Phe Leu Ala Glu Trp Ser Glu Leu Ser Glu Phe
            660                 665                 670

Gly Glu Ala Phe Glu Gly Phe Asn Ile Lys Leu Thr Val Thr Xaa Glu
        675                 680                 685

Ser Leu Ala Glu Leu Asn Xaa Pro Val Pro Lys Pro Pro Asn Val
    690                 695                 700

Asn Arg Pro Val Asn Thr Gly Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
            740                 745                 750

Glu Ala Glu Lys Leu His Lys Ser Lys Pro Asp Asp Pro Asp Ala Asp
        755                 760                 765

Trp Phe Glu Arg Ser Glu Thr Leu Ser Asp Leu Leu Glu Lys Ala Asp
770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
            805                 810                 815

Val Lys Asn Pro Gln Thr Ala Ser Asn Pro Val Val Gly Leu His Leu
        820                 825                 830

Pro Ala Lys Arg Ala Thr Gly Val Gln Ala Ala Leu Leu Gly Ala Gly
    835                 840                 845

Thr Ser Arg Pro Met Gly Met Glu Ala Pro Thr Arg Ser Lys Asn Ala
    850                 855                 860

Val Lys Met Ala Lys Arg Gln Arg Gln Lys Glu Ser Arg Gln Xaa
865                 870                 875                 880

Xaa

<210> SEQ ID NO 82
<211> LENGTH: 881
<212> TYPE: PRT
<213> ORGANISM: Infectious bursal disease virus
<220> FEATURE:
<221> NAME/KEY: DOMAIN
<222> LOCATION: (1)..(881)
<223> OTHER INFORMATION: Sequence of IBDV CEF94-VP1

<400> SEQUENCE: 82

Met Ser Asp Ile Phe Asn Ser Pro Gln Ala Arg Ser Thr Ile Ser Ala
1               5                   10                  15

Ala Phe Gly Ile Lys Pro Thr Ala Gly Gln Asp Val Glu Glu Leu Leu
            20                  25                  30
```

```
Ile Pro Lys Val Trp Val Pro Glu Asp Pro Leu Ala Ser Pro Ser
         35                  40                  45

Arg Leu Ala Lys Phe Leu Arg Glu Asn Gly Tyr Lys Val Leu Gln Pro
 50                  55                  60

Arg Ser Leu Pro Glu Asn Glu Glu Tyr Glu Thr Asp Gln Ile Leu Pro
 65                  70                  75                  80

Asp Leu Ala Trp Met Arg Gln Ile Glu Gly Ala Val Leu Lys Pro Thr
                 85                  90                  95

Leu Ser Leu Pro Ile Gly Asp Gln Glu Tyr Phe Pro Lys Tyr Tyr Pro
                100                 105                 110

Thr His Arg Pro Ser Lys Glu Lys Pro Asn Ala Tyr Pro Pro Asp Ile
            115                 120                 125

Ala Leu Leu Lys Gln Met Ile Tyr Leu Phe Leu Gln Val Pro Glu Ala
        130                 135                 140

Asn Glu Gly Leu Lys Asp Glu Val Thr Leu Leu Thr Gln Asn Ile Arg
145                 150                 155                 160

Asp Lys Ala Tyr Gly Ser Gly Thr Tyr Met Gly Gln Ala Thr Arg Leu
                165                 170                 175

Val Ala Met Lys Glu Val Ala Thr Gly Arg Asn Pro Asn Lys Asp Pro
                180                 185                 190

Leu Lys Leu Gly Tyr Thr Phe Glu Ser Ile Ala Gln Leu Leu Asp Ile
            195                 200                 205

Thr Leu Pro Val Gly Pro Pro Gly Glu Asp Lys Pro Trp Val Pro
        210                 215                 220

Leu Thr Arg Val Pro Ser Arg Met Leu Val Leu Thr Gly Asp Val Asp
225                 230                 235                 240

Gly Asp Phe Glu Val Glu Asp Tyr Leu Pro Lys Ile Asn Leu Lys Ser
                245                 250                 255

Ser Ser Gly Leu Pro Tyr Val Gly Arg Thr Lys Gly Glu Thr Ile Gly
            260                 265                 270

Glu Met Ile Ala Ile Ser Asn Gln Phe Leu Arg Glu Leu Ser Thr Leu
        275                 280                 285

Leu Lys Gln Gly Ala Gly Thr Lys Gly Ser Asn Lys Lys Leu Leu
290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335

Ile Trp Ser Ala Pro Ser Pro Thr His Leu Met Ile Ser Met Ile Thr
            340                 345                 350

Trp Pro Val Met Ser Asn Ser Pro Asn Asn Val Leu Asn Ile Glu Gly
        355                 360                 365

Cys Pro Ser Leu Tyr Lys Phe Asn Pro Phe Arg Gly Gly Leu Asn Arg
        370                 375                 380

Ile Val Glu Trp Ile Leu Ala Pro Glu Pro Lys Ala Leu Val Tyr
385                 390                 395                 400

Ala Asp Asn Ile Tyr Ile Val His Ser Asn Thr Trp Tyr Ser Ile Asp
                405                 410                 415

Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
        435                 440                 445
```

-continued

Phe Asn Gln Thr Trp Ala Thr Phe Ala Met Asn Ile Ala Pro Ala Leu
    450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Arg Gln Pro Arg Pro
            500                 505                 510

Asp Ser Glu Glu Phe Lys Ser Ile Glu Asp Lys Leu Gly Ile Asn Phe
        515                 520                 525

Lys Ile Glu Arg Ser Ile Asp Asp Ile Arg Gly Lys Leu Arg Gln Leu
    530                 535                 540

Val Leu Leu Ala Gln Pro Gly Tyr Leu Ser Gly Gly Val Glu Pro Glu
545                 550                 555                 560

Gln Ser Ser Pro Thr Val Glu Leu Asp Leu Leu Gly Trp Ser Ala Thr
                565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
        595                 600                 605

Lys Ser Lys Val Gly Ile Glu Gln Ala Tyr Lys Val Val Arg Tyr Glu
    610                 615                 620

Ala Leu Arg Leu Val Gly Gly Trp Asn Tyr Pro Leu Leu Asn Lys Ala
625                 630                 635                 640

Cys Lys Asn Asn Ala Gly Ala Ala Arg His Leu Glu Ala Lys Gly
                645                 650                 655

Phe Pro Leu Asp Glu Phe Leu Ala Glu Trp Ser Glu Leu Ser Glu Phe
            660                 665                 670

Gly Glu Ala Phe Glu Gly Phe Asn Ile Lys Leu Thr Val Thr Ser Glu
        675                 680                 685

Ser Leu Ala Glu Leu Asn Lys Pro Val Pro Pro Lys Pro Pro Asn Val
    690                 695                 700

Asn Arg Pro Val Asn Thr Gly Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
            740                 745                 750

Glu Ala Glu Lys Leu His Lys Ser Lys Pro Asp Asp Pro Asp Ala Asp
        755                 760                 765

Trp Phe Glu Arg Ser Glu Thr Leu Ser Asp Leu Leu Glu Lys Ala Asp
    770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
                805                 810                 815

Val Lys Asn Pro Gln Thr Ala Ser Asn Pro Val Val Gly Leu His Leu
            820                 825                 830

Pro Ala Lys Arg Ala Thr Gly Val Gln Ala Ala Leu Leu Gly Ala Gly
        835                 840                 845

Thr Ser Arg Pro Met Gly Met Glu Ala Pro Thr Arg Ser Lys Asn Ala
    850                 855                 860

Val Lys Met Ala Lys Arg Arg Gln Arg Gln Lys Glu Ser Arg Gln Gln

<210> SEQ ID NO 83
<211> LENGTH: 879
<212> TYPE: PRT
<213> ORGANISM: Infectious bursal disease virus
<220> FEATURE:
<221> NAME/KEY: DOMAIN
<222> LOCATION: (1)..(879)
<223> OTHER INFORMATION: Sequence of IBDV D6948-VP1

<400> SEQUENCE: 83

```
Met Ser Asp Val Phe Asn Ser Pro Gln Ala Arg Ser Lys Ile Ser Ala
 1               5                  10                  15

Ala Phe Gly Ile Lys Pro Thr Ala Gly Gln Asp Val Glu Glu Leu Leu
            20                  25                  30

Ile Pro Lys Val Trp Val Pro Glu Asp Pro Leu Ala Ser Pro Ser
        35                  40                  45

Arg Leu Ala Lys Phe Leu Arg Glu Asn Gly Tyr Lys Ile Leu Gln Pro
    50                  55                  60

Arg Ser Leu Pro Glu Asn Glu Glu Tyr Glu Thr Asp Gln Ile Leu Pro
65                  70                  75                  80

Asp Leu Ala Trp Met Arg Gln Ile Glu Gly Ala Val Leu Lys Pro Thr
                85                  90                  95

Leu Ser Leu Pro Ile Gly Asp Gln Glu Tyr Phe Pro Lys Tyr Tyr Pro
            100                 105                 110

Thr His Arg Pro Ser Lys Glu Lys Pro Asn Ala Tyr Pro Pro Asp Ile
        115                 120                 125

Ala Leu Leu Lys Gln Met Ile Tyr Leu Phe Leu Gln Val Pro Glu Ala
    130                 135                 140

Thr Asp Asn Leu Lys Asp Glu Val Thr Leu Leu Thr Gln Asn Ile Arg
145                 150                 155                 160

Asp Lys Ala Tyr Gly Ser Gly Thr Tyr Met Gly Gln Ala Thr Arg Leu
                165                 170                 175

Val Ala Met Lys Glu Val Ala Thr Gly Arg Asn Pro Asn Lys Asp Pro
            180                 185                 190

Leu Lys Leu Gly Tyr Thr Phe Glu Ser Ile Ala Gln Leu Leu Asp Ile
        195                 200                 205

Thr Leu Pro Val Gly Pro Pro Gly Glu Asp Lys Pro Trp Val Pro
    210                 215                 220

Leu Thr Arg Val Pro Ser Arg Met Leu Val Leu Thr Gly Asp Val Asp
225                 230                 235                 240

Gly Glu Phe Glu Val Glu Asp Tyr Leu Pro Lys Ile Asn Leu Lys Ser
                245                 250                 255

Ser Ser Gly Leu Pro Tyr Val Gly Arg Thr Lys Gly Glu Thr Ile Gly
            260                 265                 270

Glu Met Ile Ala Ile Ser Asn Gln Phe Leu Arg Glu Leu Ser Ala Leu
        275                 280                 285

Leu Lys Gln Gly Ala Gly Thr Lys Gly Ser Asn Lys Lys Leu Leu
    290                 295                 300

Ser Met Leu Ser Asp Tyr Trp Tyr Leu Ser Cys Gly Leu Leu Phe Pro
305                 310                 315                 320

Lys Ala Glu Arg Tyr Asp Lys Ser Thr Trp Leu Thr Lys Thr Arg Asn
                325                 330                 335
```

-continued

Ile Trp Ser Ala Pro Ser Pro Thr His Leu Met Ile Ser Met Ile Thr
                340                 345                 350

Trp Pro Val Met Ser Asn Ser Pro Asn Asn Val Leu Asn Ile Glu Gly
            355                 360                 365

Cys Pro Ser Leu Tyr Lys Phe Asn Pro Phe Arg Gly Gly Leu Asn Arg
        370                 375                 380

Ile Val Glu Trp Ile Met Ala Pro Asp Glu Pro Lys Ala Leu Val Tyr
385                 390                 395                 400

Ala Asp Asn Ile Tyr Ile Val His Ser Asn Thr Trp Tyr Ser Ile Asp
                405                 410                 415

Leu Glu Lys Gly Glu Ala Asn Cys Thr Arg Gln His Met Gln Ala Ala
            420                 425                 430

Met Tyr Tyr Ile Leu Thr Arg Gly Trp Ser Asp Asn Gly Asp Pro Met
        435                 440                 445

Phe Asn Gln Thr Trp Ala Thr Phe Ala Met Asn Ile Ala Pro Ala Leu
    450                 455                 460

Val Val Asp Ser Ser Cys Leu Ile Met Asn Leu Gln Ile Lys Thr Tyr
465                 470                 475                 480

Gly Gln Gly Ser Gly Asn Ala Ala Thr Phe Ile Asn Asn His Leu Leu
                485                 490                 495

Ser Thr Leu Val Leu Asp Gln Trp Asn Leu Met Lys Gln Pro Ser Pro
            500                 505                 510

Asp Ser Glu Glu Phe Lys Ser Ile Glu Asp Lys Leu Gly Ile Asn Phe
        515                 520                 525

Lys Ile Glu Arg Ser Ile Asp Asp Ile Arg Gly Lys Leu Arg Gln Leu
    530                 535                 540

Val Pro Leu Ala Gln Pro Gly Tyr Leu Ser Gly Gly Val Glu Pro Glu
545                 550                 555                 560

Gln Pro Ser Pro Thr Val Glu Leu Asp Leu Leu Gly Trp Ser Ala Thr
                565                 570                 575

Tyr Ser Lys Asp Leu Gly Ile Tyr Val Pro Val Leu Asp Lys Glu Arg
            580                 585                 590

Leu Phe Cys Ser Ala Ala Tyr Pro Lys Gly Val Glu Asn Lys Ser Leu
        595                 600                 605

Lys Ser Lys Val Gly Ile Glu Gln Ala Tyr Lys Val Val Arg Tyr Glu
    610                 615                 620

Ala Leu Arg Leu Val Gly Gly Trp Asn Tyr Pro Leu Leu Asn Lys Ala
625                 630                 635                 640

Cys Lys Asn Asn Ala Ser Ala Ala Arg Arg His Leu Glu Ala Lys Gly
                645                 650                 655

Phe Pro Leu Asp Glu Phe Leu Ala Glu Trp Ser Glu Leu Ser Glu Phe
            660                 665                 670

Gly Glu Ala Phe Glu Gly Phe Asn Ile Lys Leu Thr Val Thr Pro Glu
        675                 680                 685

Ser Leu Ala Glu Leu Asn Arg Pro Val Pro Lys Pro Pro Asn Val
    690                 695                 700

Asn Arg Pro Val Asn Thr Gly Gly Leu Lys Ala Val Ser Asn Ala Leu
705                 710                 715                 720

Lys Thr Gly Arg Tyr Arg Asn Glu Ala Gly Leu Ser Gly Leu Val Leu
                725                 730                 735

Leu Ala Thr Ala Arg Ser Arg Leu Gln Asp Ala Val Lys Ala Lys Ala
            740                 745                 750

Glu Ala Glu Lys Leu His Lys Ser Lys Pro Asp Asp Pro Asp Ala Asp

```
                755                 760                 765

Trp Phe Glu Arg Ser Glu Thr Leu Ser Asp Leu Leu Glu Lys Ala Asp
    770                 775                 780

Ile Ala Ser Lys Val Ala His Ser Ala Leu Val Glu Thr Ser Asp Ala
785                 790                 795                 800

Leu Glu Ala Val Gln Ser Thr Ser Val Tyr Thr Pro Lys Tyr Pro Glu
                805                 810                 815

Val Lys Asn Pro Gln Thr Ala Ser Asn Pro Val Val Gly Leu His Leu
                820                 825                 830

Pro Ala Lys Arg Ala Thr Gly Val Gln Ala Ala Leu Leu Gly Ala Gly
                835                 840                 845

Thr Ser Arg Pro Met Gly Met Glu Ala Pro Thr Arg Ser Lys Asn Ala
850                 855                 860

Val Lys Met Ala Lys Arg Arg Gln Arg Gln Lys Glu Ser Arg Gln
865                 870                 875

<210> SEQ ID NO 84
<211> LENGTH: 145
<212> TYPE: PRT
<213> ORGANISM: Infectious bursal disease virus
<220> FEATURE:
<221> NAME/KEY: DOMAIN
<222> LOCATION: (1)..(145)
<223> OTHER INFORMATION: Consensus sequence of IBDV VP5
<220> FEATURE:
<221> NAME/KEY: MISC_FEATURE
<222> LOCATION: (14)
<223> OTHER INFORMATION: The 'Xaa' at position 14 may be any amino acid
<220> FEATURE:
<221> NAME/KEY: MISC_FEATURE
<222> LOCATION: (45)
<223> OTHER INFORMATION: The 'Xaa' at position 45 may be any amino acid
<220> FEATURE:
<221> NAME/KEY: MISC_FEATURE
<222> LOCATION: (74)
<223> OTHER INFORMATION: The 'Xaa' at position 74 may be any amino acid
<220> FEATURE:
<221> NAME/KEY: MISC_FEATURE
<222> LOCATION: (125)
<223> OTHER INFORMATION: The 'Xaa' at position 125 may be any amino acid
<220> FEATURE:
<221> NAME/KEY: MISC_FEATURE
<222> LOCATION: (133)
<223> OTHER INFORMATION: The 'Xaa' at position 133 may be any amino acid

<400> SEQUENCE: 84

Met Val Ser Arg Asp Gln Thr Asn Asp Arg Ser Asp Asp Xaa Pro Ala
1               5                   10                  15

Arg Ser Asn Pro Thr Asp Cys Ser Val His Thr Glu Pro Ser Asp Ala
                20                  25                  30

Asn Asn Arg Thr Gly Val His Ser Gly Arg His Pro Xaa Glu Ala His
            35                  40                  45

Ser Gln Val Arg Asp Leu Asp Leu Gln Phe Asp Cys Gly Gly His Arg
        50                  55                  60

Val Arg Ala Asn Cys Leu Phe Pro Trp Xaa Pro Trp Leu Asn Cys Gly
65              70                  75                  80

Cys Ser Leu His Thr Ala Glu Gln Trp Glu Leu Gln Val Arg Ser Asp
                85                  90                  95

Ala Pro Asp Cys Pro Glu Pro Thr Gly Gln Leu Gln Leu Leu Gln Ala
                100                 105                 110

Ser Glu Ser Glu Ser His Ser Glu Val Lys His Thr Xaa Trp Trp Arg
            115                 120                 125
```

```
Leu Cys Thr Lys Xaa His His Lys Arg Arg Asp Leu Pro Arg Lys Pro
    130                 135                 140

Glu
145

<210> SEQ ID NO 85
<211> LENGTH: 145
<212> TYPE: PRT
<213> ORGANISM: Infectious bursal disease virus
<220> FEATURE:
<221> NAME/KEY: DOMAIN
<222> LOCATION: (1)..(145)
<223> OTHER INFORMATION: Sequence of IBDV D6948-VP5

<400> SEQUENCE: 85

Met Val Ser Arg Asp Gln Thr Asn Asp Arg Ser Asp Asp Glu Pro Ala
  1               5                  10                  15

Arg Ser Asn Pro Thr Asp Cys Ser Val His Thr Glu Pro Ser Asp Ala
             20                  25                  30

Asn Asn Arg Thr Gly Val His Ser Gly Arg His Pro Arg Glu Ala His
         35                  40                  45

Ser Gln Val Arg Asp Leu Asp Leu Gln Phe Asp Cys Gly Gly His Arg
    50                  55                  60

Val Arg Ala Asn Cys Leu Phe Pro Trp Phe Pro Trp Leu Asn Cys Gly
 65                  70                  75                  80

Cys Ser Leu His Thr Ala Glu Gln Trp Glu Leu Gln Val Arg Ser Asp
                 85                  90                  95

Ala Pro Asp Cys Pro Glu Pro Thr Gly Gln Leu Gln Leu Leu Gln Ala
            100                 105                 110

Ser Glu Ser Glu Ser His Ser Glu Val Lys His Thr Pro Trp Trp Arg
        115                 120                 125

Leu Cys Thr Lys Trp His His Lys Arg Arg Asp Leu Pro Arg Lys Pro
    130                 135                 140

Glu
145

<210> SEQ ID NO 86
<211> LENGTH: 145
<212> TYPE: PRT
<213> ORGANISM: Infectious bursal disease virus
<220> FEATURE:
<221> NAME/KEY: DOMAIN
<222> LOCATION: (1)..(145)
<223> OTHER INFORMATION: Sequence of IBDV CEF94-VP5

<400> SEQUENCE: 86

Met Val Ser Arg Asp Gln Thr Asn Asp Arg Ser Asp Asp Lys Pro Ala
  1               5                  10                  15

Arg Ser Asn Pro Thr Asp Cys Ser Val His Thr Glu Pro Ser Asp Ala
             20                  25                  30

Asn Asn Arg Thr Gly Val His Ser Gly Arg His Pro Gly Glu Ala His
         35                  40                  45

Ser Gln Val Arg Asp Leu Asp Leu Gln Phe Asp Cys Gly Gly His Arg
    50                  55                  60

Val Arg Ala Asn Cys Leu Phe Pro Trp Ile Pro Trp Leu Asn Cys Gly
 65                  70                  75                  80

Cys Ser Leu His Thr Ala Glu Gln Trp Glu Leu Gln Val Arg Ser Asp
                 85                  90                  95

Ala Pro Asp Cys Pro Glu Pro Thr Gly Gln Leu Gln Leu Leu Gln Ala
```

-continued

```
                   100                 105                 110
Ser Glu Ser Glu Ser His Ser Glu Val Lys His Thr Ser Trp Trp Arg
            115                 120                 125

Leu Cys Thr Lys Arg His His Lys Arg Arg Asp Leu Pro Arg Lys Pro
        130                 135                 140

Glu
145

<210> SEQ ID NO 87
<211> LENGTH: 149
<212> TYPE: PRT
<213> ORGANISM: Infectious bursal disease virus
<220> FEATURE:
<221> NAME/KEY: DOMAIN
<222> LOCATION: (1)..(149)
<223> OTHER INFORMATION: Sequence of IBDV D6948-VP5

<400> SEQUENCE: 87

Met Leu Ser Leu Met Val Ser Arg Asp Gln Thr Asn Asp Arg Ser Asp
  1               5                  10                  15

Asp Glu Pro Ala Arg Ser Asn Pro Thr Asp Cys Ser Val His Thr Glu
             20                  25                  30

Pro Ser Asp Ala Asn Asn Arg Thr Gly Val His Ser Gly Arg His Pro
         35                  40                  45

Arg Glu Ala His Ser Gln Val Arg Asp Leu Asp Leu Gln Phe Asp Cys
     50                  55                  60

Gly Gly His Arg Val Arg Ala Asn Cys Leu Phe Pro Trp Phe Pro Trp
 65                  70                  75                  80

Leu Asn Cys Gly Cys Ser Leu His Thr Ala Glu Gln Trp Glu Leu Gln
                 85                  90                  95

Val Arg Ser Asp Ala Pro Asp Cys Pro Glu Pro Thr Gly Gln Leu Gln
            100                 105                 110

Leu Leu Gln Ala Ser Glu Ser Glu Ser His Ser Glu Val Lys His Thr
        115                 120                 125

Pro Trp Trp Arg Leu Cys Thr Lys Trp His His Lys Arg Arg Asp Leu
    130                 135                 140

Pro Arg Lys Pro Glu
145
```